US012516127B2

(12) United States Patent
Gupta et al.

(10) Patent No.: US 12,516,127 B2
(45) Date of Patent: Jan. 6, 2026

(54) ANTI-SIRP-ALPHA ANTIBODIES

(71) Applicants: Boehringer Ingelheim International GmbH, Ingelheim am Rhein (DE); OSE Immunotherapeutics SA, Nantes (FR)

(72) Inventors: Pankaj Gupta, Scarsdale, NY (US); Priyanka Gupta, Danbury, CT (US); Habtom Habte, LaFayette Hill, PA (US); Yining Huang, Belmont, MA (US); Sandeep Kumar, Ridgefield, CT (US); Kathryn Phoenix, Burlington, CT (US); Kerry-Leigh Ralph, Bethel, CT (US); Wing Pan Kenny Tsang, Bronx, NY (US); Eduardo Sergio Trombetta, Guilford, CT (US)

(73) Assignees: Boehringer ingelheim International GmbH, Ingelheim am Rhein (DE); OSE Immunotherapeutics SA, Nantes (FR)

( * ) Notice: Subject to any disclaimer, the term of this patent is extended or adjusted under 35 U.S.C. 154(b) by 560 days.

(21) Appl. No.: 18/055,352

(22) Filed: Nov. 14, 2022

(65) Prior Publication Data

US 2023/0203188 A1 Jun. 29, 2023

Related U.S. Application Data

(63) Continuation of application No. 17/831,245, filed on Jun. 2, 2022, now Pat. No. 11,572,412.

(60) Provisional application No. 63/339,326, filed on May 6, 2022, provisional application No. 63/325,828, filed on Mar. 31, 2022, provisional application No. 63/197,259, filed on Jun. 4, 2021.

(51) Int. Cl.

*C07K 16/00* (2006.01)
*A61P 35/00* (2006.01)
*C07K 16/28* (2006.01)

(52) U.S. Cl.

CPC .......... *C07K 16/2896* (2013.01); *A61P 35/00* (2018.01); *C07K 2317/21* (2013.01); *C07K 2317/565* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 6,037,454 A | 3/2000 | Jardieu et al. | |
| 6,054,297 A | 4/2000 | Carter et al. | |
| 6,407,213 B1 | 6/2002 | Carter et al. | |
| 11,401,338 B2 * | 8/2022 | Pons | C07K 16/2896 |
| 2010/0215640 A1 | 8/2010 | Clemmons et al. | |
| 2010/0233251 A1 | 9/2010 | Von Andrian et al. | |
| 2012/0039896 A1 | 2/2012 | Clemmons et al. | |
| 2012/0070461 A1 | 3/2012 | Singh et al. | |
| 2014/0141002 A1 | 5/2014 | Clemmons et al. | |
| 2014/0242095 A1 | 8/2014 | Wang et al. | |
| 2019/0359707 A1 | 11/2019 | Pincetic et al. | |
| 2022/0275084 A1 | 9/2022 | Wernig et al. | |

FOREIGN PATENT DOCUMENTS

| | | |
|---|---|---|
| CN | 105085679 A | 11/2015 |
| CN | 111995682 A | 11/2020 |
| CN | 112574310 A | 3/2021 |
| IN | 112010979 A | 12/2020 |
| WO | 199005144 A1 | 5/1990 |
| WO | 199013646 A1 | 11/1990 |
| WO | 199632478 A1 | 10/1996 |
| WO | 2005077042 A2 | 8/2005 |
| WO | 2007005874 A2 | 1/2007 |
| WO | 2009131453 A1 | 10/2009 |
| WO | 2010077634 A1 | 7/2010 |
| WO | 2010130053 A1 | 11/2010 |
| WO | 2012092374 A2 | 7/2012 |
| WO | 2012149416 A3 | 1/2013 |
| WO | 2013056352 A1 | 4/2013 |
| WO | 2013079174 A1 | 6/2013 |
| WO | 2015048312 A1 | 4/2015 |
| WO | 2015138600 A3 | 11/2015 |
| WO | 2017178653 A2 | 10/2017 |
| WO | 2018057669 A1 | 3/2018 |

(Continued)

OTHER PUBLICATIONS

European Patent Office, Internationa Preliminary Report on Patentability in International Patent Application No. PCT/IB20222/055170, 16 pp. (Nov. 24, 2022).
European Patent Office, International Search Report in International Patent Application No. PCT/IB2024/059746, 5 pp. (Feb. 13, 2025).
European Patent Office, International Search Report in International Patent Application No. PCT/IB2024/059756, 5 pp. (Feb. 13, 2025).
European Patent Office, Written Opinion in International Patent Application No. PCT/IB2022/055170, 14 pp. (Aug. 4, 2022).
European Patent Office, Written Opinion in International Patent Application No. PCT/IB2024/059746, 6 pp. (Feb. 13, 2025).
European Patent Office, Written Opinion in International Patent Application No. PCT/IB2027/059756, 6 pp. (Feb. 13, 2025).

(Continued)

*Primary Examiner* — Meera Natarajan
(74) *Attorney, Agent, or Firm* — Morgan, Lewis & Bockius LLP

(57) ABSTRACT

The present invention relates to anti-SIRPα (Signal regulatory protein alpha) antibodies and antigen-binding fragments thereof for therapeutic and diagnostic methods and compositions using them.

19 Claims, 52 Drawing Sheets
(2 of 52 Drawing Sheet(s) Filed in Color)

Specification includes a Sequence Listing.

(56) References Cited

FOREIGN PATENT DOCUMENTS

| | | | |
|---|---|---|---|
| WO | 2018107058 | A1 | 6/2018 |
| WO | 2018190719 | A2 | 10/2018 |
| WO | 2018210793 | A2 | 11/2018 |
| WO | 2019023347 | A1 | 1/2019 |
| WO | 2019073080 | A1 | 4/2019 |
| WO | 2019183266 | A1 | 9/2019 |
| WO | 2019226973 | A1 | 11/2019 |
| WO | 2020013170 | A1 | 1/2020 |
| WO | 2020033646 | A1 | 2/2020 |
| WO | 2020068752 | A1 | 4/2020 |
| WO | 2020099653 | A1 | 5/2020 |
| WO | 2020102422 | A1 | 5/2020 |
| WO | 2020180811 | A1 | 9/2020 |
| WO | 2021032078 | A1 | 2/2021 |
| WO | 2021185273 | A1 | 9/2021 |
| WO | 2022254379 | A1 | 12/2022 |

OTHER PUBLICATIONS

Shi et al., "CD47-SIRPα axis bloackade in NASH promotes necroptic hepatocyte clearance by liver macrophages and decreases hepatic fibrosis," Science Translational Medicine, 14 (672), 27 pp. (Nov. 23, 2022).

Son et al., "Inhibition of the CD47_SIRPα axis for cancer therapy: A systematic review and meta-analysis of emerging clinical data," Frontiers in Immunology, 13, 11 pp. (Nov. 11, 2022).

Abdiche et al., "High-Throughput Epitope Binning Assays on Label-Free Array-Based Biosensors Can Yield Exquisite Epitope Discrimination That Facilitates the Selection of Monoclonal Antibodies with Functional Activity", PLOS ONE, 2014, vol. 9, No. 3, pp. e92451.

Ahmed et al., "Intrinsic physicochemical profile of marketed antibody-based biotherapeutics", Proceedings of the National Academy of Sciences, 2021, vol. 118, No. 37, p. e2020577118.

Alblas et al., "Signal Regulatory Protein Ligation Induces Macrophage Nitric Oxide Production Through JAK/STAT and Phosphatidylinositol 3-Kinase/Racl/NAPDH Oxidase/H2O2-Dependent Pathways", Molecular and Cellular Biology, Aug. 15, 2005, vol. 25, No. 16, pp. 7181-7192.

Almagro et al., "Antibody modeling assessment", Proteins: Structure, Function, and Bioinformatics, 2011, vol. 79, No. 11, pp. 3050-3066.

Almagro et al., "Humanization of antibodies.", Frontiers in Bioscience?: A Journal and Virtual Library, 2008, vol. 13, pp. 1619-1633.

Altschul et al., "Basic local alignment search tool", Journal of Molecular Biology, 1990, vol. 215, No. 3, pp. 403-410.

Altschul et al., "Gapped BLAST and PSI-BLAST: a new generation of protein database search programs", Nucleic Acids Research, 1997, vol. 25, No. 17, pp. 3389-3402.

Ansell et al., "Targeting Immune Checkpoints in Lymphoma", Current Opinion in Hematology, 2015, pp. 337-342, vol. 22, No. 4.

Barclay et al., "The Counterbalance Theory for Evolution and Function of Paired Receptors", Immunity, 2008, vol. 29, No. 5, pp. 675-678.

Barclay et al., "The Interaction Between Signal Regulatory Protein Alpha (SIRPa) and CD47: Structure, Function, and Therapeutic Target", Annu Rev Immunol., Nov. 6, 2013, pp. 25-50.

Brahmer et al., "Safety and Activity of Anti-PD-L 1 Antibody in Patients with Advanced Cancer", N Eng J_ Med, 2012, vol. 366, No. 26.

Brennan et al., "Preparation of Bispecific Antibodies by Chemical Recombination of Monoclonal Immunoglobulin G1 Fragments", Science, 1985, vol. 229, No. 4708, pp. 81-83.

Brooke et al., "Human Lymphocytes Interact Directly with CD47 through a Novel Member of the Signal Regulatory Protein (SIRP) Family", The Journal of Immunology, 2004, vol. 173, No. 4, pp. 2562-2570.

Brown et al., "Assessing the binding properties of the anti-PD-1 antibody landscape using label-free biosensors", PLOS ONE, 2020, vol. 15, No. 3, pp. e0229206.

Bruggemann et al., "Production of human antibody repertoires in transgenic mice", Current Opinion in Biotechnology, 1997, vol. 8, No. 4, pp. 455-458.

Carmen et al., "Concepts in antibody phage display", Briefings in Functional Genomics, 2002, vol. 1, No. 2, pp. 189-203.

Carter et al., "High Level Escherichia coli Expression and Production of a Bivalent Humanized Antibody Fragment", Bio/Technology, 1992, vol. 10, No. 2, pp. 163-167.

Chao et al., "Response: Mechanisms of targeting CD47-SIRP [alpha] in hematologic malignancies", Blood American Society of Hematology, US, vol. 119, No. 18, May 3, 2012 (May 3, 2012), pp. 4334-4335.

Chothia et al., "Canonical structures for the hypervariable regions of immunoglobulins", Journal of Molecular Biology, 1987, vol. 196, No. 4, pp. 901-917.

Chothia et al., "Domain association in immunoglobulin molecules The packing of variable domains", Journal of Molecular Biology, 1985, vol. 186, No. 3, pp. 651-663.

Clackson et al., "Making antibody fragments using phage display libraries", Nature, 1991, vol. 352, No. 6336, pp. 624-628.

Crepeau et al., "Challenges and Opportunities in Targeting the CD28/CTLA-4 Pathway in Transplantation and Autoimmunity", Expert Opin. Biol. Ther, 2017,pp. 1001-1012, vol. 17, No. 8.

Dahal et al., "Fc?R requirements leading to successful immunotherapy", Immunological Reviews, 2015, vol. 268, No. 1, pp. 104-122.

Edge et al., "Deglycosylation of glycoproteins by trifluoromethanesulfonic acid", Analytical Biochemistry, 1981, vol. 118, No. 1, pp. 131-137.

Gabrilovich et al., (Nat. Rev. Immunol., Mar. 2009, 9(3): 162-174.

Gauttier et al., "Dual Targeting of Adaptive and Innate Immune Checkpoints Induce Potent Memory Anti-Tumor Response". European Journal of Cancer, Jul. 11, 2016, pp. S216-S217, vol. 61, Supplement 1.

Gilbreth et al., "Crystal Structure of the Human 4-1 BB/4-1 BBL Complex", J Biol Chem., 2018, pp. 9880-9891, vol. 293, No. 25.

Girard et al., "CD80 and CD86 IgC Domains are Important for Quaternary Structure, Receptor Binding and Co-Signaling Function", Immunology Letters, 2014.

Graham et al., "Characteristics of a Human Cell Line Transformed by DNA from Human Adenovirus Type 5", Journal of General Virology, 1977, vol. 36, No. 1, pp. 59-72.

Hatherly et al., "The Structure of the Macrophage Signal Regulatory Protein (SIRP) Inhibitory Receptor Reveals a Binding Face Reminiscent of That Used by T Cell Receptors", Journal of Biological Chemistry, Mar. 6, 2007, pp. 14567-14575, vol. 282, No. 19.

Higgins et al., "[22] Using CLUSTAL for multiple sequence alignments", Methods in Enzymology, 1996, vol. 266, pp. 383-402.

Ishida et al., " Induced Expression of PD-1, A Novel Member of the immunoglobulin Gene Superfamily, Upon Programmed Cell Death", EMBO J., 1992, pp. 3887-3895, vol. 11, No. 11.

Jones et al., "The INNs and outs of antibody nonproprietary names", MABS, 2015, vol. 8, No. 1, pp. 1-9.

Justice et al., "Using the mouse to model human disease: increasing validity and reproducibility", Disease, Models & Mechanisms 9:101-103 (2016).

Karlin et al., "Applications and statistics for multiple high-scoring segments in molecular sequences.", Proceedings of the National Academy of Sciences, 1993, vol. 90, No. 12, pp. 5873-5877.

Karlin et al., "Methods for assessing the statistical significance of molecular sequence features by using general scoring schemes.", Proceedings of the National Academy of Sciences, 1990, vol. 87, No. 6, pp. 2264-2268.

Knappik et al., "Fully synthetic human combinatorial antibody libraries (HuCAL) based on modular consensus frameworks and CDRs randomized with trinucleotides 1 1 Edited by I. A. Wilson", Journal of Molecular Biology, 2000, vol. 296, No. 1, pp. 57-86.

Kohler, "Continuous cultures of fused cells secreting antibody of predefined specificity", Nature, 1975, vol. 256, pp. 495-497.

(56) References Cited

OTHER PUBLICATIONS

Lee et al., "Novel Structural Determinants on SIRP Alpha That Mediate Binding to CD47", Journal of Immunology, Jan. 1, 2007, pp. 7741-7750.
Lefranc, "Unique database numberings system for immunogenetic analysis", Immunology Today, 1997, vol. 18, No. 11, pp. 509.
Lin et al., "The PD-1/PD-1L Complex Resembles the Antigen-Binding Fv Domains of Antibodies and T Cell Receptors", PNAS, 2008, pp. 3011-3016, vol. 15, No. 8.
Liu et al., "Functional Elements on SIRPa IgV Domain Mediate Cell Surface Binding to CD47", Journal of Molecular Biology, 2007, vol. 365, No. 3, pp. 680-693.
Liu et al., "Signal Regulatory Protein (SIRPalpha), a Cellular Ligand for CD47, Regulates Neutrophil Transmigration," Journal of Biological Chemistry, Mar. 15, 2002, vol. 277, No. 12, pp. 10028-10036.
Lonberg et al., "Human Antibodies from Transgenic Mice", International Reviews of Immunology, 2009, vol. 13, No. 1, pp. 65-93.
Maier et al., "Assessment of fully automated antibody homology modeling protocols in molecular operating environment", Proteins: Structure, Function, and Bioinformatics, 2014, vol. 82, No. 8, pp. 1599-1610.
Marks et al., "By-passing immunization Human antibodies from V-gene libraries displayed on phage", Journal of Molecular Biology, 1991, vol. 222, No. 3, pp. 581-597.
Mather et al., "Culture of Testicular Cells in Hormone? Supplemented Serum?Free Medium*", Annals of the New York Academy of Sciences, 1982, vol. 383, No. 1, pp. 44-68.
Mather, "Establishment and Characterization of Two Distinct Mouse Testicular Epithelial Cell Line", Biology of Reproduction, 1980, vol. 23, No. 1, pp. 243-252.
Morimoto et al., "Single-step purification of F(ab?)2 fragments of mouse monoclonal antibodies (immunoglobulins G1) by hydrophobic interaction high performance liquid chromatography using TSKgel Phenyl-5PW", Journal of Biochemical and Biophysical Methods, 1992, vol. 24, No. 1-2, pp. 107-117.
Morrison et al., "Chimeric human antibody molecules: mouse antigen-binding domains with human constant region domains.", Proceedings of the National Academy of Sciences, 1984, vol. 81, No. 21, pp. 6851-6855.
Champiat et al., "Safety, pharmacokinetics, efficacy, and preliminary biomarker data of first-in-class BI 765063, a selective SIRPα inhibitor: Results of monotherapy dose escalation in phase 1 study in patients with advanced solid tumors.", Journal of Clinical Oncology, 2021, vol. 39, No. 15_suppl, p. 2623.
Delord et al., "A Phase 1 Study Evaluating BI 765063, a First in Class Selective Myeloid Sirpa Inhibitor, As Stand-Alone and in Combination with BI 754091, a Programmed Death-1 (PD-1) Inhibitor, in Patients with Advanced Solid Tumours", Blood, 2019, vol. 134, No. Supplement_1, p. 1040.
Gauttier et al., "Selective SIRPα blockade reverses tumor T cell exclusion and overcomes cancer immunotherapy resistance", Journal of Clinical Investigation, 2020, vol. 130, No. 11, pp. 6109-6123.
Kotecki et al., "34th Annual Meeting & Pre-Conference Programs of the Society for Immunotherapy of Cancer (SITC 2019): part 1", Journal for Immunotherapy of Cancer, 2019, vol. 7, No. Suppl 1, p. 428.
Kotecki et al., "983P Phase I dose escalation study in patients (pts) with advanced solid tumours receiving first-in-class BI 765063, a selective signal-regulatory protein α (SIRPα) inhibitor, in combination with ezabenlimab (BI 754091), a programmed cell death protein 1 (PD-1) inhibitor", Annals of Oncology, 2021, vol. 32, pp. S841-S842.
International Search Report for corresponding application PCT/IB2022/055170, date of mailing Sep. 2, 2022.
Mosser, David M., and Justin P. Edwards. "Exploring the full spectrum of macrophage activation." Nature reviews Immunology 8.12(2008): 958-969. (Year: 2008).
Myers et al., "Optimal alignments in linear space", CABIOS, 1988, vol. 4, pp. 11-17.
Nicolaou et al., "Calicheamicin ?: A Rationally Designed Molecule with Extremely Potent and Selective DNA Cleaving Properties and Apoptosis Inducing Activity." Angewandte Chemie International Edition in English 33.2 (1994): 183-186.
Nielsen et al., "Alternative Splice Variants of the Human PD-1-Gene", Cell Immunol, 2005, pp. 109-116, vol. 235.
North et al., "A New Clustering of Antibody CDR Loop Conformations", Journal of Molecular Biology, 2011, vol. 406, No. 2, pp. 228-256.
Ochando et al., "Myeloid-derived suppressor cells in transplantation and cancer", Immunol Res., Dec. 2012, 54 (1-3), pp. 275-285.
Oldenborg et al, "Role of CD47 as a Marker of Self on Red Blood Cells", Science Magazine, Jun. 16, 2000, pp. 2051-2054, vol. 288.
Pan et al., "Signal Regulatory Protein [Alpha] is Associated with Tumor-Polarized Macrophages Phenotype Switch and Plays a Pibotal Role in Tumor Progression", Hepatology, Aug. 1, 203, pp. 680-691 , vol. 58, No. 2.
Pardoll et al., "The Blockade of Immune Checkpoints in Cancer Immunotherapy", Nature Reviews Cancer, 2012, vol. 12, No. 4.
Peach et al, "Both Extracellular Immunoglobin-Like Domains of CD80 Contains Residues Critical for Binding T-Cell Surface Receptors CTLA-4 and CD28", J. Biol. Chem., 1995, pp. 21181-21187.
Pearson et al., "Improved tools for biological sequence comparison. ", Proceedings of the National Academy of Sciences, 1988, vol. 85, No. 8, pp. 2444-2448.
Pluckthun, "The Pharmacology of Monoclonal Antibodies", Handbook of Experimental Pharmacology, 1994, pp. 269-315.
Powles et al, "MPDL3280A {Anti-PD-L 1_ Treatment Leads to Clinical Activity in Metastatic Bladder Cancer", Nature, 2014, vol. 515, No. 7528.
Reichert et al., "The future of antibodies as cancer drugs", Drug Discovery Today, 2012, vol. 17, No. 17-18, pp. 954-963.
Reuter et al., "Diet-induced models for obesity and type 2 diabetes. Drug Discovery Today", Disease Models, vol. 4/1 :3-8 (2007).
Rudikoff et al., "Single amino acid substitution altering antigen-binding specificity." Proceedings of the National Academy of Sciences 79.6 (1982): 1979-1983.
Sakamoto et al., "Anticancer efficacy of monotherapy with antibodies to SIRPa/SIRPβ1 mediated by induction of antitumorigenic macrophages", Proceedings of the National Academy of Sciences, 2022, 119.1, pp. 1-10.
Seiffert et al., "Signal-Regulatory Protein ? (SIRP?) but not SIRP? is Involved in T-cell Activation, Binds to CD47 with High Affinity, and is Expressed on Immature CD34+CD38" "Hematopoietic Cells", Blood, May 2001, pp. 2741-2749, vol. 97, No. 9.
Sharma et al., "Immune Checkpoint Targeting in Cancer Therapy: Towards Combination Strategies with Curative Potential", Cell, 2015, pp. 205-214, vol. 161, No. 2.
Sim et al, "Discovery of high affinity, pan allelic, and pan-mammalian reactive antibodies against the myeloid checkpoint receptor SIRPa", MABS, 2019, pp. 1036-1052, vol. 11, No. 6.
Sojar et al., "A chemical method for the deglycosylation of proteins", Archives of Biochemistry and Biophysics, 1987, vol. 259, No. 1, pp. 52-57.
Stefanidakis et al., "Endothelial CD47 interaction with SIRPy is required for human T-cell transendothelial 5 migration under shear flow conditions in vitro", The American Society of Hematology, Blood, Aug. 15, 2008, pp. 1280-1289, vol. 112, No. 4.
Takenaka et al., "Polymorphism in Sira Modulates Engraftment of Human Hematopoietic Stem Cells", Nature Immunology, Nature Publishing Group US, New York, Dec. 1, 2007, vol. 8, No. 12, pp. 1313-1323.
Thotakura et al., "[28] Enzymatic deglycosylation of glycoproteins", Methods in Enzymology, 1987, vol. 138, pp. 350-359.
Topalian et al, "Safety, Activity, and Immune Correlates of Anti-PD-1 Antibody in Cancer", The new England Journal of Medicine, 2012, pp. 2443-2454, vol. 366, No. 26.
Torelli et al., "ADVANCE and ADAM: two algorithms for the analysis of global similarity between homologous informational sequences", Bioinformatics, 1994, vol. 10, No. 1, pp. 3-5.

(56) References Cited

OTHER PUBLICATIONS

Treffers et al., "Genetic variation of human neutrophil Fc? receptors and SIRP? in antibody?dependent cellular cytotoxicity towards cancer cells", European Journal of Immunology, 2018, vol. 48, No. 2, pp. 344-354.
Turkbeyler et al., "Prolidase Could Act as a Diagnosis and Treatment Mediator in Lung Fibrosis" Inflammation, vol. 35, No. 5, pp. 1747-1752 (Oct. 2012).
Ueda et al, "Association of the T-Cell Regulatory Gene CTLA4 with Susceptibility to Autoimmune Disease", Nature, 2003, pp. 506-511, vol. 423.
UniProt Sequence Accession Q75144 for PDCD1_HUMAN; retrieved from the internet site https://uniprot.org/uniprot/ on Mar. 26, 2020.
UniProt Sequence Accession P23510 for PDCD1_HUMAN; retrieved from the internet site https://uniprot.org/uniprot/ on Mar. 26, 2020.
UniProt Sequence Accession P33681 for PDCD1_HUMAN; retrieved from the internet site https://uniprot.org/uniprot/ on Mar. 26, 2020.
UniProt Sequence Accession P41273 for PDCD1_HUMAN; retrieved from the internet site https://uniprot.org/uniprot/ on Mar. 26, 2020.
UniProt Sequence Accession P42081 for PDCD1_HUMAN; retrieved from the internet site https://uniprot.org/uniprot/ on Mar. 26, 2020.
UniProt Sequence Accession Q15116 for PDCD1_HUMAN; retrieved from the internet site https://uniprot.org/uniprot/ on Mar. 26, 2020.
UniProt Sequence Accession Q9NZQ7 for PDCD1_HUMAN; retrieved from the internet site https://uniprot.org/uniprot/ on Mar. 26, 2020.
Urlaub et al., "Isolation of Chinese hamster cell mutants deficient in dihydrofolate reductase activity.", Proceedings of the National Academy of Sciences, 1980, vol. 77, No. 7, pp. 4216-4220.
Vargas-Madrazo et al., "An improved model of association for VH-VL immunoglobulin domains: Asymmetries between VH and VL in the packing of some interface residues", Journal of Molecular Recognition, 2003, vol. 16, No. 3, pp. 113-120.
Vinay et al., "Therapeutic Potential of Anti-CD137 (4-18B) Monoclonal Antibodies", Expert Opin. Ther Targets., 2016, pp. 361-373, vol. 20, No. 3.
Wakabayashi et al., "Prevention of metastasis by a polyamine synthesis inhibitor in an animal bone metastasis model", Oncology, 59:75-80 (2000).
Wan et al., "Aberrant Regulation of Synovial TC ell Activation by Soluble Costimulatory molecules in Rheumatoid Arthritis", J_ Immunol, 2006, pp. 8844-8850, vol. 177.
Wang et al., "Immune Regulation by4-1BB and 4-1BBL: Complexities and Challenges", Immunol Rev, 2009, pp. 192-215, vol. 229, No. 1.
Weiskopf et al., "Direct SIRPa Blockade Augments Macrophage Responses to Therapeutic Anticancer Antibodies", Blood Journal, Dec. 2014, vol. 124, No. 21.
Willoughby et al., "OX40: Structure and Function—What Questions Remain?", Mol. Immunol, 2017, pp. 13-22, vol. 83.
Wood et al., "Antibody Drug Discovery", Antibody Drug Discovery, 2011, pp. i-xv.
Yanagita et al, "Anti-SIRPa Antibodies as a Potential New Tool for Cancer Immunotherapy", JCI Insight, Jan. 2017, pp. 1-15, vol. 2, No. 1, e89140.
Zak et al., "Structure of the Complex of Human Programmed Death 1, PD-1, and Its Ligand PD-L1 ", Structure, 2015, pp. 2341-2348, vol. 23, No. 12.
Zapata et al., "Engineering linear F(ab') 2 fragments for efficient production in *Escherichia coli* and enhanced antiproliferative activity", "Protein Engineering, Design and Selection," 1995, vol. 8, No. 10, pp. 1057-1062.
Zhao et al., "CD47-Singal Regulatory Protein-(SIRP) Interactions Form a Barrier for Antibody-Mediated Tumor Cell Destruction", Proceedings of the National Academy of Sciences, Nov. 8, 2011 , vol. 108, No. 45, pp. 18342-18347.
Champiat et al., "Abstract 1993: Biomarker analyses from the Phase I clinical trial of the first-in-class SIRPa immune checkpoint inhibitor BI765063 in patients with advanced solid tumors", Cancer Research, 2022, vol. 82, No. 12_Supplement, pp. 1993-1993.

* cited by examiner

FIG. 37A SIRPαV1

FIG. 37B SIRPαV2

FIG. 37C SIRPβ1

FIG. 37D SIRPβL

FIG. 37E SIRPγ

| | | | | | | | | |
|---|---|---|---|---|---|---|---|---|
| SIRPαV1 | R | K | G | S | P | D | D | V |
| SIRPαV2 | R | K | G | S | P | D | - | T |
| SIRPβ1 | R | K | G | S | P | D | D | V |
| SIRPβL | R | K | G | S | P | D | H | V |
| SIRPγ | R | K | G | S | P | E | N | V |

ANTI-SIRP-ALPHA ANTIBODIES

RELATED APPLICATION DISCLOSURE

The subject application is a continuation of U.S. patent application Ser. No. 17/831,245, filed Jun. 2, 2022, which claims the benefit of U.S. Provisional Application No. 63/197,259, filed Jun. 4, 2021, U.S. Provisional Application No. 63/325,828, filed Mar. 31, 2022, and 63/339,326, filed May 6, 2022, each of which is hereby incorporated by reference in its entirety.

SEQUENCE LISTING

The instant application contains a Sequence Listing which has been submitted electronically in XML format and is hereby incorporated by reference in its entirety. Said XML copy, created on Nov. 14, 2022, is named 105218_03_5011_US01_Sequence_Listing.xml and is 417,899 bytes in size.

FIELD OF THE INVENTION

This invention generally relates to anti-SIRPα (Signal regulatory protein alpha) antibodies or antigen-binding fragments thereof for therapeutic and/or diagnostic use. More specifically, the invention relates to anti-SIPRα antibodies or antigen-binding fragments thereof and methods of their use for the treatment of various diseases or disorders, for example, cancer, inflammatory disease, autoimmune disease, respiratory disease, infectious disease, or fibrosis. Pharmaceutical compositions and kits comprising the anti-SIRPα antibodies or antigen-binding fragments thereof are also disclosed.

BACKGROUND OF THE INVENTION

SIRPα is an inhibitory receptor expressed on myeloid cells such as macrophages, neutrophils and subsets of dendritic cells. SIRPα contains three Ig-like domains, a single transmembrane domain, and a cytoplasmic tail with four tyrosine residues which form two typical immunoreceptor tyrosine based inhibitory motifs (ITIMs). The natural ligand for SIRPα is CD47, expressed on many cells including erythrocytes and platelets. Binding of SIRPα to CD47 leads to the phosphorylation of the tyrosine residues in SIRPα intracellular ITIM domain and subsequent recruitment and activation SHP-1 and SHP-2 phosphatases at the cell membrane which can then, by dephosphorylation of downstream targets, regulate cellular functions including phagocytosis or antigen presentation.

The development of an effective SIRPα antagonist is complicated by polymorphisms within the CD47 binding domain. It has been reported that there may be up to ten allelic variants in the general population (Takenaka 2007*; Nat Immunol* 2007 December; 8(12):1313-23. doi: 10.1038/ni1527.) and recent studies (Treffers, 2018*, Eur J Immunol.* 2018 February; 48(2):344-354. doi: 10.1002/eji.201747215.*; MAbs* August/September 2019; 11(6):1036-1052. doi: 10.1080/19420862.2019.1624123.) highlight that two SIRPα variants, V1 and V2, constitute the most prevalent allelic groups: homozygous V1/V1, homozygous V2/V2, and heterozygous V1/V2. These variants differ in 13 out of 118 amino acid residues in the N-terminal immunoglobulin-like domain of SIRPα responsible for CD47 binding. These polymorphic residues are located outside the CD47 binding site and, accordingly, the affinity of CD47 binding to SIRPα variants is similar (Hatherley D, 2008 *Immunity* 2008 Nov. 14; 29(5):675-8. doi: 10.1016/j.immuni.2008.10.004.). Consequently, therapeutic targeting of SIRPα in diverse patient population irrespective of SIRPα genotype necessitates pan-allelic antibodies that cross-react with the two major SIRPα alleles (V1 and V2).

In addition to considering polymorphic variants when targeting SIRPα, one also should consider SIRPα's closest relatives, SIRPβ1 and SIRPγ given their high sequence conservation particularly in N-terminal domains. SIRPβ1, like SIRPα is also expressed predominantly on cells of the myeloid lineage, but unlike SIRPα, lacks its own signaling cytoplasmic domain, but harbors a positively charged amino acid residue within the transmembrane region allowing for the stable association with ITAM-containing adapter molecule DAP12 and therefore is presumed to act as an activating receptor. SIRPβ1 does not bind CD47, and its ligands have not been identified. There are at least two isoforms of SIRPβ1 (Liu et al 2007 *J Mol Biol.* 2007 Jan. 19; 365(3):680-93. doi: 10.1016/j.jmb.2006.09.079; Brooke et al. 2004 *J Immunol.* 2004 Aug. 15; 173(4):2562-70. doi: 10.4049/jimmunol.173.4.2562.) that arose through tandem duplication of the gene within the SIRP family gene cluster. SIRPγ is exclusively expressed on T-cells and activated NK cells and does bind to CD47 with 10-fold lower affinity than SIRPα:CD47 interaction. Although it does not have intrinsic signaling capacity, there is reported evidence that it plays a role in T-cell transendothelial migration (TEM) and antigen presentation.

In view of the above, there is a need for pan-allelic anti-SIRPα antibodies capable of blocking the interaction of SIRPα with CD47 and that are selective against SIRPγ to allow for treatment of several types of cancer, inflammatory disease, autoimmune disease, respiratory disease, infectious disease, or fibrosis.

BRIEF SUMMARY OF THE INVENTION

The present invention addresses the above need by providing agents, in particular antibodies or antigen-binding fragments thereof, which bind (e.g., specifically) to SIRPα, in particular human SIRPα. In one aspect of the invention, the antibodies or antigen-binding fragments thereof, block the interaction between SIRPα and CD47. In another aspect of the invention, the antibodies or antigen-binding fragments thereof, block CD47-mediated SIRPα signaling.

The antibodies or antigen-binding fragments thereof of the invention are useful, for example, for the treatment and/or prevention of diseases or disorders that can be alleviated by modulating the interaction between SIRPα and CD47, in particular by blocking CD47-mediated SIRPα signaling. In one aspect of the invention, the antibodies or antigen-binding fragments thereof, are useful, for example for the treatment of cancer, inflammatory disease, autoimmune disease, respiratory disease, infectious disease or fibrosis, preferably cancer.

The invention provides an anti-SIRPα antibody or antigen-binding fragments thereof, having one or more of the properties described herein below.

In one aspect of the invention, the anti-SIRPα antibody or antigen-binding fragment thereof binds specifically to SIRPα, in particular human SIRPα or cynomolgus monkey SIRPα, more particularly human SIRPα. In one aspect, the anti-SIRPα antibody or antigen-binding fragment thereof binds to the V1 and/or V2 alleles of human SIRPα. In one aspect of the invention, the anti-SIRPα antibody or antigen-binding fragment thereof does not bind (e.g., there is no detectable binding or the anti-SIRPα antibody or antigen-binding fragment thereof binds with a $K_D$ of 1 μM or greater) to SIRPγ, in particular cynomolgus monkey SIRPγ or human SIRPγ, more particularly human SIRPγ. In one aspect of the invention, the anti-SIRPα antibody or antigen-binding fragment thereof, does not bind (e.g., there is no detectable binding or the anti-SIRPα antibody or antigen-binding fragment thereof binds with a $K_D$ of 1 μM or greater) to rabbit, mouse, rat, or dog SIRPα.

In one aspect of the invention, the anti-SIRPα antibody or antigen-binding fragment thereof blocks the binding of CD47 to SIRPα, in particular human SIRPα or cynomolgus monkey SIRPα, more particularly human SIRPα. In one aspect of the invention, the anti-SIRPα antibody or antigen-binding fragment thereof blocks the binding of CD47 to human SIRPα-V1 and SIRPα-V2. In one aspect of the invention, the anti-SIRPα antibody or antigen-binding fragment thereof blocks CD47-mediated SIRPα signaling. In one aspect of the invention, the anti-SIRPα antibody or antigen-binding fragment thereof enhances phagocytosis by macrophages and/or dendritic cells. In one aspect of the invention, the anti-SIRPα antibody or antigen-binding fragment thereof enhances antibody dependent cellular phagocytosis (ADCP), in combination with a tumor targeting agent, in particular a tumor targeting antibody. In one aspect of the invention, the anti-SIRPα antibody or antigen-binding fragment thereof enhances phagocytosis of tumor cells by macrophages and/or dendritic cells. In one aspect of the invention, the anti-SIRPα antibody or antigen-binding fragment thereof blocks inhibition of T-cell proliferation. In one aspect of the invention, the anti-SIRPα antibody or antigen-binding fragment thereof has favorable pharmacokinetic properties. In one aspect of the invention, an anti-SIRPα antibody or antigen-binding fragment thereof has favorable biophysical properties, for example yield, quality, stability or solubility.

In one aspect of the invention, an anti-SIRPα antibody or an antigen-binding fragment thereof comprises:

a) a heavy chain variable region comprising the amino acid sequence of SEQ ID NO: 33 (H-CDR1); the amino acid sequence of SEQ ID NO: 34 (H-CDR2); and the amino acid sequence of SEQ ID NO: 35 (H-CDR3), and
  a light chain variable region comprising the amino acid sequence of SEQ ID NO: 36 or SEQ ID NO: 37 (L-CDR1); the amino acid sequence of SEQ ID NO: 38 (L-CDR2); and the amino acid sequence of SEQ ID NO: 39 (L-CDR3),
  or
b) a heavy chain variable region comprising the amino acid sequence of SEQ ID NO: 1 or SEQ ID NO: 223 (H-CDR1); the amino acid sequence of SEQ ID NO: 2, SEQ ID NO: 3, SEQ ID NO: 4, SEQ ID NO: 5 or SEQ ID NO: 224 (H-CDR2); and the amino acid sequence of SEQ ID NO: 6 (H-CDR3); and
  a light chain variable region comprising the amino acid sequence of SEQ ID NO: 7, SEQ ID NO: 8, SEQ ID NO: 9 or SEQ ID NO: 225 (L-CDR1); the amino acid sequence of SEQ ID NO: 10, SEQ ID NO: 11 or SEQ ID NO: 226 (L-CDR2); and the amino acid sequence of SEQ ID NO: 12 or SEQ ID NO: 227 (L-CDR3),
  or
c) a heavy chain variable region comprising the amino acid sequence of SEQ ID NO: 52 (H-CDR1); the amino acid sequence of SEQ ID NO: 53 (H-CDR2); and the amino acid sequence of SEQ ID NO: 54 (H-CDR3); and
  a light chain variable region comprising the amino acid sequence of SEQ ID NO: 55 (L-CDR1); the amino acid sequence of SEQ ID NO: 56 (L-CDR2); and the amino acid sequence of SEQ ID NO: 57 (L-CDR3),
  or
d) a heavy chain variable region comprising the amino acid sequence of SEQ ID NO: 33 (H-CDR1); the amino acid sequence of SEQ ID NO: 70 (H-CDR2); and the amino acid sequence of SEQ ID NO: 71 (H-CDR3); and
  a light chain variable region comprising the amino acid sequence of SEQ ID NO: 36 (L-CDR1); the amino acid sequence of SEQ ID NO: 72 (L-CDR2); and the amino acid sequence of SEQ ID NO: 39 (L-CDR3),
  or
e) a heavy chain variable region comprising the amino acid sequence of SEQ ID NO: 262 (H-CDR1); the amino acid sequence of SEQ ID NO: 87 (H-CDR2); and the amino acid sequence of SEQ ID NO: 88 (H-CDR3); and
  a light chain variable region comprising the amino acid sequence of SEQ ID NO: 36 (L-CDR1); the amino acid sequence of SEQ ID NO: 72 (L-CDR2); and the amino acid sequence of SEQ ID NO: 89 (L-CDR3).

In one aspect of the invention, an anti-SIRPα antibody or an antigen-binding fragment thereof comprises:

a) a heavy chain variable region comprising the amino acid sequence of SEQ ID NO: 33 (H-CDR1); the amino acid sequence of SEQ ID NO: 34 (H-CDR2); the amino acid sequence of SEQ ID NO: 35 (H-CDR3); and a light chain variable region comprising the amino acid sequence of SEQ ID NO:233, wherein amino acids X1=D or G and X2=L or A (L-CDR1); the amino acid sequence of SEQ ID NO: 38, (L-CDR2); the amino acid sequence of SEQ ID NO: 39 (L-CDR3), or
b) a heavy chain variable region comprising the amino acid sequence of SEQ ID NO: 228 (H-CDR1), wherein amino acids X1=N or D; the amino acid sequence of SEQ ID NO:229, wherein X1=Y or D, X2=N or T, X3=N or Q, and X4=S or P (H-CDR2); the amino acid sequence of SEQ ID NO: 6 (H-CDR3); and a light chain variable region comprising the amino acid sequence of SEQ ID NO:230, wherein X1=K or R, X2=N or T, X3=G or A and X4=N, A or T (L-CDR1); the amino acid sequence of SEQ ID NO:231, wherein X1=L, Q or G and X2=N or S (L-CDR2); the amino acid sequence of SEQ ID NO:232, wherein X1=M or G (L-CDR3).

In one aspect of the invention, an anti-SIRPα antibody or an antigen-binding fragment thereof comprises a heavy chain variable region comprising the amino acid sequence of any one of SEQ ID NOS: 100, 110, 111, 112, 113, 114, 115, 116, or 117; and a light chain variable region comprising the amino acid sequence of any one of SEQ ID NOS: 105, 125, or 126.

In a further aspect, an anti-SIRPα antibody or an antigen-binding fragment thereof of the present invention comprises a heavy chain variable region comprising the amino acid sequence of any one of SEQ ID NOS: 104, 118, 119, 120, 121, 122, 123, 124 or 221; and a light chain variable region comprising the amino acid sequence of any one of SEQ ID NOS: 109, 127, 128, 129, 130 or 222.

In one aspect of the invention, an anti-SIRPα antibody or an antigen-binding fragment thereof comprises a heavy chain variable region comprising the amino acid sequence of any one of SEQ ID NOS: 100, 101, 102, 103, or 104; and a light chain variable region comprising the amino acid sequence of any one of SEQ ID NOS: 105, 106, 107, 108, or 109.

In one aspect of the invention, an anti-SIRPα antibody or an antigen-binding fragment thereof comprises:

a) a heavy chain variable region comprising the amino acid sequence of SEQ ID NO: 100; and a light chain variable region comprising the amino acid sequence of SEQ ID NO: 105; or
b) a heavy chain variable region comprising the amino acid sequence of SEQ ID NO: 110; and a light chain variable region comprising the amino acid sequence of SEQ ID NO: 125; or
c) a heavy chain variable region comprising the amino acid sequence of SEQ ID NO: 111; and a light chain variable region comprising the amino acid sequence of SEQ ID NO: 125; or
d) a heavy chain variable region comprising the amino acid sequence of SEQ ID NO: 112; and a light chain variable region comprising the amino acid sequence of SEQ ID NO: 125; or
e) a heavy chain variable region comprising the amino acid sequence of SEQ ID NO: 113; and a light chain variable region comprising the amino acid sequence of SEQ ID NO: 125; or
f) a heavy chain variable region comprising the amino acid sequence of SEQ ID NO: 114; and a light chain variable region comprising the amino acid sequence of SEQ ID NO: 125; or
g) a heavy chain variable region comprising the amino acid sequence of SEQ ID NO: 115; and a light chain variable region comprising the amino acid sequence of SEQ ID NO: 125; or
h) a heavy chain variable region comprising the amino acid sequence of SEQ ID NO: 116; and a light chain variable region comprising the amino acid sequence of SEQ ID NO: 125; or
i) a heavy chain variable region comprising the amino acid sequence of SEQ ID NO: 117; and a light chain variable region comprising the amino acid sequence of SEQ ID NO: 125; or
j) a heavy chain variable region comprising the amino acid sequence of SEQ ID NO: 111; and a light chain variable region comprising the amino acid sequence of SEQ ID NO: 126; or
k) a heavy chain variable region comprising the amino acid sequence of SEQ ID NO: 112; and a light chain variable region comprising the amino acid sequence of SEQ ID NO: 126; or
l) a heavy chain variable region comprising the amino acid sequence of SEQ ID NO: 113; and a light chain variable region comprising the amino acid sequence of SEQ ID NO: 126; or
m) a heavy chain variable region comprising the amino acid sequence of SEQ ID NO: 114; and a light chain variable region comprising the amino acid sequence of SEQ ID NO: 126; or
n) a heavy chain variable region comprising the amino acid sequence of SEQ ID NO: 115; and a light chain variable region comprising the amino acid sequence of SEQ ID NO: 126; or
o) a heavy chain variable region comprising the amino acid sequence of SEQ ID NO: 116; and a light chain variable region comprising the amino acid sequence of SEQ ID NO: 126; or
p) a heavy chain variable region comprising the amino acid sequence of SEQ ID NO: 117; and a light chain variable region comprising the amino acid sequence of SEQ ID NO: 126.

In one aspect of the invention, an anti-SIRPα antibody or an antigen-binding fragment thereof comprises:

a) a heavy chain variable region comprising the amino acid sequence of SEQ ID NO: 104; and a light chain variable region comprising the amino acid sequence of SEQ ID NO: 109; or
b) a heavy chain variable region comprising the amino acid sequence of SEQ ID NO: 118; and a light chain variable region comprising the amino acid sequence of SEQ ID NO: 127; or
c) a heavy chain variable region comprising the amino acid sequence of SEQ ID NO: 118; and a light chain variable region comprising the amino acid sequence of SEQ ID NO: 128; or
d) a heavy chain variable region comprising the amino acid sequence of SEQ ID NO: 119; and a light chain variable region comprising the amino acid sequence of SEQ ID NO: 127; or
e) a heavy chain variable region comprising the amino acid sequence of SEQ ID NO: 119; and a light chain variable region comprising the amino acid sequence of SEQ ID NO: 129; or
f) a heavy chain variable region comprising the amino acid sequence of SEQ ID NO: 120; and a light chain variable region comprising the amino acid sequence of SEQ ID NO: 127; or
g) a heavy chain variable region comprising the amino acid sequence of SEQ ID NO: 120; and a light chain variable region comprising the amino acid sequence of SEQ ID NO: 129; or
h) a heavy chain variable region comprising the amino acid sequence of SEQ ID NO: 121; and a light chain variable region comprising the amino acid sequence of SEQ ID NO: 127; or
i) a heavy chain variable region comprising the amino acid sequence of SEQ ID NO: 122; and a light chain variable region comprising the amino acid sequence of SEQ ID NO: 127; or
j) a heavy chain variable region comprising the amino acid sequence of SEQ ID NO: 118; and a light chain variable region comprising the amino acid sequence of SEQ ID NO: 130; or
k) a heavy chain variable region comprising the amino acid sequence of SEQ ID NO: 121; and a light chain variable region comprising the amino acid sequence of SEQ ID NO: 129; or
l) a heavy chain variable region comprising the amino acid sequence of SEQ ID NO: 122; and a light chain variable region comprising the amino acid sequence of SEQ ID NO: 129; or
m) a heavy chain variable region comprising the amino acid sequence of SEQ ID NO: 119; and a light chain variable region comprising the amino acid sequence of SEQ ID NO: 130; or
n) a heavy chain variable region comprising the amino acid sequence of SEQ ID NO: 123; and a light chain variable region comprising the amino acid sequence of SEQ ID NO: 127; or
o) a heavy chain variable region comprising the amino acid sequence of SEQ ID NO: 120; and a light chain variable region comprising the amino acid sequence of SEQ ID NO: 130; or p) a heavy chain variable region comprising the amino acid sequence of SEQ ID NO: 123; and a light chain variable region comprising the amino acid sequence of SEQ ID NO: 129; or q) a heavy chain variable region comprising the amino acid sequence of SEQ ID NO: 121; and a light chain variable region comprising the amino acid sequence of SEQ ID NO: 130; or r) a heavy chain variable region comprising the amino acid sequence of SEQ ID NO: 122; and a light chain variable region comprising the amino acid sequence of SEQ ID NO: 130; or s) a heavy chain variable region comprising the amino acid sequence of SEQ ID NO: 124; and a light chain variable region comprising the amino acid sequence of SEQ ID NO: 129; or t) a heavy chain variable region comprising the amino acid sequence of SEQ ID NO: 124; and a light chain variable region comprising the amino acid sequence of SEQ ID NO: 127; or u) a heavy chain variable region comprising the amino acid sequence of SEQ ID NO: 123; and a light chain variable region comprising the amino acid sequence of SEQ ID NO: 130; or v) a heavy chain variable region comprising the amino acid sequence of SEQ ID NO: 124; and a light chain variable region comprising the amino acid sequence of SEQ ID NO: 130; or w) a heavy chain variable region comprising the amino acid sequence of SEQ ID NO: 221; and a light chain variable region comprising the amino acid sequence of SEQ ID NO: 222.

In one aspect of the invention, an anti-SIRPα antibody or an antigen-binding fragment thereof comprises:

a) a heavy chain variable region comprising the amino acid sequence of SEQ ID NO: 100; and a light chain variable region comprising the amino acid sequence of SEQ ID NO: 105; or b) a heavy chain variable region comprising the amino acid sequence of SEQ ID NO: 101; and a light chain variable region comprising the amino acid sequence of SEQ ID NO: 106; or c) a heavy chain variable region comprising the amino acid sequence of SEQ ID NO: 102; and a light chain variable region comprising the amino acid sequence of SEQ ID NO: 107; or d) a heavy chain variable region comprising the amino acid sequence of SEQ ID NO: 103; and a light chain variable region comprising the amino acid sequence of SEQ ID NO: 108; or e) a heavy chain variable region comprising the amino acid sequence of SEQ ID NO: 104; and a light chain variable region comprising the amino acid sequence of SEQ ID NO: 109.

In one aspect of the invention, an anti-SIRPα antibody comprises a heavy chain comprising the amino acid sequence of any one of SEQ ID NO: 131, 138, 139, 140, 141, 142, 143, 144, 145, 146, 148, 149, 150, 151 or 152; and a light chain comprising the amino acid sequence of any one of SEQ ID NO: 174, 181, 182, 183, 184, 185, 186, 187, 188, 189, 190, 191, 192, 193, 194, 195 or 218.

In a further aspect, an anti-SIRPα antibody of the invention comprises:

a) a heavy chain comprising the amino acid sequence of SEQ ID NO: 131; and a light chain comprising the amino acid sequence of SEQ ID NO: 174; or b) a heavy chain comprising the amino acid sequence of SEQ ID NO: 138; and a light chain comprising the amino acid sequence of SEQ ID NO: 121; or c) a heavy chain comprising the amino acid sequence of SEQ ID NO: 139; and a light chain comprising the amino acid sequence of SEQ ID NO: 182; or d) a heavy chain comprising the amino acid sequence of SEQ ID NO: 140; and a light chain comprising the amino acid sequence of SEQ ID NO: 183; or e) a heavy chain comprising the amino acid sequence of SEQ ID NO: 141; and a light chain comprising the amino acid sequence of SEQ ID NO: 184; or f) a heavy chain comprising the amino acid sequence of SEQ ID NO: 142; and a light chain comprising the amino acid sequence of SEQ ID NO: 185; or g) a heavy chain comprising the amino acid sequence of SEQ ID NO: 143; and a light chain comprising the amino acid sequence of SEQ ID NO: 186; or h) a heavy chain comprising the amino acid sequence of SEQ ID NO: 144; and a light chain comprising the amino acid sequence of SEQ ID NO: 187; or i) a heavy chain comprising the amino acid sequence of SEQ ID NO: 145; and a light chain comprising the amino acid sequence of SEQ ID NO: 188; or j) a heavy chain comprising the amino acid sequence of SEQ ID NO: 146; and a light chain comprising the amino acid sequence of SEQ ID NO: 189; or k) a heavy chain comprising the amino acid sequence of SEQ ID NO: 147; and a light chain comprising the amino acid sequence of SEQ ID NO: 190; or l) a heavy chain comprising the amino acid sequence of SEQ ID NO: 148; and a light chain comprising the amino acid sequence of SEQ ID NO: 191; or m) a heavy chain comprising the amino acid sequence of SEQ ID NO: 149; and a light chain comprising the amino acid sequence of SEQ ID NO: 192; or n) a heavy chain comprising the amino acid sequence of SEQ ID NO: 150; and a light chain comprising the amino acid sequence of SEQ ID NO: 193; or o) a heavy chain comprising the amino acid sequence of SEQ ID NO: 151; and a light chain comprising the amino acid sequence of SEQ ID NO: 194; or p) a heavy chain comprising the amino acid sequence of SEQ ID NO: 152; and a light chain comprising the amino acid sequence of SEQ ID NO: 195; or q) a heavy chain comprising the amino acid sequence of SEQ ID NO: 217; and a light chain comprising the amino acid sequence of SEQ ID NO: 218.

In one aspect of the invention, an anti-SIRPα antibody comprises a heavy chain comprising the amino acid sequence of any one of SEQ ID NO: 135, 153, 154, 155, 156, 157, 158, 159, 160, 161, 162, 163, 164, 165, 166, 167, 168, 169, 170, 171, 172, 173 or 219; and a light chain comprising the amino acid sequence of any one of SEQ ID NO: 178, 196, 197, 198, 199, 200, 201, 202, 203, 204, 205, 206, 207, 208, 209, 210, 211, 212, 213, 214, 215, 216 or 220.

In one aspect of the invention, an anti-SIRPα antibody comprises:

a) a heavy chain comprising the amino acid sequence of SEQ ID NO: 135; and a light chain comprising the amino acid sequence of SEQ ID NO: 178; or b) a heavy chain comprising the amino acid sequence of SEQ ID NO: 153; and a light chain comprising the amino acid sequence of SEQ ID NO: 196; or c) a heavy chain comprising the amino acid sequence of SEQ ID NO: 154; and a light chain comprising the amino acid sequence of SEQ ID NO: 197; or d) a heavy chain comprising the amino acid sequence of SEQ ID NO: 155; and a light chain comprising the amino acid sequence of SEQ ID NO: 198; or e) a heavy chain comprising the amino acid sequence of SEQ ID NO: 156; and a light chain comprising the amino acid sequence of SEQ ID NO: 199; or f) a heavy chain comprising the amino acid sequence of SEQ ID NO: 157; and a light chain comprising the amino acid sequence of SEQ ID NO: 200; or g) a heavy chain comprising the amino acid sequence of SEQ ID NO: 158; and a light chain comprising the amino acid sequence of SEQ ID NO: 201; or h) a heavy chain comprising the amino acid sequence of SEQ ID NO: 159; and a light chain comprising the amino acid sequence of SEQ ID NO: 202; or i) a heavy chain comprising the amino acid sequence of SEQ ID NO: 160; and a light chain comprising the amino acid sequence of SEQ ID NO: 203; or j) a heavy chain comprising the amino acid sequence of SEQ ID NO: 161; and a light chain comprising the amino acid sequence of SEQ ID NO: 204; or k) a heavy chain comprising the amino acid sequence of SEQ ID NO: 162; and a light chain comprising the amino acid sequence of SEQ ID NO: 205; or l) a heavy chain comprising the amino acid sequence of SEQ ID NO: 163; and a light chain comprising the amino acid sequence of SEQ ID NO: 206; or m) a heavy chain comprising the amino acid sequence of SEQ ID NO: 164; and a light chain comprising the amino acid sequence of SEQ ID NO: 207; or n) a heavy chain comprising the amino acid sequence of SEQ ID NO: 165; and a light chain comprising the amino acid sequence of SEQ ID NO: 208; or o) a heavy chain comprising the amino acid sequence of SEQ ID NO: 166; and a light chain comprising the amino acid sequence of SEQ ID NO: 209; or p) a heavy chain comprising the amino acid sequence of SEQ ID NO: 167; and a light chain comprising the amino acid sequence of SEQ ID NO: 210; or q) a heavy chain comprising the amino acid sequence of SEQ ID NO: 168; and a light chain comprising the amino acid sequence of SEQ ID NO: 211; or r) a heavy chain comprising the amino acid sequence of SEQ ID NO: 169; and a light chain comprising the amino acid sequence of SEQ ID NO: 212; or s) a heavy chain comprising the amino acid sequence of SEQ ID NO: 170; and a light chain comprising the amino acid sequence of SEQ ID NO: 213; or t) a heavy chain comprising the amino acid sequence of SEQ ID NO: 171; and a light chain comprising the amino acid sequence of SEQ ID NO: 214; or u) a heavy chain comprising the amino acid sequence of SEQ ID NO: 172; and a light chain comprising the amino acid sequence of SEQ ID NO: 215; or v) a heavy chain comprising the amino acid sequence of SEQ ID NO: 173; and a light chain comprising the amino acid sequence of SEQ ID NO: 216; or w) a heavy chain comprising the amino acid sequence of SEQ ID NO: 219; and a light chain comprising the amino acid sequence of SEQ ID NO: 220.

In one aspect of the invention, an anti-SIRPα antibody comprises a heavy chain comprising the amino acid sequence of any one of SEQ ID NO: 131, 133, 134, 137 or 135; and a light chain comprising the amino acid sequence of any one of SEQ ID NO:174, 176, 177, 180, or 178.

In one aspect of the invention, an anti-SIRPα antibody comprises:

a) a heavy chain comprising the amino acid sequence of SEQ ID NO: 131; and a light chain comprising the amino acid sequence of SEQ ID NO: 174; or b) a heavy chain comprising the amino acid sequence of SEQ ID NO: 133; and a light chain comprising the amino acid sequence of SEQ ID NO: 176; or c) a heavy chain comprising the amino acid sequence of SEQ ID NO: 134; and a light chain comprising the amino acid sequence of SEQ ID NO: 177; or d) a heavy chain comprising the amino acid sequence of SEQ ID NO: 137; and a light chain comprising the amino acid sequence of SEQ ID NO: 180; or e) a heavy chain comprising the amino acid sequence of SEQ ID NO: 135; and a light chain comprising the amino acid sequence of SEQ ID NO: 178.

In one aspect of the invention, the anti-SIRPα antibody or antigen-binding fragment thereof, is a human antibody or antigen-binding fragment thereof. In one aspect of the invention, the anti-SIRPα antibody or antigen-binding fragment thereof, is a monoclonal antibody. In one aspect of the invention, the anti-SIRPα antibody is a full-length antibody. In one aspect of the invention, the anti-SIRPα antibody or fragment thereof, is a human monoclonal antibody, for example a full-length human monoclonal antibody.

In a one aspect of the invention, the anti-SIRPα antibody, or an antigen-binding fragment thereof, comprises a heavy chain variable region having at least 90%, at least 95%, at least 98%, or at least 99% identity to the amino acid sequences of SEQ ID NO: 100, 110, 111, 112, 113, 114, 115, 116, or 117 and a light chain variable region having at least 90%, at least 95%, at least 98%, or at least 99% identity to the amino acid sequences of SEQ ID NO: 105, 125, or 126. In a further aspect of the invention, the antibody or antigen-binding fragment thereof that comprises a heavy chain variable region having at least 90%, at least 95%, at least 98%, or at least 99% identity to the amino acid sequences of SEQ ID NO: 100, 110, 111, 112, 113, 114, 115, 116, or 117 and a light chain variable region having at least 90%, at least 95%, at least 98%, or at least 99% identity to the amino acid sequences of SEQ ID NO: 105, 125, or 126 specifically binds to SIRPα. In a one aspect of the invention, the anti-SIRPα antibody, or an antigen-binding fragment thereof, comprises a heavy chain variable region having at least 90%, at least 95%, at least 98%, or at least 99% identity to the amino acid sequences of SEQ ID NO: 104, 118, 119, 120, 121, 122, 123, 124, or 221 and a light chain variable region having at least 90%, at least 95%, at least 98%, or at least 99% identity to the amino acid sequences of SEQ ID NO: 109, 127, 128, 129, 130, or 222. In a further aspect of the invention, the antibody or antigen-binding fragment thereof that comprises a heavy chain variable region having at least 90%, at least 95%, at least 98%, or at least 99% identity to the amino acid sequences of SEQ ID NO: 104, 118, 119, 120, 121, 122, 123, 124, or 221 and a light chain variable region having at least 90%, at least 95%, at least 98%, or at least 99% identity to the amino acid sequences of SEQ ID NO: 109, 127, 128, 129, 130, or 222 specifically binds to SIRPα. In one aspect of the invention, the anti-SIRPα antibody, or an antigen-binding fragment thereof, comprises a heavy chain variable region having at least 90%, at least 95%, at least 98%, or at least 99% identity to the amino acid sequences of SEQ ID NO: 101, 102 or 103 and a light chain variable region having at least 90%, at least 95%, at least 98%, or at least 99% identity to the amino acid sequences of SEQ ID NO: 106, 107, 108. In a further aspect of the invention, the antibody or antigen-binding fragment thereof that comprises a heavy chain variable region having at least 90%, at least 95%, at least 98%, or at least 99% identity to the amino acid sequences of SEQ ID NO: 101, 102 or 103 and a light chain variable region having at least 90%, at least 95%, at least 98%, or at least 99% identity to the amino acid sequences of SEQ ID NO: 106, 107, 108 specifically binds to SIRPα.

In one aspect of the invention, the anti-SIRPα antibody, or an antigen-binding fragment thereof, comprises a heavy chain constant region from an antibody selected from the group consisting of IgG1, IgG2, IgG3, IgG4, IgM, IgA and IgE, for example human IgG1, IgG2, IgG3, IgG4, IgM, IgA or IgE, more particularly, human IgG1, IgG2, IgG3, IgG4.

In one aspect of the invention, the anti-SIRPα antibody or an antigen-binding fragment thereof comprises a heavy chain constant region, wherein the heavy chain constant region is of an IgG4 with a S241P substitution. In one aspect of the invention, the anti-SIRPα antibody or an antigen-binding fragment thereof comprises a heavy chain lacking a C-terminal lysine residue.

In one aspect of the invention, the anti-SIRPα antibody or an antigen-binding fragment thereof comprises a heavy chain constant region wherein the heavy chain constant region is of an IgG1 with L234A and L235A substitutions.

In one aspect of the invention, the anti-SIRPα antibody or antigen-binding fragment thereof comprises a light chain constant region selected from the group consisting of a kappa and a lambda light chain.

In one aspect of the invention, the anti-SIRPα antibody or antigen-binding fragment thereof, is optionally administered in combination with an additional therapeutic agent. The additional therapeutic agent may be a chemotherapeutic agent, an anti-PD-1 or PD-L1 antibody, an anti-CTLA4 antibody, a T-cell engager, a CD137-agonist-anti-FAP bispecific antibody, a tumor-targeting antibody, a VEGF-ANG2 bispecific antibody, a STING agonist, a MDM2 antagonist, or radiation therapy.

In one aspect, the anti-SIRPα antibody or an antigen-binding fragment thereof is administered in combination with an anti-PD-1 antibody, for example, nivolumab, pembrolizumab, pidilizumab, ezabenlimab, or atezolizumab. In a further aspect, the anti-SIRPα antibody or an antigen-binding fragment thereof is administered in combination with an anti-PD-L1 antibody including, for example, avelumab or durvalumab.

In one aspect, the anti-SIRPα antibody or antigen-binding fragment thereof is administered in combination with a tumor targeting antibody, for example an antibody that targets HER2 (e.g., trastuzumab), EGFR (e.g., cetuximab, panitumumab), CD20 (e.g., rituximab, ofatumumab), or CD52 (e.g., alemtuzumab).

In one aspect, the anti-SIRPα antibody or antigen-binding fragment thereof is administered in combination with two therapeutic agents. In a further aspect, the anti-SIRPα antibody or antigen-binding fragment thereof is administered in combination with an anti-PD-1 antibody (e.g., nivolumab, pembrolizumab, pidilizumab, ezabenlimab, or atezolizumab), or an anti-PD-L1 antibody (e.g., avelumab or durvalumab) and a tumor targeting antibody, for example and antibody that targets HER2 (e.g., trastuzumab), EGFR (e.g., tetuximab, panitumumab), CD20 (e.g., rituximab, ofatumumab), or CD52 (e.g., alemtuzumab).

In one aspect of the invention, the antibody or antigen-binding fragment thereof recognizes a specific linear or conformational "SIRPα epitope" on a SIRPα protein comprising the amino acid sequence set forth in any one of SEQ ID NOs: 240-252. In one aspect of the invention, the antibody or antigen-binding fragment thereof recognizes a specific linear or conformational "SIRPα epitope" on a SIRPα protein comprising the amino acid sequence set forth in any one of SEQ ID NOs: 253-260 and 264, in particular any one or more of SEQ ID NOS: 256 and 257. In one aspect of the invention the antibody or antigen-binding fragment thereof binds to a SIRPα epitope comprising the amino acids LEU 60, ILE 61, VAL 63, GLY 64, PRO 65, GLN 82, LYS 83, GLU 84, THR 97, LYS 98, ARG 99, GLU 100, LYS 126, GLY 127, SER 128, PRO 129 and ASP 130 as set forth in SEQ ID NO: 266. In one aspect of the invention the antibody or antigen-binding fragment thereof binds to a SIRPα epitope comprising the amino acids LEU 60, ILE 61, VAL 63, GLY 64, PRO 65, GLN 82, LYS 83, GLU 84, THR 97, LYS 98, ARG 99, ASN 100, LYS 126, GLY 127, SER 128, PRO 129 and ASP 130 as set forth in SEQ ID NO: 265. In another aspect of the invention, the antibody or antigen-binding fragment thereof binds to the SIRPα epitope comprising the amino acid ASP130. In another aspect, the antibody or antigen-binding fragment thereof binds to a SIRPα epitope comprising any one or more of SEQ ID NO; 253, SEQ ID NO: 254, SEQ ID NO: 255, SEQ ID NO: 264, and SEQ ID NO: 256, in particular SEQ ID NO: 256.

In one aspect of the invention the antibody or antigen-binding fragment thereof binds to the SIRPα epitope comprising the amino acids ARG 70, GLY 71, ALA 72, GLY 73, PRO 74, ALA 75, ARG 76, GLU 77, ALA 114, ALA 116, GLY 117, THR 118, TYR 120, THR 131, GLU 132, PHE 133, SER 135 and GLU 140 as set forth in SEQ ID NO: 266. In one aspect of the invention the antibody or antigen-binding fragment thereof binds to a SIRPα epitope comprising the amino acids ARG 70, GLY 71, ALA 72, GLY 73, PRO 74, GLY 75, ARG 76, GLU 77, ALA 114, ALA 116, GLY 117, THR 118, TYR 120, VAL 132, GLU 133, PHE 134, SER 136 and GLU 141 as set forth in SEQ ID NO: 265. In another aspect of the invention, the antibody or antigen-binding fragment thereof binds to the SIRPα epitope comprising the amino acid ALA72. In another aspect, the antibody or antigen-binding fragment thereof binds to a SIRPα epitope comprising any one or more of SEQ ID NO: 257, SEQ ID NO: 258, SEQ ID NO: 259 and SEQ ID NO:260, in particular SEQ ID NO: 257. In another aspect of the invention, the antibody or antigen-binding fragment thereof blocks binding of any of Antibody A-E to SIRPα.

In another aspect, the antibody or antigen-binding fragment thereof exhibits comparable binding to (e.g., less than a 10-fold difference in affinity for) the modified SIRPαV1 polypeptide sequence of SEQ ID NO: 269 or 270, compared to its binding to the SIRPαV1 polypeptide of SEQ ID NO: 268, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits reduced binding affinity for (e.g., at least a 10-fold reduction in affinity for) the modified SIRPαV1 polypeptide sequence of SEQ ID NO: 271 or 272, compared to its binding to the SIRPαV1 polypeptide of SEQ ID NO: 268, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits comparable binding to (e.g., less than a 10-fold difference in affinity for) the modified SIRPαV2 polypeptide sequence of SEQ ID NO: 274 or 275, compared to its binding to the SIRPαV2 polypeptide of SEQ ID NO: 273, which optionally is measured at room temperature.

Preferably the antibody or antigen-binding fragment thereof is antibody A, A4, A10, or an antigen-binding fragment thereof.

In another aspect, the antibody or antigen-binding fragment thereof exhibits reduced binding affinity for (e.g., at least a 10-fold reduction in affinity for) the modified SIRPβ1 polypeptide sequence of SEQ ID NO: 277, compared to its binding to the SIRPβ1 polypeptide of SEQ ID NO: 276, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits binding to the modified polypeptide sequence of SEQ ID NO: 279, which optionally is measured at room temperature. Preferably the antibody or antigen-binding fragment thereof is antibody A, A4, A10, or an antigen-binding fragment thereof.

In another aspect, the antibody or antigen-binding fragment thereof exhibits binding to the modified polypeptide sequence of SEQ ID NO: 282 or 283, which optionally is measured at room temperature. Preferably the antibody or antigen-binding fragment thereof is antibody A, A4, A10, or an antigen-binding fragment thereof.

In one aspect, the anti-SIRPα antibody or antigen-binding fragment thereof exhibits comparable binding affinity for human SIRPαV1 and SIRPαV2, such as less than 10-fold difference (preferably less than 5-fold difference) in the binding affinity ($K_D$) for human SIRPαV1 and SIRPαV2, which optionally is measured at room temperature.

In one aspect, the present invention provides an anti-SIRPα antibody or antigen-binding fragment thereof that competes for binding to V1-SIRPα and/or V2-SIRPα, with an anti-SIRPα antibody or antigen-binding fragment thereof of the invention. In one aspect, the present invention provides an anti-SIRPα antibody or antigen-binding fragment thereof that competes for binding to V1-SIRPα and/or V2 SIRPα, with an antibody comprising a heavy chain variable region comprising the amino acid sequence of any one of SEQ ID NOS: 100, 110, 111, 112, 113, 114, 115, 116, or 117 and a light chain variable region comprising the amino acid sequence of any one of SEQ ID NOS: 105, 125, or 126; or an antibody comprising a heavy chain comprising the amino acid sequence of any one of SEQ ID NO: 131,138,139, 140, 141, 142, 143, 144, 145, 146, 147, 148, 149, 150, 151, 152, or 217 and a light chain comprising the amino acid sequence of any one of SEQ ID NO: 174, 181, 182, 183, 184, 185, 186, 187, 188, 189, 190, 191, 192, 193, 194, 195, 218.

In one aspect, the present invention provides an anti-SIRPα antibody or antigen-binding fragment thereof that competes for binding to V1-SIRPα and/or V2-SIRPα, with an anti-SIRPα antibody or antigen-binding fragment thereof of the invention. In one aspect, the present invention provides an anti-SIRPα antibody or antigen-binding fragment thereof that competes for binding to V1-SIRPα and/or V2 SIRPα, with an antibody comprising a heavy chain variable region comprising the amino acid sequence of any one of SEQ ID NOS: 104, 118, 119, 120, 121, 122, 123, 124, or 221 and a light chain variable region comprising the amino acid sequence of any one of SEQ ID NOS: 109, 127, 128, 129, 130, or 222; or an antibody comprising a heavy chain comprising the amino acid sequence of any one of SEQ ID NO: 135, 153, 154, 156, 157, 158, 159, 160, 161, 162, 163, 164, 165, 166, 167, 168, 169, 170, 171, 172, 173, or 219 and a light chain comprising the amino acid sequence of any one of SEQ ID NO: 178, 196, 197, 198, 199, 200, 201, 202, 203, 204, 205, 206, 207, 208, 209, 210, 211, 212, 213, 214, 215, 216, or 220.

In one aspect, the invention provides a pharmaceutical composition comprising an anti-SIRPα antibody or antigen-binding fragment thereof as described above, and a pharmaceutically acceptable excipient, optionally in combination with one or more (e.g., one or two) additional therapeutic agents. In a further embodiment, the additional therapeutic agent is a chemotherapeutic agent, an anti-PD-1 or PD-L1 antibody, an anti-CTLA4 antibody, a T cell engager, a CD137-agonist-anti-FAP bispecific antibody, a tumor-targeting antibody, a VEGF-ANG2 bispecific antibody, a STING agonist, or a MDM2 antagonist.

In one aspect, the invention provides an anti-SIRPα antibody or antigen-binding fragment thereof as described above for use as a medicament or in the preparation of a medicament.

In one aspect, the invention provides a method of treating a SIRPα pathway disorder comprising administering to a subject in need thereof a pharmaceutically effective amount of the anti-SIRPα antibody or antigen-binding fragment thereof as described above. In one aspect, the invention provides an anti-SIRPα antibody or antigen-binding fragment thereof as described above for use in treating a SIRPα pathway disorder. In one aspect, the invention provides the use of the anti-SIRPα antibody or antigen-binding fragment thereof as described above in manufacture of a medicament for treating a SIRPα pathway disorder.

In one aspect, the invention provides a method of modulating the interaction between SIRPα and CD47 in a subject (e.g., a human) comprising administering to the subject a composition comprising an anti-SIRPα antibody or the antigen-binding fragment as described above in an amount sufficient to block the CD47-mediated SIRPα signaling in the subject. In one embodiment, the invention provides an anti-SIRPα antibody or the antigen-binding fragment as described above for use in modulating the interaction between SIRPα and CD47 in a subject. In one embodiment, the invention provides the use of an anti-SIRPα antibody or the antigen-binding fragment as described above in the manufacture of a medicament for modulating the interaction between SIRPα and CD47 in a subject.

In one embodiment, the invention provides a method of enhancing phagocytosis comprising administering to a subject a composition comprising an anti-SIRPα antibody or the antigen-binding fragment as described above in an amount sufficient to block the CD47-mediated SIRPα signaling. In one embodiment, the invention provides an anti-SIRPα antibody or the antigen-binding fragment as described above for use in enhancing phagocytosis by macrophages and/or dendritic cells in a subject. In one embodiment, the invention provides an anti-SIRPα antibody or the antigen-binding fragment as described above for use in enhancing phagocytosis of tumor cells by macrophages and/or dendritic cells in a subject. In one embodiment, the present invention provides the use of an anti-SIRPα antibody or the antigen-binding fragment as described above in the manufacture of a medicament for a subject. In one aspect of the invention, the invention provides a method of enhancing antibody dependent cellular phagocytosis (ADCP), in combination with a tumor targeting agent, preferably a tumor targeting antibody, the method comprising administering to a subject a composition comprising an anti-SIRPα antibody or the antigen-binding fragment as described above in an amount sufficient to block the CD47-mediated SIRPα signaling in combination with a tumor targeting agent, preferably a tumor targeting antibody, more preferably a tumor targeting antibody that targets HER2 (e.g., trastuzumab), EGFR (e.g., cetuximab, panitumumab), CD20 (e.g., rituximab, ofatumumab) CD52 (e.g., alemtuzumab).

In one embodiment, in a method above, in an anti-SIRPα antibody or antigen-binding fragment thereof for use above, or in the use of an anti-SIRPα antibody or antigen-binding fragment thereof above, the disease is selected from the group consisting of cancer, inflammatory disease, autoimmune disease, respiratory disease, infectious disease or fibrosis.

In one embodiment, in the method above, in the anti-SIRPα antibody or antigen-binding fragment thereof for use above, or in the use of the anti-SIRPα antibody or antigen-binding fragment thereof above, the antibody or antigen-binding fragment thereof is administered by a parenteral route, intravenous route, or subcutaneous route of administration.

In one embodiment, the invention provides an isolated polynucleotide encoding a heavy chain variable region amino and/or a light chain variable region as described above.

In one embodiment, the invention provides an isolated polynucleotide encoding a heavy chain and/or a light chain as described above.

In one embodiment, the invention provides an isolated polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221.

In one embodiment, the invention provides an isolated polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an isolated polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221; and an isolated polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an isolated polynucleotide encoding a heavy chain region comprising the amino acid sequence of any one of SEQ NO: 131,138, 139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136.

In one embodiment, the invention provides an isolated polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides an isolated polynucleotide encoding a heavy chain region comprising the amino acid sequence of any one of SEQ NO: 131,138, 139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136; and an isolated polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides an expression vector comprising a polynucleotide as described above.

In one embodiment, the invention provides an expression vector comprising a polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221.

In one embodiment, the invention provides an expression vector comprising a polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an expression vector comprising a polynucleotide encoding a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221; and a polynucleotide encoding a light chain variable region comprising the amino acid sequence of any one of SEQ ID NOs: 105, 106, 107, 108, 109, 125, 126, 109, 127, 128, 129, 130, or 222.

In one embodiment, the invention provides an expression vector comprising a polynucleotide encoding a heavy chain region comprising the amino acid sequence of any one of SEQ NO: 131,138,139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136.

In one embodiment, the invention provides an expression vector comprising a polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides an expression vector comprising a polynucleotide encoding a heavy chain region comprising the amino acid sequence of any one of SEQ NO: 131,138,139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136; and a polynucleotide encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

In one embodiment, the invention provides a host cell comprising an expression vector as described above. In one embodiment, the host cell is a mammalian cell.

In one embodiment, the invention provides a method of manufacturing an antibody or antigen-binding fragment thereof comprising the steps of:

culturing a host cell comprising an expression vector comprising an isolated polynucleotide encoding a heavy chain variable region as described above and an expression vector comprising polynucleotide encoding light chain variable region as described above under conditions that allow formation of an antibody or antigen-binding fragment thereof comprising both the heavy and light chain variable region, and recovering said antibody or antigen-binding fragment thereof.

In one embodiment, the invention provides a method of manufacturing an antibody or antigen-binding fragment thereof comprising the steps of:

culturing a host cell comprising an expression vector comprising an isolated polynucleotide encoding a heavy chain as described above and comprising a polynucleotide encoding light chain as described above under conditions that allow formation of an antibody or antigen-binding fragment thereof comprising both the heavy and light chain variable region; and recovering said antibody or antigen-binding fragment thereof.

In one embodiment, a method above further comprises the step of purifying the antibody or antigen-binding fragment thereof. In one embodiment, a method above further comprises the step of formulating the antibody or antigen-binding fragment thereof into a pharmaceutical composition. Also provided herein are pharmaceutical formulations comprising an anti-SIRPα antibody or an antigen-binding fragment thereof as disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The summary, as well as the following detailed description, is further understood when read in conjunction with the appended drawings. For the purpose of illustrating the disclosed compositions, methods, and kits there are shown in the drawings exemplary embodiments of methods and kits; however, these should not be limited to the specific embodiments disclosed.

FIG. 1A. Antibody binding to parental CHO cells. FIG. 1B. Antibody binding to CHO cells expressing full-length human SIRPαV1 (NP_542970.1). FIG. 1C. Antibody binding to CHO cells expressing full-length human SIRPαV2-expressing CHO cells (CAA71403.1).

FIG. 2A. Antibody binding to U-937 human monocytic cell line. FIG. 2B. Antibody binding to THP-1 human monocytic cell line.

FIG. 18A. SIRPα antagonists restore monocyte-derived macrophage ability to phagocytize opsonized CD47-coated beads. FIG. 18B. SIRPα antagonists enhance monocyte-derived macrophage ability to phagocytize non-opsonized CD47-coated beads. FIG. 18C. SIRPα antagonists dose-dependently restores monocyte-derived macrophage ability to phagocytize opsonized CD47-coated beads.

FIG. 19A. SIRPα antagonists restore monocyte-derived macrophage ability to phagocytize opsonized CD47-coated beads. FIG. 19B. SIRPα antagonists restore monocyte-derived macrophage ability to phagocytize non-opsonized CD47-coated beads. FIG. 19C. SIRPα antagonists dose-dependently restores monocyte-derived macrophage ability to phagocytize opsonized CD47-coated beads.

FIG. 20A. SIRPα antagonists restore monocyte-derived macrophage ability to phagocytize opsonized CD47-coated beads. FIG. 20B. SIRPα antagonists restore monocyte-derived macrophage ability to phagocytize non-opsonized CD47-coated beads. FIG. 20C. SIRPα antagonists dose-dependently restores monocyte-derived macrophage ability to phagocytize opsonized CD47-coated beads.

FIG. 21A. SIRPα antagonists restore monocyte-derived dendritic cells' ability to phagocytize opsonized CD47-coated beads. FIG. 21B. SIRPα antagonists restore monocyte-derived dendritic cells' ability to phagocytize non-opsonized CD47-coated beads.

FIG. 22A. SIRPα antagonists restore monocyte-derived dendritic cells' ability to phagocytize opsonized CD47-coated beads. FIG. 22B. SIRPα antagonists restore monocyte-derived dendritic cells' ability to phagocytize non-opsonized CD47-coated beads.

FIG. 23A. SIRPα antagonists restore monocyte-derived dendritic cells' ability to phagocytize opsonized CD47-coated beads. FIG. 23B. SIRPα antagonists restore monocyte-derived dendritic cells' ability to phagocytize non-opsonized CD47-coated beads.

FIG. 25C. Structure of CD47 (in dark grey) bound to domain 1 of the extracellular domain of human SIRPα-V2 (PDB: 2JJS). FIGS. 25D-25F: structure of domain 1 of the extracellular domain of human SIRPα-V2 highlighting the residues contacted by the Fab fragment of Antibody E (FIG. 25D), by the Fab fragment of Antibody A (FIG. 25E), or human CD47 (FIG. 25F).

FIG. 26A depicts SIRPαV2 shown in light grey as stick representation and residues of Antibody A shown in dark grey by atom type. SIRPαV1 residues comprising atoms in a distance <4.5 Å to Fab fragments of Antibody A are marked and extended by column to the sequences of SIRPαV1 and SIRPγ, aligned by sequence with the program MOE. The interaction of SIRPαV2 D130 is highlighted as a major difference to SIRPγ, where this residue is a glutamate. FIG. 26B depicts SIRPαV2 shown in light grey as stick representation and residues and surface of Antibody E shown in dark grey by atom type. SIRPαV1 residues comprising atoms in a distance <4.5 Å to Fab fragments of Antibody E are marked and extended by column to the sequences of SIRPαV1 and SIRPγ aligned by sequence with the program MOE. The interaction of SIRPαV2 A72 is highlighted as a major difference to SIRPγ, where this residue is comprised of the larger amino acid valine.

FIG. 28A. Antibody binding to CHO cells expressing full-length cyno SIRPα (EGM-02252, clone H3A9). FIG. 28B. Antibody binding to CHO cells expressing full-length cyno SIRPα (XP_015313155, clone P3HD10). FIG. 28C.

Antibody binding to CHO cells expressing full-length cyno SIRPα (NP_001271679, clone HC6).

Figure 29A:
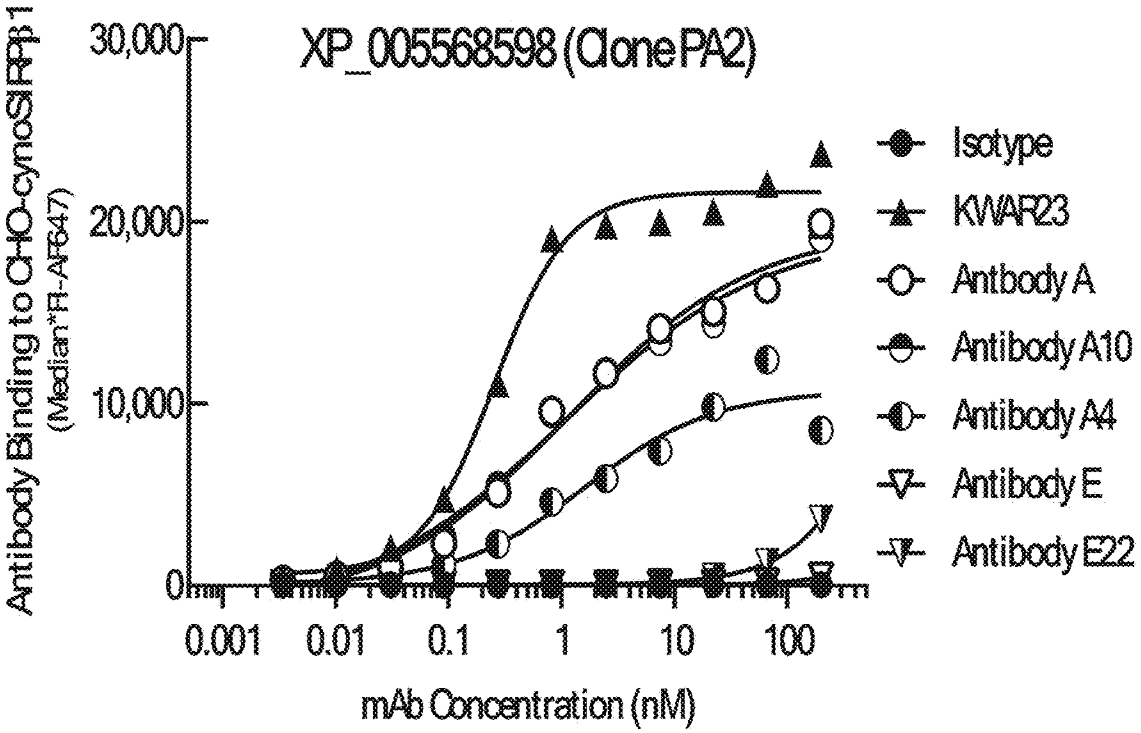
Figure 29B:
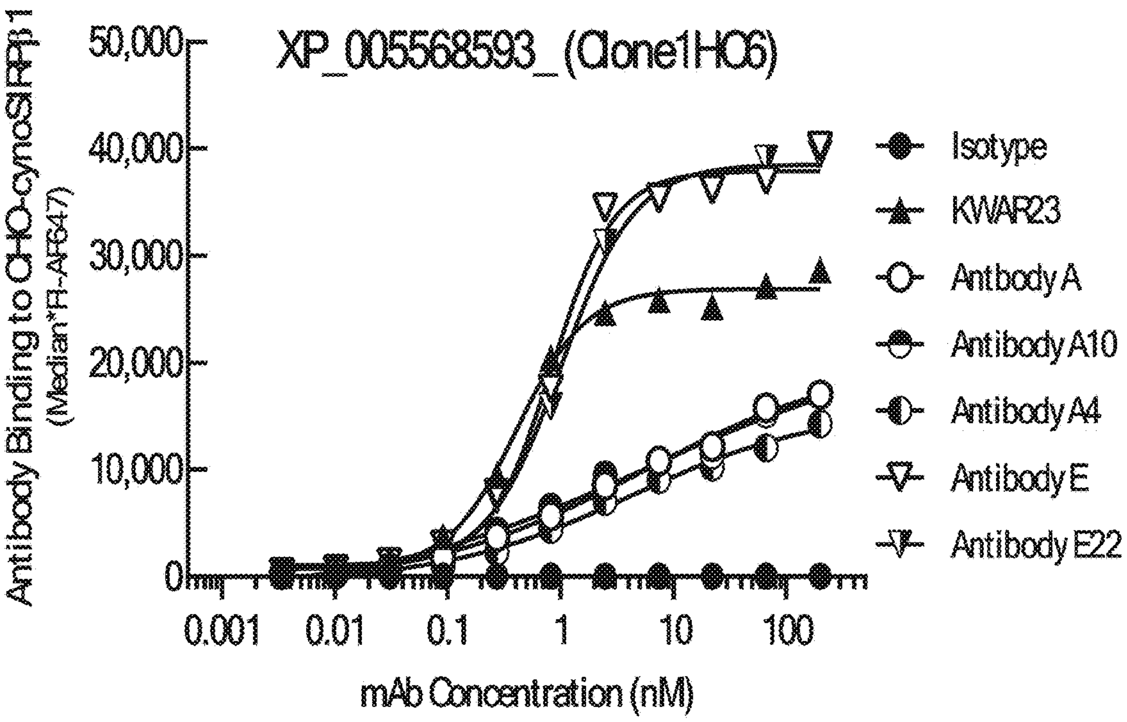

FIG. 29A and FIG. 29B are series of graphs depicting the binding of antibodies to full-length cyno SIRPβ1 expressed on CHO cells. FIG. 29A. Antibody binding to CHO cells expressing full-length cyno SIRPβ1 (XP_005568598, clone PA2). FIG. 29B. Antibody binding to CHO cells expressing full-length cyno SIRP β1v3 (XP_005568593, clone 1HC6).

Figure 30:
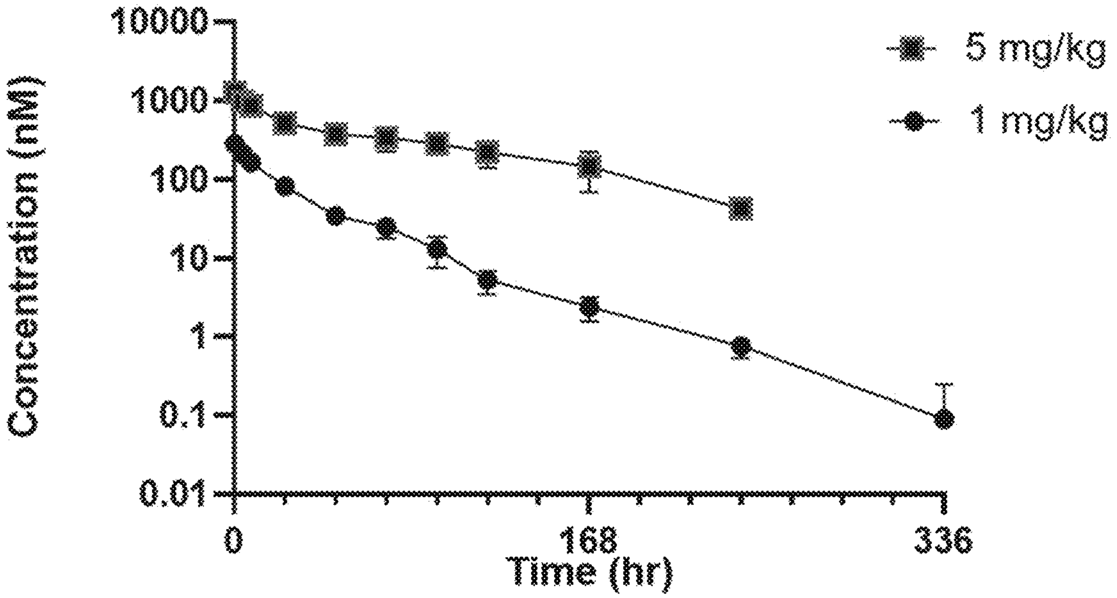

FIG. 30. Mean (SD) serum concentration-time profiles of Antibody A10 following IV administration in cynomolgus monkey at 5 mg/kg (filled squares) or 1 mg/kg (filled circles).

Figure 31A:
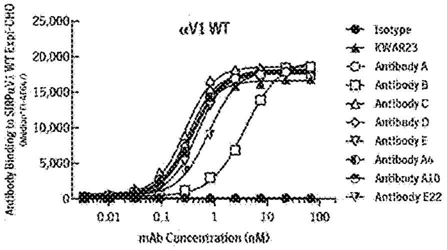
Figure 31B:
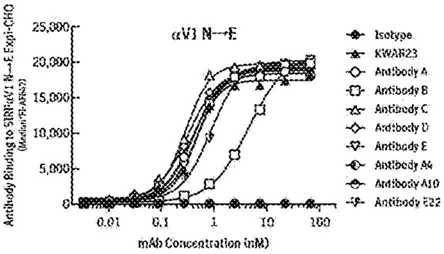
Figure 31C:
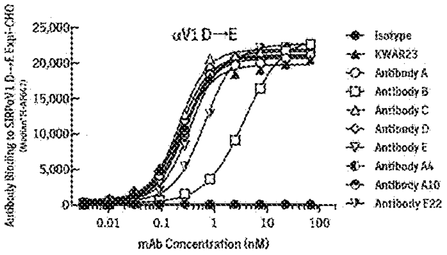
Figure 31D:
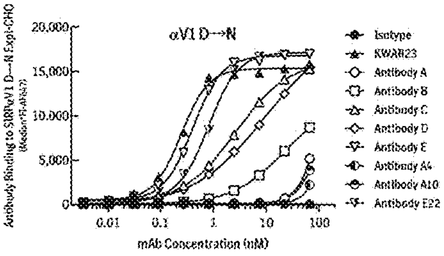
Figure 31E:
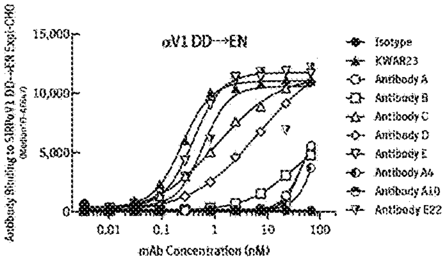
Figure 31F:
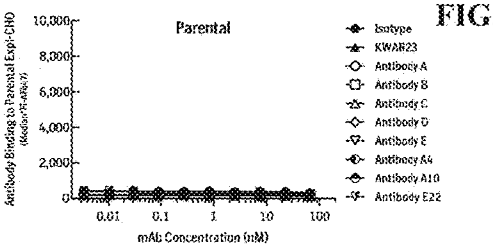

FIGS. 31A-31F show binding of antibodies to full-length human V1-SIRPα with various amino acid point mutations expressed on Expi-CHO cells. Results are shown for cells expressing full-length wild-type human SIRPαV1 (FIG. 31A), SIRPαV1 N→E (FIG. 31B), SIRPαV1 D→E (FIG. 31C), SIRPαV1 D→N (FIG. 31D), SIRPαV1 DD→EN (FIG. 31E), and parental CHO cells (FIG. 31F).

Figure 32A:
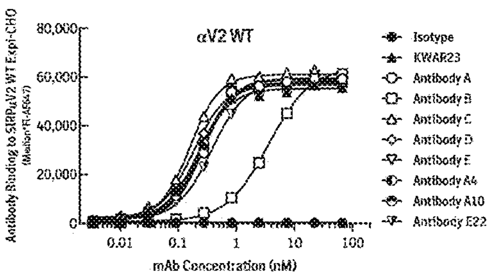
Figure 32B:
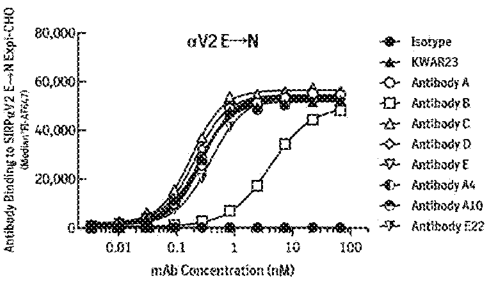
Figure 32C:
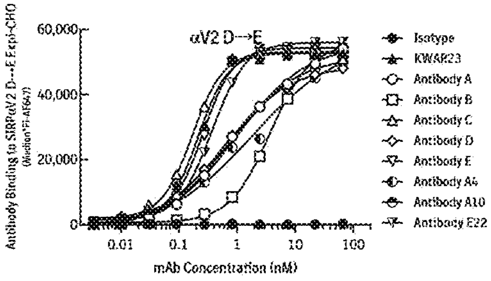

FIGS. 32A-32C show binding of antibodies to full-length human V2-SIRPα with various amino acid point mutations expressed on Expi-CHO cells. Results are shown for cells expressing full-length wild-type human SIRPαV2 (FIG. 32A), SIRPαV2 E→N (FIG. 32B), and SIRPαV2 D→E (FIG. 32C).

Figure 33A:
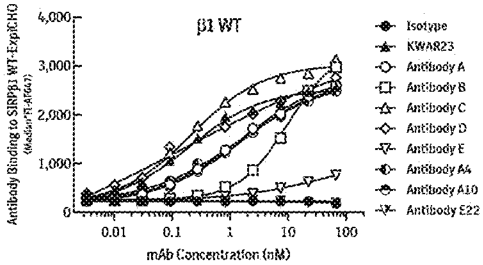
Figure 33B:
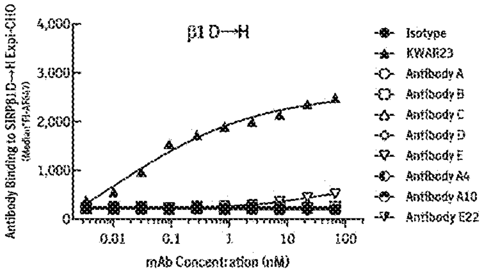

FIG. 33A and FIG. 33B show binding of antibodies to full-length human SIRPβ1 with an amino acid point mutation expressed on Expi-CHO cells. Results are shown for cells expressing full length wild-type human SIRPβ1 (FIG. 33A) and SIRPβ1 D→H (FIG. 33B).

Figure 34A:
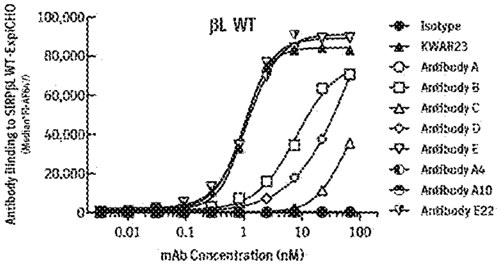
Figure 34B:
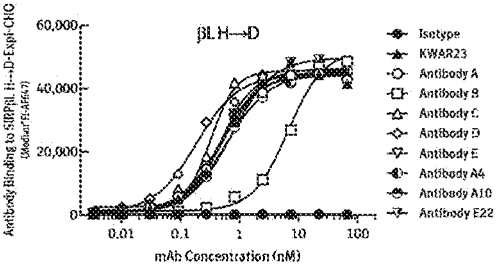

FIG. 34A and FIG. 34B show of antibodies to full-length human SIRPβL with an amino acid point mutation expressed on Expi-CHO cells. Results are shown for cells expressing wild-type SIRPβL (FIG. 34A) or SIRPβL H→D (FIG. 34B).

Figure 35A:
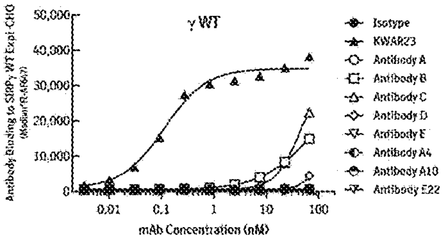
Figure 35B:
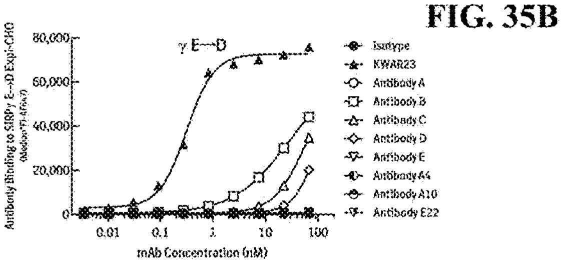
Figure 35C:
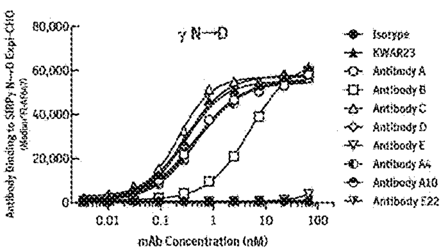
Figure 35D:
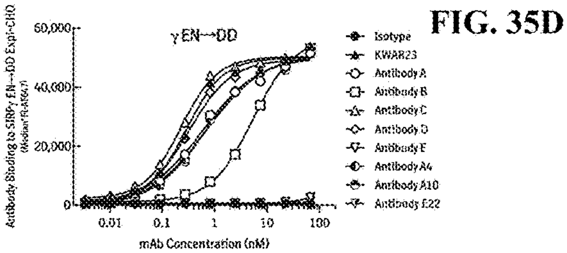

FIGS. 35A-35D show binding of antibodies to full-length human SIRPγ with various amino acid point mutations expressed on Expi-CHO cells. Results are shown for cells expressing full-length wild-type human SIRPγ (FIG. 35A), SIRPγ E→D (FIG. 35B), SIRPγ N→D (FIG. 35C), and SIRPγ EN→DD (FIG. 35D).

Figure 36A:
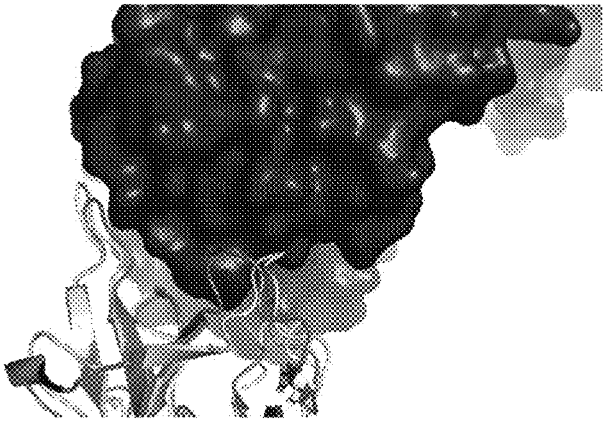

FIG. 36A. Loops of SIRPαV1 (light grey, as observed in pdbID: 4CMM), SIRPαV2 (grey, as observed in the crystal structure in complex with Antibody A) both as shown as a schematic, and Antibody A (surface in dark grey, as observed in the crystal structure in complex with SIRPαV1).

Figure 36B:
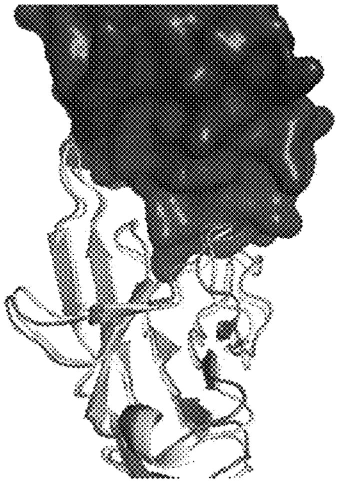
Figure 37F:
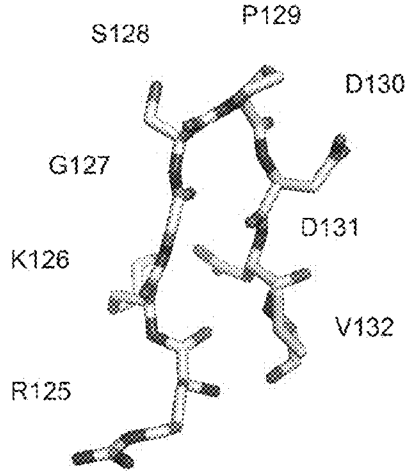
Figure 37F:
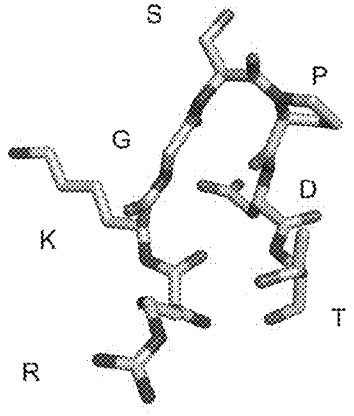
Figure 37F:
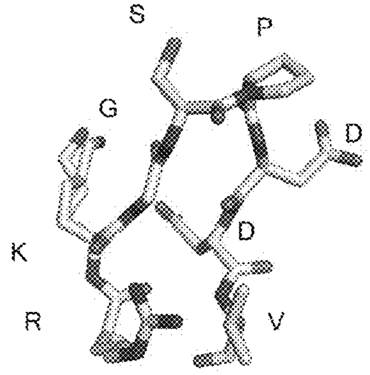
Figure 37F:
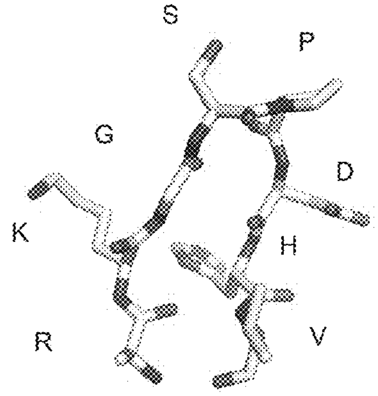
Figure 37F:
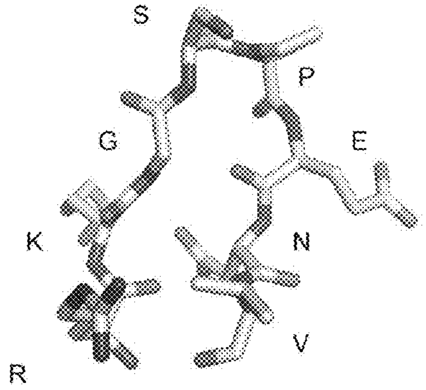

FIG. 36B. Loops of SIRPαV1 (light grey, as observed in pdbID: 4CMM), SIRPαV2 (grey, as observed in the crystal structure in complex with CD47 pdbID: 2JJS) both as shown as a schematic, and CD47 (surface in dark grey, as observed in the crystal structure in complex with SIRPαV1).

FIGS. 37A-37F. Loops of SIRP variants (light grey, color coded by atom type): conformation observed for (FIG. 37A) SIRPαV1 (pdbID: 4CMM), with numbering according to uniprot ID: P78324. (FIG. 37B) SIRPαV2 (as observed in the crystal structure in complex with Antibody A). (FIG. 37C) SIRPβ1 (pdbID: 2JJU). (FIG. 37D) SIRPβL (pdbID: 2JJV). (FIG. 37E) SIRPγ (pdbID: 2JJW). (FIG. 37F) Comparison of sequence motifs in the respective loop, with amino acid differences from SIRPαV1 that correlate with significant loss in binding being DD→EN in case of SIRPγ and D→H in case of SIRPβL.

DETAILED DESCRIPTION OF THE INVENTION

This invention relates to anti-SIRPα antibodies or antigen-binding fragments thereof. The present invention addresses the need for treatments of conditions modulated by the CD47-mediated SIRPα signaling. In one aspect, the anti-SIRPα antibodies or antigen-binding fragments thereof of the invention are for diagnostic and/or therapeutic use, for example in a subject in need thereof such as a human.

In one aspect of the invention, the anti-SIRPα antibody or antigen-binding fragment thereof specifically binds to SIRPα, in particular human or cynomolgus monkey SIRPα, more particularly human SIRPα. In one aspect, the anti-SIRPα antibody or antigen-binding fragment thereof binds to the V1 and/or V2 alleles of human SIRPα. In one aspect of the invention, the anti-SIRPα antibody or antigen-binding fragment thereof does not bind to SIRPγ, in particular cynomolgus monkey or human SIRPγ, more particularly human SIRPγ. In one aspect of the invention, the anti-SIRPα antibody or antigen-binding fragment thereof, does not bind to rabbit, mouse, rat, or dog SIRPα.

In one aspect of the invention, the anti-SIRPα antibody or antigen-binding fragment thereof has an $EC_{50}$ of 0.1 to 100 nM, 0.1 to 50 nM, 0.1 to 25 nM, 0.1 to 10 nM, or 0.1 to 5 nM. In a further aspect of the invention, the anti-SIRPα antibody or antigen-binding fragment thereof has an $EC_{50}$ of 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, or 25 nM. The $EC_{50}$ may be determined by any method known in the art including for example those set forth in the Examples.

In one aspect of the invention, the anti-SIRPα antibody or antigen-binding fragment thereof has an $IC_{50}$ of 0.01 to 100 nM, 0.01 to 50 nM, 0.01 to 25 nM, 0.01 to 10 nM, or 0.01 to 5 nM. In a further aspect of the invention, the anti-SIRPα antibody or antigen-binding fragment thereof has an $IC_{50}$ of 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, or 25 nM. The $IC_{50}$ may be determined by any method known in the art including for example those set forth in the Examples.

In one aspect of the invention, the anti-SIRPα antibody or antigen-binding fragment thereof, binds to human SIRPα-V1 and SIRPα-V2 at a high affinity. In one aspect of the invention, the anti-SIRPα antibody or antigen-binding fragment thereof, binds to human SIRPα-V1 (e.g., human SIRPα-V1 comprising the amino acid sequence set forth in SEQ ID NO:240) at a high affinity, for example at an affinity of 20 nM or less, for example 10 nM or less, for example 5 nM of less, for example 1 nM or less. In one aspect of the invention, the anti-SIRPα antibody or antigen-binding fragment thereof, binds to human SIRPα-V2 (e.g., human SIRPα-V2 comprising the amino acid sequence set forth in SEQ ID NO:241) at a high affinity, for example at an affinity of 20 nM or less, for example 10 nM or less, for example 5 nM of less, for example 1 nM or less. In another aspect of the invention, the anti-SIRPα antibody or antigen-binding fragment thereof, binds to cynomolgus monkey SIRPα. In another aspect of the invention, the anti-SIRPα antibody or antigen-binding fragment thereof, binds to cynomolgus monkey SIRPα (e.g., cynomolgus monkey SIRPα comprising the amino acid sequence set forth in SEQ ID NO:247) at an affinity of 400 nM or less, 300 nM or less, 250 nM or less, 200 or less, 100 nM or less, or 50 nM or less. In another aspect of the invention, the anti-SIRPα antibody or antigen-binding fragment thereof binds to cynomolgus monkey SIRPα (e.g., cynomolgus monkey SIRPα comprising the amino acid sequence set forth in SEQ ID NO:248) at an affinity of 400 nM or less, 300 nM or less, 200 nM or less, or 50 nM or less. In another aspect of the invention, the anti-SIRPα antibody or antigen-binding fragment thereof binds to cynomolgus monkey SIRPα (e.g., cynomolgus monkey SIRPα comprising the amino acid sequence set forth in SEQ ID NO:249) at an affinity of 400 nM or less, 300 nM or less, 200 nM or less, or 50 nM or less.

In one aspect of the invention, the anti-SIRPα antibody or antigen-binding fragment thereof does not bind to SIRPγ, for example at an affinity of 1 μM or greater. In one aspect of the invention, the anti-SIRPα antibody or antigen-binding fragment thereof does not bind to human SIRPγ, for example does not bind to human SIRPγ at an affinity of greater than 1 μM or greater. In one aspect of the invention, the anti-SIRPα antibody or antigen-binding fragment thereof does not bind to cynomolgus monkey SIRPγ, for example does not bind to cynomolgus monkey SIRPγ at an affinity of 1 μM or greater.

In one aspect, an anti-SIRPα antibody or antigen-binding fragment thereof of the invention blocks the interaction between SIRPα and CD47. In a further aspect, an anti-SIRPα antibody or antigen-binding fragment thereof of the invention blocks CD47-mediated SIRPα signaling. In some aspects, the antibody of the invention blocks the binding of CD47 to SIRPα, whereby it decreases CD47-mediated SIRPα signaling by at by at least 80%, by at least 85%, by at least 90%, or by at least 95% when compared with a comparator antibody control or in the absence of an anti-SIRPα antibody or antigen-binding fragment of the invention. In an embodiment, the comparator antibody control comprises a heavy chain variable region comprising the amino acid sequence of any one of SEQ ID NOs: 100, 101, 102, 103, 104, 105, 110, 111, 112, 113, 114, 115, 116, 117, 104, 118, 119, 120, 121, 122, 123, 124, or 221; and a light chain variable region comprising the amino acid sequence of any one of SEQ ID NOs: 105, 106, 107, 108, 109, 125, 126, 109, 127, 128, 129, 130, or 222; or a heavy chain region comprising the amino acid sequence of any one of SEQ NO: 131,138,139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136; and a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

Whether a binding domain specifically binds to a target can be tested with various methods known in the art. These methods include, Surface Plasmon Resonance or ELISA to detect binding of antibodies to purified proteins, or flow cytometry to detect binding of antibodies to cells. The ability of an antibody to block binding of CD47 can be measured by detecting purified soluble CD47 interaction with SIRPα-expressing cells. Alternatively, the blocking activity of an antibody can be measured by assessing SIRPα phosphorylation and recruitment of SHP-1 phosphatase. The blocking activity of an anti-SIRPα antibody can also be evaluated by the capacity to restore the inhibition of phagocytosis caused by CD47. Methods for determining antibody specificity and affinity by competitive inhibition are known in the art.

In one aspect, the present invention provides an anti-SIRPα antibody, in particular a monoclonal anti-SIRPα antibody, for example a human monoclonal anti-SIRPα antibody, or a full-length human monoclonal antibody.

In one aspect, an anti-SIRPα antibody or antigen-binding fragment thereof of the present invention has favorable pharmacokinetic properties. In one aspect, an anti-SIRPα antibody of the present invention has favorable biophysical properties, for example yield, quality, stability or solubility.

Antibodies

The generalized structure of antibodies or immunoglobulin is well known to those of skill in the art, these molecules are heterotetrametric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663, Vargas-Madrazo E, Paz-Garcia E. J Mol Recognit. 2003; 16(3):113-120). The variable domains are also referred herein as variable regions, and the constant domains as constant regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. IMGT and NORTH provide alternative definitions of the CDRs (see, Lefranc M P. Unique database numbering system for immunogenetic analysis. Immunol Today (1997) 18:509; and North B, Lehmann A, Dunbrack R L J. A new clustering of antibody CDR loop conformations. J Mol Biol. (2011) 406:228-56). Additionally, CDRs may be defined per the Chemical Computing Group (CCG) numbering (Almagro et al., Proteins 2011; 79:3050-3066 and Maier et al, Proteins 2014; 82:1599-1610). The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely p-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

FR residues and Ig constant domains are generally not directly involved in antigen binding but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

Definitions

The terms, "antibody", and "anti-SIRPα antibody", are used herein interchangeably and encompass monoclonal antibodies (including full length monoclonal antibodies), multispecific antibodies (e.g., bispecific antibodies), antibodies with minor modifications such as N- or C-terminal truncations and antibody fragments such as variable domains and other portions of antibodies that exhibit a desired biological activity, e.g., SIRPα binding.

The term "monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation that may be present. Monoclonal antibodies typically bind one antigenic epitope. A bispecific monoclonal antibody binds two distinct antigenic epitopes. A monoclonal antibody may be monospecific or multispecific such as bispecific, monovalent, bivalent or multivalent. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms "antibody fragment", "antigen-binding fragment", "anti-SIRPα antibody fragment", "anti-SIRPα antibody fragment", "engineered anti-SIRPα antibody fragment" refer to a portion of a full length anti-SIRPα antibody, in which a variable region or a functional capability is retained, for example, SIRPα binding. Examples of antibody fragments include, but are not limited to, a Fab, Fab', $F(ab')_2$, Fd, Fv, scFv and scFv-Fc fragment, a diabody, a linear antibody, a single-chain antibody, a minibody, a diabody formed from antibody fragments, and multispecific antibodies formed from antibody fragments.

Antibody fragments can be obtained for example by treating full-length antibodies treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a $F(ab')_2$ fragment that has two antigen-binding sites and is still capable of cross-linking antigen.

Another example of antibody fragments according to the invention are Fab' fragments. Fab' fragments differ from Fab fragments by the presence of additional residues including one or more cysteines from the antibody hinge region at the C-terminus of the $C_{H1}$ domain. $F(ab')_2$ antibody fragments are pairs of Fab' fragments linked by cysteine residues in the hinge region. Other chemical couplings of antibody fragments are also known.

A "Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

Antibody fragments may also include "single-chain Fv" or "scFv" fragments. A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Antibody fragments may also form tandem Fd segments, which comprise a pair of tandem Fd segments ($V_H$—$C_{H1}$—$V_H$—$C_{H1}$) to form a pair of antigen binding regions. These "linear antibodies" can be bispecific or monospecific as described in, for example, Zapata et al. 1995, Protein Eng. 8(10):1057-1062.

The term "human antibody" as used herein includes antibodies or fragments thereof derived from human germline immunoglobulin sequences. The term "human antibody" is not intended to include antibodies in which CDR sequences derived from the germline of another (mammalian) species, such as a mouse, rat or rabbit, have been grafted onto human framework sequences. Thus, as used herein, the term "human antibody" refers to an antibody or fragment thereof in which every part of the protein (e.g., CDR, framework, CL, CH domains (e.g., CH1, CH2, CH3), hinge, VL, VH) is substantially non-immunogenic in humans, with only minor sequence changes or variations as further described herein below.

Technologies for creating such a "human antibody" have been described and include without being limiting phage display or use of transgenic animals (www.Ablexis.com/technology-alivamab.php; WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93.; Brüggemann M, Taussig M J. "Production of human antibody repertoires in transgenic mice". Curr Opin Biotechnol. 1997 August; 8(4):455-8.).

Thus, a human antibody is distinct from e.g., a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes.

In one aspect, an anti-SIRPα antibody of the invention is a humanized antibody or antibody fragment thereof. A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. Methods of humanization of antibodies are for example described by Almagro et al., (2008) Frontiers in Bioscience 13, 1619-1633, or in WO12092374 A2.

The chimeric, humanized or human antibodies or antigen-binding fragments thereof of the present invention may further be engineered. Such engineering includes without limitation the removal or exchange of undesired amino acids, for example to reduce immunogenicity in humans, or to avoid deamidation, undesirable charges or lipophilicity or non-specific binding. Such removal or exchange of undesired amino acids can, for example, be introduced by random or site-specific mutagenesis in vitro or by somatic mutation in vivo. Moreover, in connection with chimeric or humanized antibodies, it will be understood that certain mouse FR residues may be retained in an antibody or fragment thereof.

In one aspect, an anti-SIRPα antibody comprises substantially all of at least one, and typically two, variable domains (such as contained, for example, in Fab, Fab', F(ab')2, Fabc, and Fv fragments). In another aspect, an anti-SIRPα antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

In one aspect, an anti-SIRPα antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. An alternative anti-SIRPα antibody can comprise sequences from more than one immunoglobulin class or isotype, and selecting particular modified or unmodified constant domains to optimize desired effector functions is within the ordinary skill in the art.

For example, the Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Fc engineering can be employed to optimize antibody properties suited to the pharmacology activity required of them. Where such cytotoxic activity is not desirable, such as targeting an immune cell in the treatment of cancer, the constant domain may be of isotype with reduced effector function, such as IgG4, and/or be modified with known modifications that reduce effector function. Where such cytotoxic activity is desirable, such as for destruction of a targeted tumor cell, the constant domain may be of isotype with increased effector function and/or be modified with known modifications to increase effector function. Several mutations are known to either reduce or increase effector function. See, e.g., "*The future of antibodies as cancer drugs*" Janice M Reichert, Eugen Dhimolea, Drug Discov Today (2012) September; 17(17-18):954-63—PMID: 22561895, *"Antibody Drug Discovery"* (Volume 4 of Molecular medicine and medicinal chemistry) Clive R. Wood, World Scientific, 2012 ISBN 1848166281, 9781848166288*; "FcγR requirements leading to successful immunotherapy"* Immunol Rev. (2015) November; 268(1): 104-22—PMID: 26497516.

In one aspect, the constant domain of an antibody of the present invention is IgG4Pro, which has one replacement mutation (Ser228Pro) that prevents Fab-arm exchanging. In another aspect, the constant domain of an antibody of the present invention is IgG1, which has two mutations in the constant region, Leu234Ala and Leu235Ala to reduce effector function.

The FRs and CDRs, or HVLs, of an engineered anti-SIRPα antibody or antigen-binding fragment thereof need not correspond precisely to the parental sequences. For example, a parental sequence may be altered (e.g., mutagenized) by substitution, insertion or deletion such that the resulting amino acid residue is no longer identical to the original residue in the corresponding position in either parental sequence but the antibody nevertheless retains the function of binding to SIRPα. Such alteration typically will not be extensive and will be conservative alterations. Usually, at least 75% of the engineered antibody residues will correspond to those of the parental sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of human or humanized anti-SIRPα antibodies. See, for example, U.S. Pat. Nos. 6,037,454 and 6,054,297.

An "isolated" antibody is one that has been identified and separated and/or recovered from a component of its natural environment or from a cell culture from which it was expressed. An isolated antibody or antibody fragment may have one or more co- or post-translational modifications that arise during production, purification, and/or storage of the antibody or antibody fragment. Contaminant components of the antibody's natural environment are those materials that may interfere with diagnostic or therapeutic uses of the antibody, and can be enzymes, hormones, or other proteinaceous or non-proteinaceous solutes. In one aspect, the antibody will be purified to at least greater than 95% isolation by weight of antibody, for example purified to at least greater than 95%, 96%, 97%, 98%, or 99%.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

"Multispecific" refers to a protein, such as an antibody, that specifically binds two or more distinct antigens or two or more distinct epitopes within the same antigen.

"Bispecific" refers to a protein, such as an antibody, that specifically binds two distinct antigens or two distinct epitopes within the same antigen.

In some embodiments, the antibody that specifically binds SIRPα or the antigen-binding fragment thereof of the invention is a bispecific antibody. In some embodiments, the antibody or the antigen-binding fragment thereof of the invention is a multispecific antibody. The monospecific antibodies that specifically bind SIRPα provided herein may be engineered into bispecific antibodies, which are also encompassed within the scope of the invention.

Full-length bispecific antibodies may be generated for example using Fab arm exchange (e.g., half-molecule exchange, exchanging one heavy chain-light chain pair) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond.

Bispecific antibodies may also be generated using designs such as the Triomab/Quadroma (Trion Pharma/Fresenius Biotech), Knob-in-Hole (Genentech), CrossMAbs (Roche) and the electrostatically-induced CH3 interaction (Chugai, Amgen, NovoNordisk, Oncomed), the LUZ-Y (Genentech), the Strand Exchange Engineered Domain body (SEEDbody) (EMD Serono), the Biclonic (Merus) and as DuoBody® Products (Genmab A/S).

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

A "chemotherapeutic agent" is a chemical compound useful in the treatment of cancer. Examples of such chemotherapeutic agents include alkylating agents such a thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues); cryptophycines (particularly cryptophycin 1 and cryptophycin 8); dolastatin, auristatins, (including analogues monomethyl-auristatin E and monomethyl-auristatin F); duocarmycin (including the synthetic analogues, KW-2189 and CBI-TMI); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phiI1, see for example, Agnew, Chem. Intl. Ed. Engl., 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin, and deoxydoxorubicin), epirubucin, esorubicin, idarubicin, marcellomycin, mitomycins such as mitomycin C, mycophenolic acid, nogalamycin, olivomycins, peplomycin, potfiromycin, puromycine, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above. Any one or more of these agents may be conjugated to the human antibodies or antigen-binding fragments thereof of the present invention to provide a useful therapeutic agent for the treatment of various diseases and/or disorders.

For diagnostic as well as therapeutic monitoring purposes, the antibodies or antigen-binding fragment thereof of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to an anti-SIRPα antibody or antigen-binding fragment thereof of the present invention. The label may itself be detectable (e.g., radioisotope labels or fluorescent labels) or, in the case of an enzymatic label, may catalyze chemical alteration of a substrate compound or composition that is detectable. Labeled anti-SIRPα antibodies or antigen-binding fragments thereof can be prepared and used in various applications including in vitro and in vivo diagnostics.

In various aspects of the present invention one or more domains of the anti-SIRPα antibodies or antigen-binding fragments thereof will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of anti-SIPRα antibodies or antigen-binding fragments thereof in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers, which may for example have been transfected with one or more expression vectors encoding one or more amino acids sequences of an antibody or antigen-binding fragment thereof of the present invention.

The term "mammal" for purposes of treatment according to the invention refers to any animal classified as a mammal, including humans, domesticated and farm animals, and zoo, sports, or pet animals, such as dogs, horses, cats, cows, and the like. Preferably, the mammal is a human.

A "disorder", as used herein, is any condition that would benefit from treatment with an anti-SIRPα antibody or antigen-binding fragment thereof described herein. This includes chronic and acute disorders or diseases including those pathological conditions that predispose the mammal to the disorder in question. Non-limiting examples or disorders to be treated herein include inflammatory, angiogenic, autoimmune and immunologic disorders, respiratory disorders, cancer, hematological malignancies, benign and malignant tumors, leukemias and lymphoid malignancies.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia.

As used herein, the term "SIRPα pathway disorder" or "SIRPα pathway disease" refers to a condition, which can be alleviated by modulating the interaction between SIRPα and CD47, in particular by inhibiting the SIRPα/CD47 signaling. A "SIRPα pathway disorder" or "SIRPα pathway disease" includes myeloid associated diseases where SIRPα is expressed. A "SIRPα pathway disorder" or "SIRPα pathway disease" also includes conditions characterized by reduced phagocytosis by macrophages and/or dendritic cells that express SIRPα increased immune response is desired.

Examples of SIRPα pathway disorders are cancer, inflammatory disease, autoimmune disease, respiratory disease, infectious disease or fibrosis. Examples of cancers include hematological cancer (e.g. leukemia, lymphoma, myeloma, e.g. multiple myeloma), and a metastatic lesion. Further examples include solid tumor cancers. Examples of solid tumors include malignancies, e.g. sarcomas and carcinomas, e.g. adenocarcinomas of the various organ systems, such as those affecting the lung, breast, ovarian, lymphoid, gastrointestinal (e.g. colon), anal, genitals and genitourinary tract (e.g. renal, urothelial, bladder cells, prostate), pharynx, CNS (e.g. brain, neural or glial cells), head and neck, skin (e.g. melanoma), and pancreas, as well as adenocarcinomas which include malignancies such as colon cancers, rectal cancer, renal-cell carcinoma, liver cancer, gastric cancers, non-small cell lung cancer, cancer of the small intestine and cancer of the esophagus. The cancer may be at an early, intermediate, late stage or metastatic cancer.

In some embodiments, the cancer is chosen from a lung cancer (e.g. NSCLC (e.g. a NSCLC with squamous and/or non-squamous histology, or a NSCLC adenocarcinoma)), a melanoma (e.g. an advanced melanoma), a renal cancer (e.g. a renal cell carcinoma), a liver cancer, hepatocellular carcinoma, a myeloma (e.g. a multiple myeloma), a prostate cancer, a breast cancer (e.g. a breast cancer that does not express one, two or all of estrogen receptor, progesterone receptor, or HER2/neu, e.g. a triple negative breast cancer), a colorectal cancer, a pancreatic cancer, a head and neck cancer (e.g. head and neck squamous cell carcinoma (HNSCC), anal cancer, gastro-esophageal cancer, thyroid cancer, cervical cancer, a lymphoproliferative disease (e.g. a post-transplant lymphoproliferative disease) or a hematological cancer, T-cell lymphoma, B-cell lymphoma, a non-Hodgkin lymphoma, or a leukemia (e.g. a myeloid leukemia or a lymphoid leukemia).

In some embodiments, the cancer is chosen from a carcinoma (e.g. advanced or metastatic carcinoma), melanoma or a lung carcinoma, e.g. a NSCLC.

In some embodiments, the cancer is chosen from a pancreatic cancer, prostate cancer, breast cancer, colorectal cancer, lung cancer, glioblastoma, renal cancer, preferably pancreatic cancer, prostate cancer, breast cancer, colorectal cancer or lung cancer.

In some embodiments, the cancer is pancreatic cancer, lung cancer, breast cancer, melanoma, colorectal cancer, ovarian cancer, gastric cancer, thyroid cancer, liver cancer or prostate cancer.

The terms "specifically binds" or "specific binding" in the context of a binding agent, e.g., an antibody or antigen-binding fragment thereof, refers to a binding agent that associates more frequently, more rapidly, with greater duration, with greater affinity, with greater avidity or with some combination of the above, to an antigen or an epitope within the antigen than with an unrelated antigen. In certain embodiments, an antibody or antigen-binding fragment thereof specifically binds to an antigen or epitope within an antigen with a $K_D$ of about 0.1 mM or less, preferably less than about 1 μM. Because of the sequence identity between homologous proteins in different species, or variants of a protein within a single species, specific binding can include an antibody or antigen-binding fragment thereof that recognizes a protein in more than one species (e.g., human SIRPα and cyno SIRPα). It is understood that, in certain embodiments, an antibody or antigen-binding fragment thereof that specifically binds a first protein may or may not specifically bind a second protein. As such, "specific binding" does not necessarily require (although it can include) exclusive binding, i.e. binding to a single protein. Thus, an antibody or antigen-binding fragment thereof may, in certain embodiments, specifically bind more than one protein.

Methods for determining whether two molecules specifically bind a protein are described herein or a known in the art and include, for example, equilibrium dialysis, surface plasmon resonance, and the like. In one embodiment, specific binding is characterized by a $K_D$ of about $1\times10^{-7}$ M (100 nM) or less according to the affinity binding method described in the Examples section herein. In another embodiment, specific binding is characterized by a $K_D$ of about $5\times10^{-8}$ M (50 nM) or less according to the affinity binding method described in the Examples section herein. In another embodiment, specific binding is characterized by a $K_D$ of about $1\times10^{-8}$ M (10 nM) or less according to the affinity binding method described in the Examples section herein. In another embodiment, specific binding is characterized by a $K_D$ of about $5\times10^{-9}$ M (5 nM) or less according to the affinity binding method described in the Examples section herein.

The term "subcutaneous administration" refers to introduction of a drug, for example an anti-SIRPα antibody or antigen-binding fragment thereof of the invention, under the skin of a subject such as an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug, for example an anti-SIRPα antibody or antigen-binding fragment thereof of the invention, under the skin of a subject, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of a subject, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue. For example, "subcutaneous bolus" refers to the administration of an anti-SIRPα antibody or antigen-binding fragment thereof of the invention to a subject in less than approximately 15 minutes; in another aspect, less than 5 minutes, and in still another aspect, less than 60 seconds The term "therapeutically effective amount" is used to refer to an amount of an anti-SIRPα antibody or antigen-binding fragment thereof that relieves or ameliorates one or more of the symptoms of the disorder being treated. In doing so, it is that amount that has a beneficial patient outcome. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-SIRPα antibody or antigen-binding fragment thereof prior to or following the onset of a symptom of a disease or disorder thereby preventing or removing one or more signs of the disease or disorder. As another example, the term includes the administration of an anti-SIRPα antibody or antigen-binding fragment thereof after clinical manifestation of the disease to combat the symptoms of the disease. Further, administration of an anti-SIRPα antibody or antigen-binding fragment thereof after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-SIRPα antibody or antigen-binding fragment thereof composition or antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

Described and disclosed herein are anti-SIRPα antibodies, in particular human anti-SIRPα antibodies, as well as compositions and articles of manufacture comprising anti-SIRPα antibodies of the present invention. Also described are antigen-binding fragments of an anti-SIRPα antibody. The anti-SIRPα antibodies and antigen-binding fragments thereof can be used in the treatment of a variety of diseases or disorders, in particular diseases or disorders characterized by modulation of CD47-mediated SIRPα signaling. An anti-SIRPα antibody and an antigen-binding fragment thereof each include at least a portion that specifically recognizes a SIRPα epitope.

The epitopes are most commonly proteins, short oligopeptides, oligopeptide mimics (e.g., organic compounds that mimic antibody binding properties of the SIRPα antigen), or combinations thereof. The minimum size of a peptide or polypeptide epitope for an antibody is thought to be about four to five amino acids. Peptide or polypeptide epitopes contain for example at least seven amino acids or for example at least nine amino acids or for example between about 15 to about 20 amino acids. Since an antibody can recognize an antigenic peptide or polypeptide in its tertiary form, the amino acids comprising an epitope need not be contiguous, and in some cases, may not even be on the same peptide chain. Epitopes may be determined by various techniques known in the art, such as X-ray crystallography, Hydrogen/Deuterium Exchange Mass Spectrometry (HXMS), site-directed mutagenesis, alanine scanning mutagenesis, and peptide screening methods.

The generation of anti-SIRPα antibodies and their characterization is described in the Examples. CDRs of representative anti-SIRPα antibodies of the present invention are disclosed in Tables 1-25 below. Heavy Chain CDR-1, CDR-2, CDR3 (HCDR1-3) and Light Chain CDR-1, CDR-2, CDR3 (L-CDR1-3) are provided according to the numbering systems according to Kabat, CCG, Chothia, IMGT, and North.

TABLE 1

| KABAT NOMENCLATURE | | |
|---|---|---|
| | Antibody E, E1-E22 | |
| | KABAT SEQ | SEQ ID NO: |
| HCDR1 | NYYWS | 1 |
| HCDR1-h | DYYWS | 223 |
| HCDR2 | FIYYNGRTFYNS SLKS | 2 |
| HCDR2-h | FIYYNGRTFYNPSLKS | 3 |
| HCDR2-h | FIYDNGRTFYNPSLKS | 4 |
| HCDR2-h | FIYYTGRTFYNPSLKS | 5 |
| HCR2-h | FIYYNGRTFYQS SLKS | 224 |
| HCDR3 | VRAYSGIGLDGTDV | 6 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCR1-h | RSSQSLLYSTGYTYLD | 225 |

TABLE 1-continued

| KABAT NOMENCLATURE | | | |
|---|---|---|---|
| | Antibody E, E1-E22 | | |
| | KABAT SEQ | SEQ ID NO: | |
| LCDR2 | LGSNRAS | 10 | |
| LCDR2-h | QGSNRAS | 11 | |
| LCDR2-h | GGSSRAS | 226 | |
| LCDR3 | MQALQTPLT | 12 | |
| LCDR3-h | GQALQTPLT | 227 | |
| HCDR1-Consensus | X1YYWS | 228 | wherein X1 = N or D |
| HCDR2-Consensus | FIYX1X2GRTFYX3X4SLKS | 229 | wherein X1 = Y or D; X2 = N or T; X3 = N or Q; X4 = S or P |
| LCDR1-Consensus | X1SSQSLLYSX2X3YX4YLD | 230 | wherein X1 = K or R; X2 = N or T; X3 = G or A; X4 = N, A or T |
| LCDR2-Consensus | X1GSX2RAS | 231 | wherein X1 = L, Q or G; X2 = N or S |
| LCDR3-Consensus | X1QALQTPLT | 232 | wherein X1 = M or G |

TABLE 2

| IMGT NOMENCLATURE | | |
|---|---|---|
| | Antibody E, E1-E22 | |
| | IMGT SEQ | SEQ ID NO: |
| HCDR1 | GGSIRNYY | 13 |
| HCDR2 | IYYNGRT | 14 |
| HCDR2-h | IYDNGRT | 15 |
| HCDR2-h | IYYTGRT | 16 |
| HCDR3 | ARVRAYSGIGLDGTDV | 17 |
| LCDR1 | QSLLYSNGYNY | 18 |
| LCDR1-h | QSLLYSNGYAY | 19 |
| LCDR1-h | QSLLYSNAYNY | 20 |
| LCDR2 | LGS | 21 |
| LCDR2-h | QGS | 22 |
| LCDR3 | MQALQTPLT | 12 |

TABLE 3

| CCG NOMENCLATURE | | |
|---|---|---|
| | Antibody E, E1-E22 | |
| | CCG SEQ | SEQ ID NO: |
| HCDR1 | GGSIRNYYWS | 23 |
| HCDR2 | FIYYNGRTFYNSSLKS | 2 |
| HCDR2-h | FIYYNGRTFYNPSLKS | 3 |
| HCDR2-h | FIYDNGRTFYNPSLKS | 4 |
| HCDR2-h | FIYYTGRTFYNPSLKS | 5 |
| HCDR3 | VRAYSGIGLDGTDV | 6 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCDR2 | LGSNRAS | 10 |
| LCDR2-h | QGSNRAS | 11 |
| LCDR3 | MQALQTPLT | 12 |

TABLE 4

| CHOTHIA NOMENCLATURE | | |
|---|---|---|
| | Antibody E, E1-E22 | |
| | CHOTHIA SEQ | SEQ ID NO: |
| HCDR1 | GGSIRNY | 261 |
| HCDR2 | YYNGR | 24 |
| HCDR2-h | YDNGR | 25 |
| HCDR2-h | YYTGR | 26 |
| HCDR3 | VRAYSGIGLDGTDV | 6 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCDR2 | LGSNRAS | 10 |
| LCDR2-h | QGSNRAS | 11 |
| LCDR3 | MQALQTPLT | 12 |

TABLE 5

| NORTH NOMENCLATURE | | |
|---|---|---|
| | Antibody E, E1-E22 | |
| | NORTH SEQ | SEQ ID NO: |
| HCDR1 | TVSGGSIRNYYWS | 27 |
| HCDR2 | FIYYNGRTF | 28 |
| HCDR2-h | FIYDNGRTF | 29 |
| HCDR2-h | FIYYTGRTF | 30 |

TABLE 5-continued

| NORTH NOMENCLATURE | | |
|---|---|---|
| | Antibody E, E1-E22 | |
| | NORTH SEQ | SEQ ID NO: |
| HCDR3 | ARVRAYSGIGLDGTDV | 17 |
| LCDR1 | KSSQSLLYSNGYNYLD | 7 |
| LCDR1-h | KSSQSLLYSNGYAYLD | 8 |
| LCDR1-h | KSSQSLLYSNAYNYLD | 9 |
| LCDR2 | YLGSNRAS | 31 |
| LCDR2-h | YQGSNRAS | 32 |
| LCDR3 | MQALQTPLT | 12 |

TABLE 6

| KABAT NOMENCLATURE | | | |
|---|---|---|---|
| | Antibody A, A1-A16 | | |
| | KABAT SEQ | SEQ ID NO: | |
| HCDR1 | SYDMH | 33 | |
| HCDR2 | AIGTAGDTYYTGSVKG | 34 | |
| HCDR3 | GGVWDDAFDI | 35 | |
| LCDR1 | RASQDINNYLA | 36 | |
| LCDR1-h | RASQGINNYAA | 37 | |
| LCDR2 | TASSLHS | 38 | |
| LCDR3 | QQYVSYPYT | 39 | |
| LCDR1-Consensus | RASQX1INNYX2A | 233 | wherein X1 = D or G; X2 = L or A |

TABLE 7

| IMGT NOMENCLATURE | | |
|---|---|---|
| | Antibody A, A1-A16 | |
| | IMGT SEQ | SEQ ID NO: |
| HCDR1 | GFTLSSYD | 40 |
| HCDR2 | IGTAGDT | 41 |
| HCDR3 | VRGGVWDDAFDI | 42 |
| LCDR1 | QDINNY | 43 |
| LCDR1-h | QGINNY | 44 |
| LCDR2 | TAS | 45 |
| LCDR3 | QQYVSYPYT | 39 |

TABLE 8

| CCG NOMENCLATURE | | |
|---|---|---|
| | Antibody A, A1-A16 | |
| | CCG SEQ | SEQ ID NO: |
| HCDR1 | GFTLSSYDMH | 46 |
| HCDR2 | AIGTAGDTYYTGSVKG | 34 |
| HCDR3 | GGVWDDAFDI | 35 |
| LCDR1 | RASQDINNYLA | 36 |
| LCDR1-h | RASQGINNYAA | 37 |
| LCDR2 | TASSLHS | 38 |
| LCDR3 | QQYVSYPYT | 39 |

TABLE 9

| CHOTHIA NOMENCLATURE | | |
|---|---|---|
| | Antibody A, A1-A16 | |
| | CHOTHIA SEQ | SEQ ID NO: |
| HCDR1 | GFTLSSY | 47 |
| HCDR2 | GTAGD | 48 |
| HCDR3 | GGVWDDAFDI | 35 |
| LCDR1 | RASQDINNYLA | 36 |
| LCDR1-h | RASQGINNYAA | 37 |
| LCDR2 | TASSLHS | 38 |
| LCDR3 | QQYVSYPYT | 39 |

TABLE 10

| NORTH NOMENCLATURE | | |
|---|---|---|
| | Antibody A, A1-A16 | |
| | NORTH SEQ | SEQ ID NO: |
| HCDR1 | AASGFTLSSYDMH | 49 |
| HCDR2 | AIGTAGDTY | 50 |
| HCDR3 | VRGGVWDDAFDI | 42 |
| LCDR1 | RASQDINNYLA | 36 |
| LCDR1-h | RASQGINNYAA | 37 |
| LCDR2 | YTASSLHS | 51 |
| LCDR3 | QQYVSYPYT | 39 |

TABLE 11

| KABAT NOMENCLATURE | | |
|---|---|---|
| | Antibody B | |
| | KABAT SEQ | SEQ ID NO: |
| HCDR1 | GNYMH | 52 |
| HCDR2 | WINPNSGGTNYAQKFQG | 53 |
| HCDR3 | GSGWYENYYYYGMDV | 54 |
| LCDR1 | RASQGISSWLA | 55 |
| LCDR2 | AESSLQS | 56 |
| LCDR3 | QQANSFPLT | 57 |

TABLE 12

| IMGT NOMENCLATURE | | |
|---|---|---|
| | Antibody B | |
| | IMGT SEQ | SEQ ID NO: |
| HCDR1 | GYTFTGNY | 58 |
| HCDR2 | INPNSGGT | 59 |
| HCDR3 | VSGSGWYENYYYYGMDV | 60 |
| LCDR1 | QGISSW | 61 |
| LCDR2 | AES | 62 |
| LCDR3 | QQANSFPLT | 57 |

TABLE 13

| CCG NOMENCLATURE | | |
|---|---|---|
| | Antibody B | |
| | CCG SEQ | SEQ ID NO: |
| HCDR1 | GFTFSSYDMH | 63 |
| HCDR2 | WINPNSGGTNYAQKFQG | 53 |
| HCDR3 | GSGWYENYYYYGMDV | 54 |
| LCDR1 | RASQGISSWLA | 55 |
| LCDR2 | AESSLQS | 56 |
| LCDR3 | QQANSFPLT | 57 |

TABLE 14

| CHOTHIA NOMENCLATURE | | |
|---|---|---|
| | Antibody B | |
| | CHOTHIA SEQ | SEQ ID NO: |
| HCDR1 | GYTFTGN | 64 |
| HCDR2 | NPNSGG | 65 |
| HCDR3 | GSGWYENYYYYGMDV | 54 |
| LCDR1 | RASQGISSWLA | 55 |

TABLE 14-continued

| CHOTHIA NOMENCLATURE | | |
|---|---|---|
| | Antibody B | |
| | CHOTHIA SEQ | SEQ ID NO: |
| LCDR2 | AESSLQS | 56 |
| LCDR3 | QQANSFPLT | 57 |

TABLE 15

| NORTH NOMENCLATURE | | |
|---|---|---|
| | Antibody B | |
| | NORTH SEQ | SEQ ID NO: |
| HCDR1 | KASGYTFTGNYMH | 66 |
| HCDR2 | WINPNSGGTN | 67 |
| HCDR3 | VSGSGWYENYYYYGMDV | 68 |
| LCDR1 | RASQGISSWLA | 55 |
| LCDR2 | YAESSLQS | 69 |
| LCDR3 | QQANSFPLT | 57 |

TABLE 16

| KABAT NOMENCLATURE | | |
|---|---|---|
| | Antibody C | |
| | KABAT SEQ | SEQ ID NO: |
| HCDR1 | SYDMH | 33 |
| HCDR2 | VIGIAGDTYYPGSVKG | 70 |
| HCDR3 | GGSWDDAFDI | 71 |
| LCDR1 | RASQDINNYLA | 36 |
| LCDR2 | TASSLQS | 72 |
| LCDR3 | QQYVSYPYT | 39 |

TABLE 17

| IMGT NOMENCLATURE | | |
|---|---|---|
| | Antibody C | |
| | IMGT SEQ | SEQ ID NO: |
| HCDR1 | GFTFSSYD | 73 |
| HCDR2 | IGIAGDT | 74 |
| HCDR3 | ARGGSWDDAFDI | 75 |
| LCDR1 | QDINNY | 43 |
| LCDR2 | TAS | 45 |
| LCDR3 | QQYVSYPYT | 39 |

TABLE 18

| CCG NOMENCLATURE | | |
|---|---|---|
| | Antibody C | |
| | CCG SEQ | SEQ ID NO: |
| HCDR1 | GFTFSSYDMH | 76 |
| HCDR2 | VIGIAGDTYYPGSVKG | 77 |
| HCDR3 | GGSWDDAFDI | 78 |
| LCDR1 | RASQDINNYLA | 36 |
| LCDR2 | TASSLQS | 79 |
| LCDR3 | QQYVSYPYT | 39 |

TABLE 19

| CHOTHIA NOMENCLATURE | | |
|---|---|---|
| | Antibody C | |
| | CHOTHIA SEQ | SEQ ID NO: |
| HCDR1 | GFTFSSY | 80 |
| HCDR2 | GIAGD | 81 |
| HCDR3 | GGSWDDAFDI | 82 |
| LCDR1 | RASQDINNYLA | 36 |
| LCDR2 | TASSLQS | 79 |
| LCDR3 | QQYVSYPYT | 39 |

TABLE 20

| NORTH NOMENCLATURE | | |
|---|---|---|
| | Antibody C | |
| | NORTH SEQ | SEQ ID NO: |
| HCDR1 | AASGFTFSSYDMH | 83 |
| HCDR2 | VIGIAGDTY | 84 |
| HCDR3 | ARGGSWDDAFDI | 85 |
| LCDR1 | RASQDINNYLA | 36 |
| LCDR2 | YTASSLQS | 86 |
| LCDR3 | QQYVSYPYT | 39 |

TABLE 21

| KABAT NOMENCLATURE | | |
|---|---|---|
| | Antibody D | |
| | KABAT SEQ | SEQ ID NO: |
| HCDR1 | SFDMH | 262 |
| HCDR2 | TIGIAGDTYFPGSVKG | 87 |
| HCDR3 | GGNWDDALDI | 88 |
| LCDR1 | RASQDINNYLA | 36 |

TABLE 21-continued

| KABAT NOMENCLATURE | | |
|---|---|---|
| | Antibody D | |
| | KABAT SEQ | SEQ ID NO: |
| LCDR2 | TASSLQS | 72 |
| LCDR3 | QQYNTYPYT | 89 |

TABLE 22

| IMGT NOMENCLATURE | | |
|---|---|---|
| | Antibody D | |
| | IMGT SEQ | SEQ ID NO: |
| HCDR1 | GFTFSSFD | 263 |
| HCDR2 | IGIAGDT | 74 |
| HCDR3 | ARGGNWDDALDI | 90 |
| LCDR1 | QDINNY | 43 |
| LCDR2 | TAS | 45 |
| LCDR3 | QQYNTYPYT | 89 |

TABLE 23

| CCG NOMENCLATURE | | |
|---|---|---|
| | Antibody D | |
| | CCG SEQ | SEQ ID NO: |
| HCDR1 | GFTFSSFDMH | 91 |
| HCDR2 | TIGIAGDTYFPGSVKG | 92 |
| HCDR3 | GGNWDDALDI | 93 |
| LCDR1 | RASQDINNYLA | 36 |
| LCDR2 | TASSLQS | 79 |
| LCDR3 | QQYNTYPYT | 89 |

TABLE 24

| CHOTHIA NOMENCLATURE | | |
|---|---|---|
| | Antibody D | |
| | CHOTHIA SEQ | SEQ ID NO: |
| HCDR1 | GFTFSSF | 94 |
| HCDR2 | GIAGD | 81 |
| HCDR3 | GGNWDDALDI | 95 |
| LCDR1 | RASQDINNYLA | 36 |
| LCDR2 | TASSLQS | 79 |
| LCDR3 | QQYNTYPYT | 89 |

TABLE 25

| NORTH NOMENCLATURE | | |
|---|---|---|
| | Antibody D | |
| | NORTH SEQ | SEQ ID NO: |
| HCDR1 | AASGFTFSSFDMH | 96 |
| HCDR2 | TIGIAGDTY | 97 |
| HCDR3 | ARGGNWDDALDI | 98 |
| LCDR1 | RASQDINNYLA | 99 |
| LCDR2 | YTASSLQS | 86 |
| LCDR3 | QQYNTYPYT | 89 |

Anti-SIRPα Antibody Sequences

Heavy and light chain variable regions of representative anti-SIRPα antibodies of the present invention are disclosed in Tables 26-27 below.

TABLE 26

| Heavy Chain Variable Region (VH) Amino Acid Sequences |
|---|
| >Antibody A<br>EVQLVESGGGLVQPGGSLRLSCAASGFTLSSYDMHWVRQATGKGLEWVSA<br>IGTAGDTYYTGSVKGRFTISRENAKNSLYLQMNSLRAGDTAVYYCVRGGV<br>WDDAFDIWGQGTMVTVSS (SEQ ID NO: 100) |
| >Antibody B<br>QVQLVQSGAEVKKPGASVKVSCKASGYTFTGNYMHWVRQAPGQGLEWMGW<br>INPNSGGTNYAQKFQGRVTMTRDTSISTAYMELSRLRSDDTAVYYCVSGS<br>GWYENYYYYGMDVWGQGTTVTVSS (SEQ ID NO: 101) |
| >Antibody C<br>EVQLVESGGGLVQPGGSLRLSCAASGFTFSSYDMHWVRQATGKGLEWVSV<br>IGIAGDTYYPGSVKGRFTISRENAKNSLYLQMNSLRVGDTAVYYCARGGS<br>WDDAFDIWGQGTMVTVSS (SEQ ID NO: 102) |
| >Antibody D<br>EVQLVESGGGLVQPGGSLRLSCAASGFTFSSFDMHWVRQPTGKGLEWVST<br>IGIAGDTYFPGSVKGRFTISRENAKNSLYLQMNSLRAGDTAVYYCARGGN<br>WDDALDIWGQGTMVTVSS (SEQ ID NO: 103) |
| >Antibody E<br>QVQLQESGPGLVRPSETLSLTCTVSGGSIRNYYWSWIRQPPGKGLEWIGF<br>IYYNGRTFYNSSLKSRVTISLDMSMNQFSLKMTSVTAADTAVYYCARVRA<br>YSGIGLDGTDVWGQGTTVTVSSARFTVDKSSSTAYMQFSSLTSEDTAVYF<br>CARSGPYSYYAGGYALDYWGQGTSVTVSS (SEQ ID NO: 104) |

TABLE 27

| Light Chain Variable Region Amino Acid Sequences |
|---|
| >Antibody A<br>DIQMTQSPSSLSASVGDRVTITCRASQDINNYLAWFQQKPGKAPKSLIYT<br>ASSLHSGVPSKFSGSGSGTDFTLTISSLQPEDFATYYCQQYVSYPYTFGQ<br>GTKLEIK (SEQ ID NO: 105) |
| >Antibody B<br>DIQMTQSPSSVSASVGDRVTITCRASQGISSWLAWYQQKPGKAPKLLIYA<br>ESSLQSGVPSRFSGSGSGTDFTLTISSLQPEDFATYYCQQANSFPLTFGG<br>GTKVEIK (SEQ ID NO: 106) |
| >Antibody C<br>DIQMTQSPSSLSASIGDKVTITCRASQDINNYLAWFQQKPGKAPKSLIYT<br>ASSLQSGVPSKFSGSGSGTDFTLTISSLQPEDFATYYCQQYVSYPYTFGQ<br>GTKLEIK (SEQ ID NO: 107) |

TABLE 27-continued

| Light Chain Variable Region Amino Acid Sequences |
|---|
| >Antibody D<br>DIQMTQSPSSLSASVGDRVTITCRASQDINNYLAWFQQKPGKAPKSLIYTASSLQSGVPSKFSGSGSGTDFTLTISSLQPEDFATYYCQQYNTYPYTFGQGTKLEIK (SEQ ID NO: 108) |
| >Antibody E<br>DIVMTQSPLSLPVTPGEPASISCKSSQSLLYSNGYNYLDWYLQRPGQSPQLLIYLGSNRASGVPDRFSGSGSGTDFTLKISRVEAEDVGVFYCMQALQTPLTFGGGTKVEIK (SEQ ID NO: 109) |

Representative anti-SIRPα antibodies of the present invention have the light and/or heavy chain variable regions sequences as set forth in Tables 28 or 29.

TABLE 28

Heavy Chain Variable Region (VH) Amino Acid Sequences

| CLONE NAME | VH SEQUENCE | SEQ ID NO: |
|---|---|---|
| Antibody A1<br>Antibody A9 | EVQLVESGGGLVQPGGSLRLSCAASGFTLSSYDMHWVRQAPGKGLEWVSAIGTAGDTYYTGSVKGRFTISRENAKNSLYLQMNSLRADDTAVYYCVRGGVWDDAFDIWGQGTMVTVSS | 110 |
| Antibody A2<br>Antibody A10<br>Antibody A11 | EVQLVESGGGLVQPGGSLRLSCAASGFTLSSYDMHWVRQATGKGLEWVSAIGTAGDTYYTGSVKGRFTISRENAKNSLYLQMNSLRAADTAVYYCVRGGVWDDAFDIWGQGTMVTVSS | 111 |
| Antibody A3<br>Antibody A12 | EVQLVESGGGLVQPGGSLRLSCAASGFTLSSYDMHWVRQATGKGLEWVSAIGTAGDTYYTGSVKGRFTISRENAKNSLYLQMNSLRASDTAVYYCVRGGVWDDAFDIWGQGTMVTVSS | 112 |
| Antibody A4<br>Antibody A13 | EVQLVESGGGLVQPGGSLRLSCAASGFTLSSYDMHWVRQAPGKGLEWVSAIGTAGDTYYTGSVKGRFTISRENAKNSLYLQMNSLRAADTAVYYCVRGGVWDDAFDIWGQGTMVTVSS | 113 |
| Antibody A5<br>Antibody A14 | EVQLVESGGGLVQPGGSLRLSCAASGFTLSSYDMHWVRQAPGKGLEWVSAIGTAGDTYYTGSVKGRFTISRENAKNSLYLQMNSLRASDTAVYYCVRGGVWDDAFDIWGQGTMVTVSS | 114 |
| Antibody A6<br>Antibody A15 | EVQLVESGGGLVQPGGSLRLSCAASGFTLSSYDMHWVRQAPGKGLEWVSAIGTAGDTYYTGSVKGRFTISRENAKNSLYLQMNSLRAEDTAVYYCVRGGVWDDAFDIWGQGTMVTVSS | 115 |
| Antibody A7 | EVQLVESGGGLVQPGGSLRLSCAASGFTLSSYDMHWVRQATGKGLEWVSAIGTAGDTYYTGSVKGRFTISRENAKNSLYLQMNSLRAGDTAVYYCVRGGVWDDAFDIWGQGTMVTVSS | 116 |
| Antibody A8<br>Antibody A16 | EVQLVESGGGLVQPGGSLRLSCAASGFTLSSYDMHWVRQAPGKGLEWVSAIGTAGDTYYTGSVKGRFTISRENAKNSLYLQMNSLRAGDTAVYYCVRGGVWDDAFDIWGQGTMVTVSS | 117 |
| Antibody E1<br>Antibody E2<br>Antibody E9 | QVQLQESGPGLVRPSETLSLTCTVSGGSIRNYYWSWIRQPPGKGLEWIGFIYYNGRTFYNPSLKSRVTISLDMSINQFSLKMTSVTAADTAVYYCARVRAYSGIGLDGTDVWGQGTTVTVSS | 118 |
| Antibody E3<br>Antibody E4<br>Antibody E12 | QVQLQESGPGLVRPSETLSLTCTVSGGSIRNYYWSWIRQPPGKGLEWIGFIYYNGRTFYNPSLKSRVTISLDMSKNQFSLKMTSVTAADTAVYYCARVRAYSGIGLDGTDVWGQGTTVTVSS | 119 |
| Antibody E5<br>Antibody E6<br>Antibody E14 | QVQLQESGPGLVRPSETLSLTCTVSGGSIRNYYWSWIRQPPGKGLEWIGFIYYNGRTFYNPSLKSRVTISLDKSKNQFSLKMTSVTAADTAVYYCARVRAYSGIGLDGTDVWGQGTTVTVSS | 120 |
| Antibody E7<br>Antibody E10<br>Antibody E16 | QVQLQESGPGLVRPSETLSLTCTVSGGSIRNYYWSWIRQPPGKGLEWIGFIYYNGRTFYNPSLKSRVTISLDTSKNQFSLKMTSVTAADTAVYYCARVRAYSGIGLDGTDVWGQGTTVTVSS | 121 |

TABLE 28-continued

Heavy Chain Variable Region (VH) Amino Acid Sequences

| CLONE NAME | VH SEQUENCE | SEQ ID NO: |
|---|---|---|
| Antibody E8<br>Antibody E11<br>Antibody E17 | QVQLQESGPGLVRPSETLSLTCTVSGGSIRNYYWSWIR<br>QPPGKGLEWMGFIYDNGRTFYNPSLKSRVTISLDMSM<br>NQFSLKMTSVTAADTAVYYCARVRAYSGIGLDGTDVW<br>GQGTTVTVSS | 122 |
| Antibody E13<br>Antibody E15<br>Antibody E20 | QVQLQESGPGLVRPSETLSLTCTVSGGSIRNYYWSWIR<br>QPPGKGLEWIGFIYYTGRTFYNPSLKSRVTISLDMSINQ<br>FSLKMTSVTAADTAVYYCARVRAYSGIGLDGTDVWGQ<br>GTTVTVSS | 123 |
| Antibody E18<br>Antibody E19<br>Antibody E21 | QVQLQESGPGLVRPSETLSLTCTVSGGSIRNYYWSWIR<br>QPPGKGLEWIGFIYYTGRTFYNPSLKSRVTISLDMSKN<br>QFSLKMTSVTAADTAVYYCARVRAYSGIGLDGTDVWG<br>QGTTVTVSS | 124 |
| Antibody E22 | QVQLQESGPGLVKPSETLSLTCTVSGGSIRDYYWSWIR<br>QPPGKGLEWIGFIYYNGRTFYQSSLKSRVTISLDTSKNQ<br>FSLKMTSVTAADTAVYYCARVRAYSGIGLDGTDVWGQ<br>GTTVTVSS | 221 |

TABLE 29

Light Chain Variable Region (VL) Amino Acid Sequences

| CLONE NAME | VL SEQUENCE | SEQ ID NO: |
|---|---|---|
| Antibody A1<br>Antibody A2<br>Antibody A3<br>Antibody A4<br>Antibody A5<br>Antibody A6<br>Antibody A7<br>Antibody A8 | DIQMTQSPSSLSASVGDRVTITCRASQGINNYAAWFQQ<br>KPGKAPKSLIYTASSLHSGVPSKFSGSGSGTDFTLTISS<br>LQPEDFATYYCQQYVSYPYTFGQGTKLEIK | 125 |
| Antibody A9<br>Antibody A10<br>Antibody A11<br>Antibody A12<br>Antibody A13<br>Antibody A14<br>Antibody A15<br>Antibody A16 | DIQMTQSPSSLSASVGDRVTITCRASQDINNYLAWFQQ<br>KPGKAPKSLIYTASSLHSGVPSKFSGSGSGTDFTLTISS<br>LQPEDFATYYCQQYVSYPYTFGQGTKLEIK | 126 |
| Antibody E1<br>Antibody E3<br>Antibody E5<br>Antibody E7<br>Antibody E8<br>Antibody E13<br>Antibody E19 | DIVMTQSPLSLPVTPGEPASISCKSSQSLLYSNGYAYLD<br>WYLQRPGQSPQLLIYQGSNRASGVPDRFSGSGSGTDF<br>TLKISRVEAEDVGVFYCMQALQTPLTFGGGTKVEIK | 127 |
| Antibody E2 | DIVMTQSPLSLPVTPGEPASISCKSSQSLLYSNGYAYLD<br>WYLQRPGQSPQLLIYLGSNRASGVPDRFSGSGSGTDF<br>TLKISRVEAEDVGVYYCMQALQTPLTFGGGTKVEIK | 128 |
| Antibody E4<br>Antibody E6<br>Antibody E10<br>Antibody E11<br>Antibody E15<br>Antibody E18 | DIVMTQSPLSLPVTPGEPASISCKSSQSLLYSNGYAYLD<br>WYLQRPGQSPQLLIYLGSNRASGVPDRFSGSGSGTDF<br>TLKISRVEAEDVGVYYCMQALQTPLTFGGGTKVEIK | 129 |
| Antibody E9<br>Antibody E12<br>Antibody E14<br>Antibody E16<br>Antibody E17<br>Antibody E20<br>Antibody E21 | DIVMTQSPLSLPVTPGEPASISCKSSQSLLYSNAYNYLD<br>WYLQRPGQSPQLLIYLGSNRASGVPDRFSGSGSGTDF<br>TLKISRVEAEDVGVYYCMQALQTPLTFGGGTKVEIK | 130 |

TABLE 29-continued

| Light Chain Variable Region (VL) Amino Acid Sequences | | |
|---|---|---|
| CLONE NAME | VL SEQUENCE | SEQ ID NO: |
| Antibody E22 | DIVMTQSPLSLPVTPGEPASISCRSSQSLLYSTGYTYLD<br>WYLQRPGQSPQLLIYGGSSRASGVPDRFSGSGSGTDF<br>TLKISRVEAEDVGVFYCGQALQTPLTFGQGTKVEIK | 222 |

Representative anti-SIRPα antibodies of the present invention may comprise a heavy and/or light chain as set forth in Tables 30 or 31 below.

TABLE 30

| FULL LENGTH HC SEQUENCES OF ANTI-SIRPα ANTIBODIES. | | |
|---|---|---|
| Antibody | Sequence | SEQ ID NO: |
| Antibody A | EVQLVESGGGLVQPGGSLRLSCAASGFTLSSYDMHWVRQATGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 131 |
| Antibody F | EVQLVESGGGLVQPGGSLRLSCAASGFTLSSYDMHWVRQATGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGG<br>PSVFLFPPKPKDTLMISRTPEVTCVVVDVSQEDPEVQFNWYVDGVE<br>VHNAKTKPREEQFNSTYRVVSVLTVLHQDWLNGKEYKCKVSNKGLP<br>SSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFS<br>CSVMHEALHNHYTQKSLSLSLG | 132 |
| Antibody B | QVQLVQSGAEVKKPGASVKVSCKASGYTFTGNYMHWVRQAPGQG<br>LEWMGWINPNSGGTNYAQKFQGRVTMTRDTSISTAYMELSRLRSD<br>DTAVYYCVSGSGWYENYYYYGMDVWGQGTTVTVSSASTKGPSVFP<br>LAPSSKSTSGGTAALGCLVKDYFPEPVTVSWNSGALTSGVHTFPAVL<br>QSSGLYSLSSVVTVPSSSLGTQTYICNVNHKPSNTKVDKRVEPKSCDK<br>THTCPPCPAPEAAGGPSVFLFPPKPKDTLMISRTPEVTCVVVDVSHE<br>DPEVKFNWYVDGVEVHNAKTKPREEQYNSTYRVVSVLTVLHQDWL<br>NGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKL<br>TVDKSRWQQGNVFSCSVMHEALHNHYTQKSLSLSPG | 133 |
| Antibody C | EVQLVESGGGLVQPGGSLRLSCAASGFTFSSYDMHWVRQATGKGLE<br>WVSVIGIAGDTYYPGSVKGRFTISRENAKNSLYLQMNSLRVGDTAVY<br>YCARGGSWDDAFDIWGQGTMVTVSSASTKGPSVFPLAPSSKSTSGG<br>TAALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAPEA<br>AGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNK<br>ALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGN<br>VFSCSVMHEALHNHYTQKSLSLSPG | 134 |
| Antibody E | QVQLQESGPGLVRPSETLSLTCTVSGGSIRNYYWSWIRQPPGKGLE<br>WIGFIYYNGRTFYNSSLKSRVTISLDMSMNQFSLKMTSVTAADTAVY<br>YCARVRAYSGIGLDGTDVWGQGTTVTVSSASTKGPSVFPLAPSSKST<br>SGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPCP<br>APEAAGGPSVFLFPPKPKDTLMISRTPEVTCVVVDVSHEDPEVKFNW<br>YVDGVEVHNAKTKPREEQYNSTYRVVSVLTVLHQDWLNGKEYKCKV<br>SNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQ<br>QGNVFSCSVMHEALHNHYTQKSLSLSPG | 135 |
| Antibody G | QVQLQESGPGLVRPSETLSLTCTVSGGSIRNYYWSWIRQPPGKGLE<br>WIGFIYYNGRTFYNSSLKSRVTISLDMSMNQFSLKMTSVTAADTAVY<br>YCARVRAYSGIGLDGTDVWGQGTTVTVSSASTKGPSVFPLAPCSRST<br>SESTAALGCLVKDYFPEPVTVSWNSGALTSGVHTFPAVLQSSGLYSLS | 136 |

TABLE 30-continued

FULL LENGTH HC SEQUENCES OF ANTI-SIRPα ANTIBODIES.

| Antibody | Sequence | SEQ ID NO: |
|---|---|---|
| | SVVTVPSSSLGTKTYTCNVDHKPSNTKVDKRVESKYGPPCPPCPAPEF LGGPSVFLFPPKPKDTLMISRTPEVTCVVVDVSQEDPEVQFNWYVD GVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPS DIAVEWESNGQPENNYKTTPPVLDSDGSFFLYSRLTVDKSRWQEGN VFSCSVMHEALHNHYTQKSLSLSLG | |
| Antibody D | EVQLVESGGGLVQPGGSLRLSCAASGFTFSSFDMHWVRQPTGKGLE WVSTIGIAGDTYFPGSVKGRFTISRENAKNSLYLQMNSLRAGDTAVY YCARGGNWDDALDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 137 |
| Antibody A1 | EVQLVESGGGLVQPGGSLRLSCAASGFTLSSYDMHWVRQAPGKGLE WVSAIGTAGDTYYTGSVKGRFTISRENAKNSLYLQMNSLRADDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 138 |
| Antibody A2 | EVQLVESGGGLVQPGGSLRLSCAASGFTLSSYDMHWVRQATGKGLE WVSAIGTAGDTYYTGSVKGRFTISRENAKNSLYLQMNSLRAADTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 139 |
| Antibody A3 | EVQLVESGGGLVQPGGSLRLSCAASGFTLSSYDMHWVRQATGKGLE WVSAIGTAGDTYYTGSVKGRFTISRENAKNSLYLQMNSLRASDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 140 |
| Antibody A4 | EVQLVESGGGLVQPGGSLRLSCAASGFTLSSYDMHWVRQAPGKGLE WVSAIGTAGDTYYTGSVKGRFTISRENAKNSLYLQMNSLRAADTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 141 |
| Antibody A5 | EVQLVESGGGLVQPGGSLRLSCAASGFTLSSYDMHWVRQAPGKGLE WVSAIGTAGDTYYTGSVKGRFTISRENAKNSLYLQMNSLRASDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 142 |
| Antibody A6 | EVQLVESGGGLVQPGGSLRLSCAASGFTLSSYDMHWVRQAPGKGLE WVSAIGTAGDTYYTGSVKGRFTISRENAKNSLYLQMNSLRAEDTAVY YCVRGGVWDDAFDIWGQGTMVTVSSASTKGPSVFPLAPSSKSTSG | 143 |

TABLE 30-continued

FULL LENGTH HC SEQUENCES OF ANTI-SIRPα ANTIBODIES.

| Antibody | Sequence | SEQ ID NO: |
|---|---|---|
| | GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | |
| Antibody A7 | EVQLVESGGGLVQPGGSLRLSCAASGFTLSSYDMHWVRQATGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 144 |
| Antibody A8 | EVQLVESGGGLVQPGGSLRLSCAASGFTLSSYDMHWVRQAPGKGLE<br>WVSAIGTAGDTYYTGSVKGRFTISRENAKNSLYLQMNSLRAGDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 145 |
| Antibody A9 | EVQLVESGGGLVQPGGSLRLSCAASGFTLSSYDMHWVRQAPGKGLE<br>WVSAIGTAGDTYYTGSVKGRFTISRENAKNSLYLQMNSLRADDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 146 |
| Antibody A10 | EVQLVESGGGLVQPGGSLRLSCAASGFTLSSYDMHWVRQATGKGLE<br>WVSAIGTAGDTYYTGSVKGRFTISRENAKNSLYLQMNSLRAADTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 147 |
| Antibody A11 | EVQLVESGGGLVQPGGSLRLSCAASGFTLSSYDMHWVRQATGKGLE<br>WVSAIGTAGDTYYTGSVKGRFTISRENAKNSLYLQMNSLRAADTAVY<br>YCVRGGVWDDAFDIWGQGTMVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPEFLGG<br>PSVFLFPPKPKDTLMISRTPEVTCVVVDVSQEDPEVQFNWYVDGVE<br>VHNAKTKPREEQFNSTYRVVSVLTVLHQDWLNGKEYKCKVSNKGLP<br>SSIEKTISKAKGQPREPQVYTLPPSQEEMTKNQVSLTCLVKGFYPSDIA<br>VEWESNGQPENNYKTTPPVLDSDGSFFLYSRLTVDKSRWQEGNVFS<br>CSVMHEALHNHYTQKSLSLSLG | 217 |
| Antibody A12 | EVQLVESGGGLVQPGGSLRLSCAASGFTLSSYDMHWVRQATGKGLE<br>WVSAIGTAGDTYYTGSVKGRFTISRENAKNSLYLQMNSLRASDTAVY<br>YCVRGGVWDDAFDIWGQGTMVTVSSASTKGPSVFPLAPSSKSTSG<br>GTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 148 |
| Antibody A13 | EVQLVESGGGLVQPGGSLRLSCAASGFTLSSYDMHWVRQAPGKGLE<br>WVSAIGTAGDTYYTGSVKGRFTISRENAKNSLYLQMNSLRAADTAVY | 149 |

TABLE 30-continued

FULL LENGTH HC SEQUENCES OF ANTI-SIRPα ANTIBODIES.

| Antibody | Sequence | SEQ ID NO: |
|---|---|---|
| | YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | |
| Antibody A14 | EVQLVESGGGLVQPGGSLRLSCAASGFTLSSYDMHWVRQAPGKGLE WVSAIGTAGDTYYTGSVKGRFTISRENAKNSLYLQMNSLRASDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 150 |
| Antibody A15 | EVQLVESGGGLVQPGGSLRLSCAASGFTLSSYDMHWVRQAPGKGLE WVSAIGTAGDTYYTGSVKGRFTISRENAKNSLYLQMNSLRAEDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 151 |
| Antibody A16 | EVQLVESGGGLVQPGGSLRLSCAASGFTLSSYDMHWVRQAPGKGLE WVSAIGTAGDTYYTGSVKGRFTISRENAKNSLYLQMNSLRAGDTAVY YCVRGGVWDDAFDIWGQGTMVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 152 |
| Antibody E1 | QVQLQESGPGLVRPSETLSLTCTVSGGSIRNYYWSWIRQPPGKGLE WIGFIYYNGRTFYNPSLKSRVTISLDMSINQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 153 |
| Antibody E2 | QVQLQESGPGLVRPSETLSLTCTVSGGSIRNYYWSWIRQPPGKGLE WIGFIYYNGRTFYNPSLKSRVTISLDMSINQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 154 |
| Antibody E3 | QVQLQESGPGLVRPSETLSLTCTVSGGSIRNYYWSWIRQPPGKGLE WIGFIYYNGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 155 |

TABLE 30-continued

FULL LENGTH HC SEQUENCES OF ANTI-SIRPα ANTIBODIES.

| Antibody | Sequence | SEQ ID NO: |
|---|---|---|
| Antibody E4 | QVQLQESGPGLVRPSETLSLTCTVSGGSIRNYYWSWIRQPPGKGLE<br>WIGFIYYNGRTFYNPSLKSRVTISLDMSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 156 |
| Antibody E5 | QVQLQESGPGLVRPSETLSLTCTVSGGSIRNYYWSWIRQPPGKGLE<br>WIGFIYYNGRTFYNPSLKSRVTISLDKSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 157 |
| Antibody E6 | QVQLQESGPGLVRPSETLSLTCTVSGGSIRNYYWSWIRQPPGKGLE<br>WIGFIYYNGRTFYNPSLKSRVTISLDKSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 158 |
| Antibody E7 | QVQLQESGPGLVRPSETLSLTCTVSGGSIRNYYWSWIRQPPGKGLE<br>WIGFIYYNGRTFYNPSLKSRVTISLDTSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 159 |
| Antibody E8 | QVQLQESGPGLVRPSETLSLTCTVSGGSIRNYYWSWIRQPPGKGLE<br>WMGFIYDNGRTFYNPSLKSRVTISLDMSMNQFSLKMTSVTAADTAV<br>YYCARVRAYSGIGLDGTDVWGQGTTVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKRVEPKSCDKTHTCPPC<br>PAPEAAGGPSVFLFPPKPKDTLMISRTPEVTCVVVDVSHEDPEVKFN<br>WYVDGVEVHNAKTKPREEQYNSTYRVVSVLTVLHQDWLNGKEYKC<br>KVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSR<br>WQQGNVFSCSVMHEALHNHYTQKSLSLSPG | 160 |
| Antibody E9 | QVQLQESGPGLVRPSETLSLTCTVSGGSIRNYYWSWIRQPPGKGLE<br>WIGFIYYNGRTFYNPSLKSRVTISLDMSINQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 161 |
| Antibody E10 | QVQLQESGPGLVRPSETLSLTCTVSGGSIRNYYWSWIRQPPGKGLE<br>WIGFIYYNGRTFYNPSLKSRVTISLDTSKNQFSLKMTSVTAADTAVYY<br>CARVRAYSGIGLDGTDVWGQGTTVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPA<br>PEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQ<br>QGNVFSCSVMHEALHNHYTQKSLSLSPG | 162 |

TABLE 30-continued

FULL LENGTH HC SEQUENCES OF ANTI-SIRPα ANTIBODIES.

| Antibody | Sequence | SEQ ID NO: |
|---|---|---|
| Antibody E11 | QVQLQESGPGLVRPSETLSLTCTVSGGSIRNYYWSWIRQPPGKGLE WMGFIYDNGRTFYNPSLKSRVTISLDMSMNQFSLKMTSVTAADTAV YYCARVRAYSGIGLDGTDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPPC PAPEAAGGPSVFLFPPKPKDTLMISRTPEVTCVVVDVSHEDPEVKFN WYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG | 163 |
| Antibody E12 | QVQLQESGPGLVRPSETLSLTCTVSGGSIRNYYWSWIRQPPGKGLE WIGFIYYNGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 164 |
| Antibody E13 | QVQLQESGPGLVRPSETLSLTCTVSGGSIRNYYWSWIRQPPGKGLE WIGFIYYTGRTFYNPSLKSRVTISLDMSINQFSLKMTSVTAADTAVYYC ARVRAYSGIGLDGTDVWGQGTTVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 165 |
| Antibody E14 | QVQLQESGPGLVRPSETLSLTCTVSGGSIRNYYWSWIRQPPGKGLE WIGFIYYNGRTFYNPSLKSRVTISLDKSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 166 |
| Antibody E15 | QVQLQESGPGLVRPSETLSLTCTVSGGSIRNYYWSWIRQPPGKGLE WIGFIYYTGRTFYNPSLKSRVTISLDMSINQFSLKMTSVTAADTAVYYC ARVRAYSGIGLDGTDVWGQGTTVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 167 |
| Antibody E16 | QVQLQESGPGLVRPSETLSLTCTVSGGSIRNYYWSWIRQPPGKGLE WIGFIYYNGRTFYNPSLKSRVTISLDTSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 168 |
| Antibody E17 | QVQLQESGPGLVRPSETLSLTCTVSGGSIRNYYWSWIRQPPGKGLE WMGFIYDNGRTFYNPSLKSRVTISLDMSMNQFSLKMTSVTAADTAV YYCARVRAYSGIGLDGTDVWGQGTTVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKRVEPKSCDKTHTCPPC PAPEAAGGPSVFLFPPKPKDTLMISRTPEVTCVVVDVSHEDPEVKFN | 169 |

TABLE 30-continued

| FULL LENGTH HC SEQUENCES OF ANTI-SIRPα ANTIBODIES. | | |
|---|---|---|
| Antibody | Sequence | SEQ ID NO: |
| | WYVDGVEVHNAKTKPREEQYNSTYRVVSVLTVLHQDWLNGKEYKC KVSNKALPAPIEKTISKAKGQPREPQVYTLPPSREEMTKNQVSLTCLV KGFYPSDIAVEWESNGQPENNYKTTPPVLDSDGSFFLYSKLTVDKSR WQQGNVFSCSVMHEALHNHYTQKSLSLSPG | |
| Antibody E18 | QVQLQESGPGLVRPSETLSLTCTVSGGSIRNYYWSWIRQPPGKGLE WIGFIYYTGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 170 |
| Antibody E19 | QVQLQESGPGLVRPSETLSLTCTVSGGSIRNYYWSWIRQPPGKGLE WIGFIYYTGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 171 |
| Antibody E20 | QVQLQESGPGLVRPSETLSLTCTVSGGSIRNYYWSWIRQPPGKGLE WIGFIYYTGRTFYNPSLKSRVTISLDMSINQFSLKMTSVTAADTAVYYC ARVRAYSGIGLDGTDVWGQGTTVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 172 |
| Antibody E21 | QVQLQESGPGLVRPSETLSLTCTVSGGSIRNYYWSWIRQPPGKGLE WIGFIYYTGRTFYNPSLKSRVTISLDMSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 173 |
| Antibody E22 | QVQLQESGPGLVKPSETLSLTCTVSGGSIRDYYWSWIRQPPGKGLE WIGFIYYNGRTFYQSSLKSRVTISLDTSKNQFSLKMTSVTAADTAVYY CARVRAYSGIGLDGTDVWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKRVEPKSCDKTHTCPPCPA PEAAGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPG | 219 |

TABLE 31

| FULL LENGTH LC SEQUENCES OF ANTI-SIRP-α ANTIBODIES. | | |
|---|---|---|
| Antibody | Sequence | SEQ ID NO: |
| Antibody A | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 174 |

TABLE 31-continued

FULL LENGTH LC SEQUENCES OF ANTI-SIRP-α ANTIBODIES.

| Antibody | Sequence | SEQ ID NO: |
|---|---|---|
| Antibody F | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 175 |
| Antibody B | DIQMTQSPSSVSASVGDRVTITCRASQGISSWLAWYQQKPGKAPKL LIYAESSLQSGVPSRFSGSGSGTDFTLTISSLQPEDFATYYCQQANSFP LTFGGGTKVEIKRTVAAPSVFIFPPSDEQLKSGTASVVCLLNNFYPREA KVQWKVDNALQSGNSQESVTEQDSKDSTYSLSSTLTLSKADYEKHKV YACEVTHQGLSSPVTKSFNRGEC | 176 |
| Antibody C | DIQMTQSPSSLSASIGDKVTITCRASQDINNYLAWFQQKPGKAPKSLI YTASSLQSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 177 |
| Antibody E | DIVMTQSPLSLPVTPGEPASISCKSSQSLLYSNGYNYLDWYLQRPGQS PQLLIYLGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 178 |
| Antibody G | DIVMTQSPLSLPVTPGEPASISCKSSQSLLYSNGYNYLDWYLQRPGQS PQLLIYLGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 179 |
| Antibody D | DIQMTQSPSSLSASVGDRVTITCRASQDINNYLAWFQQKPGKAPKSL IYTASSLQSGVPSKFSGSGSGTDFTLTISSLQPEDFATYYCQQYNTYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 180 |
| Antibody A1 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 181 |
| Antibody A2 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 182 |
| Antibody A3 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 183 |
| Antibody A4 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 184 |
| Antibody A5 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 185 |
| Antibody A6 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 186 |
| Antibody A7 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK | 187 |

TABLE 31-continued

FULL LENGTH LC SEQUENCES OF ANTI-SIRP-α ANTIBODIES.

| Antibody | Sequence | SEQ ID NO: |
|---|---|---|
| | VQWKVDNALQSGNSQESVTEQDSKDSTYSLSSTLTLSKADYEKHKVY ACEVTHQGLSSPVTKSFNRGEC | |
| Antibody A8 | DIQMTQSPSSLSASVGDRVTITCRASQGINNYAAWFQQKPGKAPKS LIYTASSLHSGVPSKFSGSGSGTDFTLTISSLQPEDFATYYCQQYVSYPY TFGQGTKLEIKRTVAAPSVFIFPPSDEQLKSGTASVVCLLNNFYPREAK VQWKVDNALQSGNSQESVTEQDSKDSTYSLSSTLTLSKADYEKHKVY ACEVTHQGLSSPVTKSFNRGEC | 188 |
| Antibody A9 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 189 |
| Antibody A10 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 190 |
| Antibody A11 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 218 |
| Antibody A12 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 191 |
| Antibody A13 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 192 |
| Antibody A14 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 193 |
| Antibody A15 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 194 |
| Antibody A16 | DIQMTQSPSSLSASVGDRVTITCRASQDINNYLAWFQQKPGKAPKSL IYTASSLHSGVPSKFSGSGSGTDFTLTISSLQPEDFATYYCQQYVSYPYT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVYA CEVTHQGLSSPVTKSFNRGEC | 195 |
| Antibody E1 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 196 |
| Antibody E2 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 197 |
| Antibody E3 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 198 |

TABLE 31-continued

FULL LENGTH LC SEQUENCES OF ANTI-SIRP-α ANTIBODIES.

| Antibody | Sequence | SEQ ID NO: |
|---|---|---|
| Antibody E4 | DIVMTQSPLSLPVTPGEPASISCKSSQSLLYSNGYAYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 199 |
| Antibody E5 | DIVMTQSPLSLPVTPGEPASISCKSSQSLLYSNGYAYLDWYLQRPGQS<br>PQLLIYQGSNRASGVPDRFSGSGSGTDFTLKISRVEAEDVGVFYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 200 |
| Antibody E6 | DIVMTQSPLSLPVTPGEPASISCKSSQSLLYSNGYAYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 201 |
| Antibody E7 | DIVMTQSPLSLPVTPGEPASISCKSSQSLLYSNGYAYLDWYLQRPGQS<br>PQLLIYQGSNRASGVPDRFSGSGSGTDFTLKISRVEAEDVGVFYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 202 |
| Antibody E8 | DIVMTQSPLSLPVTPGEPASISCKSSQSLLYSNGYAYLDWYLQRPGQS<br>PQLLIYQGSNRASGVPDRFSGSGSGTDFTLKISRVEAEDVGVFYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 203 |
| Antibody E9 | DIVMTQSPLSLPVTPGEPASISCKSSQSLLYSNAYNYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 204 |
| Antibody E10 | DIVMTQSPLSLPVTPGEPASISCKSSQSLLYSNGYAYLDWYLORPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 205 |
| Antibody E11 | DIVMTQSPLSLPVTPGEPASISCKSSQSLLYSNGYAYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 206 |
| Antibody E12 | DIVMTQSPLSLPVTPGEPASISCKSSQSLLYSNAYNYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 207 |
| Antibody E13 | DIVMTQSPLSLPVTPGEPASISCKSSQSLLYSNGYAYLDWYLQRPGQS<br>PQLLIYQGSNRASGVPDRFSGSGSGTDFTLKISRVEAEDVGVFYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 208 |
| Antibody E14 | DIVMTQSPLSLPVTPGEPASISCKSSQSLLYSNAYNYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 209 |
| Antibody E15 | DIVMTQSPLSLPVTPGEPASISCKSSQSLLYSNGYAYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF<br>YPREAKVQWKVDNALQSGNSQESVTEQDSKDSTYSLSSTLTLSKADY<br>EKHKVYACEVTHQGLSSPVTKSFNRGEC | 210 |
| Antibody E16 | DIVMTQSPLSLPVTPGEPASISCKSSQSLLYSNAYNYLDWYLQRPGQS<br>PQLLIYLGSNRASGVPDRFSGSGSGTDFTLKISRVEAEDVGVYYCMQ<br>ALQTPLTFGGGTKVEIKRTVAAPSVFIFPPSDEQLKSGTASVVCLLNNF | 211 |

TABLE 31-continued

| FULL LENGTH LC SEQUENCES OF ANTI-SIRP-α ANTIBODIES. | | |
|---|---|---|
| Antibody | Sequence | SEQ ID NO: |
| | YPREAKVQWKVDNALQSGNSQESVTEQDSKDSTYSLSSTLTLSKADY EKHKVYACEVTHQGLSSPVTKSFNRGEC | |
| Antibody E17 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 212 |
| Antibody E18 | DIVMTQSPLSLPVTPGEPASISCKSSQSLLYSNGYAYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 213 |
| Antibody E19 | DIVMTQSPLSLPVTPGEPASISCKSSQSLLYSNGYAYLDWYLQRPGQS PQLLIYQGSNRASGVPDRFSGSGSGTDFTLKISRVEAEDVGVFYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 214 |
| Antibody E20 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 215 |
| Antibody E21 | DIVMTQSPLSLPVTPGEPASISCKSSQSLLYSNAYNYLDWYLQRPGQS PQLLIYLGSNRASGVPDRFSGSGSGTDFTLKISRVEAEDVGVYYCMQ ALQTPLTFGGGTKVEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC | 216 |
| Antibody E22 | DIVMTQSPLSLPVTPGEPASISCRSSQSLLYSTGYTYLDWYLQRPGQS PQLLIYGGSSRASGVPDRFSGSGSGTDFTLKISRVEAEDVGVFYCGQA LQTPLTFGQGTKVEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC | 220 |

TABLE 32

| EXAMPLE HC AND LC SEQUENCES OF THE CONSTANT REGIONS OF ANTI-SIRPα ANTIBODIES. | | |
|---|---|---|
| Antibody | Sequence | SEQ ID NO: |
| IgG1-HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSKLTVDKSRWQQGNVFSCSVMHEALHNHYTQKSLSLSPGK | 234 |
| IgG1-LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC | 235 |
| IgG4-HC | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGK | 236 |
| IgG4-LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC | 237 |

TABLE 32-continued

EXAMPLE HC AND LC SEQUENCES OF THE CONSTANT REGIONS OF ANTI-SIRPα ANTIBODIES.

| Antibody | Sequence | SEQ ID NO: |
|---|---|---|
| IgG1-KO-HC | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDS DGSFFLYSKLTVDKSRWQQGNVFSCSVMHEALHNHYTQKSLSLSPG K | 238 |
| IgG1-KO-LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC | 239 |

Amino Acid Sequence Variants

Variant anti-SIRPα antibodies and antibody fragments thereof can be engineered based on a set of CDRs depicted in Tables 1-25. It is to be understood that in the variant anti-SIRPα antibodies and antibody fragments the amino acid sequence of the CDRs remain unchanged or have minimal changes (e.g., 1-5 changes), but the surrounding regions, e.g., FR regions can be engineered. Amino acid sequence variants of the anti-SIRPα antibody can be prepared by introducing appropriate nucleotide changes into the anti-SIRPα antibody DNA, or by peptide synthesis. Such variants include, for example, deletions from, and/or insertions into and/or substitutions of, residues within the amino acid sequences of the anti-SIRPα antibodies of the examples herein. Any combination of deletions, insertions, and substitutions is made to arrive at the final construct, provided that the final construct possesses the desired characteristics. The amino acid changes also may alter post-translational processes of the human or variant anti-SIRPα antibody, such as changing the number or position of glycosylation sites.

In some embodiments, the present invention includes anti-SIRPα antibodies or antibody fragments thereof having a variable heavy chain and a variable light chain, wherein the variable heavy chain amino acid sequence and the variable light chain amino acid sequence are at least at least 90%, at least 92.5%, at least 95%, at least 98%, or at least 99% identical to the amino acid sequences disclosed in Tables 26-29 provided that the antibody or fragments thereof retain binding to SIRPα-V1 and/or SIRPα-V2.

In some embodiments, the present invention includes anti-SIRPα antibodies or antibody fragments thereof having a variable heavy chain and a variable light chain, wherein the variable heavy chain amino acid sequence and the variable light chain amino acid sequence are at least 80%, at least 85%, at least 90%, at least 92.5%, at least 95%, at least 98%, or at least 99% identical to the amino acid sequences of SEQ ID Nos: 100, 101, 102, 103, 110, 111, 112, 113, 114, 115, 116, 117, 104, 118, 119, 120, 121, 122, 123, 124, or 221, and SEQ ID Nos: 105, 106, 107, 108,109, 126, 127, 128, 129, 130, or 222, respectively.

In some embodiments, the present invention includes anti-SIRPα antibodies having a heavy chain and a light chain, wherein the heavy chain amino acid sequence and the light chain amino acid sequence are at least 95%, at least 98%, or at least 99% identical to the amino acid sequences disclosed in Tables 30 and 31 provided that the antibody or fragments thereof retain binding to SIRPα-V1 and/or SIRPα-V2.

In some embodiments, the anti-SIRPα antibodies or antibody fragments thereof comprise a variable heavy chain sequence that comprises an amino acid sequence with at least about 95%, about 96%, about 97%, about 98%, or about 99%, sequence identity to the amino acid sequence set forth in SEQ ID NOs: 100, 101, 102, 103, 110, 111, 112, 113, 114, 115, 116, 117, 104, 118, 119, 120, 121, 122, 123, 124, or 221. In other embodiments, the anti-SIRPα antibodies or antibody fragments thereof retains the binding and/or functional activity of an anti-SIRPα antibody or antibody fragment thereof that comprises the variable heavy chain sequence of SEQ ID NOs: 100, 101, 102, 103, 110, 111, 112, 113, 114, 115, 116, 117, 104, 118, 119, 120, 121, 122, 123, 124, or 221. In still further embodiments, the anti-SIRPα antibodies or antibody fragments thereof comprise the variable heavy chain sequence of SEQ ID NOs: 100, 101, 102, 103, 110, 111, 112, 113, 114, 115, 116, 117, 104, 118, 119, 120, 121, 122, 123, 124, or 221 and have one or more conservative amino acid substitutions, e.g., 1, 2, 3, 4, 5, 1-2, 1-3, 1-4 or 1-5 conservative amino acid substitutions in the heavy chain variable sequence. In yet further embodiments, the one or more conservative amino acid substitutions fall within one or more framework regions in SEQ ID NOs: 100, 101, 102, 103, 110, 111, 112, 113, 114, 115, 116, 117, 104, 118, 119, 120, 121, 122, 123, 124, or 221 (based on the numbering system of Kabat).

In some embodiments, the anti-SIRPα antibody or antibody fragment thereof comprises a variable heavy chain sequence with at least about 95%, about 96%, about 97%, about 98%, or about 99% sequence identity to the anti-SIRPα heavy chain variable region sequence set forth in 100, 101, 102, 103, 110, 111, 112, 113, 114, 115, 116, 117, 104, 118, 119, 120, 121, 122, 123, 124, or 221 comprises one or more conservative amino acid substitutions in a framework region (based on the numbering system of Kabat), and retains the binding and/or functional activity of an anti-SIRPα antibody or antibody fragment thereof that comprises a variable heavy chain sequence as set forth in SEQ ID NOs: 100, 101, 102, 103, 110, 111, 112, 113, 114, 115, 116, 117, 104, 118, 119, 120, 121, 122, 123, 124, or 221 and a variable light chain sequence as set forth in SEQ ID NOs: 105, 106, 107, 108,109, 126, 127, 128, 129, 130, or 222.

In some embodiments, the anti-SIRPα antibodies or antibody fragments thereof comprise a variable light chain sequence that comprises an amino acid sequence with at least about 95%, about 96%, about 97%, about 98%, or about 99%, sequence identity to the amino acid sequence set forth in SEQ ID NOs: 105, 106, 107, 108,109, 126, 127, 128, 129, 130, or 222. In other embodiments, the anti-SIRPα antibodies or antibody fragments thereof retains the binding and/or functional activity of an anti-SIRPα antibody or antibody fragment thereof that comprises the variable light chain sequence of SEQ ID NOs: 105, 106, 107, 108,109, 126, 127, 128, 129, 130, or 222. In still further embodiments, the anti-SIRPα antibodies or antibody fragments thereof comprise the variable light chain sequence of SEQ ID NOs: 105, 106, 107, 108,109, 126, 127, 128, 129, 130, or 222 and have one or more conservative amino acid substitutions, e.g., 1, 2, 3, 4, 5, 1-2, 1-3, 1-4 or 1-5 conservative amino acid substitutions in the light chain variable sequence. In yet further embodiments, the one or more conservative amino acid substitutions fall within one or more framework regions in SEQ ID NOs: 105, 106, 107, 108,109, 127, 128, 129, 130, or 222 (based on the numbering system of Kabat).

In some embodiments, the anti-SIRPα antibody or antibody fragment thereof comprises a variable light chain sequence with at least about 95%, about 96%, about 97%, about 98%, or about 99% sequence identity to the anti-SIRPα light chain variable region sequence set forth in SEQ ID NOs: 105, 106, 107, 108,109, 126, 127, 128, 129, 130, or 222 comprises one or more conservative amino acid substitutions in a framework region (based on the numbering system of Kabat), and retains the binding and/or functional activity of an anti-SIRPα antibody or antibody fragment thereof that comprises a variable heavy chain sequence as set forth in SEQ ID NOs: 100, 101, 102, 103, 110, 111, 112, 113, 114, 115, 116, 117, 104, 118, 119, 120, 121, 122, 123, 124, or 221 and a variable light chain sequence as set forth in SEQ ID NOs: 105, 106, 107, 108,109, 126, 127, 128, 129, 130, or 222.

In some embodiments, the present invention includes anti-SIRPα antibodies or antigen-binding fragments thereof having an amino acid substitution. These variants have at least one amino acid residue in the anti-SIRPα antibody or antigen-binding fragment thereof removed and a different residue inserted in its place. The sites of greatest interest for substitutional mutagenesis include the hypervariable regions, but FR alterations are also contemplated. Conservative substitutions are shown in Table 33 under the heading of "preferred substitutions". If such substitutions result in a change in biological activity, then more substantial changes, denominated "exemplary substitutions", or as further described below in reference to amino acid classes, may be introduced and the products screened.

TABLE 33

Exemplary amino acid substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gin | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |

TABLE 33-continued

Exemplary amino acid substitutions

| Original Residue | Exemplary Substitutions | Preferred Substitutions |
|---|---|---|
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-SIRPα antibody or antigen-binding fragment thereof also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody or antigen-binding fragment thereof to improve its stability (particularly where the antibody is an antibody fragment such as an Fv fragment).

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody. For example, an antibody may comprise an amino acid substitution at position 297 of the human IgG1 heavy chain to abrogate oligosaccharyltransferase enzyme complex-mediated glycosylation by replacing the asparagine 297 (e.g. N297A, N297G).

In some aspects, the present invention includes nucleic acid molecules that encode the amino acid sequence variants of the anti-SIRPα antibodies or antigen-binding fragments thereof described herein. Nucleic acid molecules encoding amino acid sequence variants of an anti-SIRPα antibody or antigen-binding fragment thereof are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-SIRPα antibody or antigen-binding fragment thereof. For example, nucleic acid molecules according to the invention also encompass nucleic acid molecules which hybridize under stringent conditions to nucleic acid molecules as disclosed herein, whereby the term "stringent conditions" within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C.

In certain embodiments, the anti-SIRPα antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from *E. coli* and chemically coupled to form $F(ab')_2$ fragments (see, e.g., Carter et al., 1992, Bio/Technology 10:163-167). By another approach, $F(ab')_2$ fragments can be isolated directly from recombinant host cell culture. Other techniques for the production of antibody fragments will be apparent to a skilled practitioner.

In one aspect, the anti-SIRPα antibodies and antigen-binding fragments thereof can include modifications, such as glycosylation, oxidation, or deamidation.

In certain embodiments, it may be desirable to use an anti-SIRPα antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis (see, e.g., WO 96/32478). For example, antibody fragments of the invention may also be fused to human serum albumin to increase the serum half-life, if the use of a full-length IgG scaffold is undesirable. Such fusion proteins of the antibody fragment with human serum albumin may be advantageous in situations in which two different antibody fragments need to be fused to increase avidity, or to generate a bispecific binding protein with extended serum half-life (see e.g. WO 05/077042 A2).

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670,417, 4,791,192 and 4,179,337.

Biophysical Properties

In one aspect, the present invention provides an anti-SIRPα antibody or antigen-binding fragment thereof having one or more favorable biophysical properties. In one aspect, a human anti-SIRPα antibody or antigen-binding fragment thereof of the present invention is present in at least 90% monomer form, or in at least 92% monomer form, or in at least 95% monomer form, or in at least 96% monomer form, or in at least 97% monomer form, or in at least 98% monomer form, or in at least 99% monomer form in a buffer. In a further aspect, a human anti-SIRPα antibody or antigen-binding fragment thereof of the present invention remains in at least 90% monomer form, or in at least 92% monomer form, or in at least 95% monomer form, or in at least 96% monomer form, or in at least 97% monomer form, or in at least 98% monomer form, or in at least 99% monomer form in a buffer for one week, one month, or for four months. Said percentage of monomer may be determined after one or more purification steps are performed, e.g., Protein A purification optionally followed by cation exchange chromatography. Said percentage of monomer may be determined following a low pH treatment, e.g., pH 3.5 treatment. Said percentage of monomer may be determined following one week, one month, or four months in a buffer at room temperature, e.g., 25° C., or an elevated temperature, e.g., 40° C.

In another aspect, an anti-SIRPα antibody or antigen-binding fragment thereof of the invention is stable at high concentrations.

In another aspect, an anti-SIRPα antibody or antigen-binding fragment thereof of the invention has low viscosity.

Epitope Binding

In another aspect, the invention relates to an antibody or antigen-binding fragment thereof that recognizes a specific linear and/or conformational "SIRPα antigen epitope" and "SIRPα epitope".

As used herein, the terms "SIRPα antigen epitope" and "SIRPα epitope" refer to a molecule (e.g., a peptide) or a fragment of a molecule capable of binding to an anti-SIRPα antibody or antigen-binding fragment thereof. These terms further include, for example, a SIRPα antigenic determinant recognized by any of the antibodies or antibody fragments of the present invention or key points of contact between the molecule and antibody.

SIRPα antigen epitopes can be included in proteins, protein fragments, peptides or the like. The epitopes are most commonly proteins, short oligopeptides, oligopeptide mimics (e.g., organic compounds that mimic antibody binding properties of the SIRPα antigen), or combinations thereof.

In one aspect of the invention, the antibody or antigen-binding fragment thereof recognizes a specific linear or conformational "SIRPα epitope" on a SIRPα protein comprising the amino acid sequence set forth in any one of SEQ ID NOs: 240-252. In one aspect of the invention, the antibody or antigen-binding fragment thereof recognizes a specific linear or conformational "SIRPα epitope" on a SIRPα protein comprising the amino acid sequence set forth in any one of SEQ ID NOs: 253-260 and 264, in particular any one or more of SEQ ID NOS: 256 and 257. In one aspect of the invention the antibody or antigen-binding fragment thereof binds to a SIRPα epitope comprising the amino acids LEU 60, ILE 61, VAL 63, GLY 64, PRO 65, GLN 82, LYS 83, GLU 84, THR 97, LYS 98, ARG 99, GLU 100, LYS 126, GLY 127, SER 128, PRO 129 and ASP 130 as set forth in SEQ ID NO: 266. In one aspect of the invention the antibody or antigen-binding fragment thereof binds to a SIRPα epitope comprising the amino acids LEU 60, ILE 61, VAL 63, GLY 64, PRO 65, GLN 82, LYS 83, GLU 84, THR 97, LYS 98, ARG 99, ASN 100, LYS 126, GLY 127, SER 128, PRO 129 and ASP 130 as set forth in SEQ ID NO: 265. In another aspect of the invention, the antibody or antigen-binding fragment thereof binds to the SIRPα epitope comprising the amino acid ASP130. In another aspect, the antibody or antigen-binding fragment thereof binds to a SIRPα epitope comprising any one or more of SEQ ID NO; 253, SEQ ID NO: 254, SEQ ID NO: 255, SEQ ID NO: 264, and SEQ ID NO: 256, in particular SEQ ID NO: 256.

In one aspect of the invention the antibody or antigen-binding fragment thereof binds to the SIRPα epitope comprising the amino acids ARG 70, GLY 71, ALA 72, GLY 73, PRO 74, ALA 75, ARG 76, GLU 77, ALA 114, ALA 116, GLY 117, THR 118, TYR 120, THR 131, GLU 132, PHE 133, SER 135 and GLU 140 as set forth in SEQ ID NO: 266. In one aspect of the invention the antibody or antigen-binding fragment thereof binds to a SIRPα epitope comprising the amino acids ARG 70, GLY 71, ALA 72, GLY 73, PRO 74, GLY 75, ARG 76, GLU 77, ALA 114, ALA 116, GLY 117, THR 118, TYR 120, VAL 132, GLU 133, PHE 134, SER 136 and GLU 141 as set forth in SEQ ID NO: 265.

In another aspect of the invention, the antibody or antigen-binding fragment thereof binds to the SIRPα epitope comprising the amino acid ALA72. In another aspect, the antibody or antigen-binding fragment thereof binds to a SIRPα epitope comprising any one or more of SEQ ID NO: 257, SEQ ID NO: 258, SEQ ID NO: 259 and SEQ ID NO:260, in particular SEQ ID NO: 257. In another aspect of the invention, the antibody or antigen-binding fragment thereof blocks binding of any of Antibody A-E to SIRPα.

In a further embodiment, the epitope is present on a SIRPα protein set forth in Table 34 or 35 below.

TABLE 34

Sequences of SIRP proteins

| Protein | Sequence (Extracellular Domain) | SEQ ID NO: |
|---|---|---|
| Human SIRPαV1 (NP_542970.1) | EEELQVIQPDKSVLVAAGETATLRCTATSLIPVGPIQWFR GAGPGRELIYNQKEGHFPRVTTVSDLTKRNNMDFSIRIG NITPADAGTYYCVKFRKGSPDDVEFKSGAGTELSVRAKPS APVVSGPAARATPQHTVSFTCESHGFSPRDITLKWFKNG NELSDFQTNVDPVGESVSYSIHSTAKVVLTREDVHSQVIC EVAHVTLQGDPLRGTANLSETIRVPPTLEVTQQPVRAEN QVNVTCQVRKFYPQRLQLTWLENGNVSRTETASTVTEN KDGTYNWMSWLLVNVSAHRDDVKLTCQVEHDGQPAV SKSHDLKVSAHPKEQGSNTAAENTGSNERNIYGGSG | 240 |
| Human SIRPαV2 (CAA71403.1) | EEELQVIQPDKSVSVAAGESAILHCTVTSLIPVGPIQWFRG AGPARELIYNQKEGHFPRVTTVSESTKRENMDFSISISNIT PADAGTYYCVKFRKGSPDTEFKSGAGTELSVRAKPSAPVV SGPAARATPQHTVSFTCESHGFSPRDITLKWFKNGNELS DFQTNVDPVGESVSYSIHSTAKVVLTREDVHSQVICEVAH VTLQGDPLRGTANLSETIRVPPTLEVTQQPVRAENQVNV TCQVRKFYPQRLQLTWLENGNVSRTETASTVTENKDGTY NWMSWLLVNVSAHRDDVKLTCQVEHDGQPAVSKSHDL KVSAHPKEQGSNTAAENTGSNERNIYGGSG | 241 |
| Human SIRPβ1 (NP_006056.2). | EDELQVIQPEKSVSVAAGESATLRCAMTSLIPVGPIMWFR GAGAGRELIYNQKEGHFPRVTTVSELTKRNNLDFSISISNI TPADAGTYYCVKFRKGSPDDVEFKSGAGTELSVRAKPSAP VVSGPAVRATPEHTVSFTCESHGFSPRDITLKWFKNGNEL SDFQTNVDPAGDSVSYSIHSTARVVLTRGDVHSQVICEIA HITLQGDPLRGTANLSEAIRVPPTLEVTQQPMRAENQAN VTCQVSNFYPRGLQLTWLENGNVSRTETASTLIENKDGT YNWMSWLLVNTCAHRDDVVLTCQVEHDGQQAVSKSY ALEISAHQKEHGSDITHEAALAPTAPLGGSG | 242 |
| Human SIRPβL/SIRPβ1v3 (NP_001129316.1) | EEELQVIQPDKSISVAAGESATLHCTVTSLIPVGPIQWFRG AGPGRELIYNQKEGHFPRVTTVSDLTKRNNMDFSIRISNI TPADAGTYYCVKFRKGSPDHVEFKSGAGTELSVRAKPSAP VVSGPAARATPQHTVSFTCESHGFSPRDITLKWFKNGNE LSDFQTNVDPAGDSVSYSIHSTAKVVLTREDVHSQVICEV AHVTLQGDPLRGTANLSETIRVPPTLEVTQQPVRAENQV NVTCQVRKFYPQRLQLTWLENGNVSRTETASTLTENKDG TYNWMSWLLVNVSAHRDDVKLTCQVEHDGQPAVSKSH DLKVSAHPKEQGSNTAPGPALASAAPLGGSG | 243 |
| human SIRPγ (NP_061026.2) | EEELQMIQPEKLLLVTVGKTATLHCTVTSLLPVGPVLWFR GVGPGRELIYNQKEGHFPRVTTVSDLTKRNNMDFSIRISSI TPADVGTYYCVKFRKGSPENVEFKSGPGTEMALGAKPSA PVVLGPAARTTPEHTVSFTCESHGFSPRDITLKWFKNGNE LSDFQTNVDPTGQSVAYSIRSTARVVLDPWDVRSQVICE VAHVTLQGDPLRGTANLSEAIRVPPTLEVTQQPMRVGN QVNVTCQVRKFYPQSLQLTWSENGNVCQRETASTLTEN KDGTYNWTSWFLVNISDQRDDVVLTCQVKHDGQLAVS KRLALEVTVHQKDQSSDATP | 244 |
| Human CD47 (NP_942088) | WQPPLLFNKTKSVEFTFGNDTVVIPCFVTNMEAQNTTEV YVKWKFKGRDIYTFDGQANKSTVPTDFSSAKIEVSQLLKG DASLKMDKSDAVSHTGNYTCEVTELTREGETIIELKYRVVS | 245 |
| Mouse SIRPα (NP 031573) | KELKVTQPEKSVSVAAGDSTVLNCTLTSLLPVGPIKWYRG VGQSRLLIYSFTGEHFPRVTNVSDATKRNNMDFSIRISNV TPEDAGTYYCVKFQKGPSEPDTEIQSGGGTEVYVLAKPSP PEVSGPADRGIPDQKVNFTCKSHGFSPRNITLKWFKDGQ ELHHLETTVNPSGKNVSYNISSTVRVVLNSMDVHSKVICE | 246 |

TABLE 34-continued

| Sequences of SIRP proteins | | |
|---|---|---|
| Protein | Sequence (Extracellular Domain) | SEQ ID NO: |
| | VAHITLDRSPLRGIANLSNFIRVSPTVKVTQQSPTSMNQV NLTCRAERFYPEDLQLIWLENGNVSRNDTPKNLTKNTDG TYNYTSLFLVNSSAHREDVVFTCQVKHDQQPAITRNHTV LGLAHSSDQGSMQTFPGNNATHNWN | |
| CySIRPα NP_001271679 | EEELQVIQPEKSVSVAAGDSATLNCTVSSLIPVGPIQWFR GAGPGRELIYNLKEGHFPRVTAVSDPTKRNNMDFSIRISN ITPADAGTYYCVKFRKGSPDVELKSGAGTELSVRAKPSAP VVSGPAVRATAEHTVSFTCESHGFSPRDITLKWFKNGNEL SDVQTNVDPAGKSVSYSIRSTARVLLTRRDVHSQVICEVA HVTLQGDPLRGTANLSEAIRVPPFLEVTQQSMRADNQV NVTCQVTKFYPQRLQLTWLENGNVSRTEMASALPENKD GTYNWTSWLLVNVSAHRDDVKLTCQVEHDGQPAVNKS FSVKVSAHPKEQGSNTAAENTGTNERNIYGGSG | 247 |
| CySIRPα EGM_02252 | EEELQVIQPEKSVSVAAGESATLNCTATSLIPVGPIQWFR GVGPGRELIYHQKEGHFPRVTPVSDPTKRNNMDFSIRISN ITPADAGTYYCVKFRKGSPDVELKSGAGTELSVRAKPSAP VVSGPAVRATAEHTVSFTCESHGFSPRDITLKWFKNGNEL SDFQTNVDPAGKSVSYSIRSTARVVLTRRDVHSQVICEVA HVTLQGDPLRGTANLSEAIRVPPFLEFTQQSMRADNQV NVTCQVMKFYPQRLQLTWLENGNVSRTEMASALPENK DGTYNWTSWLLVNVSAHRDDVKLTCQVEHDGQPAVNK SFSVKVSAHPKEQGSNTAAENTGTNERNIYGGSG | 248 |
| CySIRPα XP_015313155 | EEELQVIQPEKSVSVAAGDSATLNCTVSSLIPVGPIQWFR GAGPGRELIYNLKEGHFPRVTPVSDPTKRNNMDFSIRISN ITPADAGTYYCVKFRKGSPDVELKSGAGTELSVRAKPSAP VVSGPAVRATAEHTVSFTCESHGFSPRDITLKWFKNGNEL SDFQTNVDPAGKSVSYSIRSTARVVLTRRDVHSQVICEVA HVTLQGDPLRGTANLSEAIRVPPFLEVTQQSMRADNQV NVTCQVTKFYPQRLQLTWLENGNVSRTEMASALPENKD GTYNWTSWLLVNVSAHRDDVKLTCQVEHDGQPAVNKS FSVKVSAHPKEQGSNTAAENTGTNERNIYGGSG | 249 |
| Cyno SIRPβ1v3 XP_005568593 | EEELQVIQPEKSVSVTAGESATLNCTVTSLIPVGPIQWFRG AGPGRELIYNLKEGHFPRVTTVLDPTKRNNMDFSIHISNIT PADAGTYYCVKFRKGSPDVELKSGAGTELSVRAKPSAPVV SGPTARATPEHTVSFTCESHGFSPRDITLKWFKNGNELSD FQTNVDPAGKSVSYSIRSTARVVLTRRDVHSQVICEVAHV TLQGDPLRGTANLSEAIRVPPTLEVFQRPMRAENQVNVT CQVRKFYPQRLLLTWLENGNVSQTETASTLTENKDGTYN WRSWLLVNTCAHRDGVVLTCQVEHDGQPAVSKSHALE VSAHQKEQCSDTTSGPVLAPTAPLGGSG | 250 |
| Cyno SIRPβ1 XP_005568598 | EEELQVIQPEKSISVAAGESATLNCTVTSLIPVGPIQWFRG VGPGRELIFNLQEGHFPRVTPVSDPTKRNNMDFSILISSIT PADAGTYYCVKFRKGSPDVELKSGAGTELSVRAKPSAPVV SGPAVRATAEHTVSFTCESHGFSPRDITLKWFKNGNELSD FQTSVDPAGKSVSYSIRSTARVVLTRRDVHSQVICEVAHV TLQGDPLRGTANLSEAIRVPPFLEVTQQSMRAENQANIT CQVSNFYPQRLLLTWLENGNVSQTETASTLTENKDGTYN WTSWLLVNICAHRDDVVLTCQVKHDGQPAVSKSHTLEIS AHQKEQDSDVTHGLALAPTAPLGGSG | 251 |
| Cyno SIRPγ XP_005568591 | EEELQMIQPEKLLLVAVGESATLNCTVTSLLPVGPVLWFR GVGPGRELIYNQKEGHFPRVTTVSDLTKRNNMDFSIRISSI TPADAGTYYCVKFRKGSPENVEFKSGPGTEMALRAKPSA PVVSGPAARATPEHTVSFTCKSHGFSPRDITLKWFKNGN ELSDFQTNVDPAGQSVSYSIRSTARVVLAPWDVRSQVTC EVAHVTLQGDPLRGTANLSEAIRVPPTLEVTQQPMRAG NQVNITYQVRNFYPQNLQLTWLENGNVCRTETASTLTEN KDGTYNWTSWLLVNTSDQRDDVVLTCQVKHDGQLAVN KSLVLEVSAHQKDQSSDATHGGSG | 252 |

TABLE 35

| Sequences of SIRPα epitopes | | |
|---|---|---|
| Protein | Sequence | SEQ ID NO: |
| Human SIRPαV1 or V2 | LIPVGP | 253 |
| Human SIRPαV1 or V2 | QKE | 254 |
| Human SIRPαV1 | TKRN | 255 |
| Human SIRPαV2 | TKRE | 264 |
| Human SIRPαV1 or V2 | KGSPD | 256 |
| Human SIRPαV1 or V2 | RGAGPGRE | 257 |
| Human SIRPαV1 or V2 | AGTYY | 258 |
| Human SIRPαV1 | VEFKSGAGTE | 259 |
| Human SIRPαV2 | TEFKSGAGTE | 260 |

The present invention also provides an anti-SIRPα antibody or antigen-binding fragment thereof that competes for binding to SIRPα with an anti-SIRPα antibody according to the present invention. In one embodiment, the present invention provides an anti-SIRPα antibody or antigen-binding fragment thereof that competes for binding to SIRPα with any one of Antibody A-Antibody E. Competition assays may be conducted for example as described in PLoS One. 2014; 9(3): e92451 using a biosensor, or PLoS One 2020 Mar. 5; 15(3):e0229206, or by a method disclosed herein.

Therapeutic Uses

In one embodiment, the anti-SIRPα antibodies of the invention or antigen-binding fragments thereof are useful for treating and/or preventing SIRPα pathway disorders.

In another embodiment, the anti-SIRPα antibodies of the invention or antigen-binding fragments thereof are useful as a medicament.

Accordingly, in one embodiment, the invention provides a method of modulating the interaction between SIRPα and CD47 in a subject comprising administering to said subject a composition comprising an anti-SIRPα antibody or antigen-binding fragment thereof according to the invention in an amount sufficient to block CD47-mediated SIRPα signaling in said subject. In one embodiment, the present invention provides an anti-SIRPα antibody or antigen-binding fragment thereof according to the present invention for use in modulating the interaction between SIRPα and CD47 in a subject. In one embodiment, the invention provides the use of an anti-SIRPα antibody or antigen-binding fragment thereof according to the present invention in the manufacture of a medicament for modulating the interaction between SIRPα and CD47 in a subject.

In one embodiment, the invention provides a method of enhancing myeloid cell phagocytosis in a subject comprising administering to said subject a composition comprising an anti-SIRPα antibody or antigen-binding fragment thereof according to the invention in an amount sufficient to enhance an immune response in said subject. In one embodiment, the present invention provides an anti-SIRPα antibody or antigen-binding fragment thereof according to the invention for use in enhancing myeloid cell activity in a subject. In one embodiment, the present invention provides the use of an anti-SIRPα antibody or antigen-binding fragment thereof according to the present invention in the manufacture of a medicament for enhancing myleloid cell phagocytosis in a subject.

In one embodiment, a SIRPα pathway disease or disorder in a subject comprising administering to said subject a composition comprising an anti-SIRPα antibody or antigen-binding fragment thereof according to the present invention. In one embodiment, the present invention provides an anti-SIRPα antibody or antigen-binding fragment thereof according to the present invention for use in treating or preventing cancer, inflammatory disease, autoimmune disease, respiratory disease, infectious disease or fibrosis. in a subject. In one embodiment, the present invention provides the use of an anti-SIRPα antibody or antigen-binding fragment thereof according to the present invention in the manufacture of a medicament for treating or preventing cancer, inflammatory disease, autoimmune disease, respiratory disease, infectious disease or fibrosis in a subject.

Accordingly, in one embodiment, the invention provides a method of treating or preventing one of the above diseases or disorders in a subject comprising administering to said subject a composition comprising an anti-SIRPα antibody or antigen-binding fragment thereof according to the invention. In one embodiment, the present invention provides an anti-SIRPα antibody or antigen-binding fragment thereof according to the invention for use in treating or preventing one of the above diseases or disorders in a subject. In one embodiment, the present invention provides the use of an anti-SIRPα antibody or antigen-binding fragment thereof according to the present invention in the manufacture of a medicament for treating and/or preventing one of the above diseases or disorders in a subject.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the SIRPα protein (or fragment thereof) to be purified, and thereafter the support is washed with a suitable solvent that will remove substantially all the material in the sample except the SIRPα protein, which is bound to the immobilized antibody. Finally, the support is washed with another suitable solvent that will release the SIRPα protein from the antibody.

The SIRPα antibodies and fragments thereof of the invention as disclosed herein are also useful in diagnostic assays to detect and/or quantify SIRPα protein, for example, detecting SIRPα expression in specific cells, tissues, or serum.

It will be advantageous in some embodiments, for example, for diagnostic purposes to label the antibody with a detectable moiety. Numerous detectable labels are available, including radioisotopes, fluorescent labels, enzyme substrate labels, quantum dots and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Diagnostic Kits

An anti-SIRPα antibody or fragment thereof can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Compositions, Combinations and Administration Thereof

A composition comprising an anti-SIRPα antibody or an antigen-binding fragment thereof according to the invention can be administered to a subject having or at risk of the SIRPα pathway diseases and/or disorders described herein. The invention further provides for the use of an anti-SIRPα antibody or an antigen-binding fragment thereof in the manufacture of a medicament for prevention or treatment of a SIRPα pathway disease or disorder. The term "subject" as used herein means any mammalian patient to which an anti-SIRPα antibody or an antigen-binding fragment thereof can be administered, including, e.g., humans and certain non-human mammals, such as primates, and dogs. Subjects specifically intended for treatment using the methods described herein include humans.

An anti-SIRPα antibody or an antigen-binding fragment thereof may be administered on their own or in combination with one or more additional therapeutic agents, such as state-of-the-art or standard-of-care compounds, such as e.g. cytostatic or cytotoxic substances, cell proliferation inhibitors, anti-angiogenic substances, steroids, immune modulators/checkpoint inhibitors, and the like.

In one aspect, the present invention also provides pharmaceutical compositions administered as pharmaceutical compositions comprising a therapeutically effective amount of the anti-SIRPα antibody or an antigen-binding fragment thereof and one or more pharmaceutically compatible ingredients, and optionally one or more additional therapeutic agents.

A further aspect of the invention provides a binding molecule of the invention for use in the therapy of cancer (e.g. an individual suffering from cancer or being at risk of developing cancer) wherein said therapy comprises one or more pharmacologically active substances.

A further aspect of the invention provides the use of one or more active ingredients in the manufacture of a medicament for the therapy of cancer and/or tumors (e.g. an individual suffering from cancer or being at risk of developing cancer) wherein said medicament comprises the binding molecule of the invention.

Cytostatic and/or cytotoxic active substances which may be administered in combination with an anti-SIRPα antibody or antigen-binding fragment thereof of the invention include, without being restricted thereto, hormones, hormone analogues and anti-hormones, aromatase inhibitors, LHRH agonists and antagonists, inhibitors of growth factors (e.g., platelet derived growth factor (PDGF), fibroblast growth factor (FGF), vascular endothelial growth factor (VEGF), epidermal growth factor (EGF), insulin-like growth factors (IGF), human epidermal growth factor (HER, e.g. HER2, HER3, HER4) and hepatocyte growth factor (HGF)), including, for example anti-growth factor antibodies or anti-growth factor receptor antibodies and tyrosine kinase inhibitors, such as, for example, cetuximab, gefitinib, afatinib, nintedanib, imatinib, lapatinib, bosutinib and trastuzumab; antimetabolites (e.g., antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g., anthracyclins); platinum derivatives (e.g., cisplatin, oxaliplatin, carboplatin); alkylation agents (e.g., estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g., *Vinca* alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g., epipodophyllotoxins such as for example etoposide and etopophos, teniposide, amsacrin, topotecan, irinotecan, mitoxantrone), serine/threonine kinase inhibitors (e.g., PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g., PTK2/FAK inhibitors), protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g., everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g., CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; and/or cyclin-dependent kinase 9 inhibitors.

In one aspect of the invention, the anti-SIRPα antibody or antigen-binding fragment thereof is optionally administered in combination with an additional therapeutic agent. The additional therapeutic agent may be a chemotherapeutic agent, an anti-PD-1 or PD-L1 antibody, an anti-CTLA4 antibody, a T-cell engager, a CD137-agonist-anti-FAP bispecific antibody, a tumor-targeting antibody, a VEGF-ANG2 bispecific antibody, a STING agonist, a MDM2 antagonist, or radiation therapy.

In one aspect, the anti-SIRPα antibody or an antigen-binding fragment thereof is administered in combination with an anti-PD-1 antibody, for example, nivolumab, pembrolizumab, pidilizumab, ezabenlimab, or atezolizumab. In a further aspect, the anti-SIRPα antibody or an antigen-binding fragment thereof is administered in combination with an anti-PD-L1 antibody including, for example, avelumab or durvalumab.

In one aspect, the anti-SIRPα antibody or antigen-binding fragment thereof is administered in combination with a tumor targeting antibody targeting HER2 (e.g., trastuzumab), EGFR (e.g., cetuximab, panitumumab), CD20 (e.g., rituximab, ofatumumab), or CD52 (e.g., alemtuzumab).

In one aspect, the anti-SIRPα antibody or antigen-binding fragment thereof is administered in combination with two therapeutic agents. In a further aspect, the anti-SIRPα antibody or antigen-binding fragment thereof is administered in combination with an anti-PD-1 antibody (e.g., nivolumab, pembrolizumab, pidilizumab, ezabenlimab, or atezolizumab), or an anti-PD-L1 antibody (e.g., avelumab or durvalumab) and tumor targeting antibody targeting HER2 (e.g., trastuzumab), EGFR (e.g., tetuximab, panitumumab), CD20 (e.g., rituximab, ofatumumab), or CD52 (e.g., alemtuzumab).

Various delivery systems are known and can be used to administer the anti-SIRPα antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-SIRPα antibody or an antigen-binding fragment thereof can be administered, for example by infusion, bolus or injection, and can be administered together with other biologically active agents. Administration can be systemic or local. Formulations for such injections may be prepared in, for example, prefilled syringes. As such in an aspect of the invention, pre-filled syringes are provided that include an anti-SIRPα antibody or an antigen-binding fragment thereof.

To be used in therapy, the anti-SIRPα antibody of the invention is formulated into pharmaceutical compositions appropriate to facilitate administration to animals or humans. Typical formulations of the binding molecule or antibody molecule described herein can be prepared by mixing the binding molecule or antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed.

In typical embodiments, the pharmaceutical composition is formulated in accordance with routine procedures as a pharmaceutical composition adapted for intravenous or subcutaneous administration to a subject. Typically, compositions for administration by injection are solutions in sterile isotonic aqueous buffer. Where necessary, the pharmaceutical composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-SIRPα antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-SIRPα antibody or antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

In some embodiments, antibodies of the invention can be formulated to doses, which include for example a dose of 1 mg/kg to 200 mg/kg. including, for example, 1 mg/kg to 25 mg/kg, 25 mg/kg to 50 mg/kg, 50 mg/kg to 75 mg/kg, 75 mg/kg to 100 mg/kg, 100 mg/kg to 125 mg/kg, 125 mg/kg to 150 mg/kg, 150 mg/kg to 175 mg/kg, or 175 mg/kg to 200 mg/kg. With respect to therapeutic regimens for combinatorial administration, in a specific embodiment, an anti-SIRPα antibody or antigen-binding fragment thereof is administered concurrently with a second and/or third therapeutic agent. In another specific embodiment, the second and/or third therapeutic agent is administered prior or subsequent to administration of the anti-SIRPα antibody or antigen-binding fragment thereof.

Polynucleotides, Vectors, and Host Cells

The present invention relates to isolated polynucleotides that comprise a sequence encoding an anti-SIRPα antibody or antigen-binding fragment thereof, vectors, and host cells comprising the polynucleotides, and recombinant techniques for production of the antibody. The isolated polynucleotides can encode any desired form of the anti-SIRPα antibody including, for example, full length monoclonal antibodies, Fab, Fab', $F(ab')_2$, and Fv fragments, diabodies, linear antibodies, single-chain antibody molecules, and multispecific antibodies formed from antibody fragments.

The polynucleotide(s) that comprise a sequence encoding an anti-SIRPα antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-SIRPα antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (e.g., cleaved by a signal peptidase) by the host cell. For prokaryotic host cells that do not recognize and process the anti-SIRPα antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and

*Kluyveromyces* α-factor leaders), acid phosphatase, *C. albicans* glucoamylase, or the signal described in WO 90/13646. In mammalian cells, mammalian signal sequences as well as viral secretory leaders, for example, the herpes simplex gD signal, can be used. The DNA for such precursor region is ligated in reading frame to DNA encoding the anti-SIRPα antibody.

Anti-SIRPα antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-SIRPα antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia* pastors (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated anti-SIRPα antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The anti-SIRPα antibodies or antigen-binding fragments thereof can also be incorporated in viral vectors, e.g. the polynucleotide encoding for the anti-SIRPα antibody or antigen-binding fragment thereof is introduced into the viral vector and then expressed in the body of the subject after infection with the virus.

In another aspect, expression of the anti-SIRPα antibody or antigen-binding fragment thereof is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/−DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Also included are nucleic acids that hybridize under low, moderate, and high stringency conditions, in particular under high stringency conditions, as defined herein, to all or a portion (e.g., the portion encoding the variable region) of the nucleotide sequence represented by isolated polynucleotide sequence(s) that encode an anti-SIRPα antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, at least 98%, or at least 99% identical to the sequence of a portion or all of a nucleic acid encoding an anti-SIRPα polypeptide (e.g., a heavy chain or light chain variable region), or its complement. Hybridizing nucleic acids of the type described herein can be used, for example, as a cloning probe, a primer, e.g., a PCR primer, or a diagnostic probe. In one aspect, "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

In one embodiment, the present invention relates to an isolated polynucleotide comprising a nucleotide sequence encoding a heavy chain variable region comprising the amino acid sequence of any one of SEQ ID NOs: 100, 101, 102, 103, 104, 105, 110, 111, 112, 113, 114, 115, 116, 117, 118, 119, 120, 121, 122, 123, 124, or 221.

In one embodiment, the present invention relates to an isolated polynucleotide comprising a nucleotide sequence encoding a light chain variable region comprising the amino acid sequence of any one of SEQ ID NOs: 105, 106, 107, 108, 109, 125, 126, 109, 127, 128, 129, 130, or 222.

In one embodiment, the present invention relates to an isolated polynucleotide comprising a nucleotide sequence encoding a heavy chain region comprising the amino acid sequence of any one of SEQ NO: 131,138,139, 140, 141, 142, 143, 144, 145, 146, 147, 148, 149, 150, 151, 152, 217, 135,153, 154, 156, 157, 158, 159, 160, 161, 162, 163, 164, 165, 166, 167, 168, 169, 170, 171, 172, 173, 219, 133, 134, 137, 132, or 136.

In one embodiment, the present invention relates to an isolated polynucleotide comprising the nucleotide sequence encoding of a light chain region comprising the amino acid sequence of any one any one of SEQ NO: 174, 181, 182, 183, 184, 185, 186, 187, 188, 189, 190, 191, 192, 193, 194, 195, 218, 178, 196, 197, 198, 199, 200, 201, 202, 203, 204, 205, 206, 207, 208, 209, 210, 211, 212, 213, 214, 215, 216, 220, 176, 177, 180, 175, or 179.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-SIRPα antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

EXAMPLES

The present disclosure is now described with reference to the following Examples. These Examples are provided for the purpose of illustration only and the disclosure should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present invention, and are not to be construed as limiting in any way the remainder of the disclosure.

Example 1: Generation of Anti-SIRPα Antibodies

Phage and Yeast Display.

Initial efforts to generate anti-SIRPα antibodies of desired selectivity, i.e., being able to block hSIRPαV1 and hSIRPαV2 and lacking binding to hSIRPγ, are conducted using phage display. Biotinylated extracellular domains of hSIRPαV1, hSIRPαV2, and cynomologus SIRPα proteins are used as the target proteins in three sequential screening rounds. Unlabeled hSIRPγ extracellular domain is included in each screening round as a deselecting agent in order to remove antibodies that could bind to hSIRPγ extracellular domain.

Phage display yielded thirteen candidate antibodies that were further characterized. Four of the candidate antibodies could block hSIRPαV1 and hSIRPαV2, but each of these antibodies was determined to also bind to hSIRPγ. Nine of the candidate antibodies did not bind to hSIRPγ, but also could only block hSIRPαV1 or hSIRPαV2 but not both. Thus, it was determined that none of the thirteen candidate antibodies possessed the desired selectivity.

A similar effort to generate anti-SIRPα antibodies of desired selectivity is conducted using yeast display. The majority of the candidate antibodies identified by yeast display (59 out of 66) could block hSIRPαV1 and hSIRPαV2 but also bound to hSIRPγ. The remaining seven antibodies did not bind to hSIRPγ, but could only block hSIRPαV1 but not hSIRPαV2. Thus, similarly to the phage display, it was determined that none of the candidate antibodies possessed the desired selectivity.

Immunization.

AlivaMab kappa mice are immunized subcutaneously with combinations of recombinantly produced extracellular domains of human and cynomologus SIRPα proteins [NP 542970, CAA71403 and NP 001271679] following standard laboratory immunization techniques. Briefly, mice are immunized subcutaneously once per week for four weeks with protein and adjuvant mixtures. An aqueous adjuvant is used and is expected to improve generation of antibodies with the desired selectivity by decreasing the exposure of sites that are internal to the native protein confirmation. After four immunizations, antibody titers are determined by ELISA methods. Animals that display a strong antibody response against all antigens are selected for antibody recovery.

B-Cell Recovery and Recombinant Antibody Production.

Antigen-specific memory B-cell recovery is performed via single B-cell flow cytometry and cell sorting. Recovered antibody sequences are synthesized and screened for various charateristics, including but not limited to, affinity to SIRPα, binding to huSIRPα-V1 and huSIRPα-V2 CHO cell lines, and blocking of SIRPα:CD47 interaction. Representative antibodies exhibiting the desired properties are shown in Table 26-27: Antibody A, Antibody B, Antibody C, Antibody D, and Antibody E.

Example 2. Removal of Sequence Liabilities for Antibody a and Antibody E

Fragment antibody (Fab) clones of the parent antibodies are prepared. Libraries are prepared with certain position variations so as to remove potential sequence liabilities (i.e. amino acid residues that may be immunogenic or that may create potential manufacturing problems). These mutated libraries usually have 5 to 10 binary positions per V-region. Separate saturation libraries are also made apart from single or double mutation libraries to address specific positions in more complex V-regions. Such libraries are prepared using standard methods known in the art and can be readily used by the skilled person.

The engineered Fabs are tested for desired properties, including affinity to huSIRPα-V1 and huSIRPα-V2. Representative variable regions for engineered antibodies for Antibody A and Antibody E are shown in Table 28-29.

Example 3. Binding Affinities (SPR $K_D$) of Antibodies to Purified Recombinant Human SIRPα, SIRPβ1, SIRPγ Proteins The binding affinity of anti-SIRPα antibodies to the various SIRPα analytes is determined by surface plasmon resonance (SPR) using a ProteOn XPR36 (Bio-Rad). The running buffer for this experiment and all dilutions (except where stated) are done in 1×HBS-EP+. The CM5 sensorchip is activated with equal mixture of EDC/NHS for 420 sec at a flow rate of 10 μl/min and immobilized with Protein A/G beads (50 μg/ml in 10 mM acetate pH 4.5) for 420 sec at a flowrate of 10 μl/min resulting in ~2600-2900 RU of Protein A/G on the surface. The sensorchip is deactivated with 1M ethanolamine HCl for 420 sec at a flowrate of 10 μl/min.

Each antibody is captured on the Protein A/G surface for 60 sec at a flowrate of 10 μl/min resulting in capture levels of ~280 RU. The analyte is injected over the captured antibody for 300 sec at a flowrate of 30 μl/min. The dissociation is done for 600 sec. Two-fold serial dilutions of each SIRP protein (Extracellular Domain+His-Tag) are injected as analyte with the highest concentrations indicated in table 36 below.

| Analyte (Extracellular Domain + His-Tag) | Accession Number | Highest Concentration (nM) in experiment |
|---|---|---|
| hSIRPαVI | NP_542970.1 | 100 |
| hSIRPαV2 | CAA71403.1 | 100 |
| hSIRPβ1 | NP_006056.2 | 1000 |
| hSIRPβ1v3 | NP_001129316.1 | 100 |
| hSIRPγ | NP_061026.2 | 1000 |
| cynoSIRPα | NP 001271679 | 1000 |
| cynoSIRPα | EGM_02252 | 1000 |
| cynoSIRPα | XP_015313155 | 1000 |
| cynoSIRPβ1 | XP_005568598 | 1000 |
| cynoSIRPβ1v3 | XP_005568593 | 1000 |
| cynoSIRPγ | XP_005568591 | 1000 |

Once each analyte injection is complete, the sensor surface is regenerated by injecting 0.85% phosphoric acid for 30 sec at a flowrate of 30 μl/min.

The analyte interaction with sensor surface (flow cell 1) and blank (HBS-EP+) are subtracted from the raw data. Sensorgrams are then fit globally to 1:1 Langmuir binding to provide on-rate ($k_a$), off-rate ($k_D$), and affinity ($K_D$) values as well as the steady state binding mode to provide the equilibrium affinity ($K_D$).

The above procedure is used to measure the binding affinity to the following analytes: human SIRPαV1, human SIRPαV2, human SIRPβ1, human SIRPβ1v3, human SIRPγ, cynomolgus (cyno) SIRPα, cyno SIRPβ1, cyno SIRPβ1v3, cyno SIRPγ, mouse SIRPα The results for binding affinities of SIRPα antibodies are shown in Tables 37-42 below.

TABLE 37

Binding affinity of SIRPa antibodies (Antibodies A-G) to human SIRP proteins.

| Antibodies | HuSIRPαV1 (M) | HuSIRPαV2 (M) | HuSIRPβ1 (M) | HuSIRPβ1v3 (M) | HuSIRPγ (M) |
|---|---|---|---|---|---|
| Antibody A | 8.81E−09 | 1.31E−08 | 7.82E−08 | NB | NB |
| Antibody B | 1.74E−08 | 7.15E−08 | NB | NB | NB |
| Antibody C | 6.27E−10 | 9.69E−11 | 2.14E−09 | NB | NB |
| Antibody D | 4.04E−09 | 4.05E−09 | 1.65E−08 | NB | NB |
| Antibody E | 4.56E−10 | 4.2E−10 | 1.23E−06 | 1.16E−09 | NB |
| Antibody F | 9.30E−09 | 1.41E−08 | 8.40E−08 | NB | NB |
| Antibody G | 4.97E−10 | 4.65E−10 | 1.27E−06 | 1.27E−09 | NB |

NB = No binding at highest concentration

TABLE 38

Binding affinity of SIRPa antibodies (Antibodies A-G) to cyno and mouse SIRP proteins.

| Antibodies | Mouse NP_031573 SIRPα (M) | CySIRPα NP_ 001271679 (M) | CySIRPa EGM_ 02252 (M) | CySIRPα XP_ 005568593 (M) |
|---|---|---|---|---|
| Antibody A | NB | 4.53E−07 | 2.01E−07 | 2.01E−07 |
| Antibody B | NB | NB | NA | NA |
| Antibody C | NB | 1.43E−08 | NA | NA |
| Antibody D | NB | NB | NA | NA |
| Antibody E | NB | 9.21E−09 | NB | 6.98E−09 |
| Antibody F | NB | 5.06E−07 | 2.30E−07 | 2.27E−07 |
| Antibody G | NB | 1.01E−08 | NB | 7.62E−09 |

NB = No binding at highest concentration
NA = Data Not Available

TABLE 39

Binding affinity of SIRPα antibodies (Antibodies A, A1-A16) to human SIRP proteins.

| Antibodies | HuSIRPα V1 (M) | HuSIRPαV2 (M) | HuSIRPβ1 (M) | HuSIRPβ1v3 (M) | HuSIRPγ (M) |
|---|---|---|---|---|---|
| Antibody A | 7.72E−09 | 9.03E−09 | 6.48E−08 | NB | NB |
| Antibody A15 | 7.06E−09 | 7.91E−09 | 5.88E−08 | NB | NB |
| Antibody A13 | 7.28E−09 | 8.36E−09 | 6.10E−08 | NB | NB |
| Antibody A9 | 7.34E−09 | 8.25E−09 | 5.88E−08 | NB | NB |
| Antibody A12 | 7.83E−09 | 8.96E−09 | 6.44E−08 | NB | NB |
| Antibody A10 | 7.95E−09 | 9.17E−09 | 6.90E−08 | NB | NB |
| Antibody A16 | 7.98E−09 | 8.22E−09 | 6.27E−08 | NB | NB |
| Antibody A14 | 8.13E−09 | 7.95E−09 | 5.83E−08 | NB | NB |
| Antibody A6 | 8.28E−09 | 1.81E−08 | 6.51E−08 | NB | NB |
| Antibody A4 | 8.46E−09 | 1.83E−08 | 6.72E−08 | NB | NB |
| Antibody A8 | 8.53E−09 | 1.88E−08 | 6.96E−08 | NB | NB |
| Antibody A1 | 8.60E−09 | 1.86E−08 | NB | NB | NB |
| Antibody A5 | 8.75E−09 | 1.78E−08 | 6.42E−08 | NB | NB |
| Antibody A3 | 9.06E−09 | 1.96E−08 | 7.03E−08 | NB | NB |

TABLE 39-continued

Binding affinity of SIRPα antibodies (Antibodies A, A1-A16) to human SIRP proteins.

| Antibodies | HuSIRPα V1 (M) | HuSIRPαV2 (M) | HuSIRPβ1 (M) | HuSIRPβ1v3 (M) | HuSIRPγ (M) |
|---|---|---|---|---|---|
| Antibody A7 | 9.38E−09 | 2.04E−08 | 7.22E−08 | NB | NB |
| Antibody A2 | 9.39E−09 | 2.09E−08 | 7.75E−08 | NB | NB |

NB = No binding at highest concentration

TABLE 40

Binding affinity of SIRPα antibodies (Antibodies A, A1-A16) to cyno SIRP proteins.

| Antibodies | CySIRPα NP_001271679 (M) | CySIRPα EGM_02252 (M) | CySIRPα XP_015313155 (M) | Cyno SIRPβ1 XP_005568598 (M) | Cyno SIRPβ1v3 XP_005568593 (M) | Cyno SIRPγ XP_005568591 (M) |
|---|---|---|---|---|---|---|
| Antibody A | 3.36E−07 | 2.58E−07 | 1.65E−07 | NB | 2.46E−07 | NB |
| Antibody A15 | 3.17E−07 | 2.23E−07 | 1.54E−07 | NB | 2.32E−07 | NB |
| Antibody A13 | 3.30E−07 | 2.26E−07 | 1.60E−07 | NB | 2.38E−07 | NB |
| Antibody A9 | 3.46E−07 | 2.27E−07 | 1.56E−07 | NB | 2.57E−07 | NB |
| Antibody A12 | 3.84E−07 | 2.49E−07 | 1.82E−07 | NB | 2.79E−07 | NB |
| Antibody A10 | 3.78E−07 | 2.49E−07 | 1.80E−07 | NB | 2.71E−07 | NB |
| Antibody A16 | 3.06E−07 | 2.25E−07 | 1.51E−07 | NB | 2.25E−07 | NB |
| Antibody A14 | 3.16E−07 | 2.22E−07 | 1.53E−07 | NB | 2.35E−07 | NB |
| Antibody A6 | 6.84E−07 | 5.38E−07 | 3.66E−07 | NB | 4.69E−07 | NB |
| Antibody A4 | 6.69E−07 | 5.08E−07 | 3.74E−07 | NB | 4.60E−07 | NB |
| Antibody A8 | 6.39E−07 | 5.35E−07 | 3.50E−07 | NB | 4.49E−07 | NB |
| Antibody A1 | 7.80E−07 | 5.43E−07 | 3.69E−07 | NB | 5.57E−07 | NB |
| Antibody A5 | 6.65E−07 | 5.33E−07 | 3.47E−07 | NB | 4.65E−07 | NB |
| Antibody A3 | 8.57E−07 | 5.71E−07 | 4.38E−07 | NB | 5.64E−07 | NB |
| Antibody A7 | 7.41E−07 | 6.09E−07 | 3.89E−07 | NB | 4.94E−07 | NB |
| Antibody A2 | 8.87E−07 | 5.84E−07 | 4.24E−07 | NB | 5.52E−07 | NB |

NB = No binding at highest concentration
NA = Data Not Available

TABLE 41

Binding affinity of SIRPα antibodies (Antibodies E, E1-E22) to human SIRP proteins.

| Antibodies | HuSIRPα V1 (M) | huSIRPαV2 (M) | huSIRPβ1 (M) | huSIRPβ1v3 (M) | huSIRPγ (M) |
|---|---|---|---|---|---|
| Antibody E | 4.25E−10 | 3.30E−10 | 7.71E−07 | 8.10E−10 | NB |
| Antibody E1 | 7.23E−10 | 6.30E−10 | 1.48E−06 | 1.81E−09 | NB |
| Antibody E2 | 9.12E−10 | 6.87E−10 | NB | 1.93E−09 | NB |
| Antibody E3 | 9.64E−10 | 7.75E−10 | 2.14E−06 | 1.76E−09 | NB |
| Antibody E4 | 9.88E−10 | 8.24E−10 | 1.34E−06 | 1.95E−09 | NB |

TABLE 41-continued

Binding affinity of SIRPα antibodies (Antibodies E, E1-E22) to human SIRP proteins.

| Antibodies | HuSIRPα V1 (M) | huSIRPαV2 (M) | huSIRPβ1 (M) | huSIRPβ1v3 (M) | huSIRPγ (M) |
|---|---|---|---|---|---|
| Antibody E5 | 1.02E−09 | 8.73E−10 | 1.38E−06 | 2.72E−09 | NB |
| Antibody E6 | 1.03E−09 | 8.75E−10 | NB | 2.72E−09 | NB |
| Antibody E7 | 1.20E−09 | 1.18E−09 | 8.74E−07 | 2.21E−09 | NB |
| Antibody E8 | 1.21E−09 | 5.42E−10 | 2.42E−06 | 2.58E−09 | NB |
| Antibody E9 | 1.22E−09 | 9.41E−10 | NB | 3.16E−09 | NB |

TABLE 41-continued

Binding affinity of SIRPα antibodies (Antibodies E, E1-E22) to human SIRP proteins.

| Antibodies | HuSIRPα V1 (M) | huSIRPαV2 (M) | huSIRPβ1 (M) | huSIRPβ1v3 (M) | huSIRPγ (M) |
|---|---|---|---|---|---|
| Antibody E10 | 1.23E−09 | 1.20E−09 | 1.57E−06 | 2.37E−09 | NB |
| Antibody E11 | 1.41E−09 | 5.68E−10 | 3.28E−06 | 2.99E−09 | NB |
| Antibody E12 | 1.67E−09 | 1.26E−09 | 1.67E−06 | 3.43E−09 | NB |
| Antibody E13 | 1.70E−09 | 6.90E−10 | NB | 4.17E−09 | NB |
| Antibody E14 | 1.84E−09 | 1.36E−09 | NB | 4.80E−09 | NB |
| Antibody E15 | 1.91E−09 | 7.37E−10 | NB | 4.56E−09 | NB |
| Antibody E16 | 2.15E−09 | 1.93E−09 | 4.24E−06 | 4.02E−09 | NB |

TABLE 41-continued

Binding affinity of SIRPα antibodies (Antibodies E, E1-E22) to human SIRP proteins.

| Antibodies | HuSIRPα V1 (M) | huSIRPαV2 (M) | huSIRPβ1 (M) | huSIRPβ1v3 (M) | huSIRPγ (M) |
|---|---|---|---|---|---|
| Antibody E17 | 2.36E−09 | 7.97E−10 | NB | 5.32E−09 | NB |
| Antibody E18 | 2.46E−09 | 8.98E−10 | NB | 4.80E−09 | NB |
| Antibody E19 | 2.52E−09 | 9.70E−10 | 1.66E−06 | 4.74E−09 | NB |
| Antibody E20 | 3.42E−09 | 1.11E−09 | 4.35E−07 | 8.48E−09 | NB |
| Antibody E21 | 4.46E−09 | 1.39E−09 | NB | 8.84E−09 | NB |
| Antibody E22 | 1.57E−09 | 1.47E−09 | NB | 3.19E−09 | NB |

NB = No binding at highest concentration

TABLE 42

Binding affinity of Antibody E, E1-E22 SIRPα antibodies to cyno SIRP proteins.

| Antibodies | CySIRPα NP_001271679 (M) | CySIRPα EGM_02252 (M) | CySIRPα XP_015313155 (M) | Cyno SIRPβ1 XP_005568598 (M) | Cyno SIRPβ1v3 XP_005568593 (M) | Cyno SIRPγ XP_005568591 (M) |
|---|---|---|---|---|---|---|
| Antibody E | 7.46E−09 | NB | 7.07E−09 | NB | 4.62E−09 | NB |
| Antibody E1 | 1.79E−08 | NB | 1.67E−08 | NB | 1.08E−08 | NB |
| Antibody E2 | 2.07E−08 | NB | 1.97E−08 | NB | 1.24E−08 | NB |
| Antibody E3 | 1.73E−08 | NB | 1.69E−08 | NB | 1.07E−08 | NB |
| Antibody E4 | 2.11E−08 | NB | 1.98E−08 | NB | 1.31E−08 | NB |
| Antibody E5 | 3.82E−08 | NB | 3.78E−08 | NB | 2.26E−08 | NB |
| Antibody E6 | 4.10E−08 | NB | 4.16E−08 | NB | 2.39E−08 | NB |
| Antibody E7 | 2.19E−08 | NB | 2.12E−08 | NB | 1.31E−08 | NB |
| Antibody E8 | 1.77E−08 | NB | 1.66E−08 | NB | 1.08E−08 | NB |
| Antibody E9 | 4.37E−08 | NB | 4.08E−08 | NB | 2.51E−08 | NB |
| Antibody E10 | 2.52E−08 | NB | 2.37E−08 | NB | 1.57E−08 | NB |
| Antibody E11 | 2.03E−08 | NB | 2.00E−08 | NB | 1.32E−08 | NB |
| Antibody E12 | 4.61E−08 | NB | 4.22E−08 | NB | 2.79E−08 | NB |
| Antibody E13 | 3.83E−08 | NB | 3.74E−08 | NB | 2.05E−08 | NB |
| Antibody E14 | 9.07E−08 | NB | 8.63E−08 | NB | 5.19E−08 | NB |
| Antibody E15 | 4.94E−08 | NB | 4.62E−08 | NB | 2.58E−08 | NB |
| Antibody E16 | 5.03E−08 | NB | 4.88E−08 | NB | 3.03E−08 | NB |
| Antibody E17 | 4.48 E−08 | NB | 4.32E−08 | NB | 2.70E−08 | NB |
| Antibody E18 | 5.25E−08 | NB | 5.00E−08 | NB | 2.78E−08 | NB |
| Antibody E19 | 4.66E−08 | NB | 4.47E−08 | NB | 2.50E−08 | NB |
| Antibody E20 | 1.11E−07 | NB | 1.04E−07 | NB | 5.74E−08 | NB |
| Antibody E21 | 1.07E−07 | NB | 1.08E−07 | NB | 5.65E−08 | NB |
| Antibody E22 | 1.38E−08 | NB | 1.42E−08 | NB | 1.20E−08 | NB |

NB = No binding at highest concentration

Example 4. Binding of Antibodies to Full-Length Human V1-SIRPα or V2-SIRPα Expressed on CHO Cells Antibody binding to cells expressing SIRPα is evaluated by flow cytometry. CHO-K1 parental cells (negative control), CHO-K1 cells expressing full-length human SIRPαV1 (NP_542970.1) or CHO-K1 cells expressing full-length human SIRPαV2 (CAA71403.1) are blocked with donkey IgG and incubated on ice with increasing concentrations of antibodies for 60 minutes, washed and stained with AF647-conjugated donkey $F(ab')_2$ anti-human IgG secondary reagent. Cells are washed, fixed, and analyzed by flow cytometry. Median fluorescent intensity is determined and used as a measure of antibody binding.

Figure 1A:
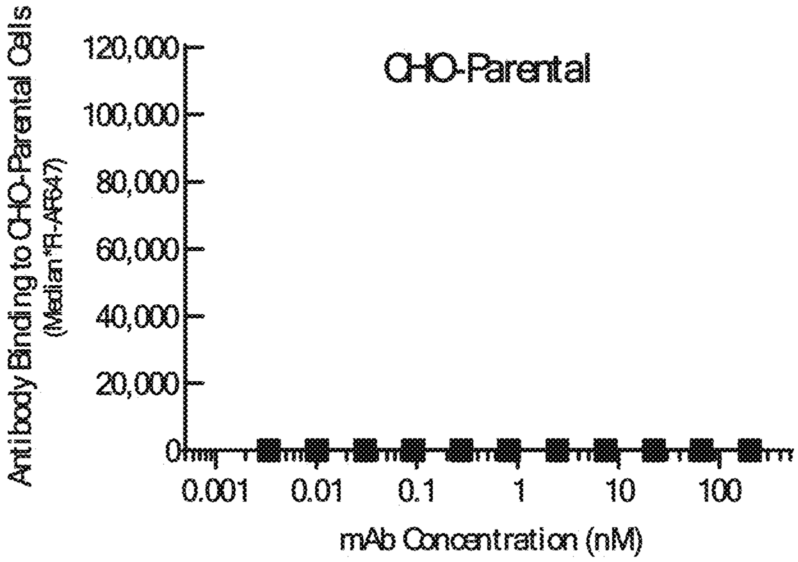
FIGS. 1A-1C are series of graphs depicting the binding of antibodies to full-length human V1-SIRPα or V2-SIRPα expressed on CHO cells.
Figure 1B:
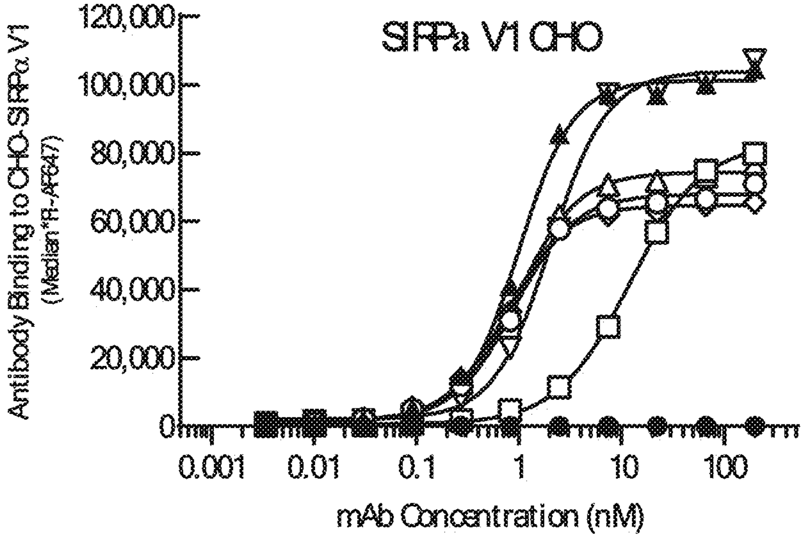
Figure 1C:
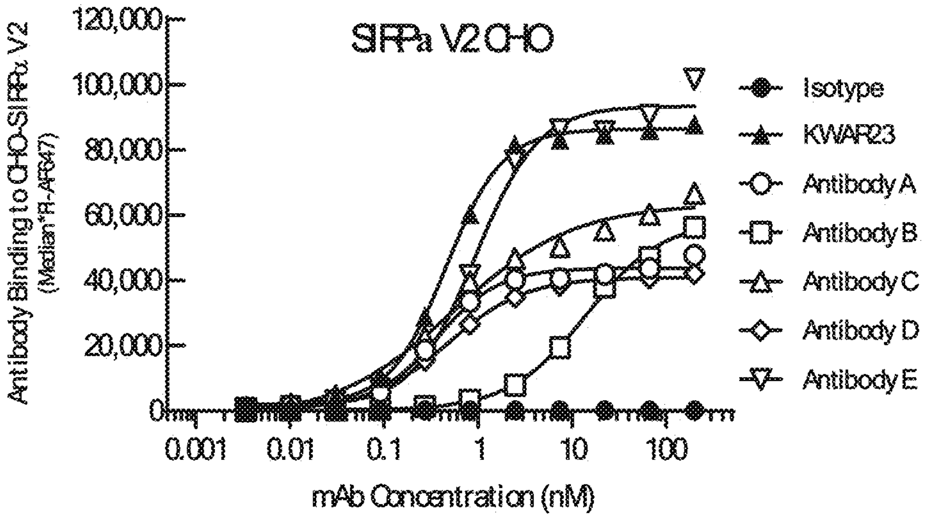

Anti-SIRPα antibody KWAR23 (WO2015138600) and antibodies A-E demonstrated dose-dependent binding to CHO cells expressing full-length human SIRPαV1 (FIG. 1B) or SIRPαV2 (FIG. 1C) with $EC_{50}$ values ranging between 0.4-14 nM (Table 43). None of the antibodies tested exhibited binding to parental CHO cells (FIG. 1A).

TABLE 43

$EC_{50}$ of Anti-SIRPα antibodies

| Antibody | Cell Binding $EC_{50}$ (nM) CHO-Parental | CHO-hSIRPαV1 | CHO-hSIRPαV2 |
|---|---|---|---|
| Isotype | NB | NB | NB |
| KWAR23 | NB | 1.0 | 0.5 |
| Antibody A | NB | 0.9 | 0.4 |
| Antibody B | NB | 12.0 | 14.2 |
| Antibody C | NB | 1.0 | 0.5 |
| Antibody D | NB | 0.7 | 0.5 |
| Antibody E | NB | 2.0 | 0.9 |

NB No binding

Example 5. Binding of Antibodies to Endogenous Human V1-SIRPα or V2-SIRPα Expressed on Human Monocytic Cell Lines Antibody binding to human monocytic cell lines homozygous for the V1-allele (U-937) or the V2-allele (THP-1) of SIRPα is assessed. U-937 or THP-1 cells are blocked with donkey IgG and incubated on ice with increasing concentrations of antibodies for 60 minutes, washed and stained with AF647-conjugated donkey $F(ab')_2$ anti-human IgG secondary reagent. Cells are washed, fixed, and analyzed by flow cytometry. Median fluorescent intensity is determined and used as a measure of antibody binding.

Figure 2A:
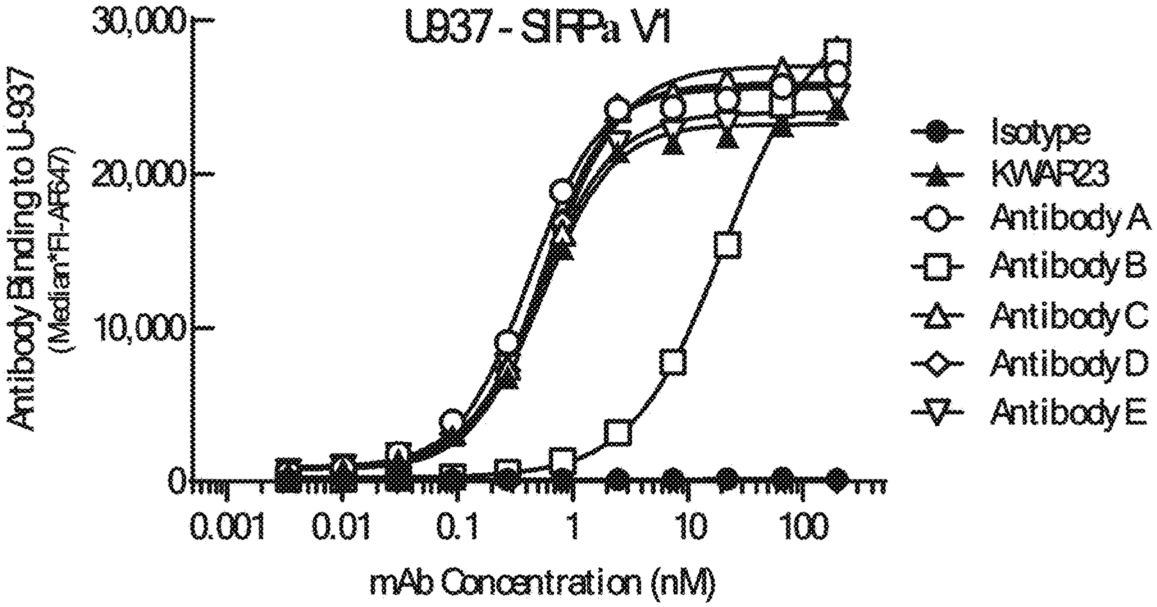
FIG. 2A and FIG. 2B are series of graphs depicting the binding of antibodies to endogenous human V1-SIRPα or V2-SIRPα expressed on human monocytic cell lines.
Figure 2B:
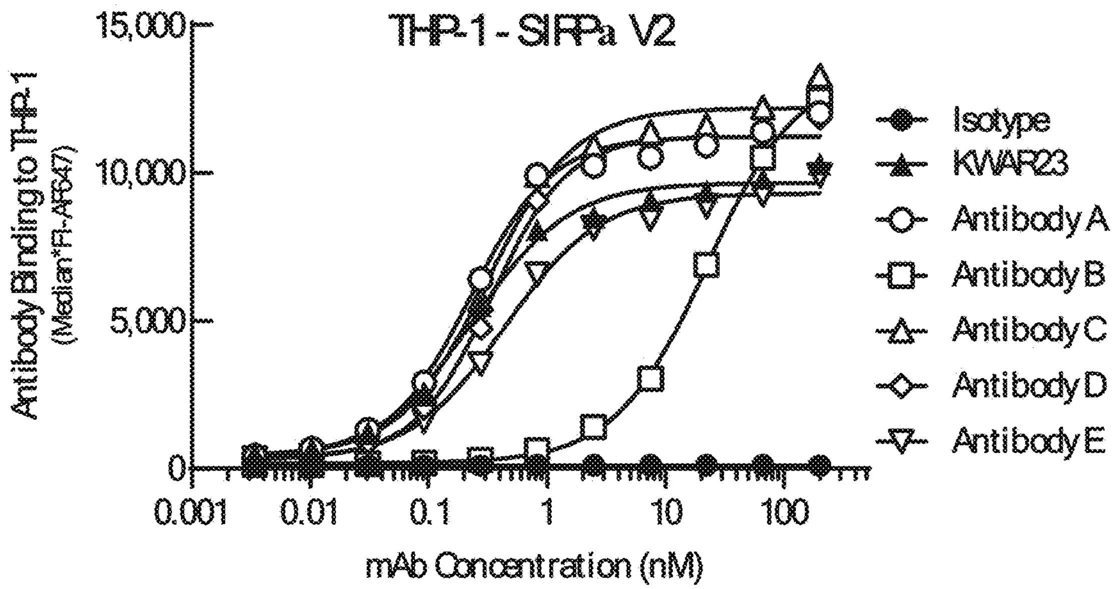
Figure 3A:
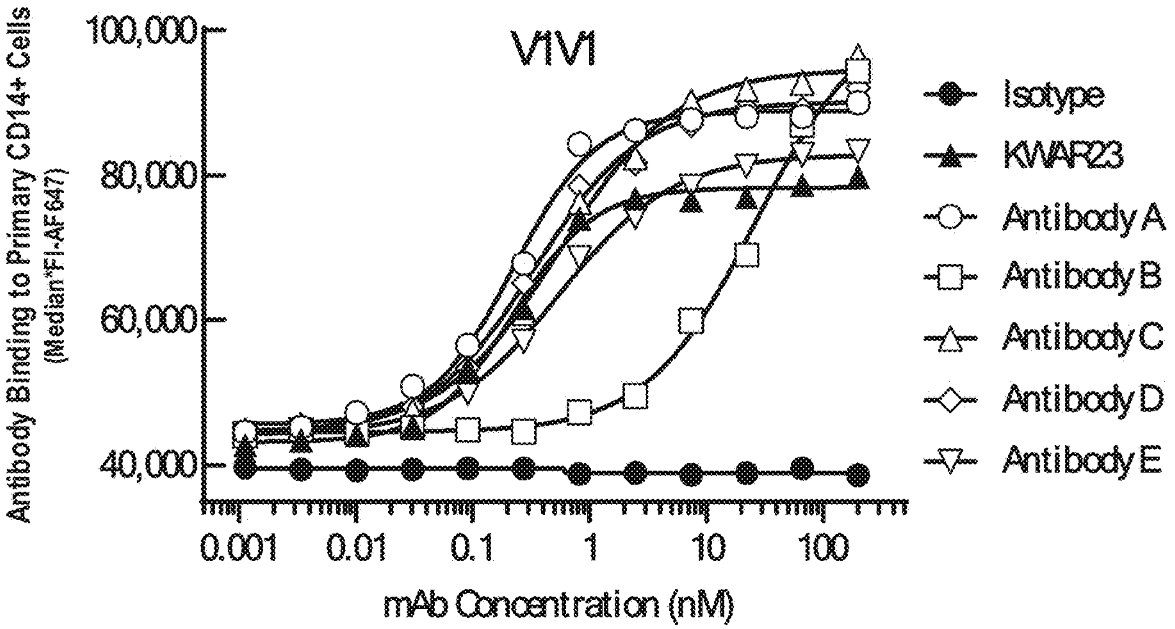
FIGS. 3A-3D are series of graphs depicting the binding of antibodies to endogenous human V1-SIRPα and/or V2-SIRPα expressed on primary human monocytes. Antibody binding to primary human CD14+ monocytes from donors homozygous for V1-SIRPα allele (FIGS. 3A-3D). Solid, dashed, and dotted lines indicate antibody molecules engineered on hIgG1 (LALA), hIgG4P, hIgG1 (K322A) backbones, respectively.
Figure 3B:
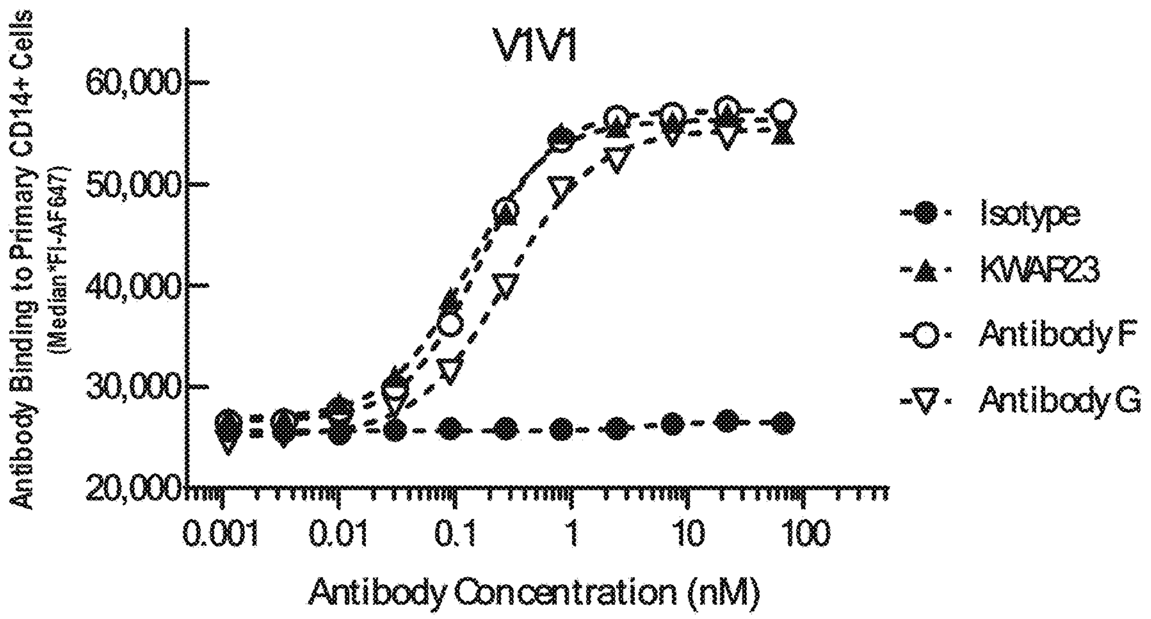
Figure 3C:
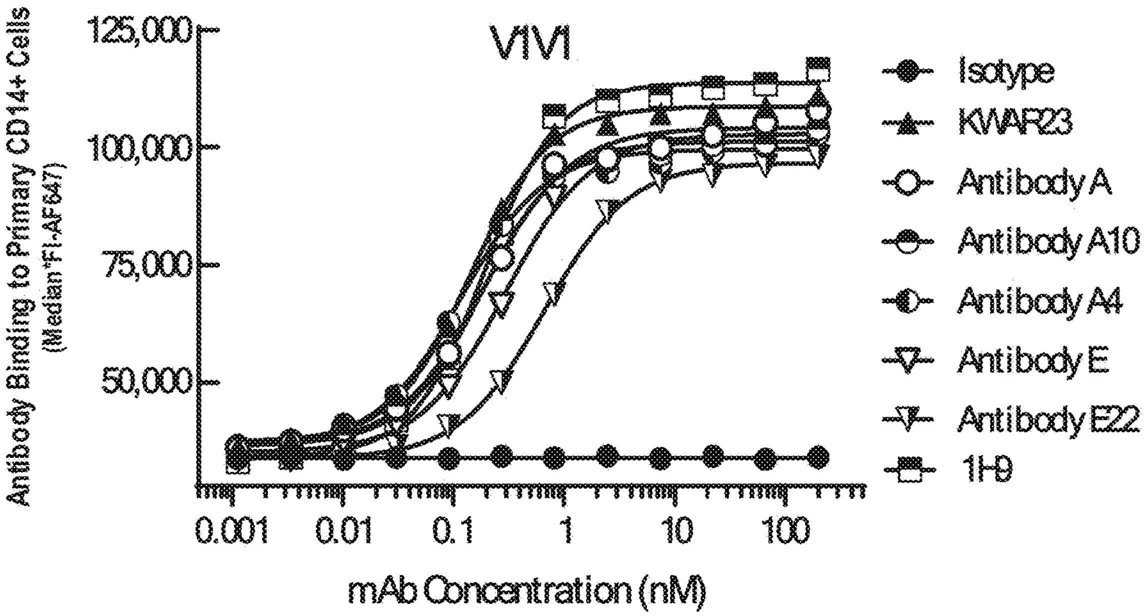
Figure 3D:
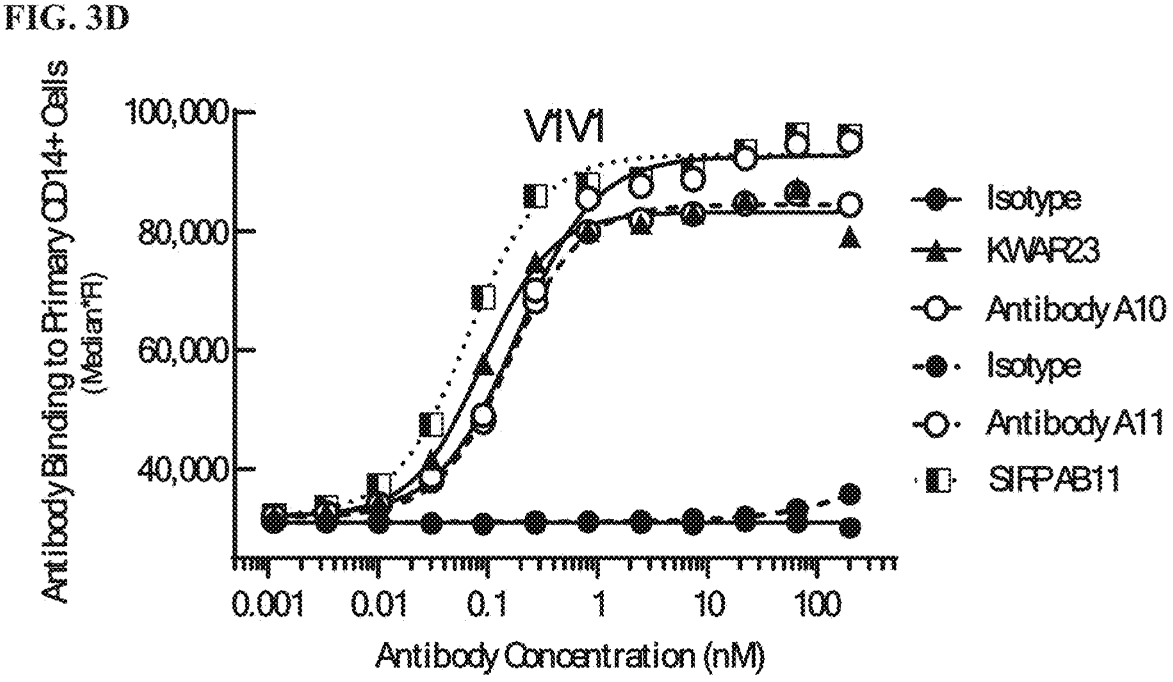
Figure 4A:
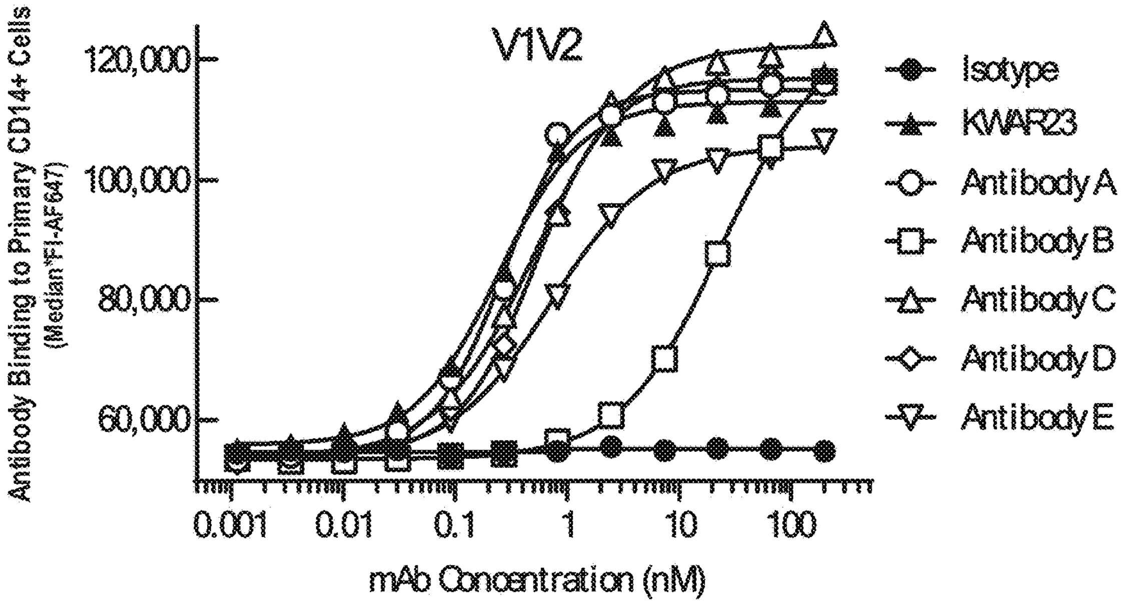
FIGS. 4A-4D are series of graphs depicting the binding of antibodies to endogenous human V1-SIRPα and/or V2-SIRPα expressed on primary human monocytes. Antibody binding to primary human CD14+ monocytes from donors heterozygous for V1- and V2-SIRPα alleles (FIGS. 4A-4D). Solid, dashed, and dotted lines indicate antibody molecules engineered on hIgG1 (LALA), hIgG4P, hIgG1 (K322A) backbones, respectively.
Figure 4B:
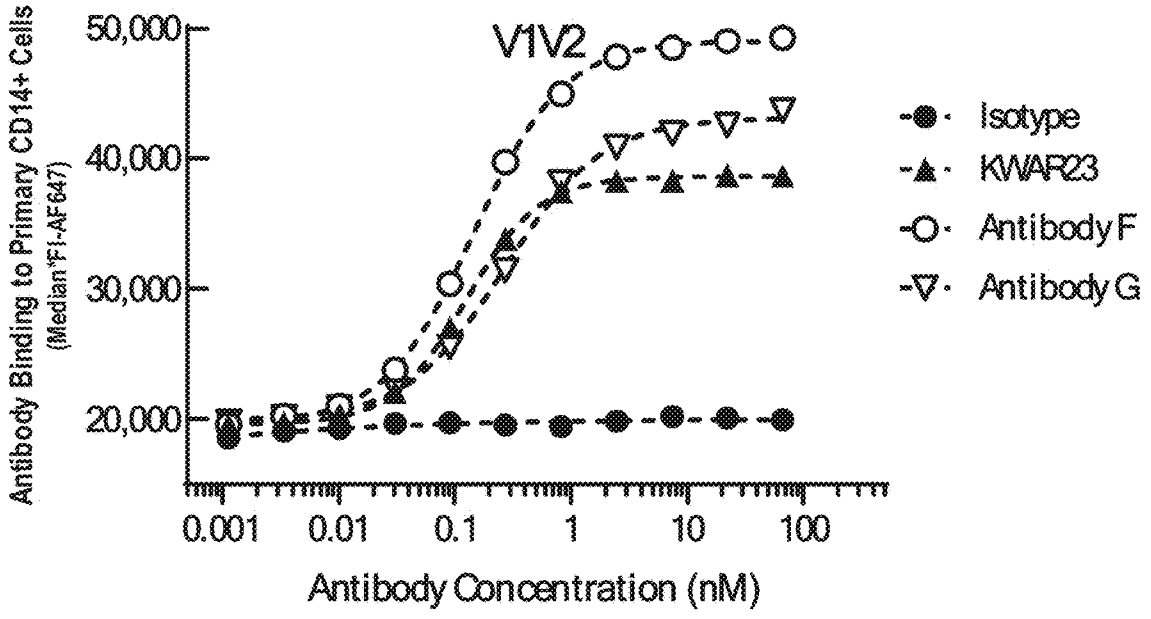
Figure 4C:
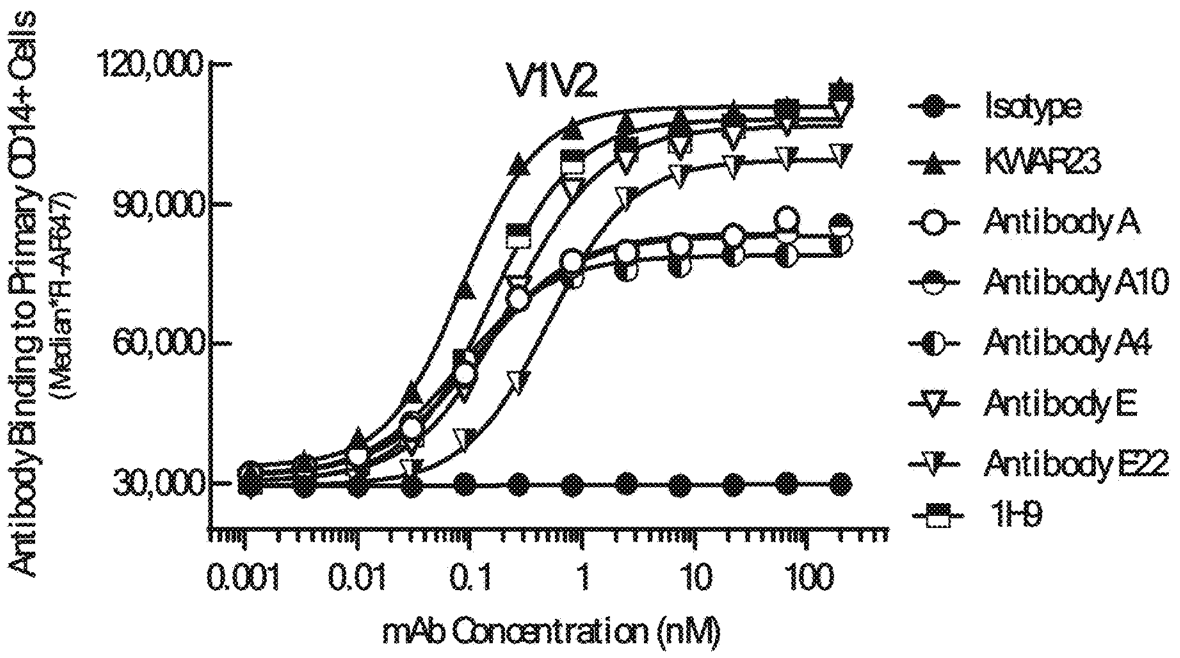
Figure 4D:
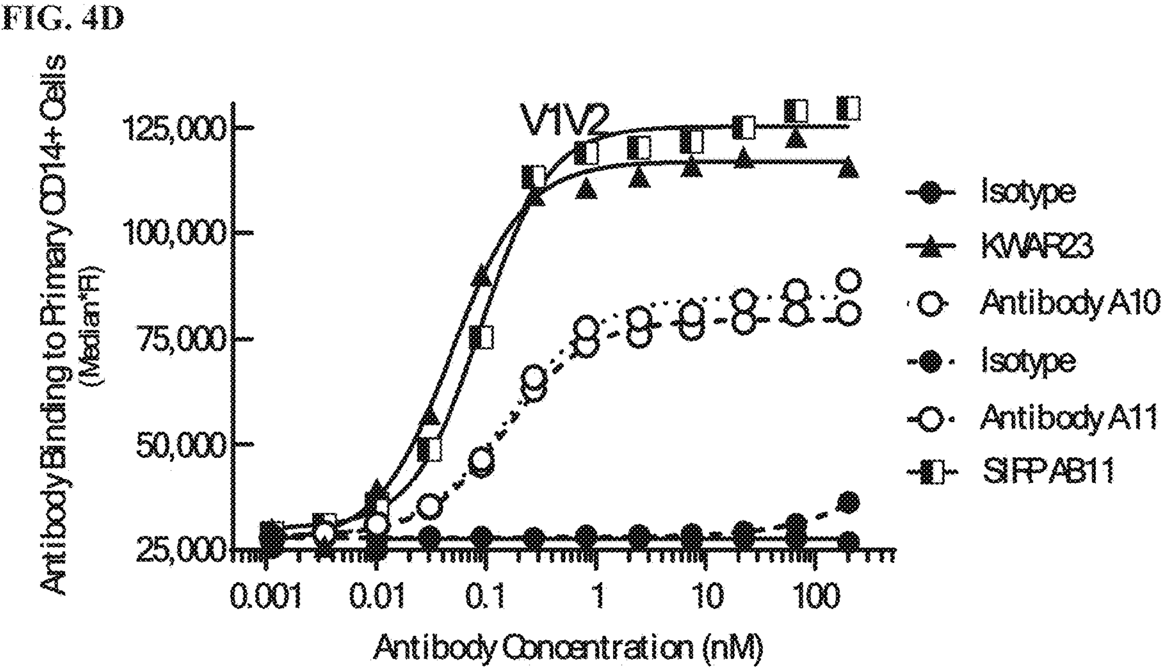
Figure 5A:
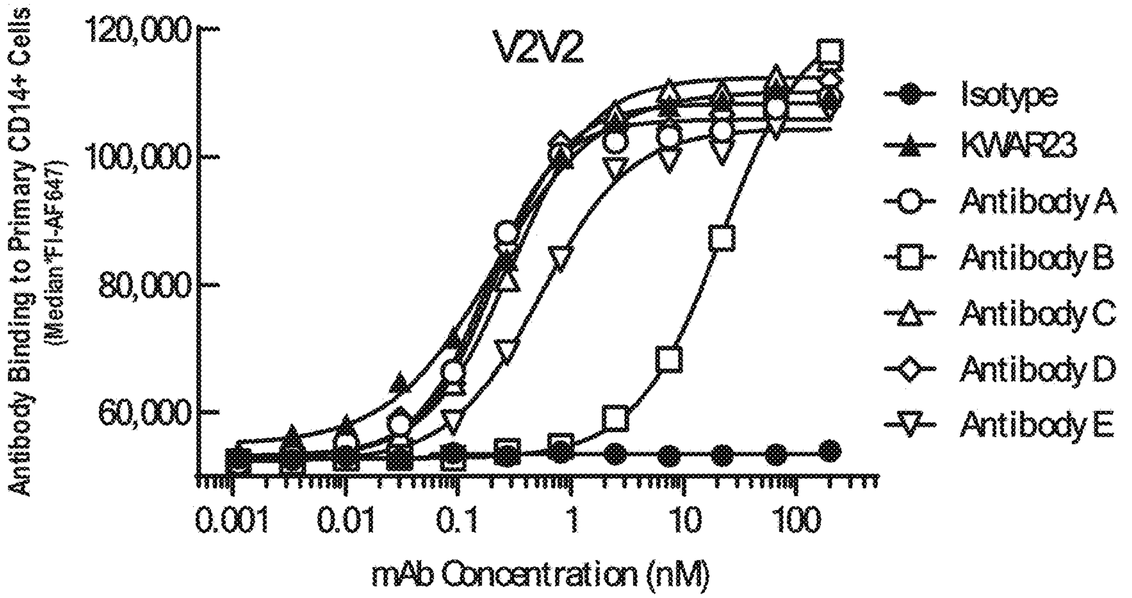
FIGS. 5A-5D are series of graphs depicting the binding of antibodies to endogenous human V1-SIRPα and/or V2-SIRPα expressed on primary human monocytes. Antibody binding to primary human CD14+ monocytes from donors homozygous for V2-SIRPα allele (FIGS. 5A-5D). Solid, dashed, and dotted lines indicate antibody molecules engineered on hIgG1 (LALA), hIgG4P, hIgG1 (K322A) backbones, respectively.
Figure 5B:
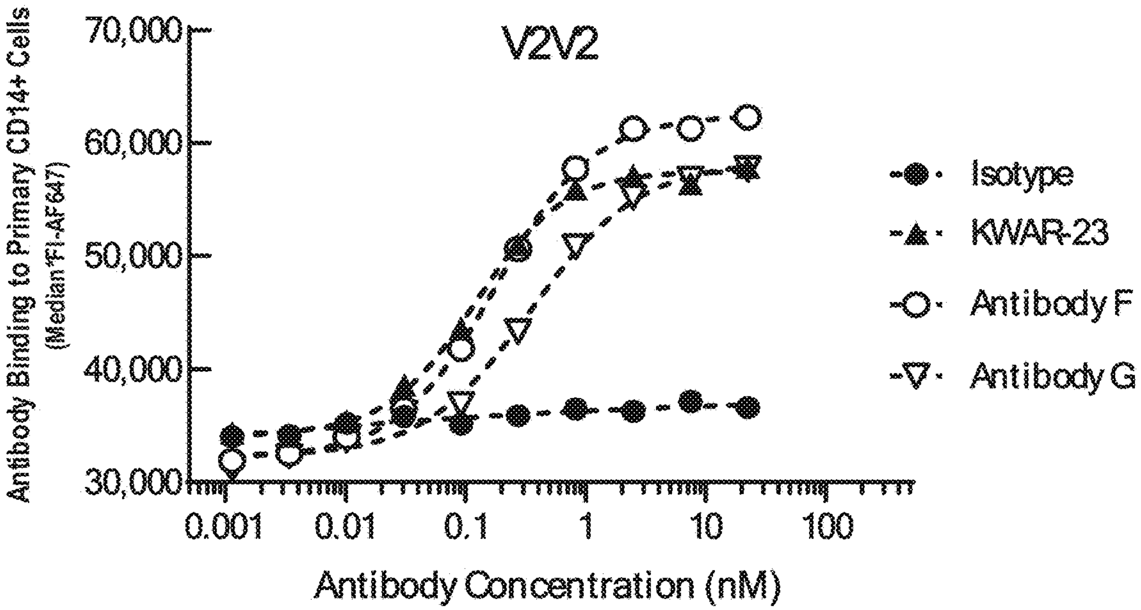
Figure 5C:
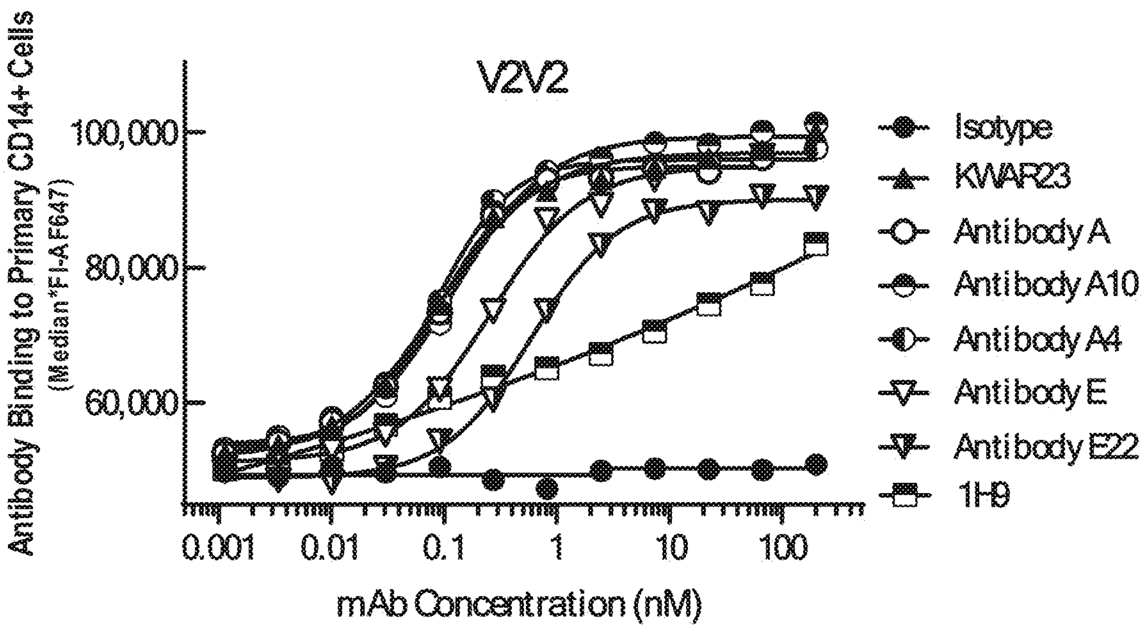
Figure 5D:
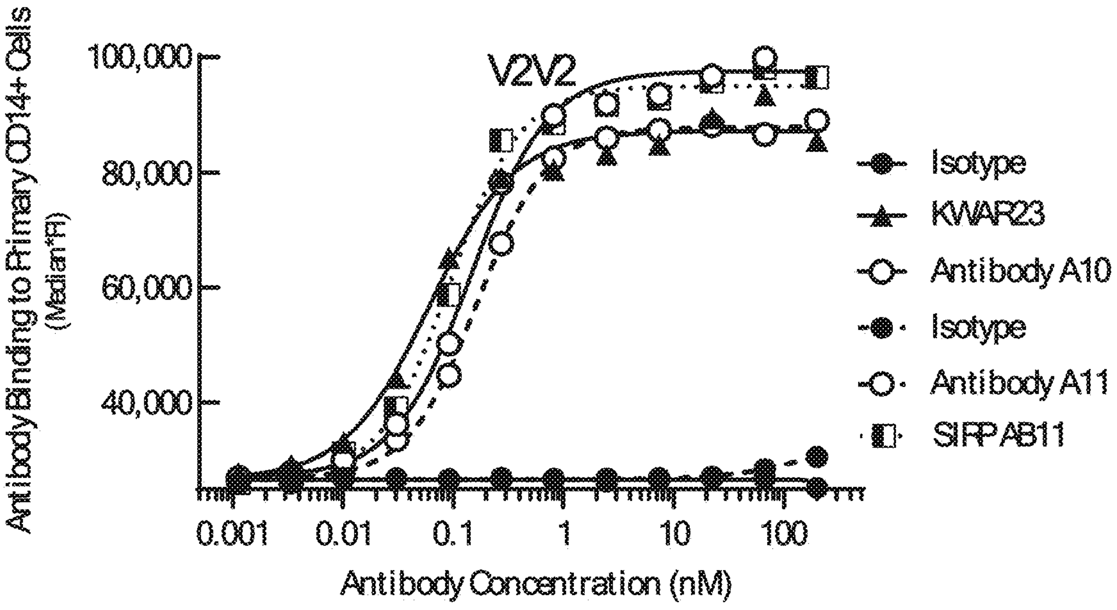
Figure 6A:
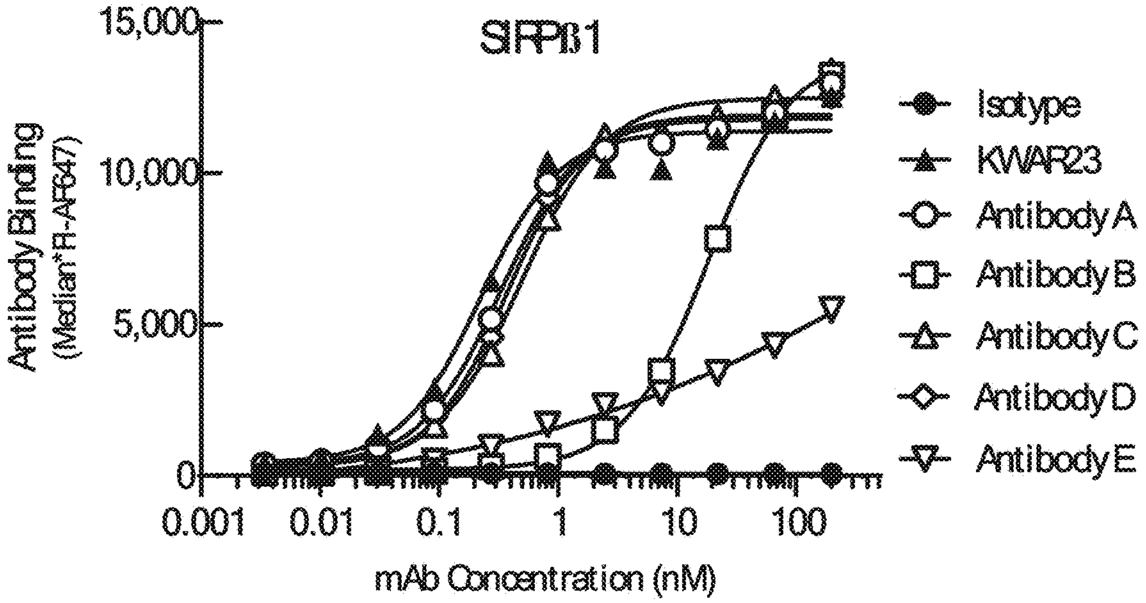
FIGS. 6A-6D are series of graphs depicting the binding of antibodies to full-length human SIRPβ1 expressed on U973$^{SIRPα\ KO}$ cells. Antibody binding to U937$^{SIRPα\ KO}$ cells expressing full-length human SIRPβ1 (NP_006056.2) (FIGS. 6A-6D). Solid, dashed, and dotted lines indicate antibody molecules engineered on hIgG1 (LALA), hIgG4P, hIgG1 (K322A) backbones, respectively.
Figure 6B:
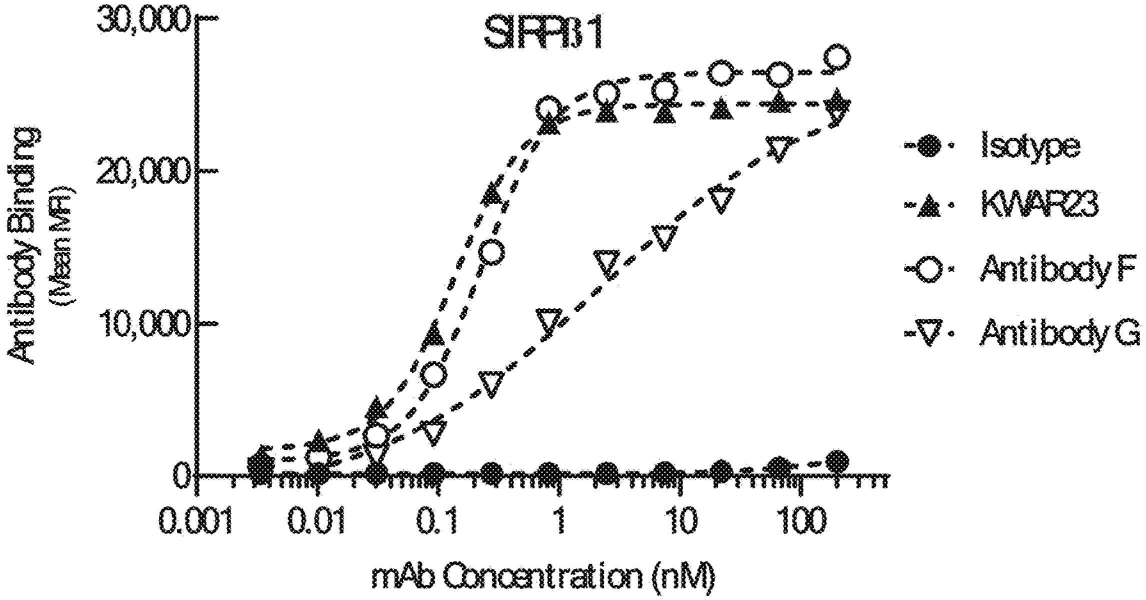
Figure 6C:
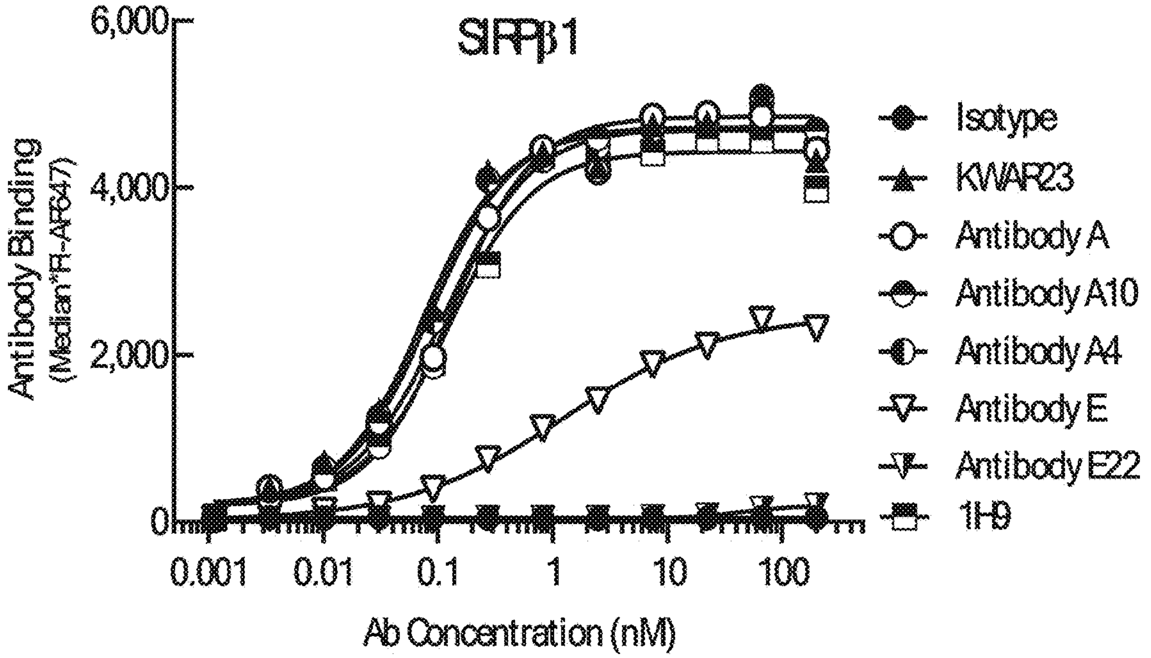
Figure 6D:
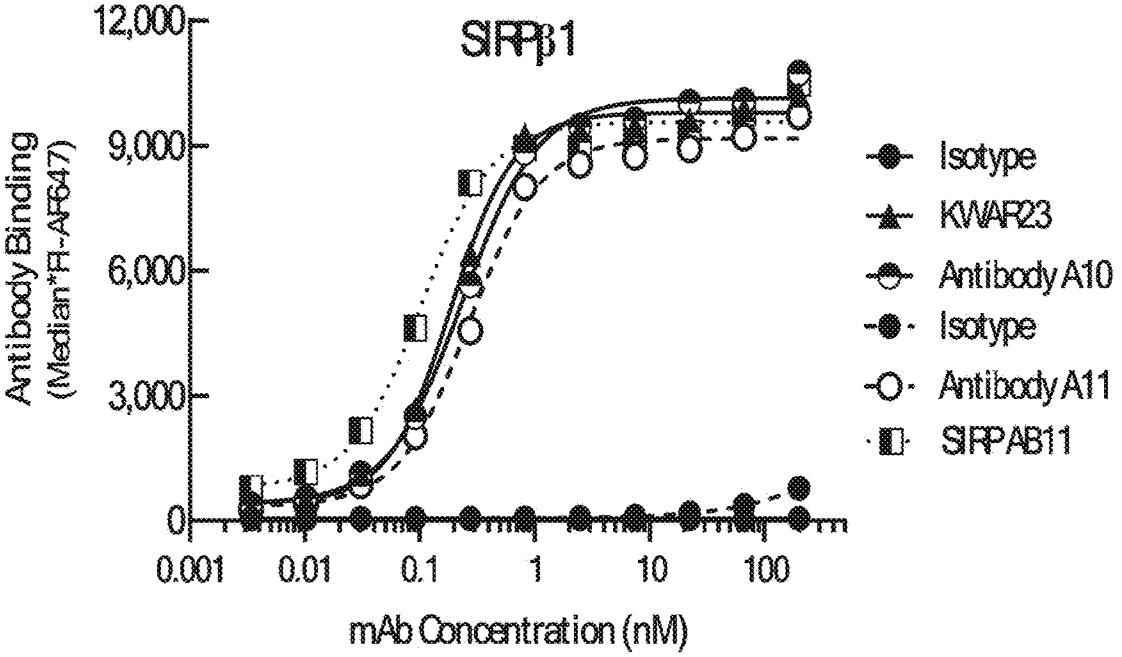
Figure 7A:
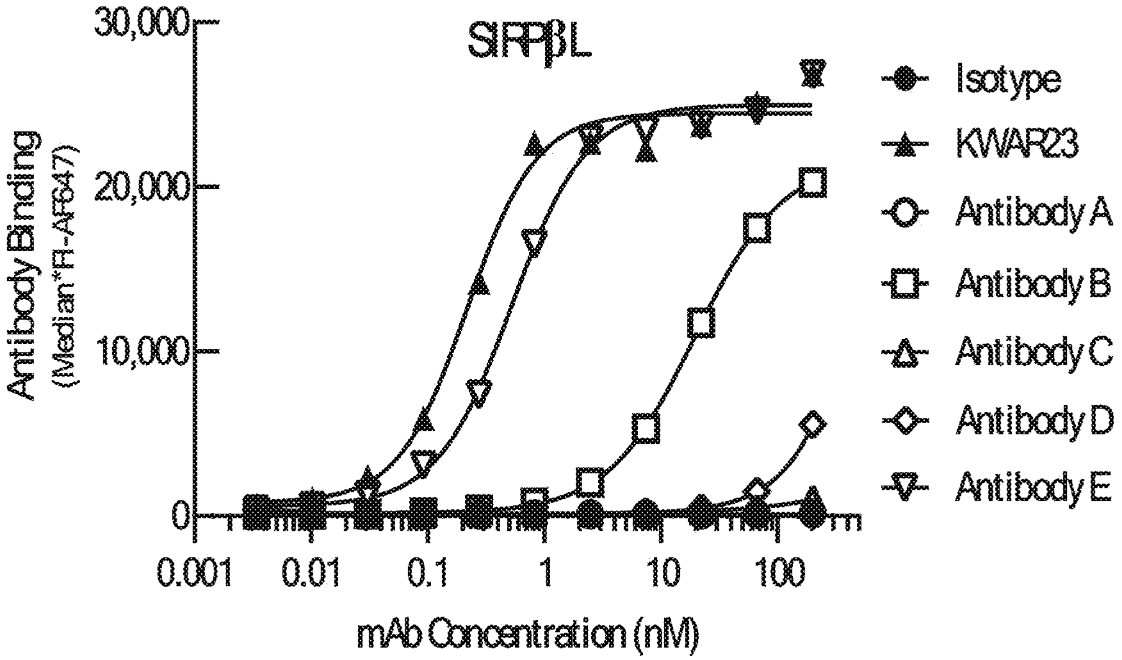
FIGS. 7A-7D are series of graphs depicting the binding of antibodies to full-length human SIRPβ1 expressed on U973$^{SIRPα\ KO}$ cells. Antibody binding to U937$^{SIRPα\ KO}$ cells expressing full-length human SIRPβL (NP_001129316.1) (FIGS. 7A-7D). Solid, dashed, and dotted lines indicate antibody molecules engineered on hIgG1 (LALA), hIgG4P, hIgG1 (K322A) backbones, respectively.
Figure 7B:
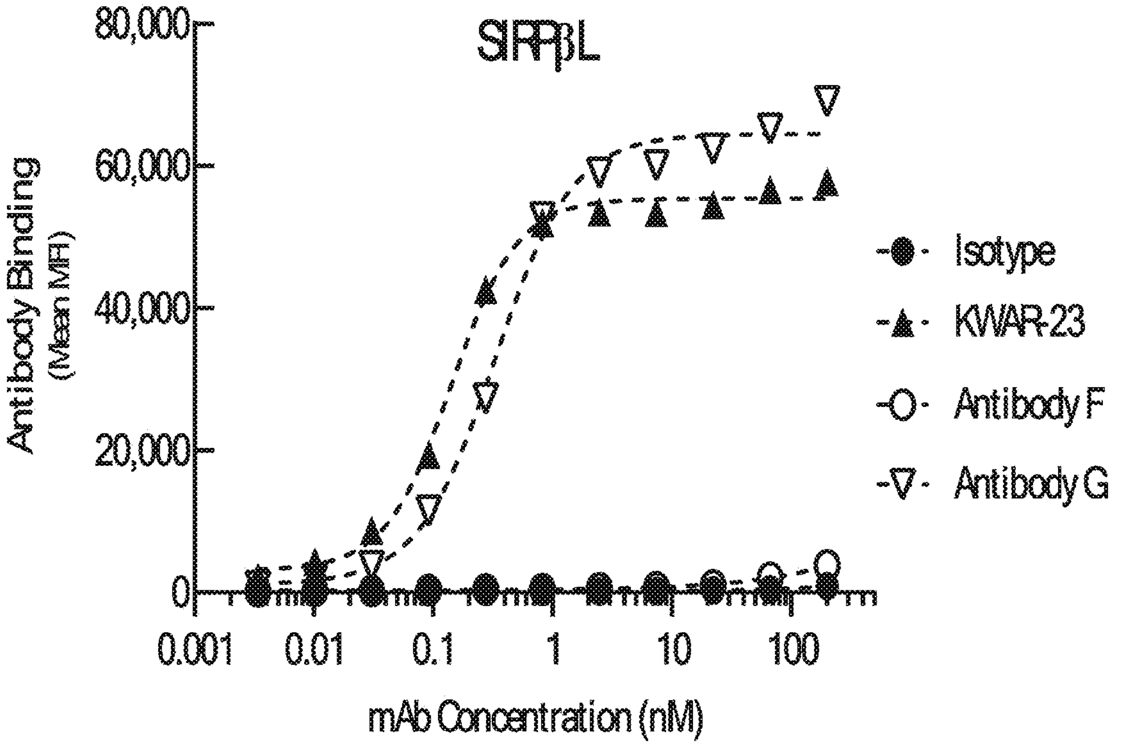
Figure 7C:
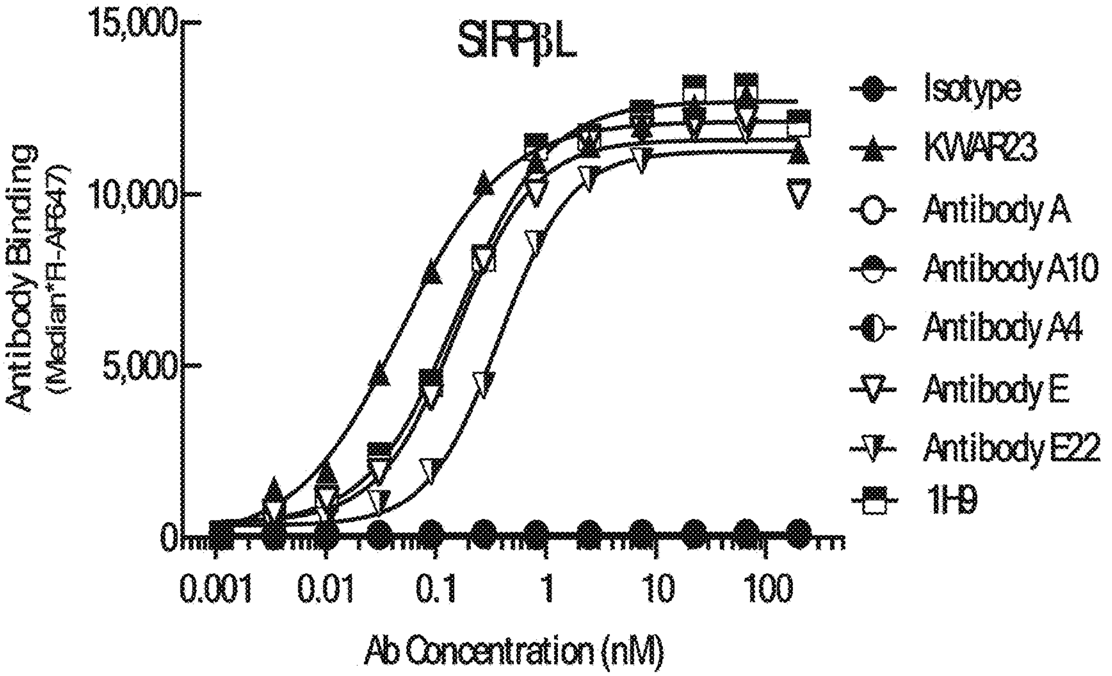
Figure 7D:
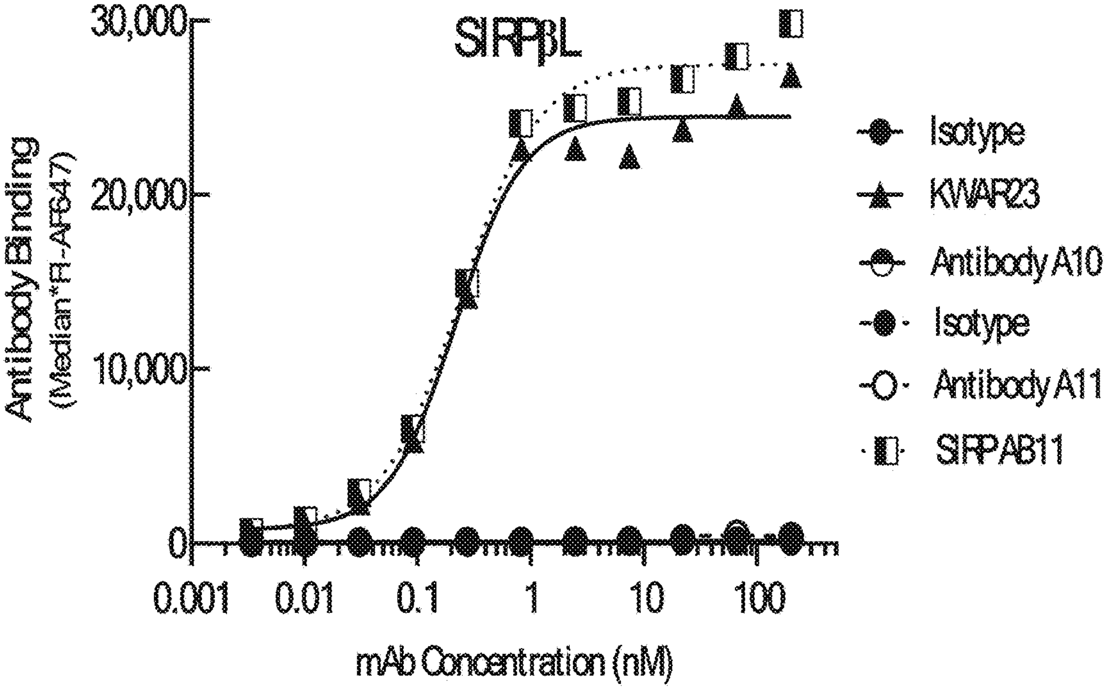

Anti-SIRPα antibody KWAR23 and antibodies A-E demonstrated dose-dependent binding to U-937 cells homozygous for human SIRPαV1 allele (FIG. 2A) and THP-1 cells homozygous for human SIRPαV2 allele (FIG. 2B) with $EC_{50}$ values ranging between 0.2-22 nM (Table 44).

TABLE 44

$EC_{50}$ of Anti-SIRPα antibodies

| Antibody | Cell Binding $EC_{50}$ (nM) U937 | THP-1 |
|---|---|---|
| Isotype | NB | NB |
| KWAR23 | 0.5 | 0.2 |
| Antibody A | 0.4 | 0.2 |
| Antibody B | 21.1 | 22.3 |
| Antibody C | 0.6 | 0.3 |
| Antibody D | 0.5 | 0.3 |
| Antibody E | 0.5 | 0.4 |

NB No Binding

Example 6. Binding of Antibodies to Endogenous Human V1-SIRPα and/or V2-SIRPα Expressed on Primary Human Monocytes Antibody binding to primary human cells expressing SIRPα is evaluated by flow cytometry. Human peripheral blood mononuclear cells (PBMCs) from donors genotyped as homozygous for the SIRPα V1 allele, V2 allele, or heterozygous for both alleles are blocked with donkey IgG and incubated on ice with increasing concentrations of antibody for 60 minutes, washed and stained with AF647-conjugated donkey $F(ab')_2$ anti-human IgG secondary reagent. Washed cells are subsequently blocked with Human TruStain FcX™ (Biolegend) and stained with BV421-conjugated anti-human CD14 (Biolegend, clone M5E2). Cells are washed, fixed, and analyzed by flow cytometry. Median fluorescent intensity of the CD14+ population was determined and used as a measure of antibody binding.

All antibodies tested (Antibody A-G, A10, A4, A11, and E22) demonstrated dose-dependent binding to primary human monocytes from donors homozygous for V1 (FIGS. 3A-3D) or V2 (FIGS. 5A-5D) alleles or heterozygous for both alleles (FIGS. 4A-4D). Table 45 highlights the primary cell binding $EC_{50}$ calculated for each of the antibodies described above. Aside from Antibody B, all antibodies exhibited subnanomolar $EC_{50}$.

Binding of known anti-SIRPα antibodies, KWAR23, 1H9 (WO 2019/023347) and SIRP AB11 (WO 2020/068752), to primary human monocytes were also assessed as described above and $EC_{50}$ results are shown in Table 45. While 1H9 exhibited dose-dependent binding and subnanomolar binding $EC_{50}$ values for primary human monocytes from donors homozygous for V1 alleles or heterozygous for both alleles (FIGS. 3C and 4C), non-saturable antibody binding was detected on primary human monocytes from donors homozygous for V2 alleles. KWAR23 and SIRP AB11 antibodies exhibited subnanomolar binding $EC_{50}$ on primary human monocytes from donors of all genotypes (FIGS. 3A-3D, 4A-4D and 5A-5D; Table 45).

TABLE 45

$EC_{50}$ of Anti-SIRPα antibodies

| Antibody | Primary Human Monocyte Cell Binding $EC_{50}$, nM ± SD (n) V1V1 | V1V2 | V2V2 |
|---|---|---|---|
| Isotype | NB | NB | NB |
| KWAR23 | 0.2 ± 0.04 (n = 7) | 0.1 ± 0.1 (n = 7) | 0.1 ± 0.05 (n = 7) |
| Antibody A | 0.2 ± 0.03 (n = 5) | 0.2 ± 0.1 (n = 5) | 0.1 ± 0.04 (n = 5) |
| Antibody B | 26.6 (n = 1) | 24.1 (n = 1) | 21.8 (n = 1) |
| Antibody C | 0.6 (n = 1) | 0.5 (n = 1) | 0.3 (n = 1) |
| Antibody D | 0.3 (n = 1) | 0.5 (n = 1) | 0.2 (n = 1) |
| Antibody E | 0.4 ± 0.1 (n = 5) | 0.4 ± 0.2 (n = 5) | 0.7 ± 0.3 (n = 5) |
| Antibody F | 0.2 (n = 1) | 0.1 (n = 1) | 0.2 (n = 1) |

TABLE 45-continued

| EC$_{50}$ of Anti-SIRPα antibodies | | | |
|---|---|---|---|
| | Primary Human Monocyte Cell Binding EC$_{50}$, nM ± SD (n) | | |
| Antibody | V1V1 | V1V2 | V2V2 |
| Antibody G | 0.3 (n = 1) | 0.3 (n = 1) | 0.4 (n = 1) |
| Antibody A10 | 0.2 ± 0.04 (n = 5) | 0.1 ± 0.05 (n = 5) | 0.1 ± 0.04 (n = 5) |
| Antibody A4 | 0.1 ± 0.01 (n = 3) | 0.1 ± 0.04 (n = 3) | 0.1 ± 0.03 (n = 3) |
| Antibody E22 | 0.8 ± 0.1 (n = 3) | 0.7 ± 0.2 (n = 3) | 0.4 ± 0.2 (n = 3) |
| Antibody A11 | 0.1 ± 0 .04 (n = 2) | 0.1 ± 0.06 (n = 2) | 0.1 ± 0.07 (n = 2) |
| 1H9 | 0.2 (n = 1) | 0.2 (n = 1) | NS (n = 1) |
| SIRP AB11 | 0.1 ± 0.01 (n = 2) | 0.1 ± 0.01 (n = 2) | 0.1 ± 0.001 (n = 2) |

NB No Binding
NS Non-saturable binding

Example 7. Binding of Antibodies to Full-Length Human SIRPβ1 or SIRPβL-Expressed on U937$^{SIRPα\ KO}$ Cells Antibody binding to cells expressing full-length human SIRPβ1 (NP_006056.2) and SIRPβL (NP_001129316.1) is evaluated by flow cytometry. SIRPβ1- or SIRPβL-expressing U937$^{SIRPα\ KO}$ cells are blocked with donkey IgG and incubated on ice with increasing concentrations of antibodies for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

Antibodies A-G, A10, A4, and A11, but not isotype control or antibody E22, demonstrated dose-dependent binding to full length human SIRPβ1 expressed on U-937$^{SIRPα\ KO}$ cells (FIGS. 6A-6D). Table 44 highlights the binding EC$_{50}$ calculated for each of the antibodies described above. While antibodies A, C, D, F, A10, A4, and A11 exhibited subnanomolar EC$_{50}$ values to these cells, binding of antibodies B, E, and G were non-saturable at concentrations as high as 200 nM and no EC$_{50}$ values determined.

Antibodies E, G, and E22 demonstrated dose-dependent binding to full length human SIRPβL expressed on U-937$^{SIRPα\ KO}$ cells (FIGS. 7A-7D) with EC$_{50}$ less than 1 nM (Table 46). No binding of antibodies A, C, D, F, A10, A4 and A11 could be detected on SIRPβL-expressing U-937$^{SIRPα\ KO}$ cells (FIGS. 7A-7D). Binding of antibody B (FIG. 7A) was detected on SIRPβL-expressing U-937$^{SIRPα\ KO}$ cells; however, binding was non-saturable at concentrations as high as 200 nM Binding of known anti-SIRPα antibodies, KWAR23, 1H9 and SIRPAB11, to SIRPβ1- or SIRPβL-expressing U937$^{SIRPα\ KO}$ cells was also assessed as described above. All 3 molecules demonstrated dose-dependent binding to both cell types (FIGS. 6A-6D and 7A-7D) with sub-nanomolar binding EC$_{50}$ values (Table 46).

TABLE 46

| EC$_{50}$ of Anti-SIRPα antibodies | | |
|---|---|---|
| | Cell Binding EC$_{50}$, nM ± SD (n) | |
| Antibody | SIRPβ1 | SIRPβL |
| Isotype | NB (n = 6) | NB (n = 6) |
| KWAR23 | 0.2 ± 0.1 (n = 6) | 0.2 ± 0.1 (n = 6) |
| Antibody A | 0.2 ± 0.1 (n = 5) | NB (n = 5) |
| Antibody B | NS (n = 1) | NS (n = 1) |
| Antibody C | 0.5 (n = 1) | NB (n = 1) |

TABLE 46-continued

| EC$_{50}$ of Anti-SIRPα antibodies | | |
|---|---|---|
| | Cell Binding EC$_{50}$, nM ± SD (n) | |
| Antibody | SIRPβ1 | SIRPβL |
| Antibody D | 0.4 (n = 1) | NB (n = 1) |
| Antibody E | NS (n = 5) | 0.3 ± 0.1 (n = 5) |
| Antibody F | 0.2 (n = 1) | NB (n = 1) |
| Antibody G | NS (n = 1) | 0.3 (n = 1) |
| Antibody A10 | 0.2 ± 0.1 (n = 4) | NB (n = 4) |
| Antibody A4 | 0.2 ± 0.1 (n = 3) | NB (n = 3) |
| Antibody E22 | NB (n = 3) | 0.6 ± 0.2 (n = 3) |
| Antibody A11 | 0.3 (n = 1) | NB (n = 1) |
| 1H9 | 0.2 ± 1.0 (n = 2) | 0.3 ± 0.2 (n = 2) |
| SIRPAB11 | 0.1 (n = 1) | 0.2 (n = 1) |

NB No binding
NS Non-saturable binding as high a 200 nM

Example 8. Binding of Antibodies to Purified Recombinant Human SIRPγ Proteins by ELISA A biochemical ELISA-based assay is utilized to evaluate the binding of antibodies to SIRPγ. Black, 96-well flat-bottom immunoassay plates are coated with recombinant human SIRPγ extracellular domain (ECD)/His protein (NP_061026.2) diluted in DPBS and incubated overnight at 4° C. Plates are washed three times and subsequently blocked for about 1-2 h at room temperature (RT). Plates are washed and serially titrated antibodies are added to respective wells for an incubation of about 1-2 h at RT. After the incubation, the plates are washed and HRPO-conjugated mouse anti-human IgG secondary reagent (Jackson Immuno Research) is added to each well and incubated for about 1-2 hours. Following the final plate washing, Amplex™ red substrate is added and incubated at RT in the dark for 15-30 minutes. Fluorescence is detected ($\lambda_{Ex}/\lambda_{Em}$=530/590 nm) using EnVision Multilabel Plate Reader (Perkin Elmer). Average fluorescence is plotted for measuring the antibody binding.

Figure 8:
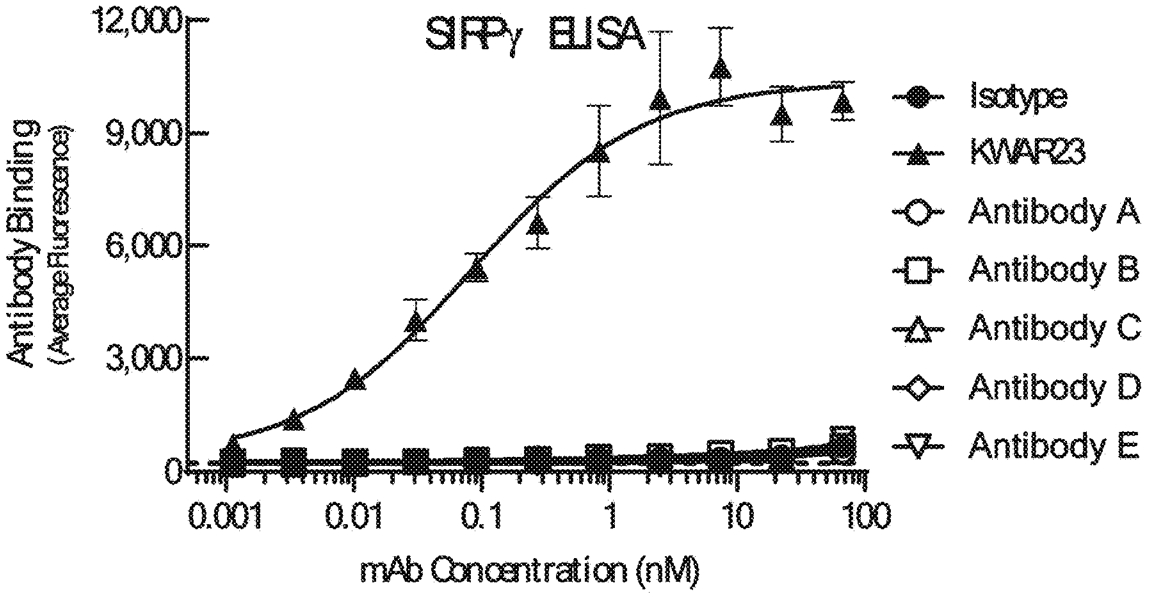
FIG. 8 is a graph depicting the binding of antibodies to recombinant SIRPγ protein. Antibody binding to immobilized recombinant His-tagged human SIRPγ extracellular domain (NP_061026.2).

Except SIRPγ-reactive mAb, KWAR23, none of the antibodies tested (Antibodies A-E) exhibited binding to immobilized recombinant human SIRPγ ECD/His protein (FIG. 8). The EC$_{50}$ value for KWAR23 was determined to be 0.1 nM (Table 47).

Example 9. Binding of Antibodies to Full-Length Human SIRPγ Expressed on CHO Cells Antibody binding to cells expressing human SIRPγ (NP_061026.2) is evaluated by flow cytometry. SIRPγ-expressing CHO cells are blocked with donkey IgG and incubated on ice with increasing concentrations of antibody for 60 minutes, washed and stained with AF647-conjugated donkey F(ab')$_2$ anti-human IgG secondary reagent. Cells are washed, fixed, and analyzed by flow cytometry. Median fluorescent intensity is determined and used as a measure of antibody binding.

Figure 9:
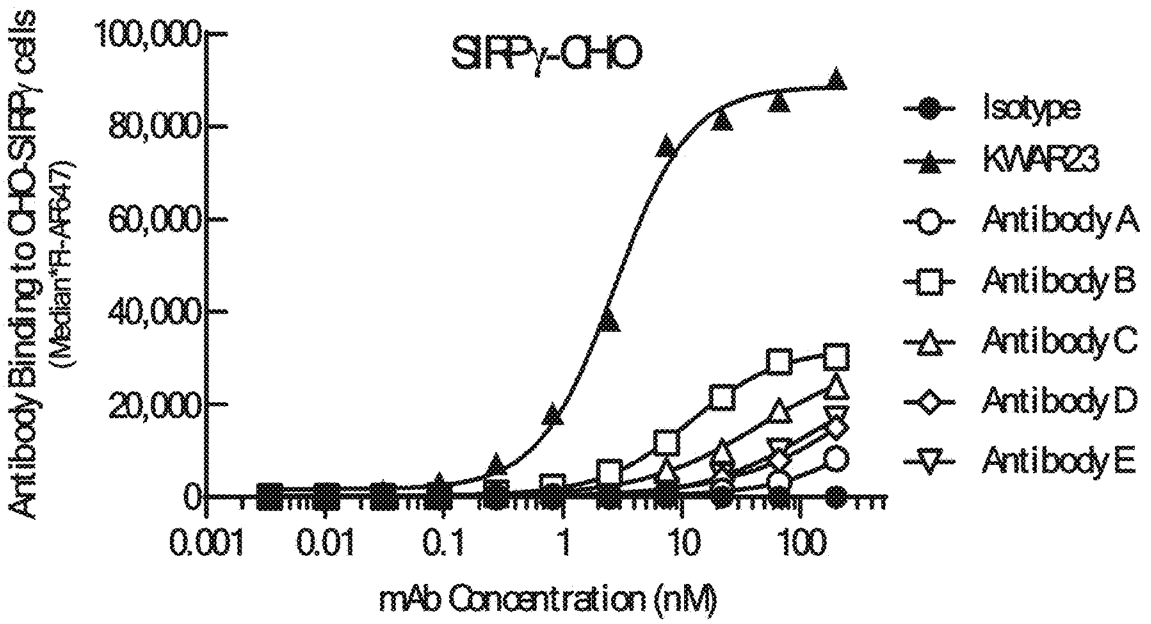
FIG. 9 is a graph depicting the binding of antibodies to full-length human SIRPγ expressed on CHO cells. Antibody binding to CHO cells expressing full-length human SIRPγ (NP_061026.2).
Figure 10A:
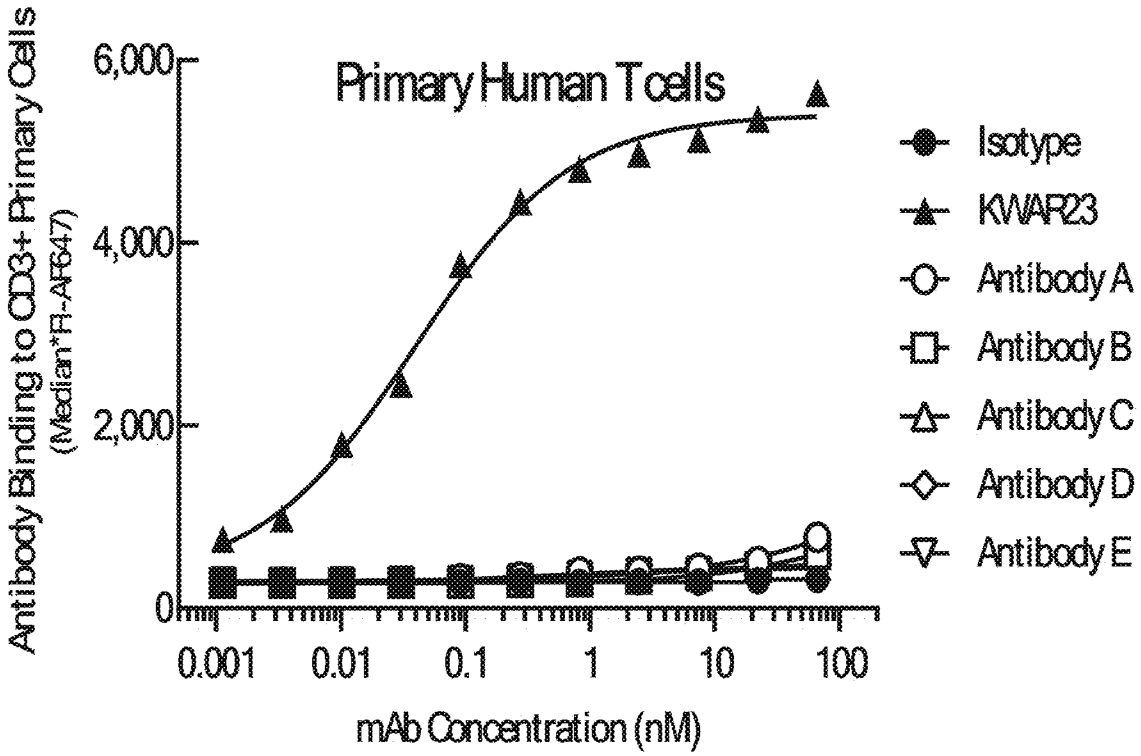
FIGS. 10A-10D are series of graphs depicting the binding of antibodies to primary human CD3+ T cells. Antibody binding to primary human CD3+ T cells (FIGS. 10A-10D). Solid, dashed, and dotted lines indicate antibody molecules engineered on hIgG1 (LALA), hIgG4P, hIgG1 (K322A) backbones, respectively.
Figure 10B:
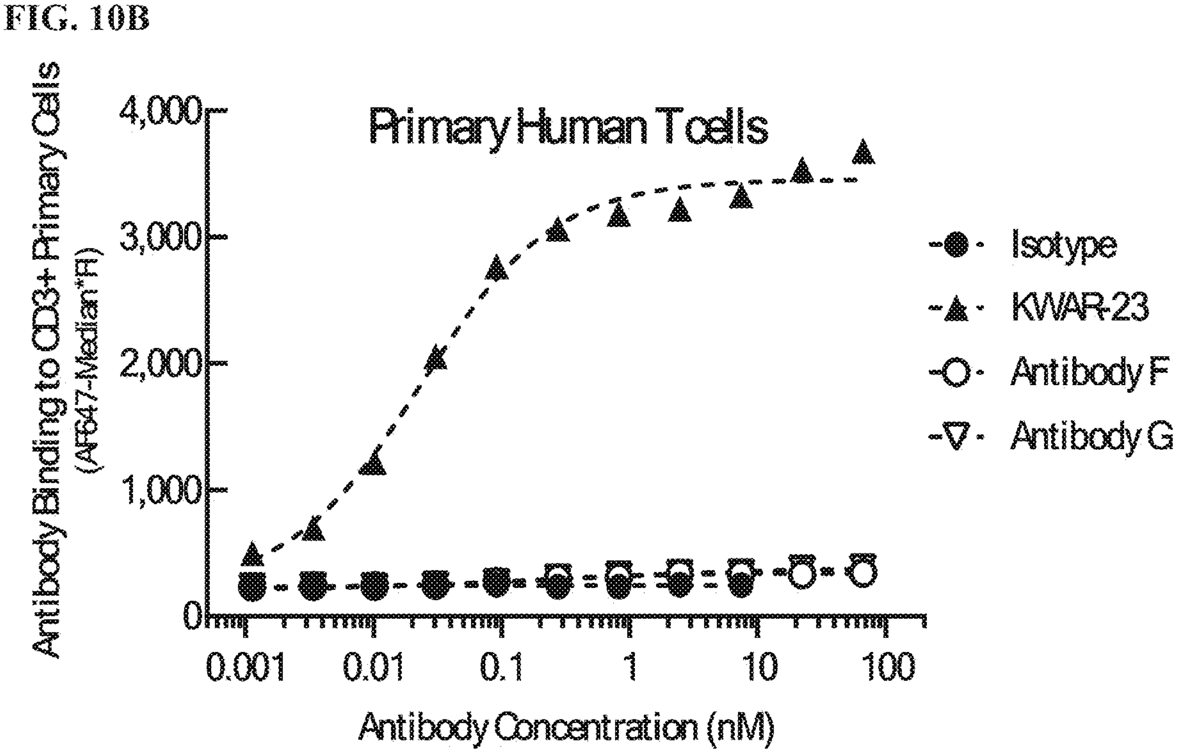
Figure 10C:
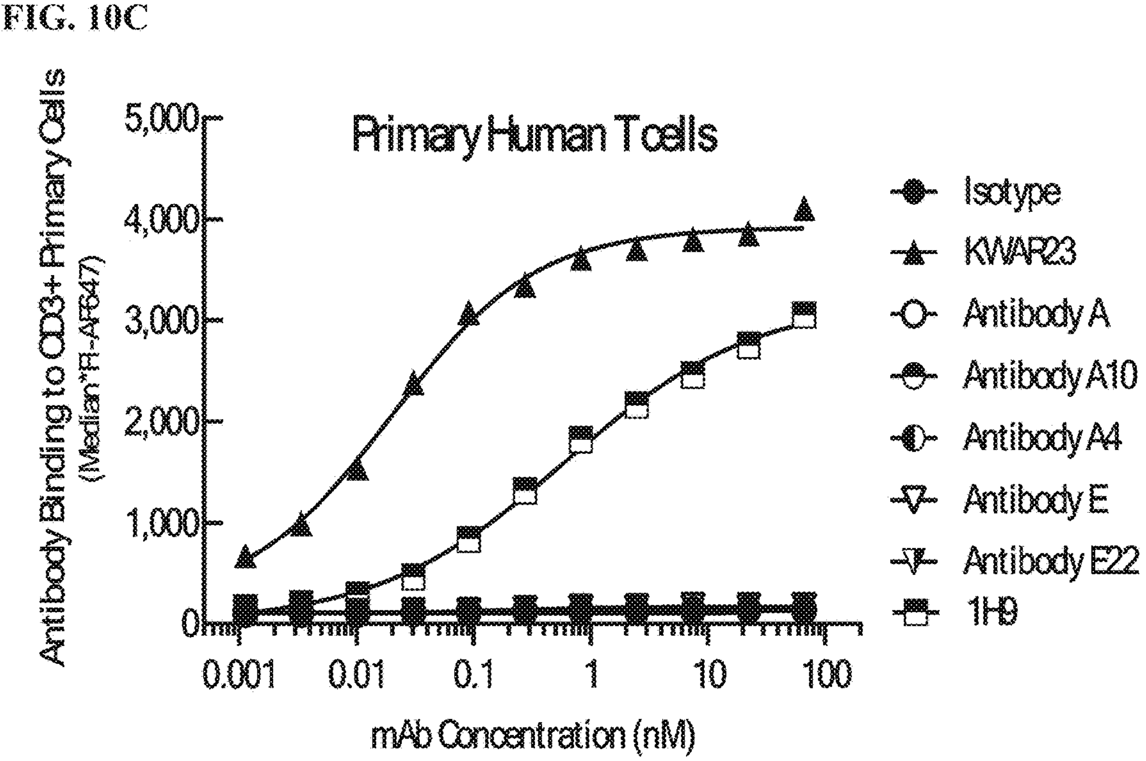
Figure 10D:
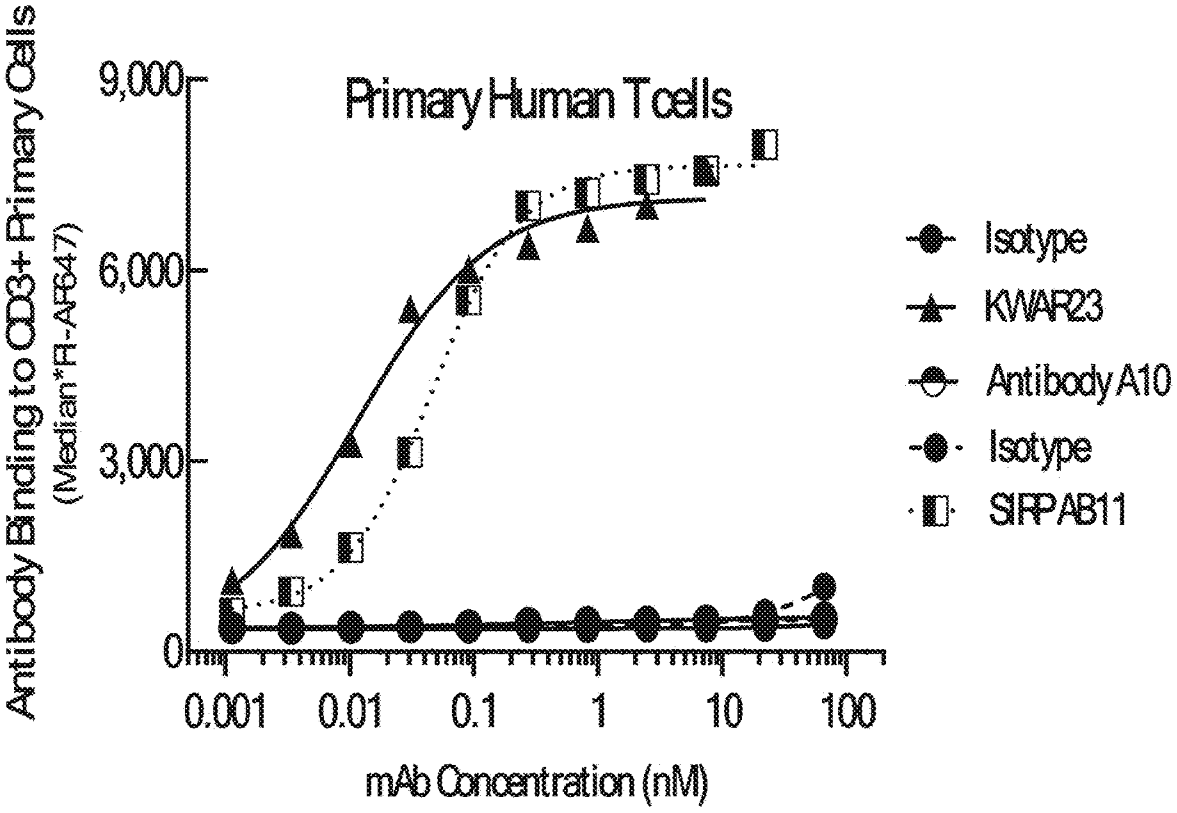

Binding for each of the antibodies on SIRPγ-expressing CHO cells was detected relative to isotype control (FIG. 9). Compared to SIRPγ-reactive mAb (KWAR23) that exhibited an EC$_{50}$ of 2.7 nM (Table 47), binding of antibodies A and C-E was non-saturable at concentrations as high as 200 nM and the magnitude of bound antibody detected was low.

Example 10. Binding of Antibodies to SIRPγ Expressed on Primary Human T Cells Antibody binding to primary human T cells expressing endogenous SIRPγ is evaluated by flow cytometry. Human peripheral blood mononuclear cells (PBMCs) are blocked with donkey IgG and incubated on ice with increasing concentrations of antibody for 60 minutes, washed and stained with AF647-conjugated donkey F(ab')$_2$ anti-human IgG secondary reagent. Human PBMCs are subsequently blocked with Human TruStain FcX™ (Biolegend) and stained with BUV395-conjugated anti-human CD3 (BD Biosciences, clone SK7). Cells are washed, fixed, and analyzed by flow cytometry. Median fluorescent intensity of CD3+ gated population is determined and used as a measure of antibody binding.

Binding of known anti-SIRPα antibodies, KWAR23, 1H9 and SIRPAB11, to primary human T cells is also assessed as described above. KWAR23, 1H9 and SIRP AB11 demonstrated dose-dependent binding to primary human CD3+ cells (FIGS. 10A-10D) with $EC_{50}$ values less than 1 nM (Table 47), while no binding by antibodies A-G, A10, A4, A11, and E22 was detected.

TABLE 47

$EC_{50}$ of Anti-SIRPα antibodies

| Antibody | $EC_{50}$; nM ± SD (n) | | |
|---|---|---|---|
| | recombinant hSIRPγ | CHO-hSIRPγ | primary CD3 + cells |
| Isotype | NB (n = 1) | NB (n = 1) | NB (n = 18) |
| KWAR23 | 0.1 (n = 1) | 2.7 (n = 1) | 0.03 ± 0.01 (n = 15) |
| Antibody A | NB (n = 1) | NS (n = 1) | NB (n = 15) |
| Antibody B | NB (n = 1) | 11.8 (n = 1) | NB (n = 3) |
| Antibody C | NB (n = 1) | NS (n = 1) | NB (n = 3) |
| Antibody D | NB (n = 1) | NS (n = 1) | NB (n = 3) |
| Antibody E | NB (n = 1) | NS (n = 1) | NB (n = 15) |
| Antibody F | NT | NT | NB (n = 3) |
| Antibody G | NT | NT | NB (n = 3) |
| Antibody A10 | NT | NT | NB (n = 12) |
| Antibody A4 | NT | NT | NB (n = 9) |
| Antibody E22 | NT | NT | NB (n = 9) |
| Antibody A11 | NT | NT | NB (n = 3) |
| 1H9 | NT | NT | 0.2 ± 0.1 (n = 2) |
| SIRPAB11 | NT | NT | 0.02 ± 0.004 (n = 3) |

NB No binding
NT Not tested
NS Non-saturable binding

Example 11. Blocking of Human CD47 Binding to Full-Length Human V1-SIRPα or V2-SIRPα Expressed on CHO Cells Human CD47 tetramers are assembled using biotinylated human CD47 (NP_942088; AcroBiosystems) and AF647-conjugated streptavidin (Biolegend). To assess antibody ligand blocking potential, CHO-K1 cells expressing full-length human SIRPαV1 (NP_542970.1) or CHO-K1 cells expressing full-length human SIRPαV2 (CAA71403.1) are co-incubated with increasing concentrations of antibody and a fixed concentration of human CD47 tetramer on ice for 60 min. Cells are washed, fixed, and analyzed by flow cytometry. Median fluorescent intensity is determined and used as a measure of CD47 binding.

Figure 11A:
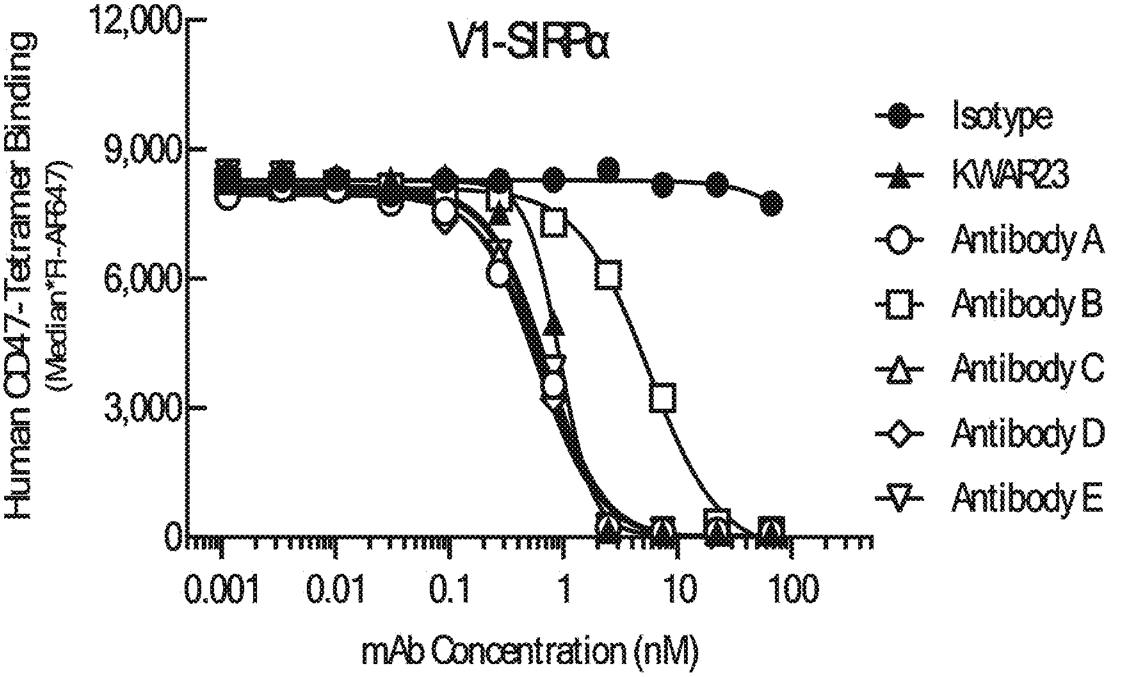
FIG. 11A and FIG. 11B are series of graphs depicting the blocking of human CD47 binding to human SIRPα. Figure A. Antibodies block human CD47 binding to CHO cells expressing full-length human SIRPαV1 (NP_542970.1). Figure B. Antibodies block human CD47 binding to CHO cells expressing full-length human SIRPαV2 (CAA71403.1).
Figure 11B:
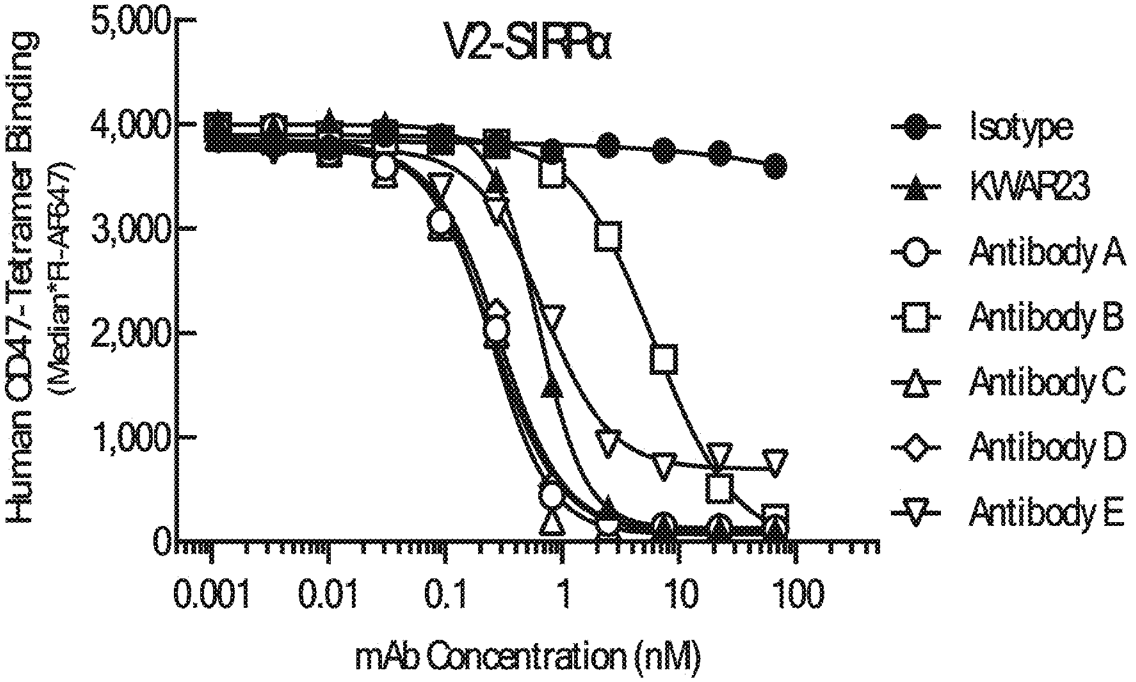
Figure 12A:
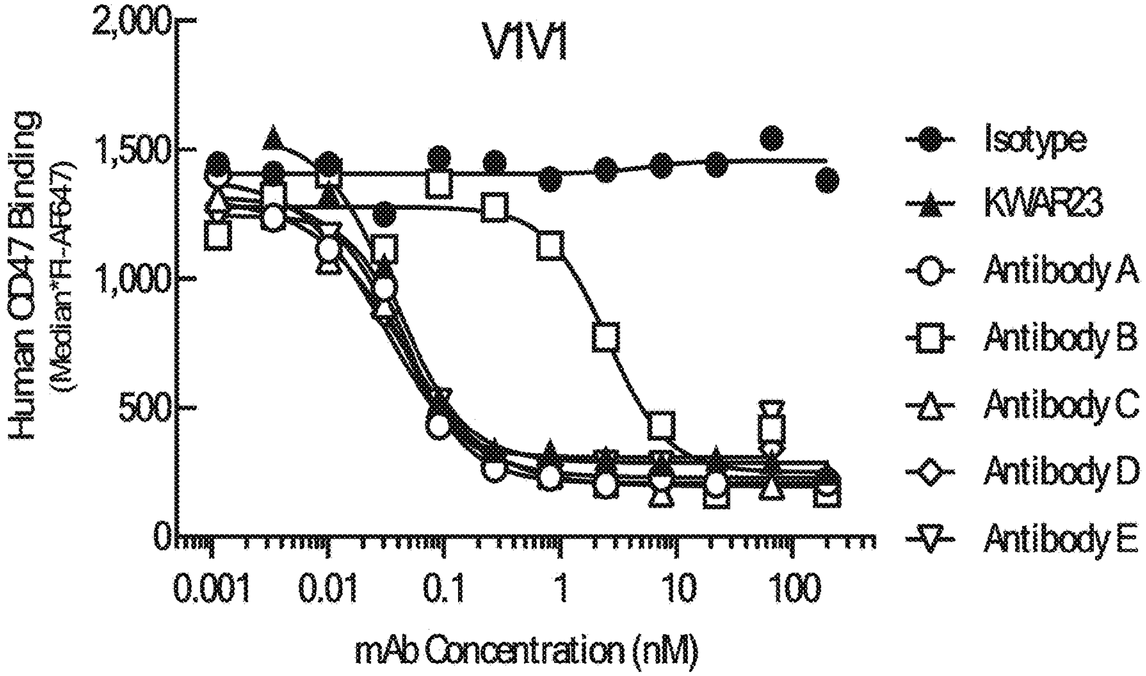
FIGS. 12A-12D are series of graphs depicting the blocking of human CD47 binding to SIRPα expressed on primary cells. Antibodies block human CD47 binding to primary human CD14+ monocytes from donors homozygous for V1 (FIGS. 12A-12D). Solid, dashed, and dotted lines indicate antibody molecules engineered on hIgG1 (LALA), hIgG4P, hIgG1 (K322A) backbones, respectively.
Figure 12B:
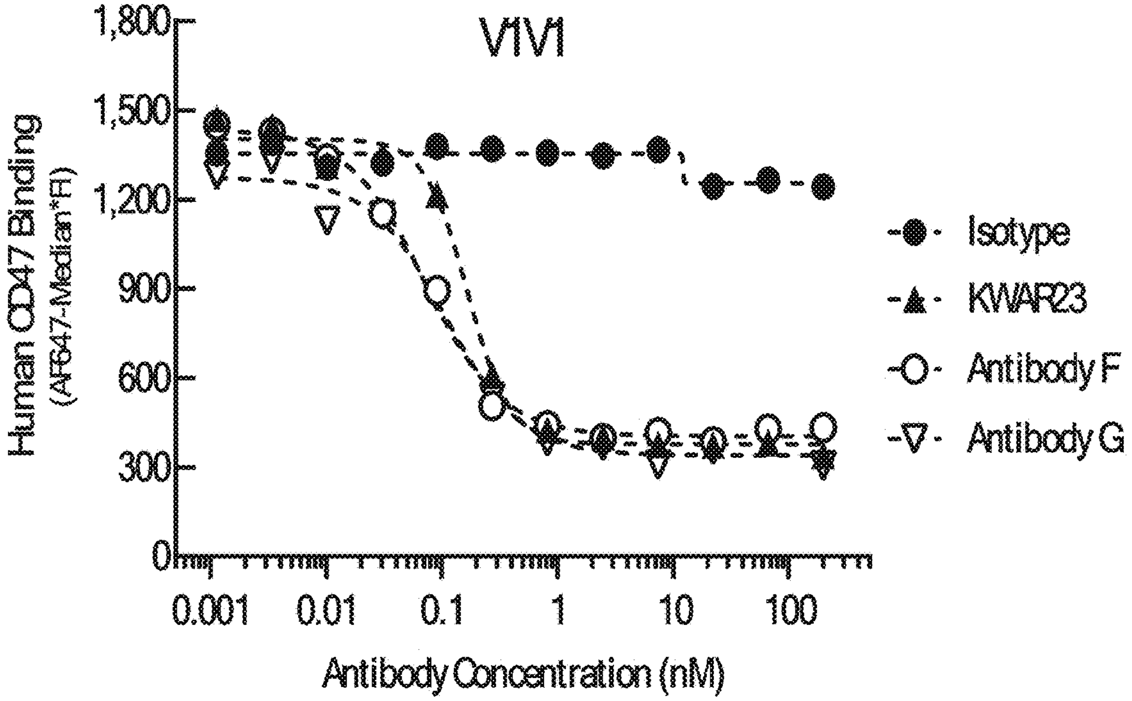
Figure 12C:
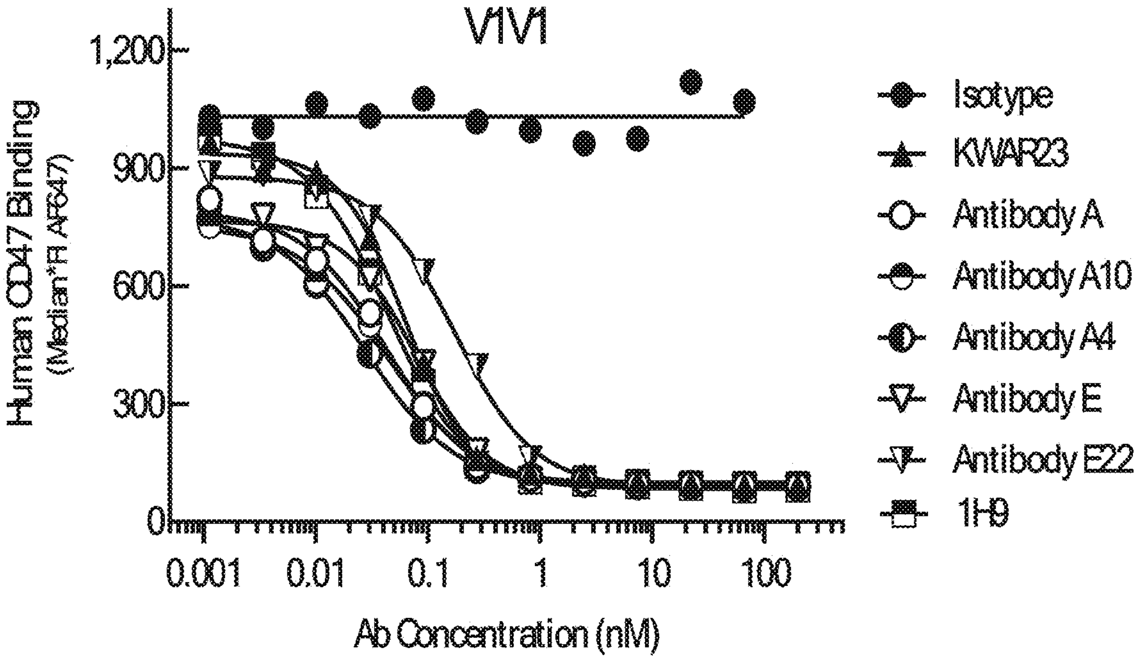
Figure 12D:
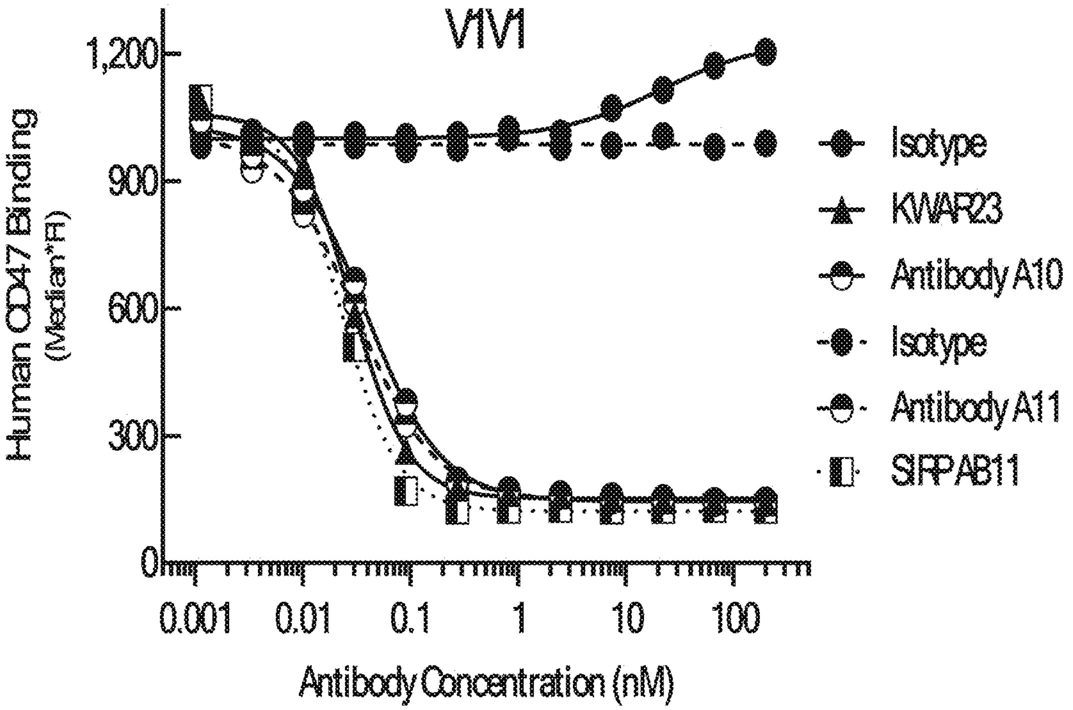
Figure 13A:
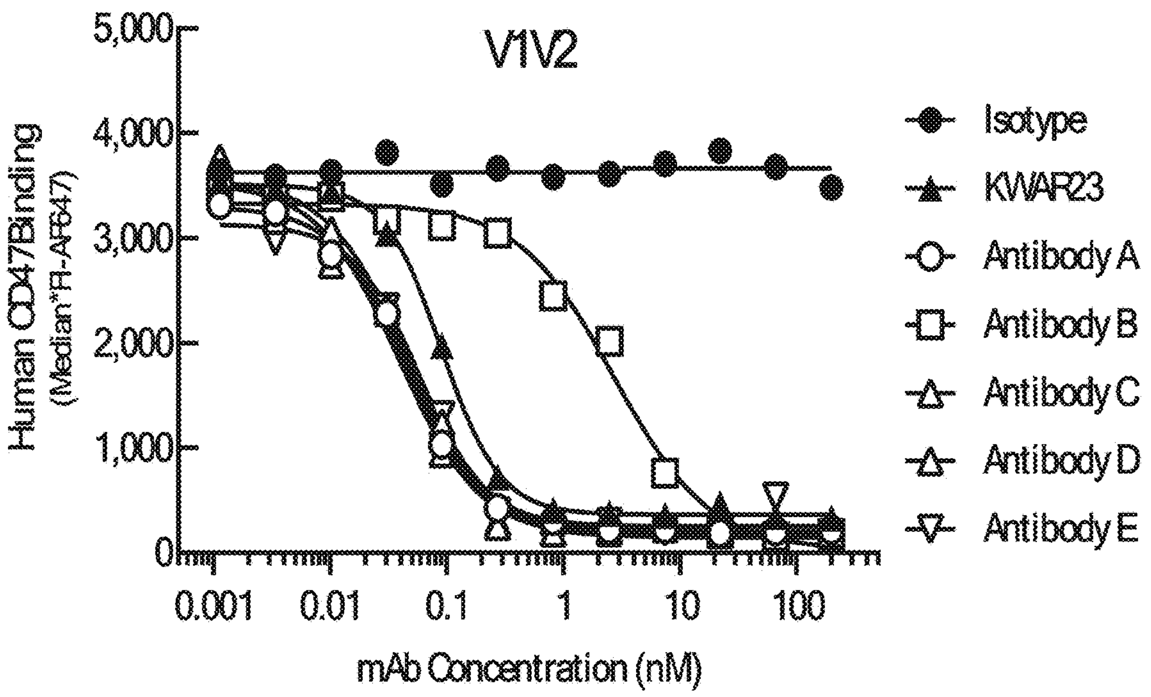
FIGS. 13A-13D are series of graphs depicting the blocking of human CD47 binding to SIRPα expressed on primary cells. Antibodies block human CD47 binding to primary human CD14+ monocytes from donors heterozygous for V1- and V2-SIRPα alleles. Solid, dashed, and dotted lines indicate antibody molecules engineered on hIgG1 (LALA), hIgG4P, hIgG1 (K322A) backbones, respectively.
Figure 13B:
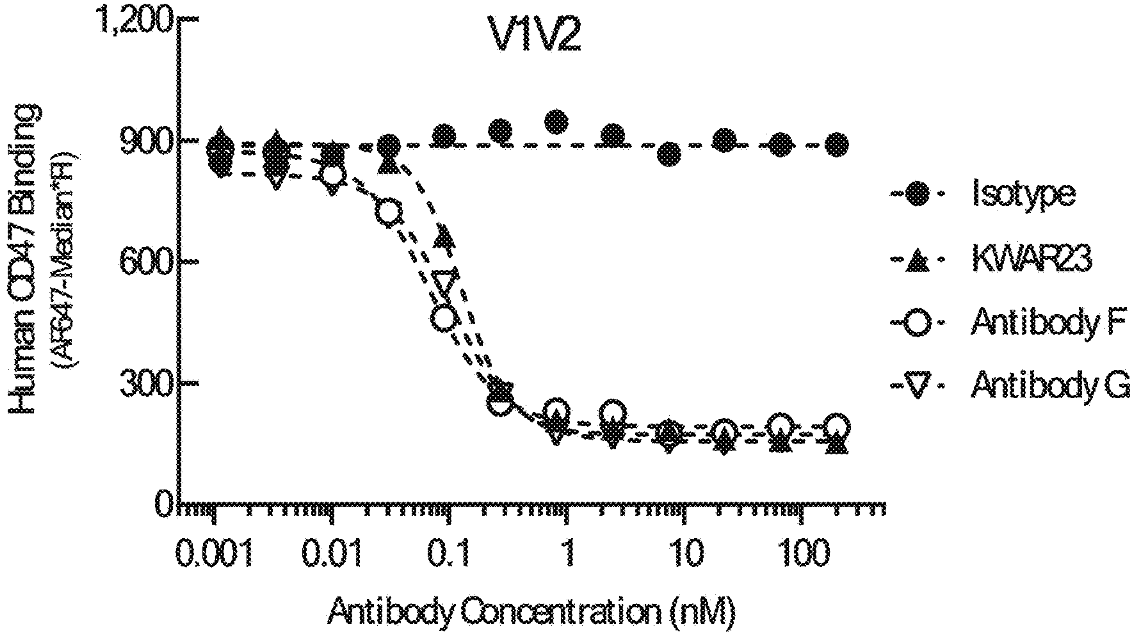
Figure 13C:
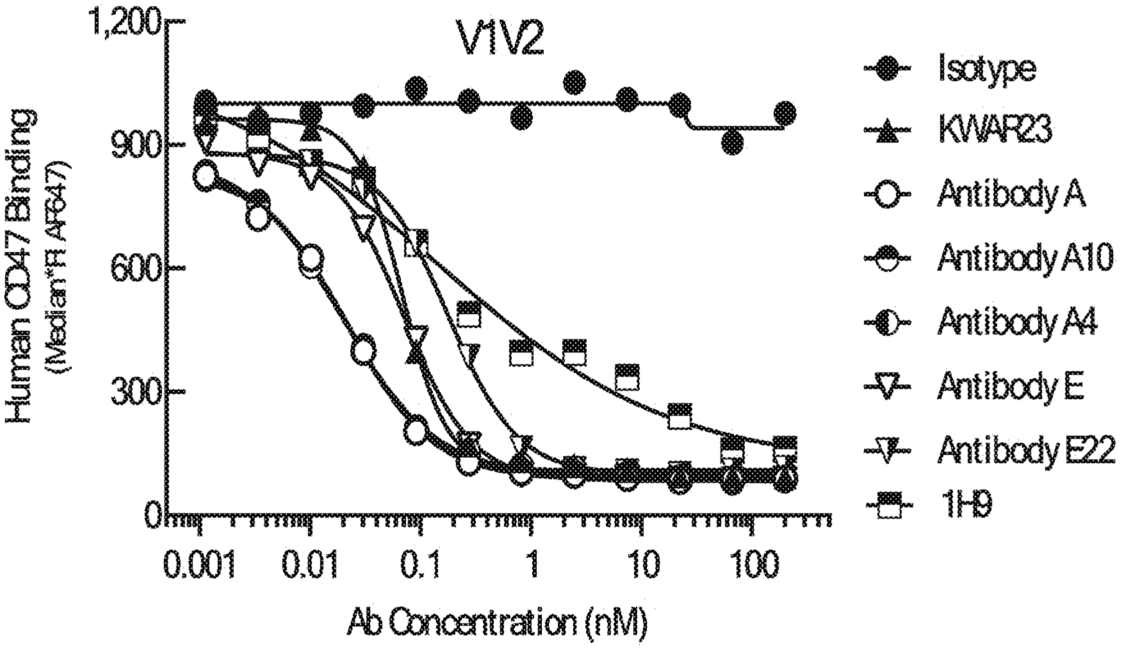
Figure 13D:
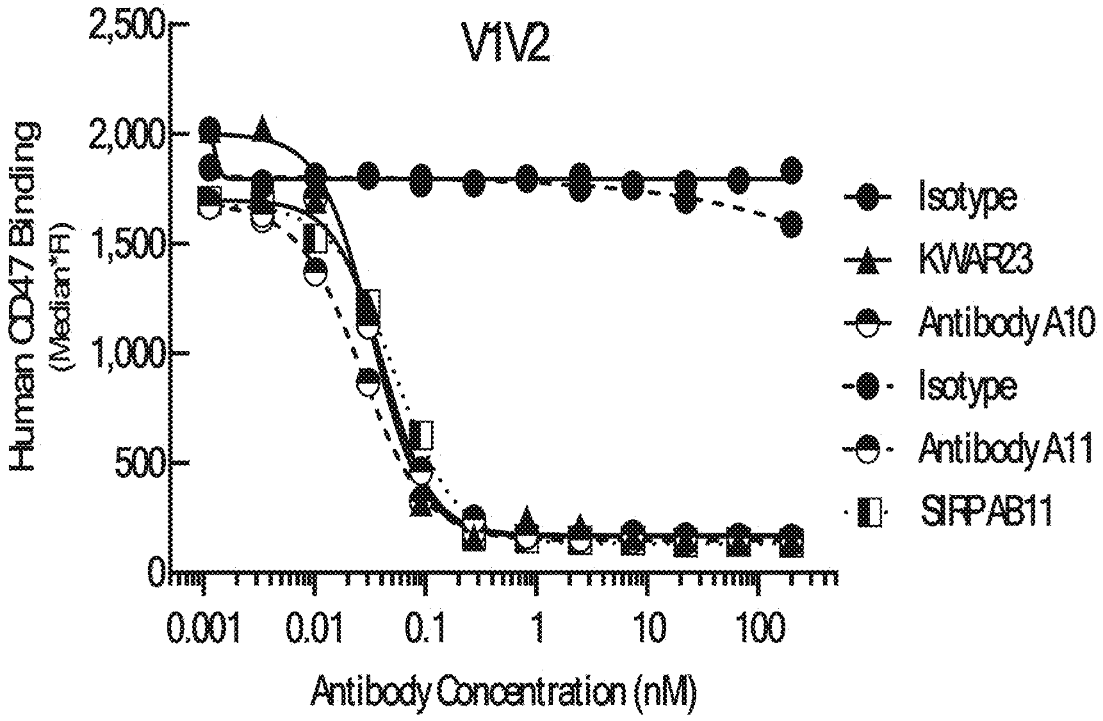

Known KWAR23 antibody and antibodies A-E dose-dependently blocked human CD47 binding to human SIRPαV1 and SIRPαV2-expressing CHO cells (FIGS. 11A and 11B) with half maximal inhibitory concentration ($IC_{50}$) values ranging between 0.3-6.0 nM (Table 48). Blockade of human CD47 binding to human SIRPαV2-expressing CHO cells by antibody E plateaued at about 80%.

TABLE 48

$IC_{50}$ of Anti-SIRPα antibodies

| Antibody | Blockade of Human CD47 Binding; $IC_{50}$ (nM) | |
|---|---|---|
| | CHO-hSIRPαV1 | CHO-hSIRPαV2 |
| Isotype | NB | NB |
| KWAR23 | 0.9 | 0.6 |
| Antibody A | 0.6 | 0.3 |
| Antibody B | 5.6 | 6.0 |
| Antibody C | 0.7 | 0.3 |
| Antibody D | 0.6 | 0.3 |
| Antibody E | 0.7 | 0.7* |

NB No blockade
*Inhibition plateaus at <100%

Example 12. Blocking of Human CD47 Binding to Endogenous Human V1-SIRPα and/or V2-SIRPα Expressed on Primary Human Monocytes Human CD47 tetramers are assembled using biotinylated human CD47 (NP_942088; AcroBiosystems) and AF647-conjugated streptavidin (Biolegend). Human peripheral blood mononuclear cells (PBMCs) from donors genotyped as homozygous for the SIRPα V1 allele, V2 allele, or heterozygous for both alleles are blocked with Human TruStain FcX™ (Biolegend) and co-incubated with increasing concentrations of antibody, a fixed concentration of human CD47 tetramer and BV421-conjugated anti-human CD14 on ice for 60 min. Cells are washed, fixed, and analyzed by flow cytometry. Median fluorescent intensity of CD14+ gated population is determined and used as a measure of CD47 binding.

Antibodies A-G, A10, A4, E22, and A11, but not isotype control, dose-dependently blocked human CD47 binding to primary human monocytes from donors homozygous for V1 (FIGS. 12A-12D) or V2 (FIGS. 14A-14D) alleles or heterozygous for both alleles (FIGS. 13A-13D). Aside from Antibody B, all antibodies exhibited $IC_{50}$ values less than 1 nM (Table 49).

Figure 14A:
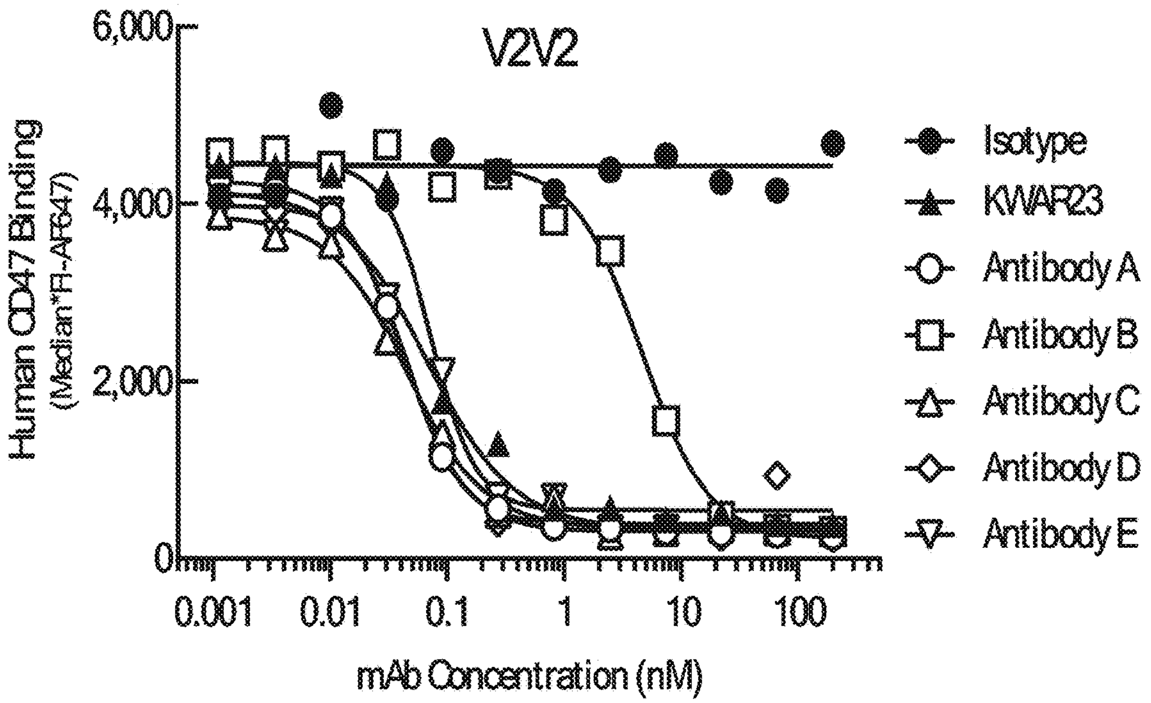
FIGS. 14A-14D are series of graphs depicting the blocking of human CD47 binding to SIRPα expressed on primary cells. Antibodies block human CD47 binding to primary human CD14+ monocytes from donors homozygous for V2 alleles. Solid, dashed, and dotted lines indicate antibody molecules engineered on hIgG1 (LALA), hIgG4P, hIgG1 (K322A) backbones, respectively.
Figure 14B:
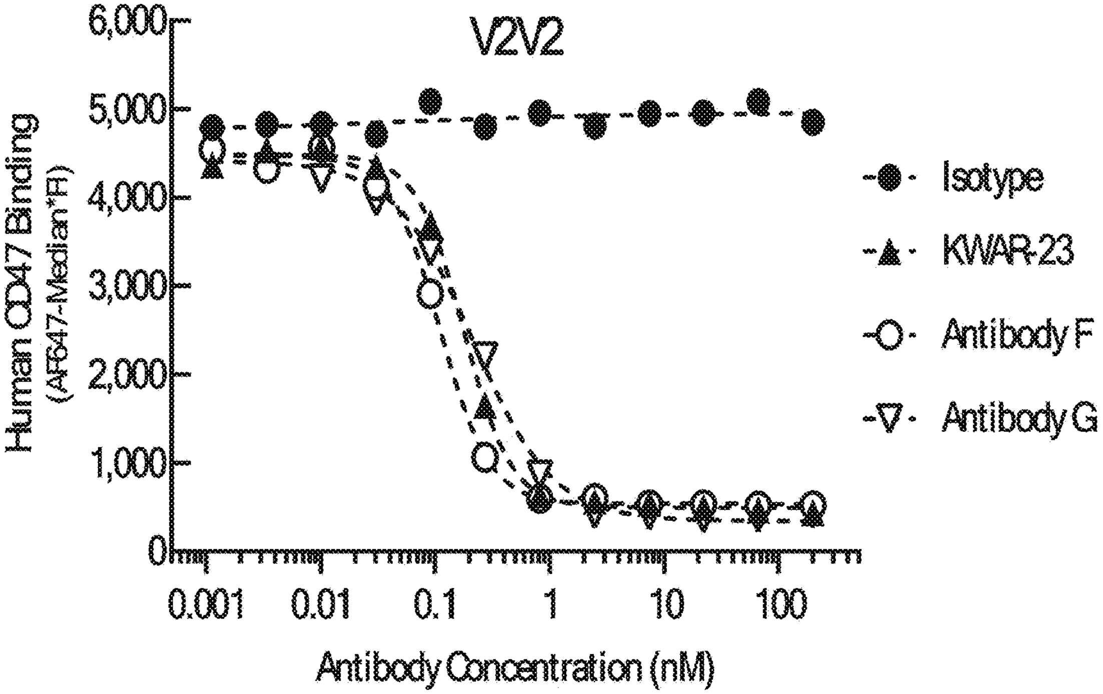
Figure 14C:
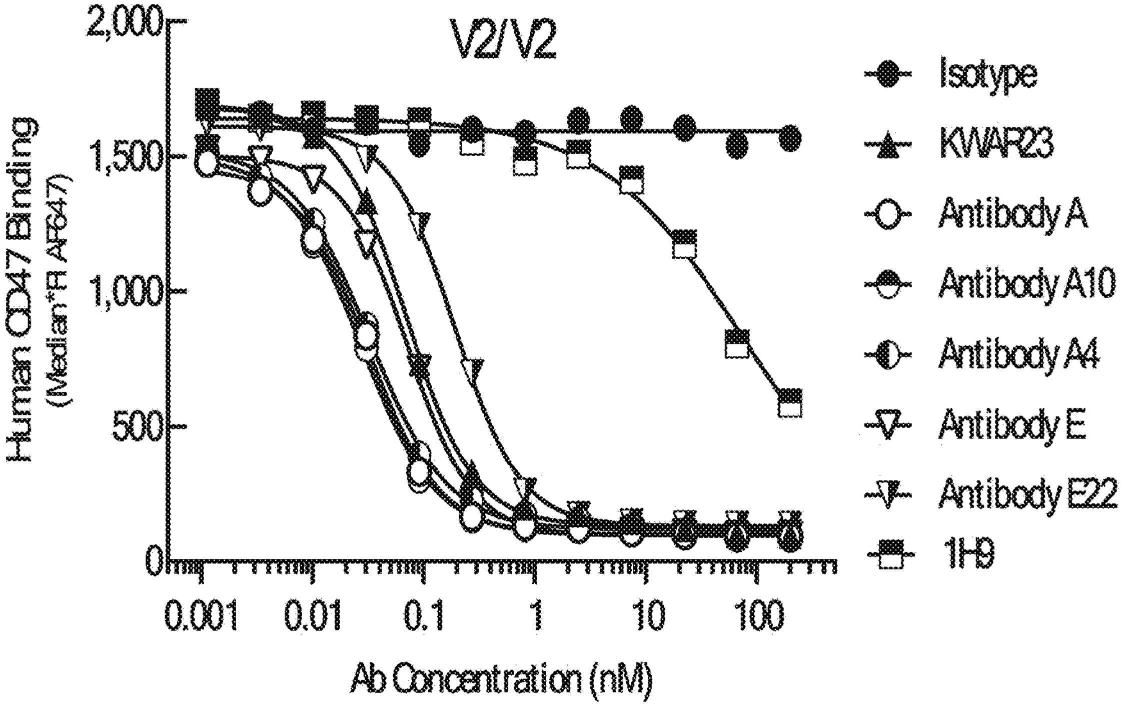
Figure 14D:
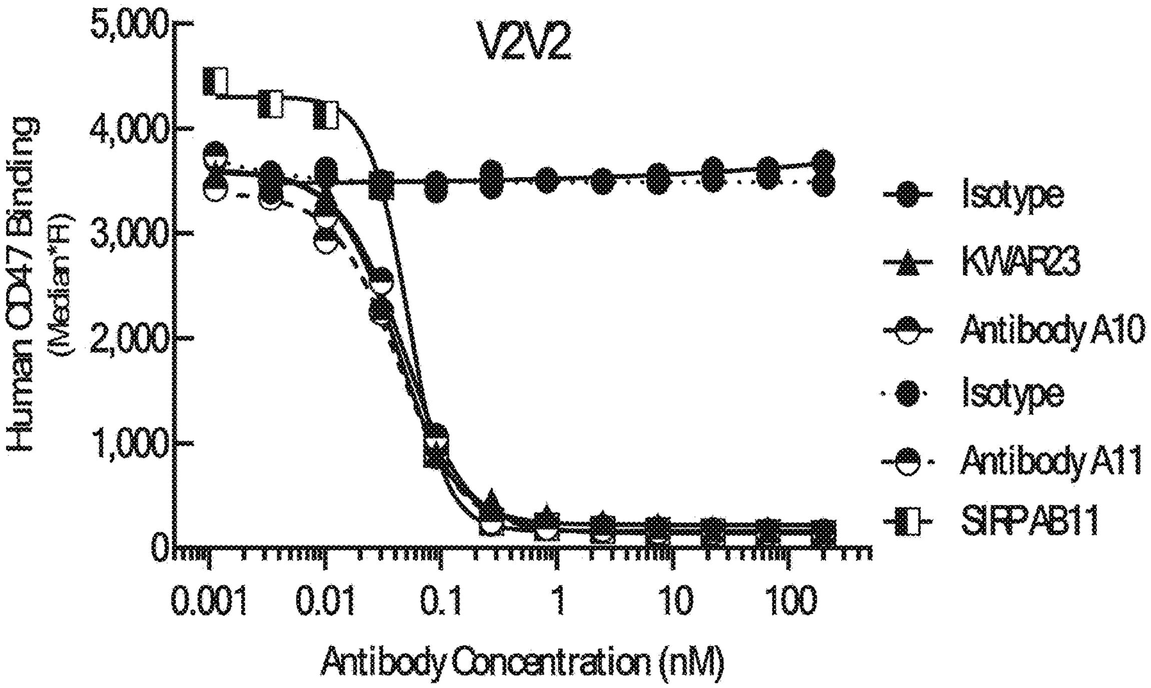
Figure 15A:
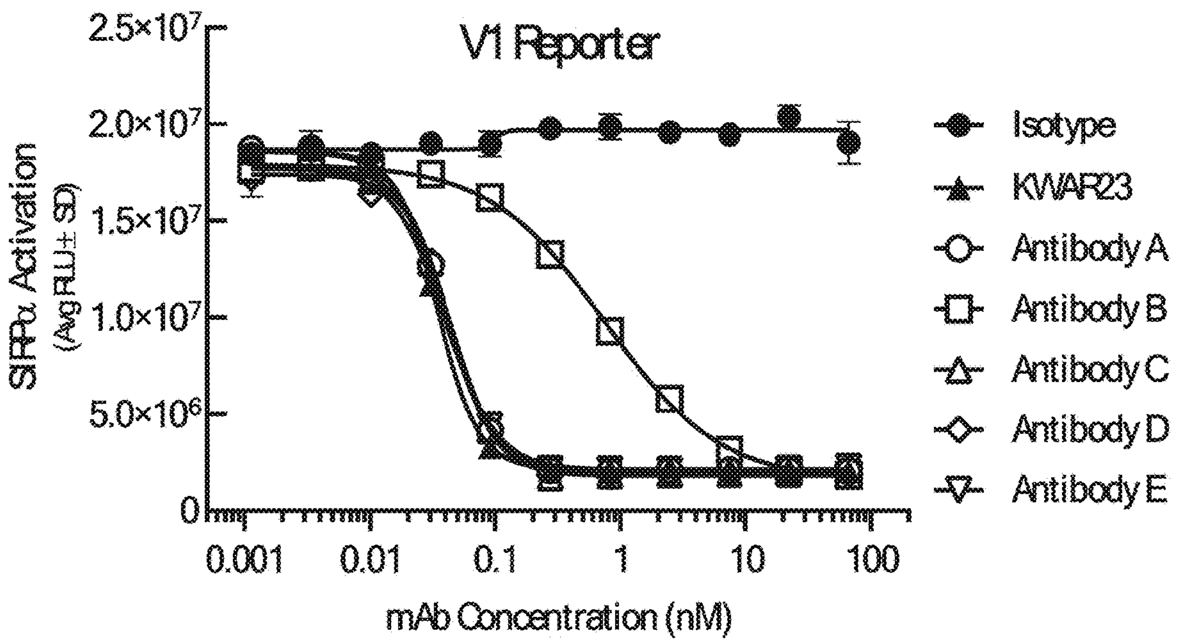
FIGS. 15A-15D are series of graphs showing that the cellular CD47-mediated SIRPα activation blocked by anti-SIRPα antibodies. Antibodies dose-dependently block cellular CD47-mediated V1-SIRPα signaling (FIGS. 15A-15D). Solid, dashed, and dotted lines indicate antibody molecules engineered on hIgG1 (LALA), hIgG4P, hIgG1 (K322A) backbones, respectively.
Figure 15B:
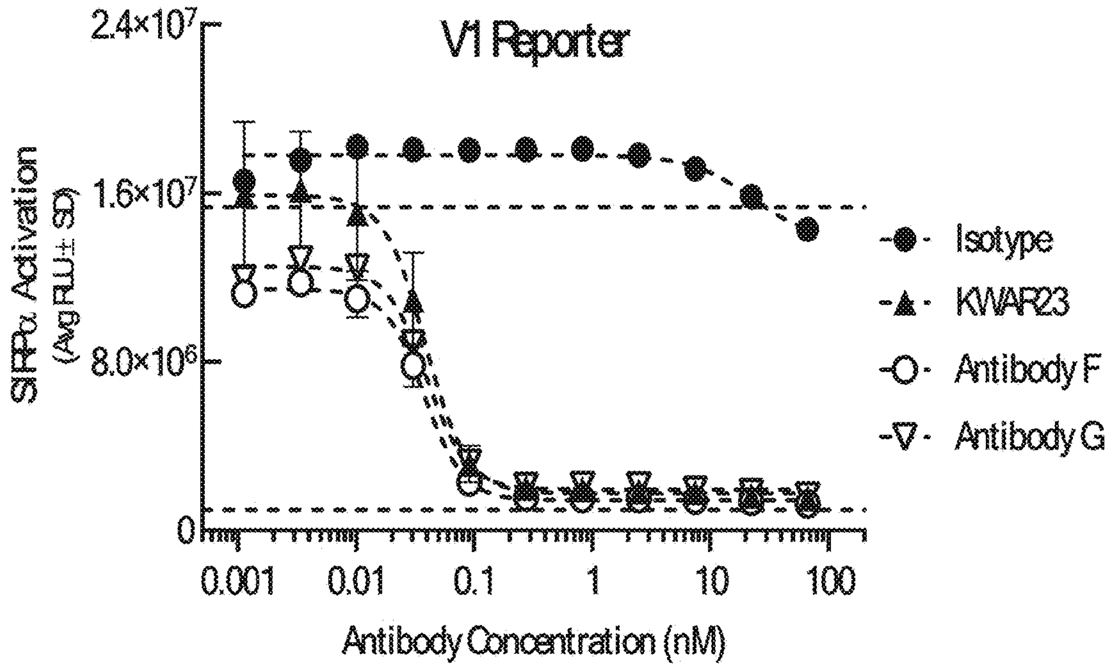
Figure 15C:
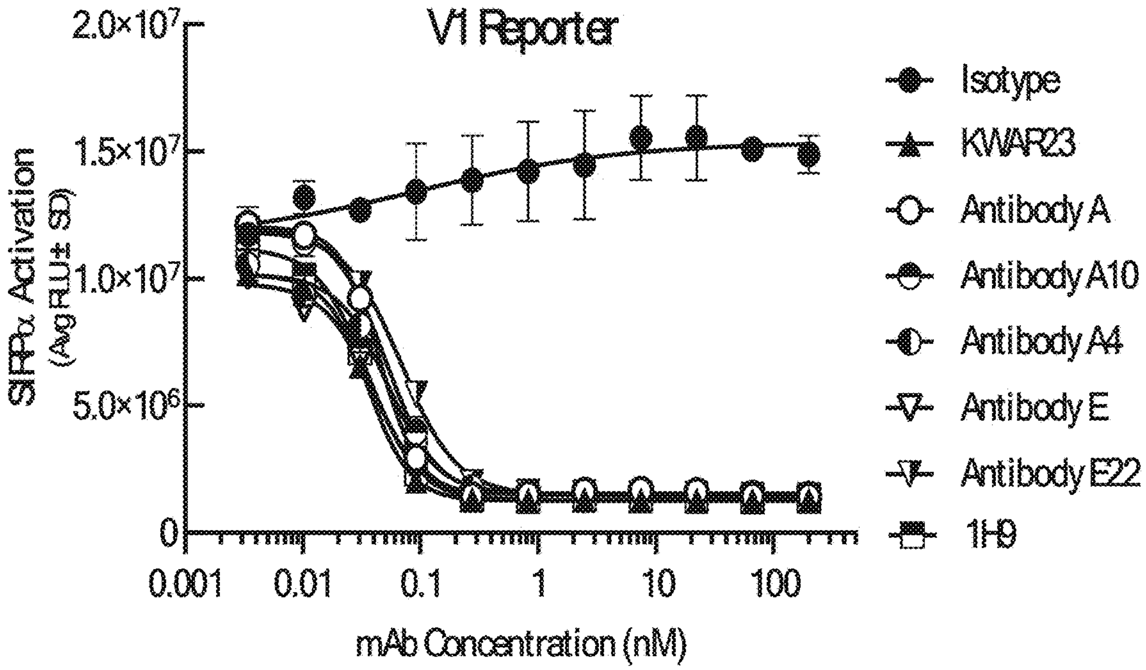
Figure 15D:
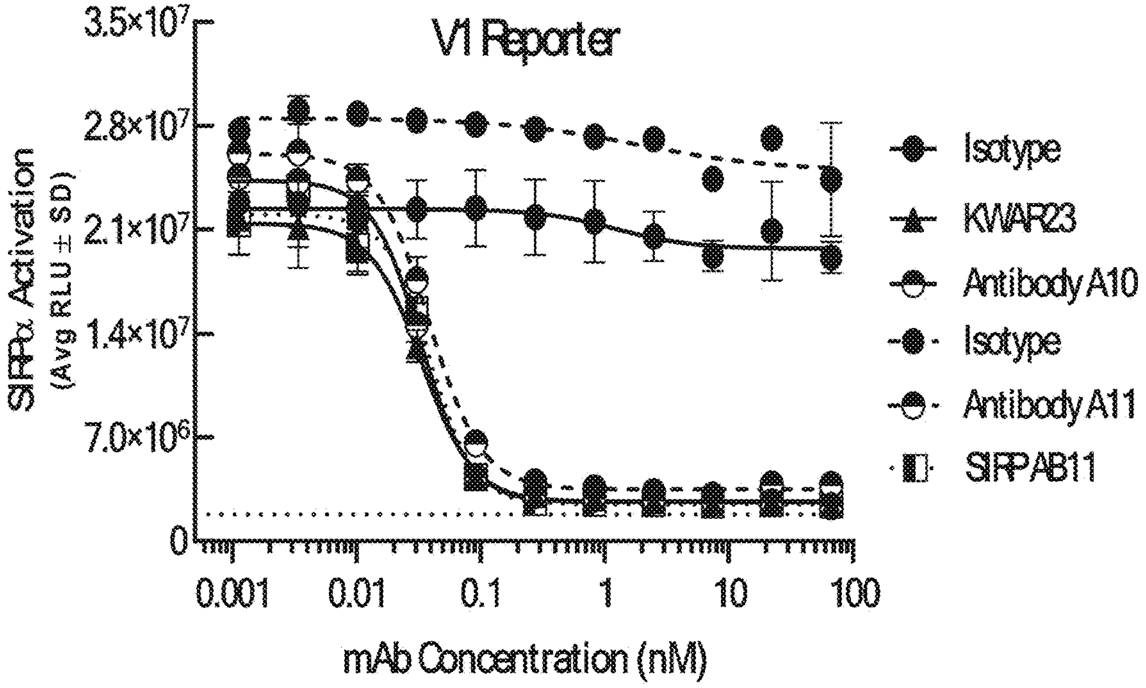
Figure 16A:
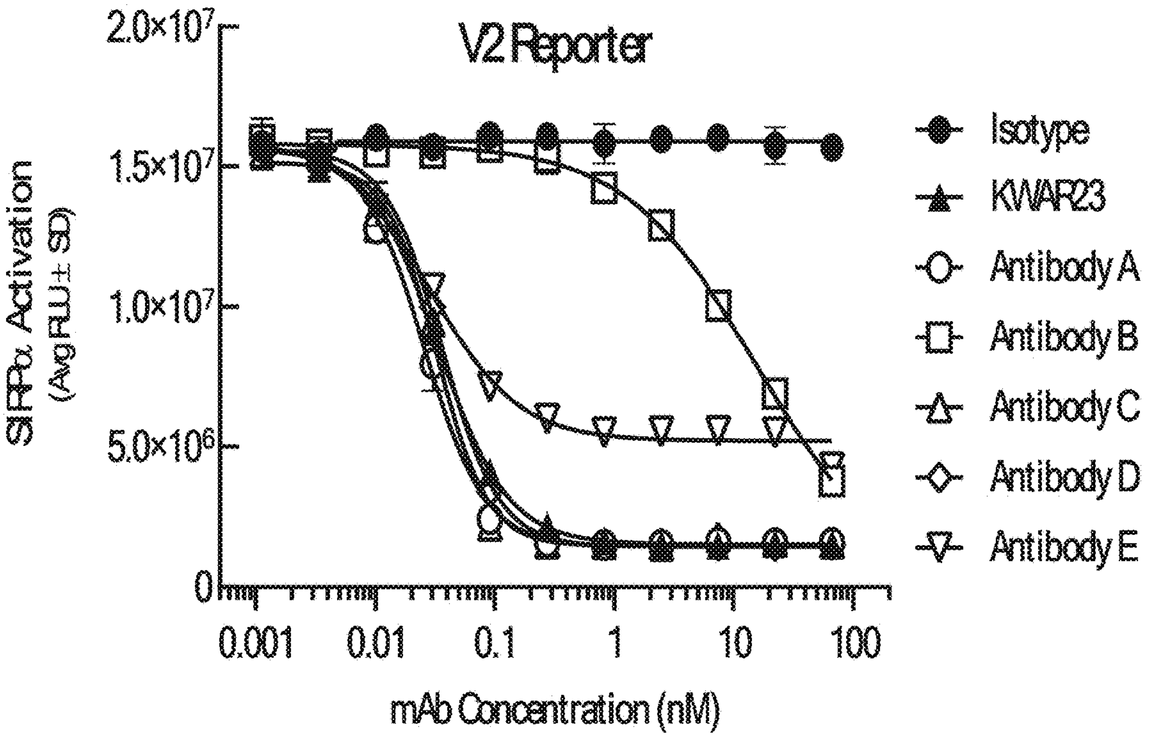
FIGS. 16A-16D are series of graphs showing that the cellular CD47-mediated SIRPα activation blocked by anti-SIRPα antibodies. Antibodies dose-dependently block cellular CD47-mediated V2-SIRPα signaling (FIGS. 16A-16D). Solid, dashed, and dotted lines indicate antibody molecules engineered on hIgG1 (LALA), hIgG4P, hIgG1 (K322A) backbones, respectively.
Figure 16B:
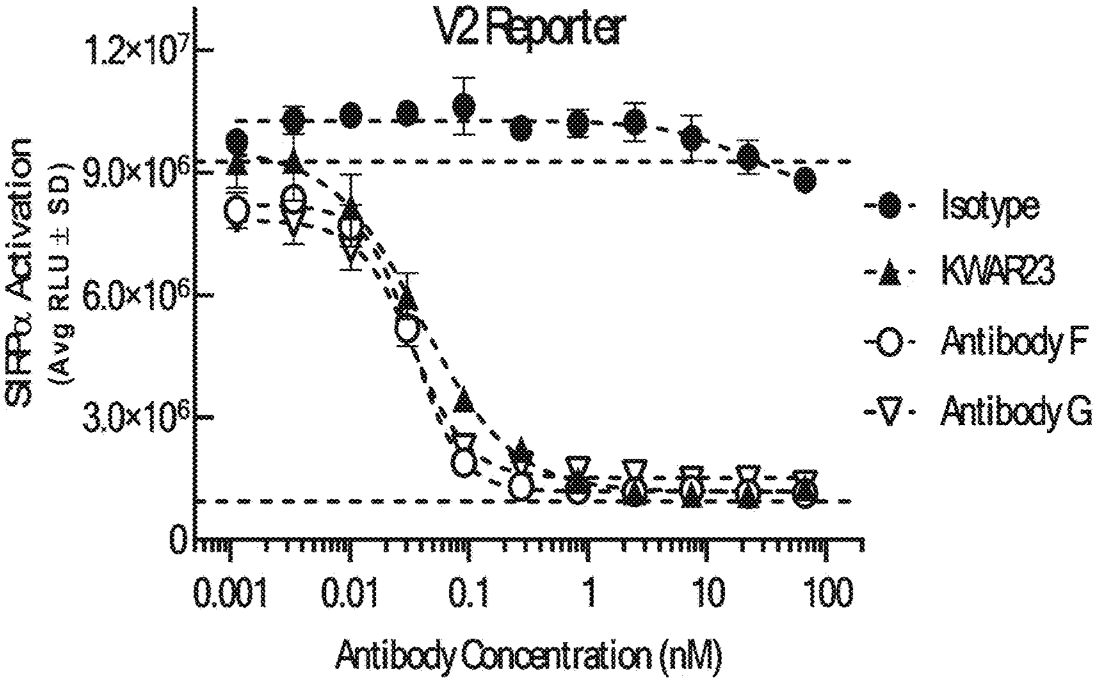
Figure 16C:
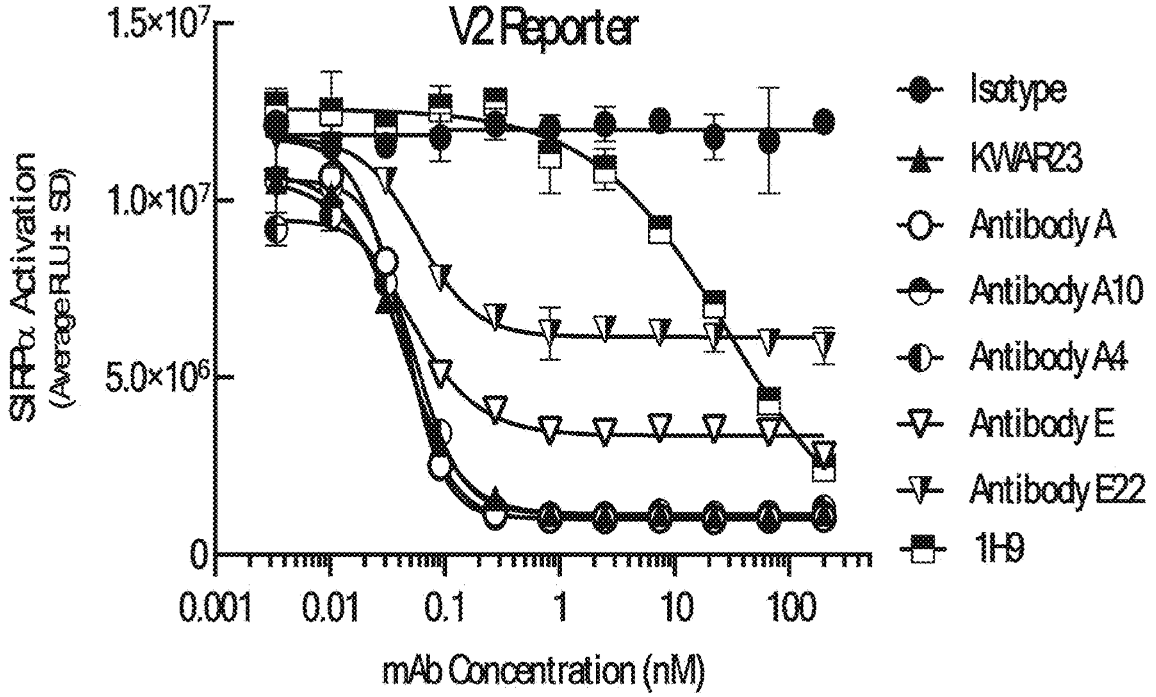
Figure 16D:
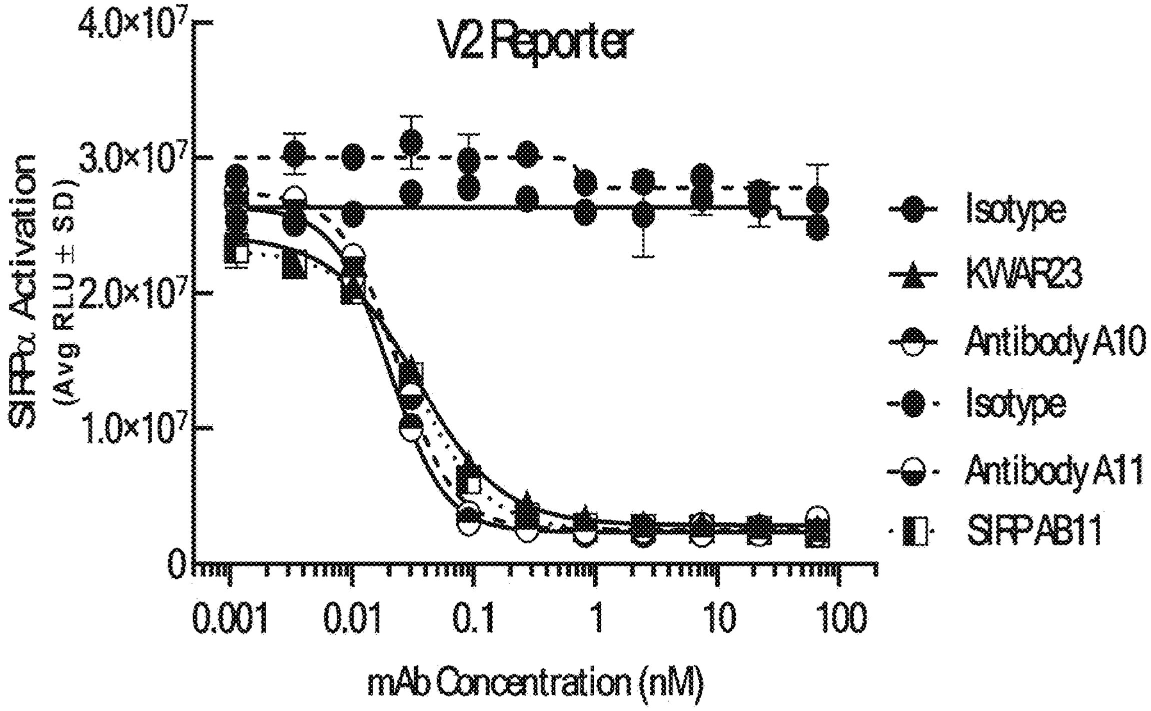

The ability of known anti-SIRPα antibodies, KWAR23, 1H9 and SIRPAB11, to block human CD47 binding to primary human monocytes is assessed as described above. While 1H9 blocked human CD47 from binding to primary human monocytes from donors homozygous for V1 alleles (FIG. 12C) or heterozygous for both alleles (FIG. 13C) with subnanomolar $IC_{50}$ values (Table 49), incomplete blockade to primary human monocytes from donors homozygous for V2 alleles was observed (FIG. 14C). KWAR23 and SIRPAB11 antibodies blocked human CD47 binding to primary human monocytes from donors of all genotypes (FIGS. 12A-12D, 13A-13D and 14A-14D; Table 49).

TABLE 49

$IC_{50}$ of Anti-SIRPα antibodies

| Antibody | Blockade of Human CD47 Binding; $IC_{50,}$ nM ± SD (n) | | |
|---|---|---|---|
| | V1V1 | V1V2 | V2V2 |
| Isotype | NB (n = 6) | NB (n = 6) | NB (n = 6) |
| KWAR23 | 0.07 ± 0.04 (n = 6) | 0.10 ± 0.06 (n = 6) | 0.11 ± 0.06 (n = 6) |
| Antibody A | 0.06 ± 0.03 (n = 5) | 0.07 ± 0.05 (n = 5) | 0.06 ± 0.03 (n = 5) |
| Antibody B | 2.55 (n = 1) | 2.77 (n = 1) | 4.60 (n = 1) |
| Antibody C | 0.04 (n = 1) | 0.04 (n = 1) | 0.05 (n = 1) |
| Antibody D | 0.03 (n = 1) | 0.04 (n = 1) | 0.05 (n = 1) |
| Antibody E | 0.09 ± 0.03 (n = 5) | 0.10 ± 0.04 (n = 5) | 0.11 ± 0.04 (n = 5) |

TABLE 49-continued

IC$_{50}$ of Anti-SIRPα antibodies

| Antibody | Blockade of Human CD47 Binding; IC$_{50}$, nM ± SD (n) | | |
|---|---|---|---|
| | V1V1 | V1V2 | V2V2 |
| Antibody F | 0.07 (n = 1) | 0.07 (n = 1) | 0.11 (n = 1) |
| Antibody G | 0.11 (n = 1) | 0.11 (n = 1) | 0.22 (n = 1) |
| Antibody A10 | 0.05 ± 0.01 (n = 4) | 0.07 ± 0.08 (n = 4) | 0.05 ± 0.02 (n = 4) |
| Antibody A4 | 0.04 ± 0.01 (n = 3) | 0.05 ± 0.04 (n = 3) | 0.07 ± 0.04 (n = 3) |
| Antibody E22 | 0.25 ± 0.10 (n = 3) | 0.36 ± 0.21 (n = 3) | 0.30 ± 0.10 (n = 3) |
| Antibody A11 | 0.03 (n = 1) | 0.03 (n = 1) | 0.05 (n = 1) |
| 1H9 | 0.04 (n = 1) | 0.15 (n = 1) | NS (n = 1) |
| SIRPAB11 | 0.02 (n = 1) | 0.05 (n = 1) | 0.05 (n = 1) |

NB No Blockade
NS Non-saturable inhibition

Example 13. Blocking Human V1-SIRPα and V2-SIRPα Signaling Dependent on Cellular CD47 Expression A SIRPα signaling assay is used to measure SIRPα engagement induced by CD47 presented via cell-cell interaction. Detection of SIRPα signaling in this assay relies on enzyme fragment complementation (EFC). EFC uses a complementation system in β-galactosidase, which consists of the enzyme donor (ED) and the enzyme acceptor (EA) fragments. Independently, these fragments have no β-gal enzymatic activity; however, when brought into proximity they form an active β-gal enzyme. The reporter Jurkat cells are devoid of CD47 and stably co-express an ED-tagged SIRPα receptor and EA-tagged SH2 domain of the SHP-1 phosphatase. When the reporter cells are exposed to donor cells (Jurkat cells expressing endogenous levels of CD47), SIRPα is phosphorylated and recruits SHP-1 phosphatase. This interaction forces ED and EA fragments complementation and formation of active β-gal enzyme that is capable of hydrolyzing substrate to generate a chemiluminescent signal as a measure of receptor activation.

Jurkat SIRPα-V1 or -αV2 signaling cells (20,000) are incubated with serially titrated antibodies in 96-well white-bottom TC treated plates for 1 h at 37° C., 5% $CO_2$ prior to the addition of Jurkat$^{Parental}$ cells (30,000) in a total volume of 100 μl in PathHunter cell plating 0 reagent. Plates are incubated in a humidified incubator for 5 hours at 37° C., 5% $CO_2$. Following the addition of PathHunter BioAssay Detection Reagents and incubation at room temperature in the dark, the plates are read on an EnVision® luminometer. Average RLU units are plotted as a measure of receptor activation.

Antibodies A-G, A10, A4, E22, and A11, but not isotype control, completely blocked cellular CD47-mediated SIRPαV1 activation (FIGS. 15A-15D) with subnanomolar IC$_{50}$ values (Table 48). Similarly, all antibodies dose-dependently blocked cellular CD47-mediated SIRPαV2 activation (FIGS. 16A-16D; Table 50), though inhibition by antibodies E and E22 plateaued at about 80% and 55%, respectively and antibody B did not achieve saturable inhibition.

The ability of known SIRPα antibodies, KWAR23, 1 H9 and SIRPAB11, to block cellular CD47-mediated SIRPα signaling is assessed as described above. While 1H9 completely blocked cellular CD47-mediated SIRPαV1 activation with an IC$_{50}$ of 0.04 nM (FIG. 15C; Table 50), blockade of cellular CD47-mediated SIRPαV2 activation did not achieve saturable inhibition (FIG. 16C; Table 50). KWAR23 and SIRP AB11 antibodies were capable of blocking cellular CD47-mediated SIRPα signaling of by cells expressing either SIRPα allele.

TABLE 50

IC$_{50}$ of Anti-SIRPα antibodies

| Antibody | Blockade of Cellular CD47-Mediated SIRPα Signaling; IC$_{50}$, nM ± SD (n) | |
|---|---|---|
| | V1V1 | V2V2 |
| Isotype | NB (n = 6) | NB (n = 6) |
| KWAR23 | 0.04 ± 0.01 (n = 6) | 0.04 ± 0.01 (n = 6) |
| Antibody A | 0.04 ± 0.01 (n = 5) | 0.04 ± 0.01 (n = 5) |
| Antibody B | 0.76 (n = 1) | NS (n = 6) |
| Antibody C | 0.04 (n = 1) | 0.03 (n = 1) |
| Antibody D | 0.04 (n = 1) | 0.04 (n = 1) |
| Antibody E | 0.04 ± 0.01 (n = 5) | 0.04 ± 0.01 (n = 5)* |
| Antibody F | 0.04 (n = 1) | 0.03 (n = 1) |
| Antibody G | 0.04 (n = 1) | 0.03 (n = 1) |
| Antibody A10 | 0.04 ± 0.01 (n = 4) | 0.04 ± 0.01 (n = 4) |
| Antibody A4 | 0.04 ± 0.01 (n = 3) | 0.05 ± 0.01 (n = 3) |
| Antibody E22 | 0.07 ± 0.01 (n = 3) | 0.07 ± 0.01 (n = 3)* |
| Antibody A11 | 0.04 (n = 1) | 0.02 (n = 1) |
| 1H9 | 0.04 (n = 1) | NS (n = 1) |
| SIRPAB11 | 0.04 (n = 1) | 0.03 (n = 1) |

NB No Blockade
NS Non-saturable inhibition
*Inhibition plateaus at <100%

Example 14. SIRPα Antagonist Revert Inhibition of Phagocytosis Caused by CD47 in Human Monocytic Cell Lines A flow-based phagocytosis assay was developed to quantify the SIRPα-mediated regulation of phagocytosis induced by CD47. U-937 cells devoid of endogenous SIRPα are transduced with lentivirus containing full-length V1- or V2-SIRPα alleles. These cells are preincubated with anti-SIRPα antibodies at the indicated concentrations in 96-well V-bottom tissue culture (TC)-treated plates for 30 minutes prior to the addition of fluorescently conjugated microbeads (Spherotech) coated with or without human CD47 (NP_942088; AcroBiosystems) and opsonized with human IgG1 antibodies to induce Fc-receptor mediated phagocytosis. Following a 2 h incubation at 37° C., 5% $CO_2$, samples are washed, blocked with Human TruStain FcX™ (Biolegend) and stained with fluorescently-conjugated antibody that recognize the external surface of the beads to enable differentiation between beads stuck on the outside of the cells and those that were inside. Cells are washed, fixed, and analyzed by flow cytometry. Phagocytosis is represented as the percentage of cells with internalized beads.

Figure 17A:
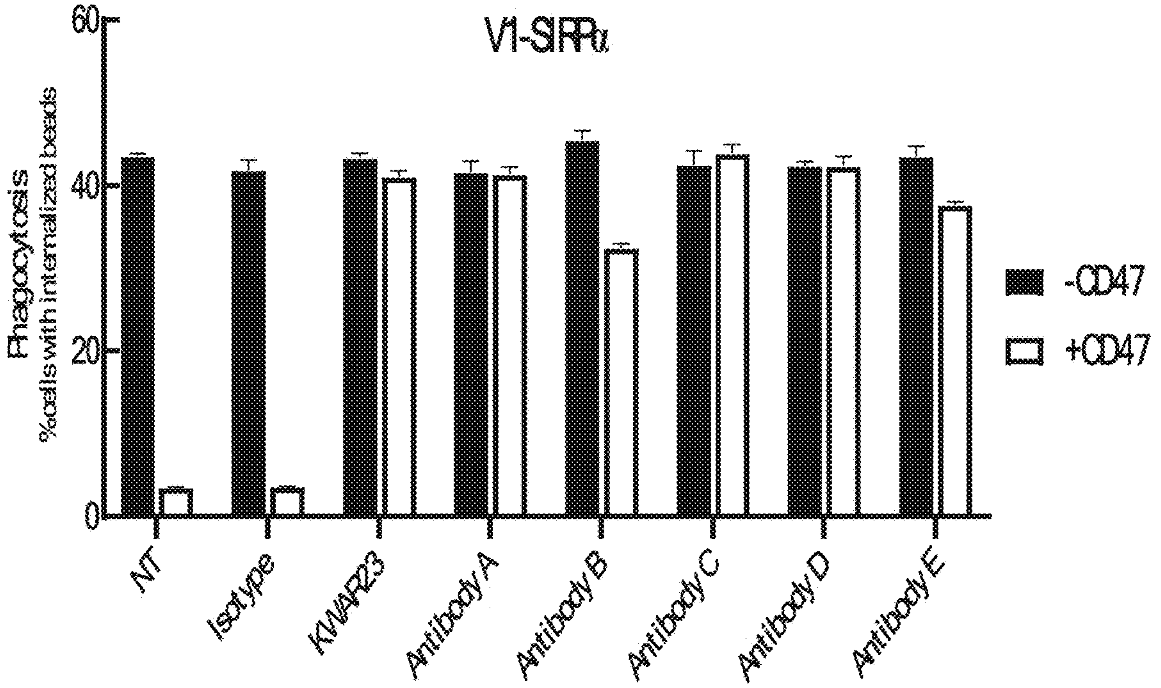
FIG. 17A and FIG. 17B are series of histograms showing that CD47-mediated inhibition of phagocytosis by human monocytic cell lines can be restored by anti-SIRPα antibodies. Anti-SIRPα antibodies restore (FIG. 17A) V1- and (FIG. 17B) V2-SIRPα expressing U937$^{SIRP\alpha\ KO}$ cell's ability to phagocytize CD47-coated beads.
Figure 17B:
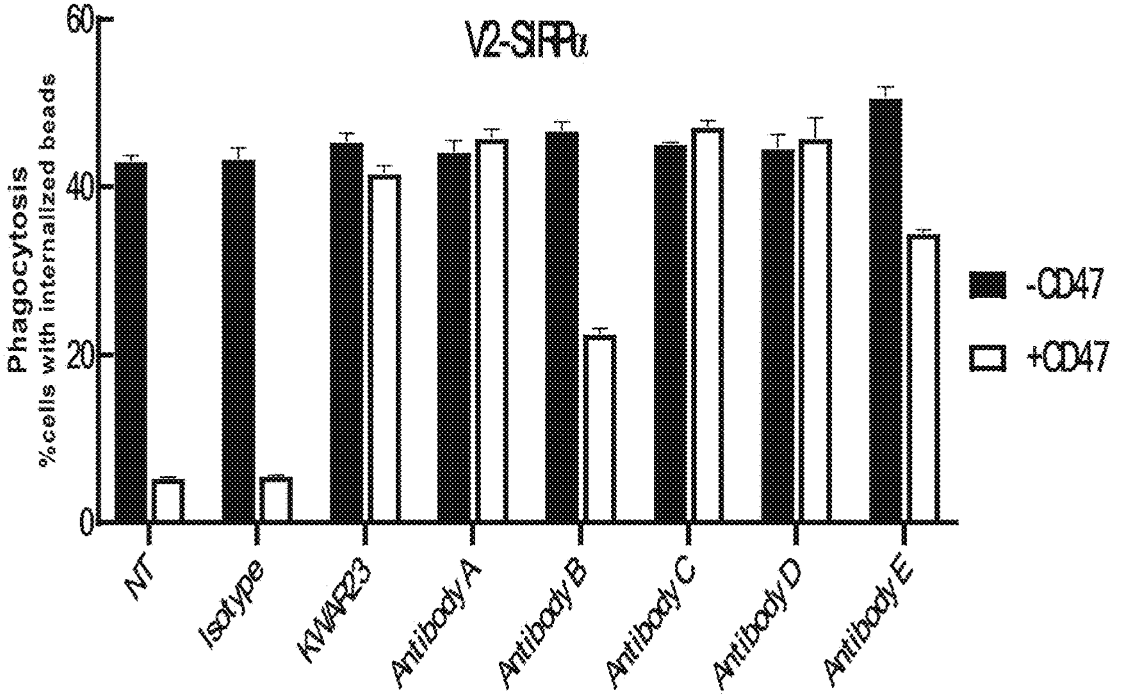

Internalization of opsonized beads by U-937 cells expressing SIRPα for either V1 or V2 alleles dropped when cells were incubated with CD47-coated beads (white bars); an effect not observed when cells were incubated with beads lacking CD47 (black bars). Pre-treatment of cells with 67 nM of the indicated antibodies restored both V1- (FIG. 17A) and V2- (FIG. 17B) SIRPα-expressing U-937 cell's ability to phagocytize CD47-coated beads (white bars) indicating that the antibodies can block CD47-mediated SIRPα signaling.

Example 15. SIRPα Antagonist Revert Inhibition of Phagocytosis Caused by CD47 in Primary Human Monocyte-Derived Macrophages of any Combination of SIRPα Alleles A flow-based phagocytosis assay was developed to quantify the SIRPα-mediated regulation of phagocytosis induced by CD47. Monocytes enriched from human PBMCs (Easy-Sep Monocyte Enrichment Kit, StemCell Technologies) from donors genotyped as homozygous for the SIRPα V1 allele, V2 allele, or heterozygous for both alleles are differentiated into macrophages following 6-7 days of culture in ImmunoCult™-SF macrophage differentiation medium spiked with 50 ng/ml human recombinant M-CSF (Peprotech). Monocyte-derived macrophages (MDMs) are preincubated with anti-SIRPα antibodies at the indicated concentrations in 96-well ultra-low attachment TC plates for 30 minutes prior to the addition of fluorescently conjugated microbeads (Spherotech) coated with or without human CD47 (NP_942088; AcroBiosystems) and with or without human IgG1 opsonization to induce Fc-receptor mediated phagocytosis. Following a 1 h incubation at 37° C., 5% $CO_2$, samples are washed, blocked with Human TruStain FcX™ (Biolegend) and stained with fluorescently-conjugated antibody that recognize the external surface of the beads to enable differentiation between beads stuck on the outside of the cells and those that were inside. Cells are washed, fixed, and analyzed by flow cytometry. Phagocytosis is represented as the percentage of cells with internalized beads.

Figure 18A:
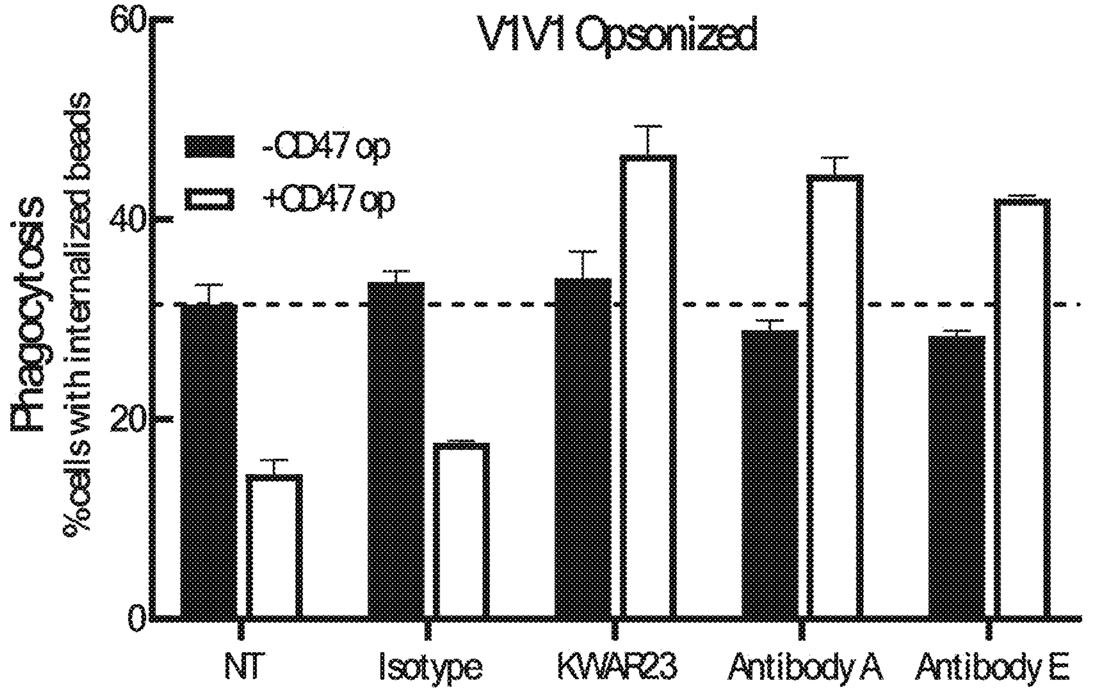
FIGS. 18A-18C are series of histograms and a graph demonstrating that anti-SIRPα antibodies restore CD47-mediated inhibition of phagocytosis by primary human macrophages derived from donors homozygous for V1-SIRPα allele.
Figure 18B:
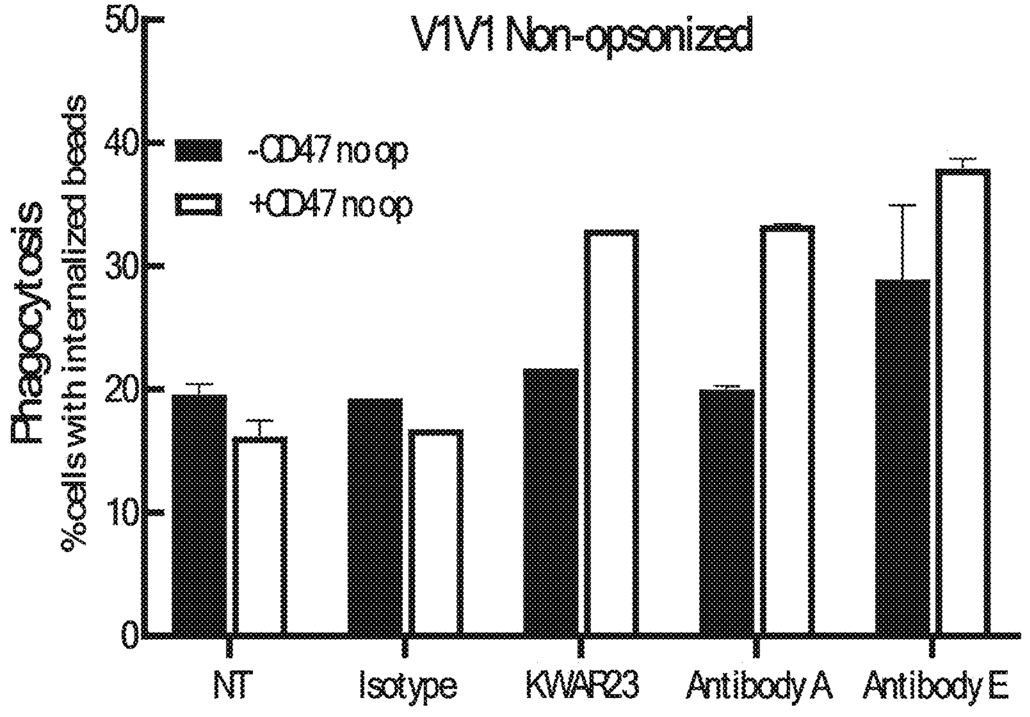
Figure 18C:
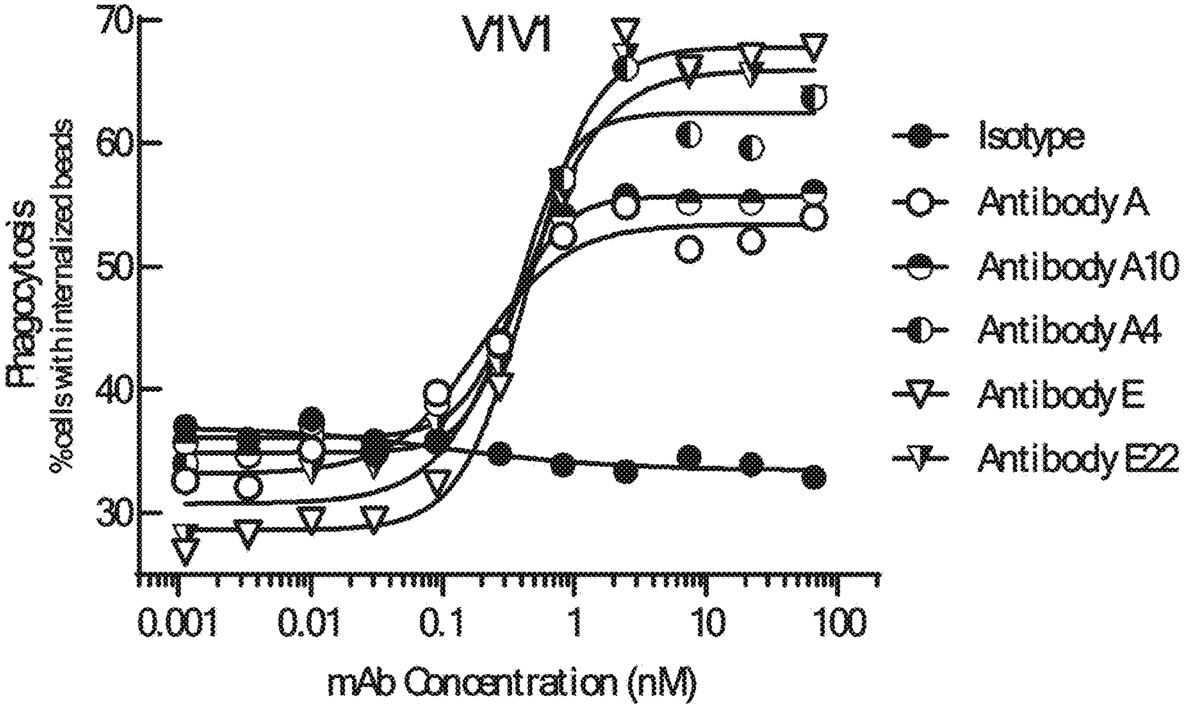
Figure 19A:
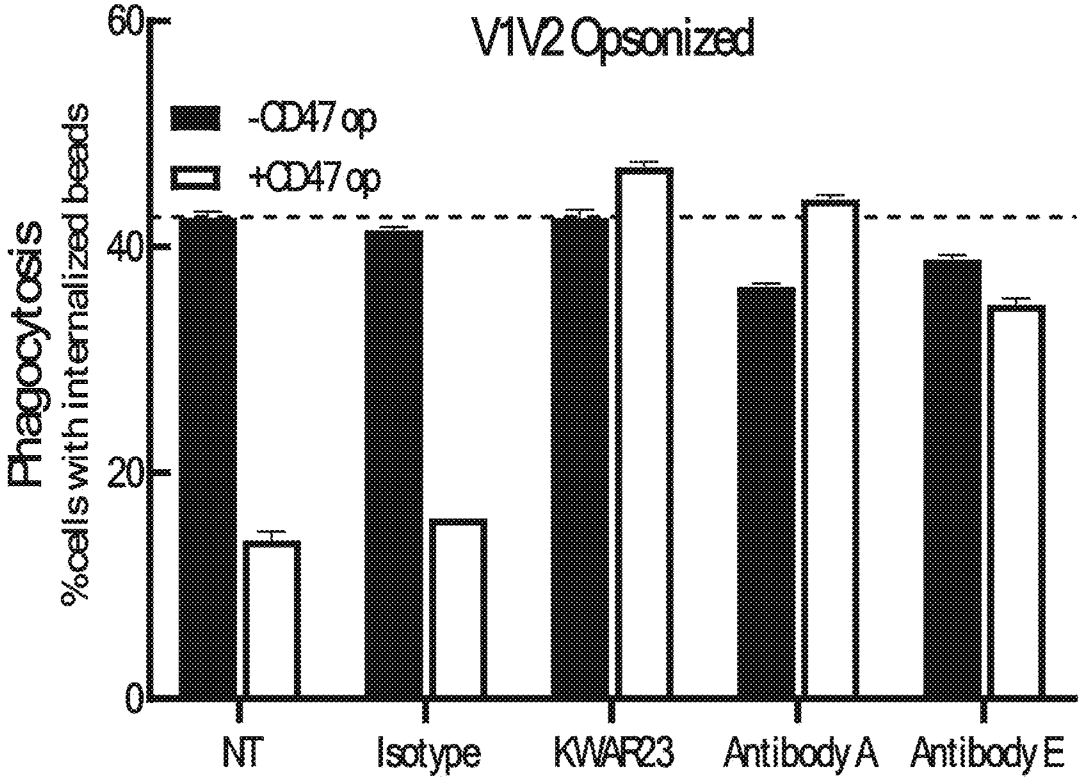
FIGS. 19A-19C are series of histograms and a graph demonstrating that anti-SIRPα antibodies restore CD47-mediated inhibition of phagocytosis by primary human macrophages derived from donors heterozygous for V1- and V2-SIRPα allele.
Figure 19B:
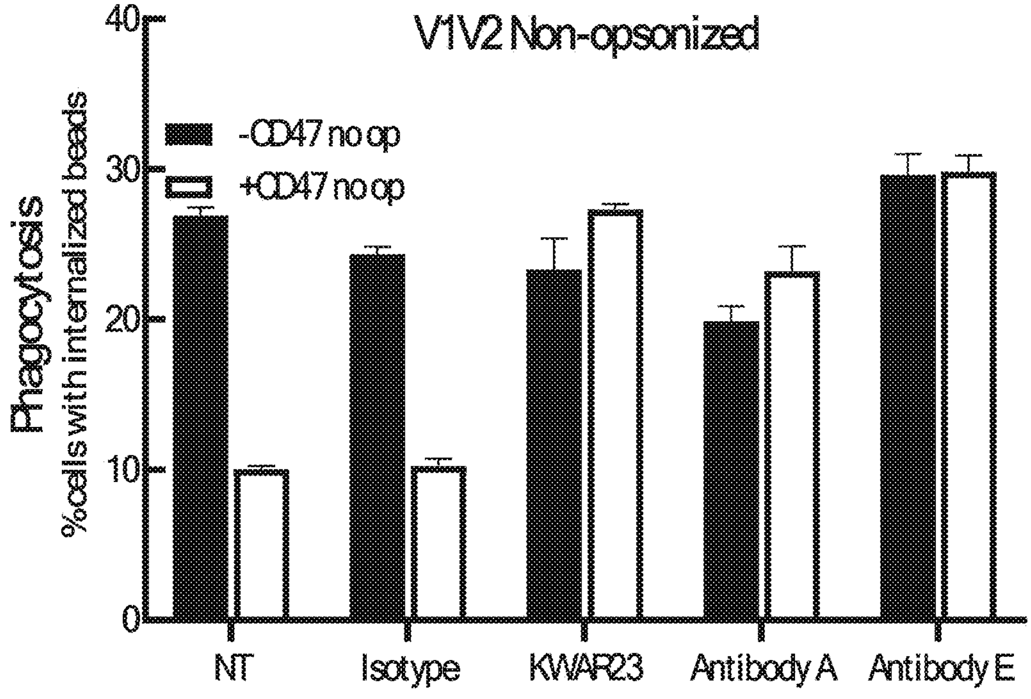
Figure 19C:
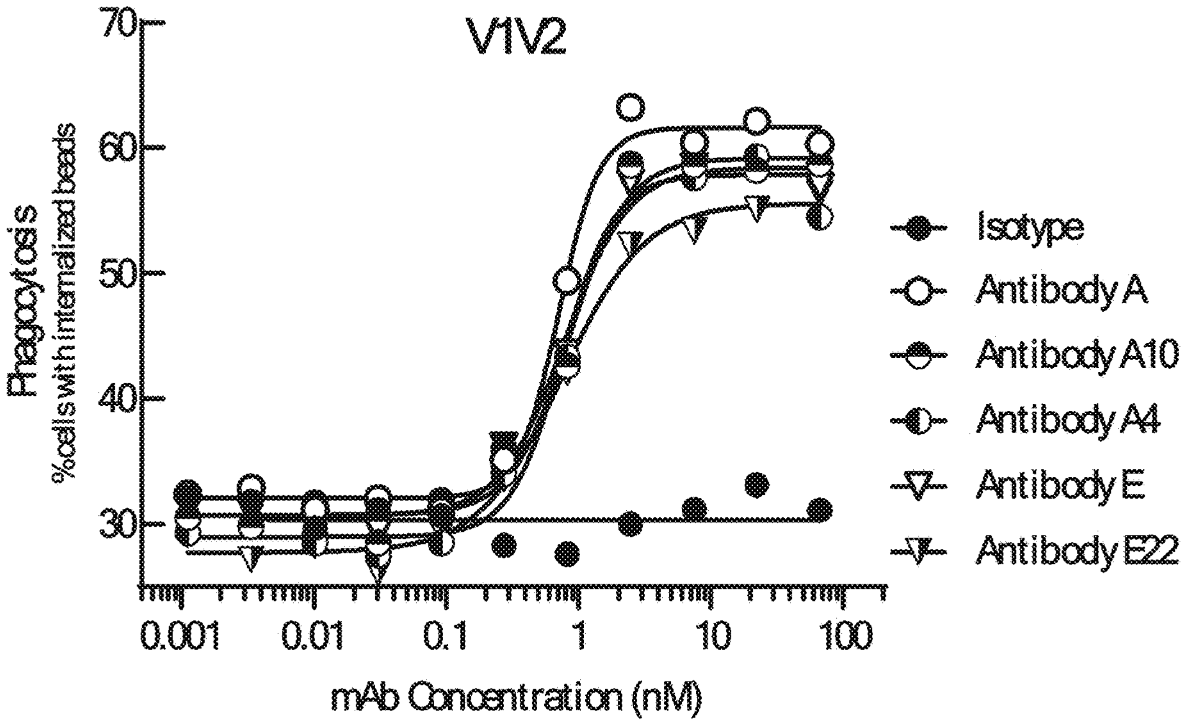
Figure 20A:
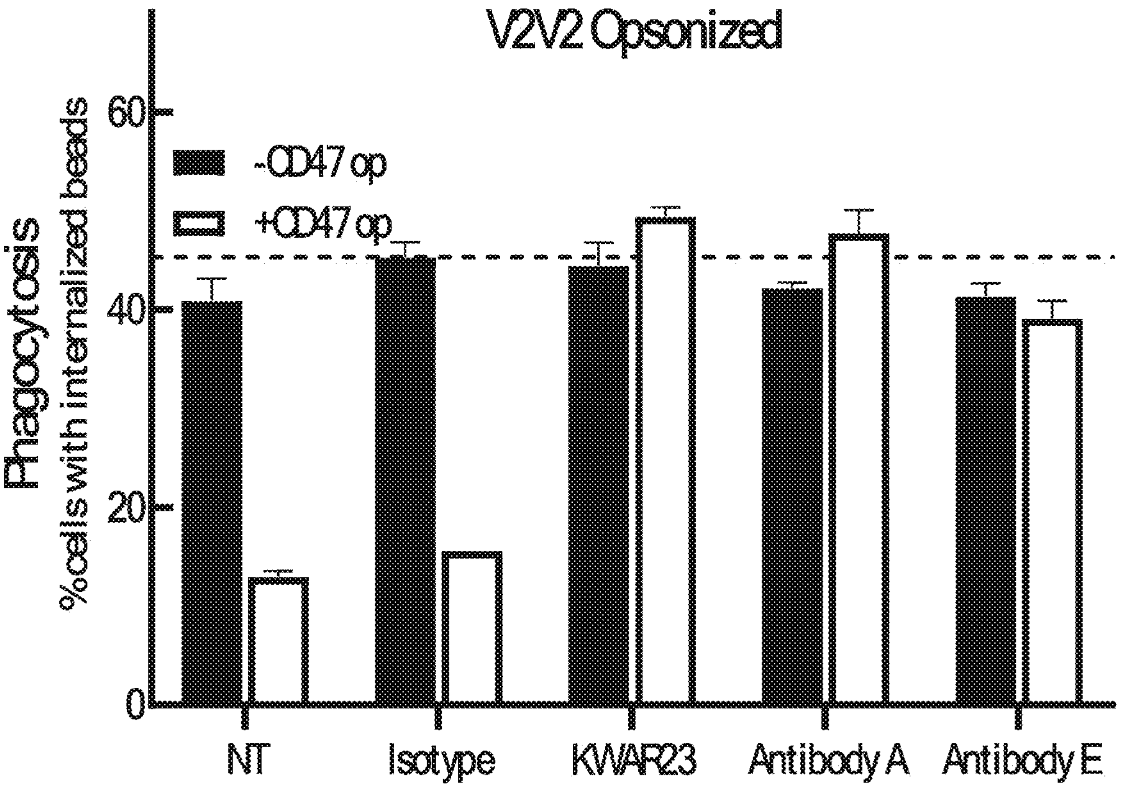
FIGS. 20A-20C are series of histograms and a graph demonstrating that anti-SIRPα antibodies restore CD47-mediated inhibition of phagocytosis by primary human macrophages derived from donors homozygous for V2-SIRPα allele.
Figure 20B:
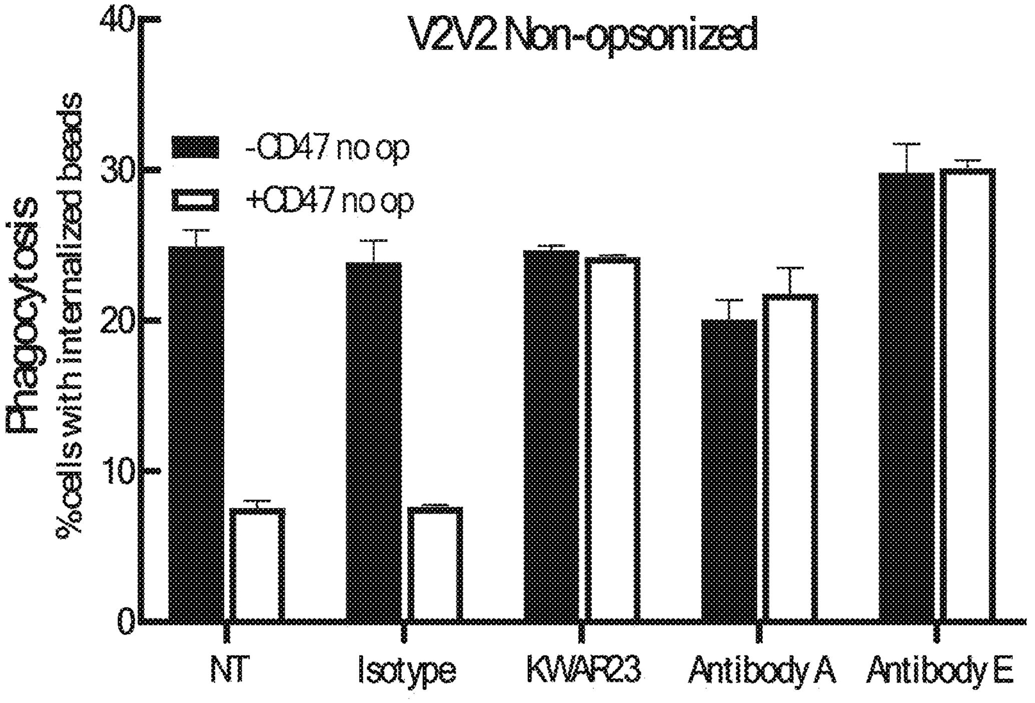
Figure 20C:
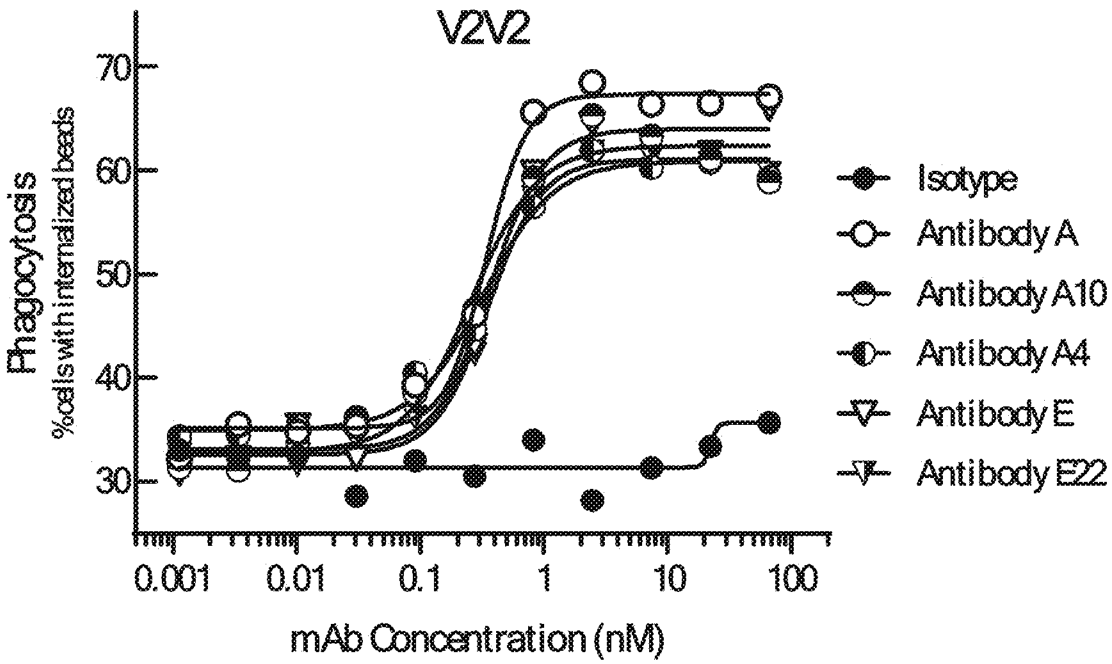

Internalization of beads (with or without opsonization) by MDMs from donors homozygous for V1 or V2 alleles (FIGS. 18A-18B and 20A-20B, respectively) or heterozygous for both alleles (FIGS. 19A-19B) dropped when cells were incubated with CD47-coated beads (white bars); an effect not observed when cells were incubated with beads lacking CD47 (black bars). Pre-treatment of cells with 67 nM of the indicated antibodies restored the cells' ability to phagocytize CD47-coated beads (white bars) with (FIGS. 18A, 19A, and 20A) and without (FIGS. 18B, 19B, and 20B) opsonization indicating that the antibodies can block CD47-mediated SIRPα signaling. Further experiments showed that anti-SIRPα antibodies could restore CD47-mediated inhibition of phagocytosis by primary MDMs derived from donors of all genotypes in a dose-dependent manner (FIGS. 18C, 19C, and 20C).

Example 16. SIRPα Antagonist Revert Inhibition of Phagocytosis Caused by CD47 in Primary Human Monocyte-Derived Dendritic Cells of any Combination of SIRPα Alleles A flow-based phagocytosis assay was developed to quantify the SIRPα-mediated regulation of phagocytosis induced by CD47. Monocytes enriched from human PBMCs (Easy-Sep™ Monocyte Enrichment Kit, StemCell Technologies) from donors genotyped as homozygous for the SIRPα V1 allele, V2 allele, or heterozygous for both alleles are differentiated into dendritic cells following 5-6 day of culture in ImmunoCult™-ACF Dendritic Cell Medium spiked with ImmunoCult™-ACF Dendritic Cell Differentiation Supplement. Monocyte-derived dendritic cells (MDDCs) are preincubated with anti-SIRPα antibodies at the indicated concentrations in 96-well ultra-low attachment TC plates for 30 minutes prior to the addition of fluorescently conjugated microbeads (Spherotech) coated with or without human CD47 (NP_942088; AcroBiosystems) and with or without human IgG1 opsonization to induce Fc-receptor mediated phagocytosis. Following a 1 h incubation at 37° C., 5% $CO_2$, samples are washed, blocked with Human TruStain FcX™ (Biolegend) and stained with fluorescently-conjugated antibody that recognize the beads to enable differentiation between beads stuck on the outside of the cells and those that were inside. Cells are washed, fixed, and analyzed by flow cytometry. Phagocytosis is represented as the percentage of cells with internalized beads.

Figure 21A:
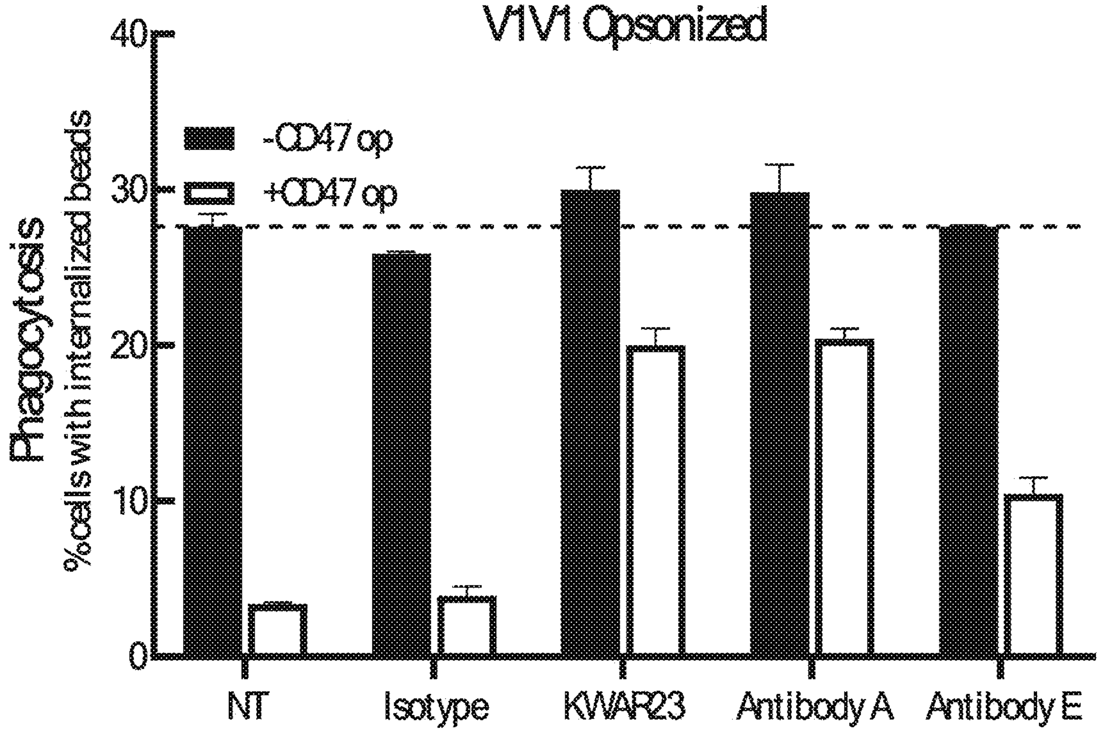
FIG. 21A and FIG. 21B are series of histograms showing that anti-SIRPα antibodies restore CD47-mediated inhibition of phagocytosis by primary human dendritic cells derived from donors homozygous for V1-SIRPα allele.
Figure 21B:
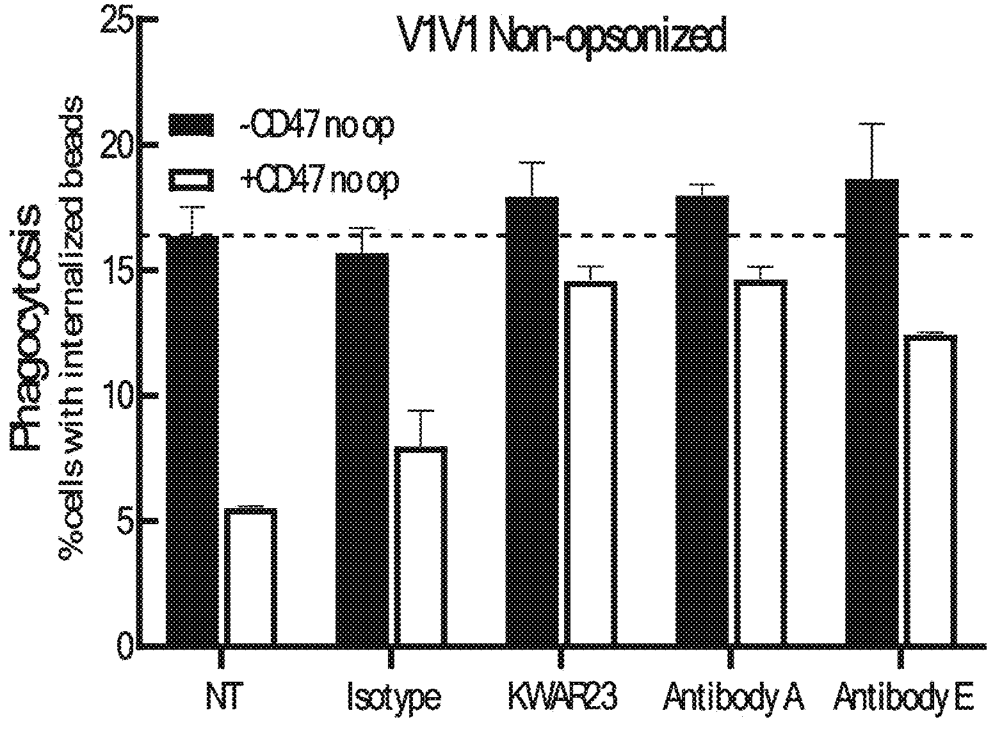
Figure 22A:
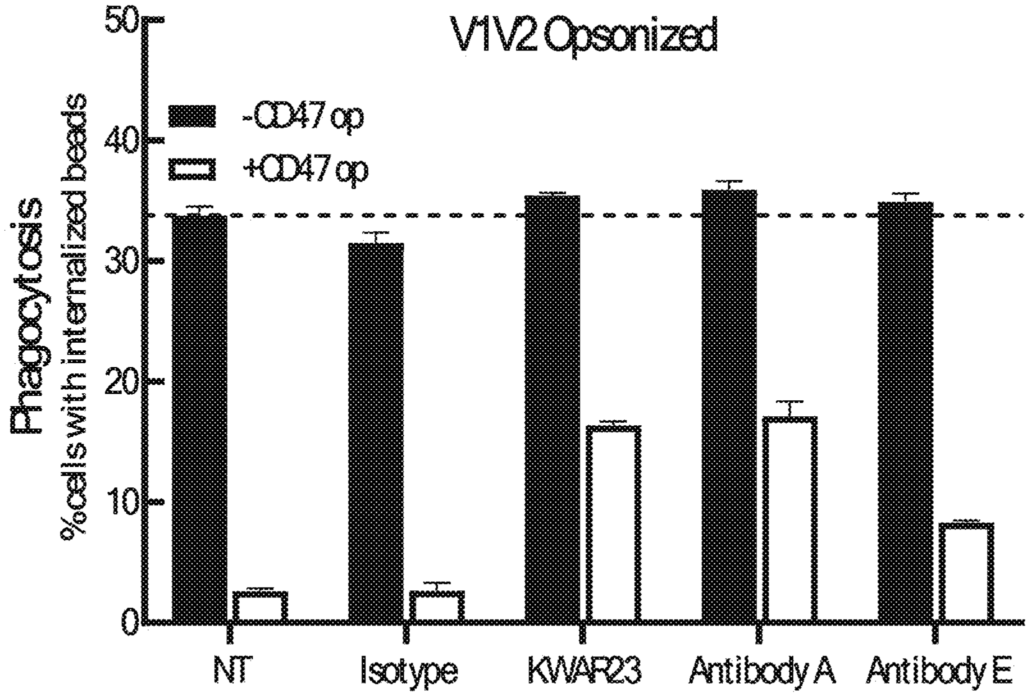
FIG. 22A and FIG. 22B are series of histograms showing that anti-SIRPα antibodies restore CD47-mediated inhibition of phagocytosis by primary human dendritic cells derived from donors heterozygous for V1- and V2-SIRPα allele.
Figure 22B:
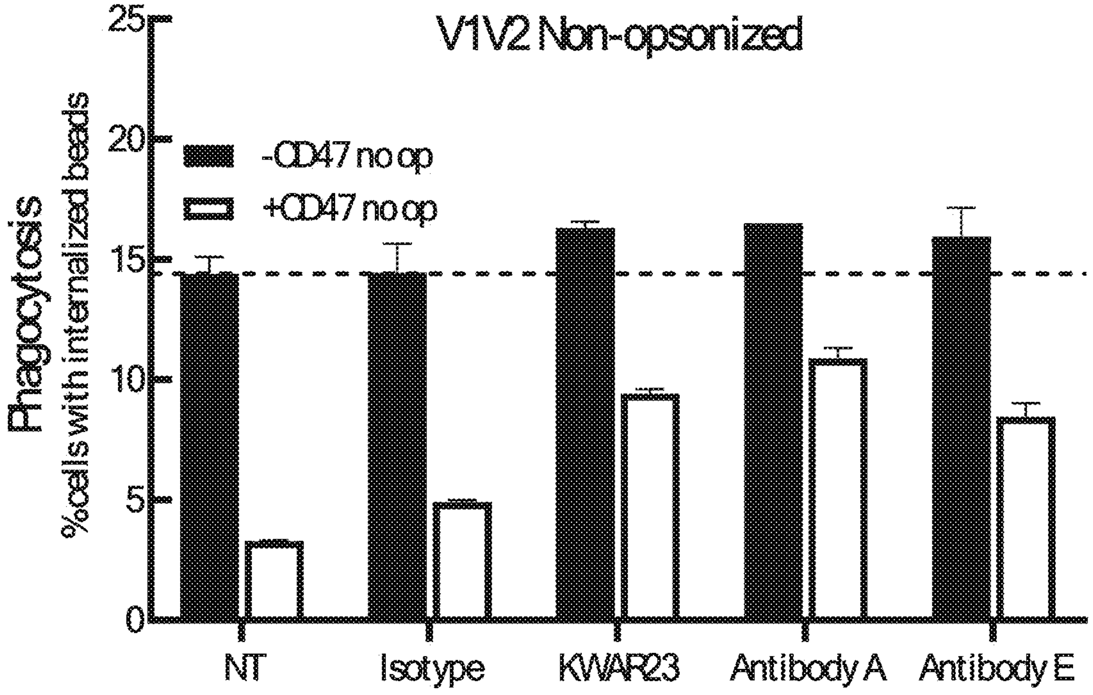
Figure 23A:
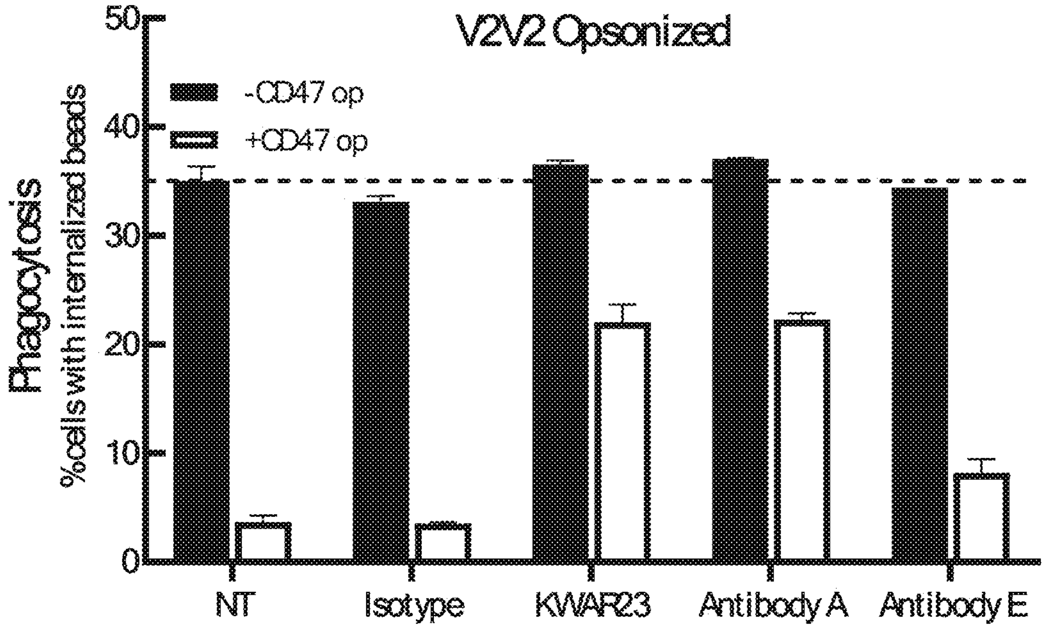
FIG. 23A and FIG. 23B are series of histograms showing that anti-SIRPα antibodies restore CD47-mediated inhibition of phagocytosis by primary human dendritic cells derived from donors homozygous for V2-SIRPα allele.
Figure 23B:
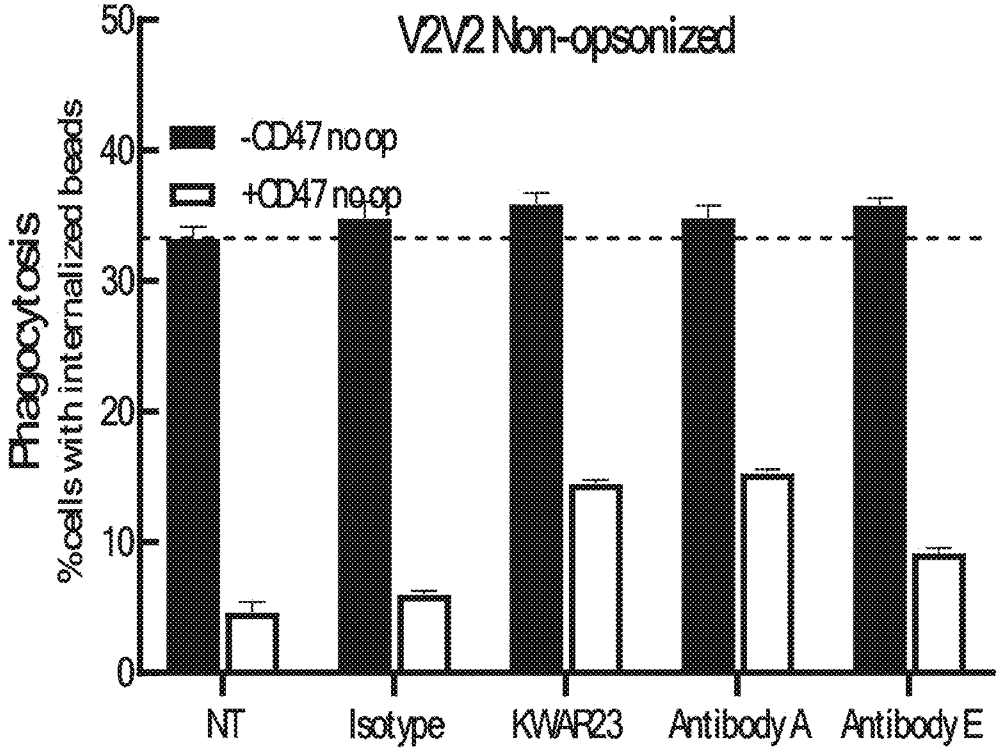

Internalization of beads (with or without opsonization) by MDDCs from donors homozygous for V1 or V2 alleles (FIGS. 21A-21B and 23A-23B, respectively) or heterozygous for both alleles (FIGS. 22A-22B) dropped when cells were incubated with CD47-coated beads (white bars); an effect not observed when cells were incubated with beads lacking CD47 (black bars). Pre-treatment of cells with 67 nM of the indicated antibodies restored the cells' ability to phagocytize CD47-coated beads (white bars) with (FIGS. 21A, 22A, and 23A) and without (FIGS. 21B, 22B, and 23B) opsonization indicating that the antibodies can block CD47-mediated SIRPα signaling.

Example 17. Anti-SIRPα Antibodies Potentiate U-937 Phagocytosis of Human Tumor Cells The functional activity of select molecules were evaluated in an antibody-dependent cellular phagocytosis assay. Raji cells (Burkitt's lymphoma cell line; ATCC), are labeled with PKH26 Red (Sigma) according to manufacturer's instructions and subsequently opsonized with Rituximab. Raji cells are washed to remove unbound Rituximab. V1- or V2-SIRPα-expressing U-937 cells (50,000) are treated with serially titrated anti-SIRPα mAb in 96-well ultra-low attachment TC plates for 30 minutes prior to the addition of 50,000 Raji target cells (±Rituximab opsonization). Following a 2 h incubation in a humidified incubator at 37° C., 5% $CO_2$, samples are washed, blocked with Human TruStain FcX™ (Biolegend) and stained with PB-conjugated anti-human CD13 (U-937 marker; clone WM15; BD Biosciences) and AF647-conjugated anti-human CD19 (Raji marker; clone HIB19; Biolegend) cocktail. Cells are washed, fixed, and analyzed by flow cytometry. Phagocytosis is represented as the percentage of CD13+ cells that stained negative for CD19 and positive for PKH26.

The results showed that V1- and V2-SIRPα-expressing U-937 cells were incapable of phagocytizing Raji cells devoid of Rituximab opsonization. Opsonization of Raji cells induced an increase in cellular phagocytosis (about 0.2% to about 6%), which was further enhanced, in a dose-dependent manner, by treatment with anti-SIRPα antibodies.

Example 18. Anti-SIRPα Antibodies Potentiate Monocyte-Derived Macrophage Phagocytosis of Human Tumor Cells The functional activity of select molecules were evaluated in an antibody-dependent cellular phagocytosis assay. Raji cells (Burkitt's lymphoma cell line; ATCC), are labeled with PKH26 Red (Sigma) according to manufacturer's instructions and subsequently opsonized with Rituximab. Raji cells are washed to remove unbound Rituximab. Monocytes enriched from human PBMCs (EasySep™ Monocyte Enrichment Kit, StemCell Technologies) from donors genotyped as homozygous for the SIRPα V1 allele, are differentiated into macrophages following 6-7 days in culture in ImmunoCult™-SF macrophage differentiation medium spiked with 50 ng/ml human recombinant M-CSF (Peprotech). Monocyte-derived macrophages (MDMs) are treated with serially titrated anti-SIRPα mAb in 96-well ultra-low attachment U-bottom plates for 30 minutes prior to the addition of 50,000 Raji target cells (±Rituximab opsonization). Following a 2 h incubation at 37° C., 5% $CO_2$, samples are washed, blocked with Human TruStain FcX™ (Biolegend) and stained with BV421-conjugated anti-human CD14 (MDM marker; clone M5E2; Biolegend) and AF647-conjugated anti-human CD19 (Raji marker; clone HIB19; Biolegend) cocktail. Cells are washed, fixed, and analyzed by flow cytometry. Phagocytosis is represented as the percentage of CD13+ cells that stained negative for CD19 and positive for PKH26.

The results showed that MDMs were incapable of phagocytizing Raji cells devoid of opsonization regardless of cell treatment. Opsonization of Raji cells induced an increase in cellular phagocytosis (about 1.3 to about 17%), which was further enhanced by anti-SIRPα antibody treatment.

Example 19. Mixed Lymphocyte Reaction

Selected molecules are evaluated in a mixed lymphocyte reaction. 96-well round bottom tissue culture treated plates were coated with recombinant human CD47 extracellular domain (ECD)/hFc protein diluted in DPBS and incubated overnight at 4° C. Plates are washed 3× in DPBS/CF. Cryopreserved human monocyte-derived dendritic cells (Astarte Biologics) are thawed, washed and resuspended at 0.1 million/ml in X-VIVO 15 media. MDDCs are then pre-incubated with various anti-SIRPα mAb together with or without anti-PD1 antagonist at a 1:1 volume ratio for 60 minutes prior to transferring MDDC±mAb treatment to respective wells of a 96-well round bottom TC plate previously coated with or without human CD47 fusion protein. Human CD4+ T cells (about 100,000), enriched from allogeneic human PBMC donors (EasySep™ Human CD4+ T Cell Isolation Kit) are added to respective wells and plates are incubated in a humidified incubator at 37° C., 5% $CO_2$ for 5 days. Sixteen to eighteen hours prior to harvest, culture wells are pulsed with 1 μCi (10 μl at 100 μCi/ml) of $^3$[H]thymidine (Moravek Biochemicals Inc.). Cells are subsequently harvested onto filter mats (Wallac) using the Molecular Devices Micro96 Harvester, dried, and then sealed in sample bags (Perkin Elmer) with 10 ml of Beta-Plate Scintillation (Perkin-Elmer, cat #1205-440). $^3$[H]Thymidine incorporation is measured using a MicroBeta2 2450 Microplate Counter (Perkin Elmer).

Figure 24A:
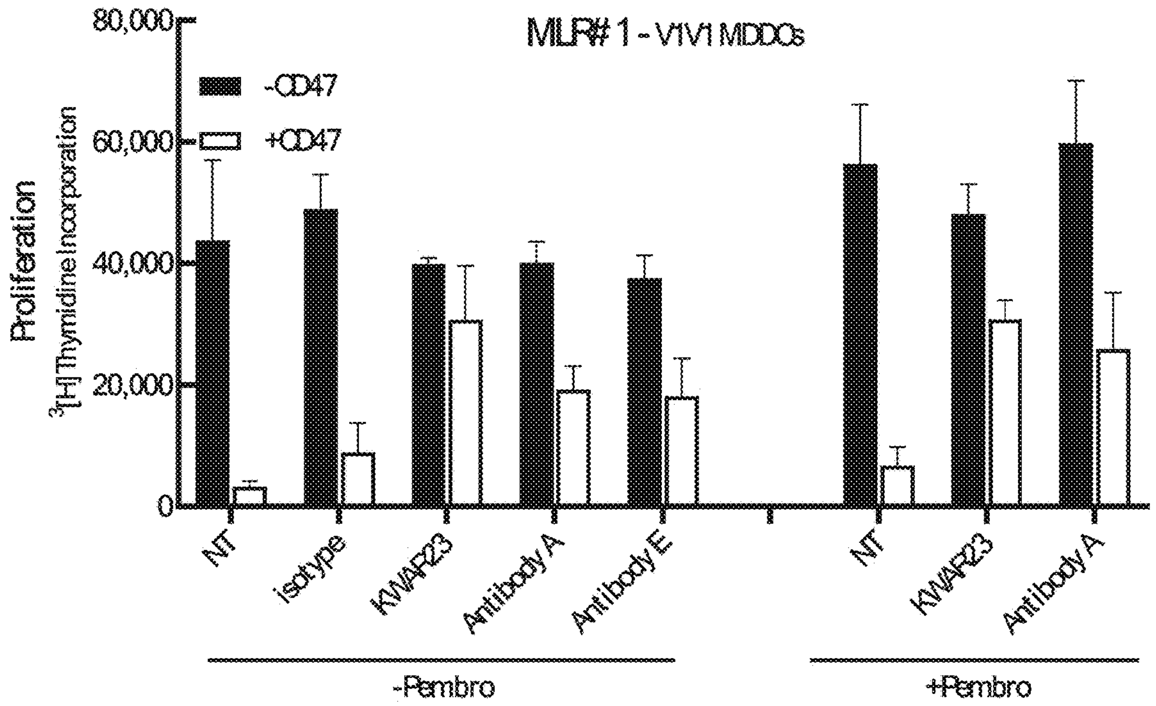
FIG. 24A and FIG. 24B are series of histograms showing that anti-SIRPα antibodies restore human CD47-mediated inhibition of MLR. Human CD47-Fc mediated immunosuppression of MLR partially restored by anti-SIRPα mAb alone or in combination with anti-PD1 antagonist, pembrolizumab (FIG. 24A and FIG. 24B).
Figure 24B:
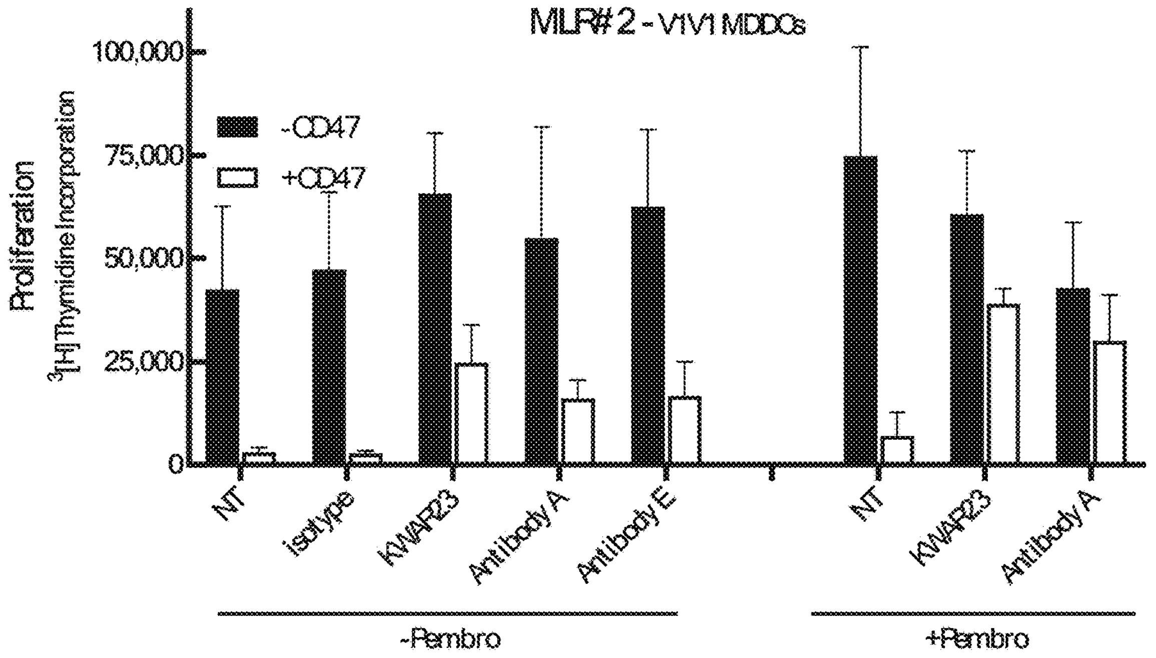
Figure 25A:
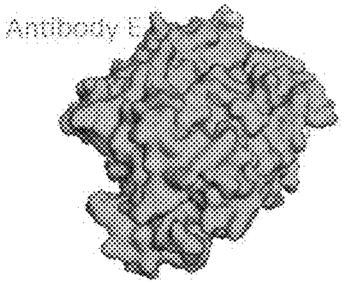
FIGS. 25A-25F are series of images depicting the epitopes recognized by anti-SIRPα antibodies. Structures of Fab fragments of Antibody E (FIG. 25A) or Antibody A (FIG. 25B) bound to domain 1 of the extracellular domain of human SIRPα-V2 (residues 1 to 115).
Figure 25B:
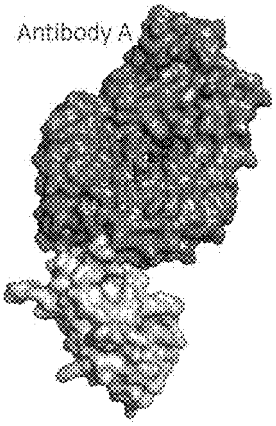
Figure 25C:
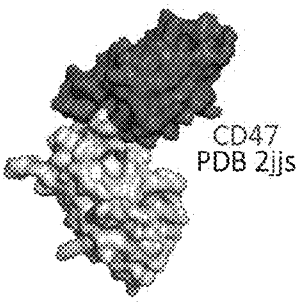
Figure 25D:
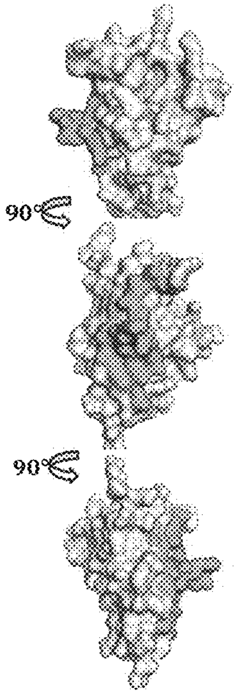
Figure 25E:
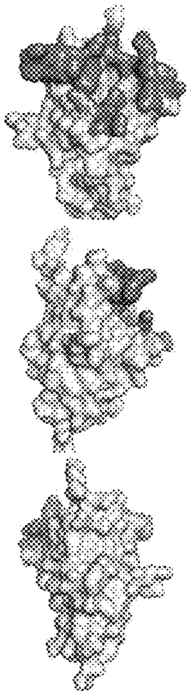
Figure 25F:
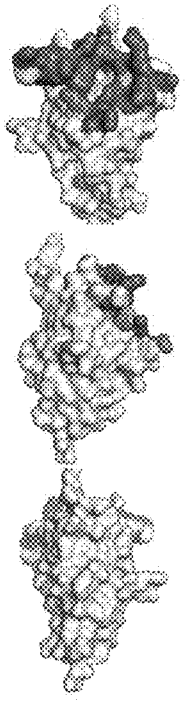
Figure 26A:
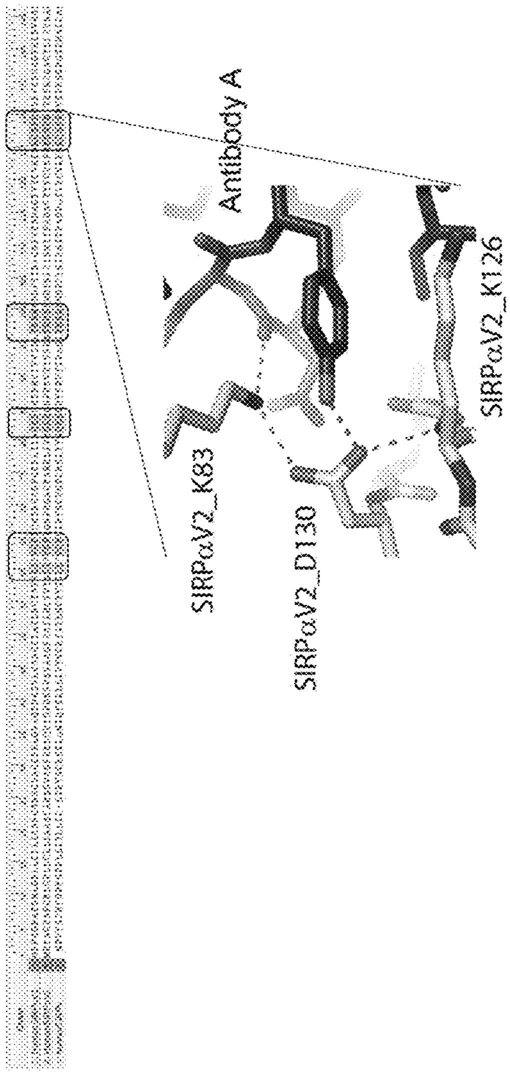
FIG. 26A and FIG. 26B are series of images depicting epitopes of Antibody A::SIRPα_V2 complex and Antibody E::SIRPα_V2 complex based on crystal structures.
Figure 26B:
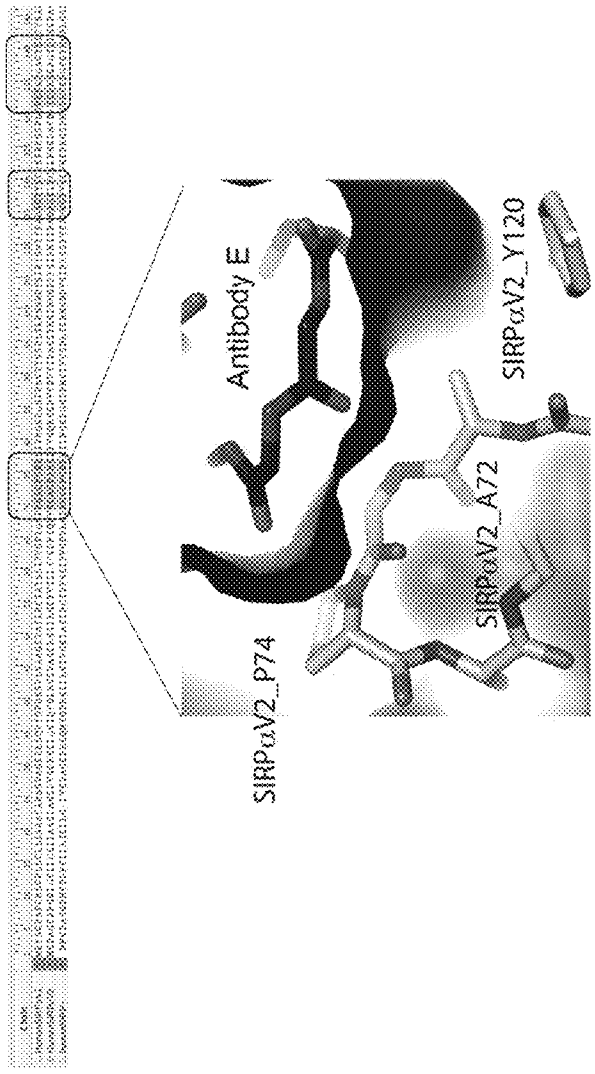

FIGS. 24A-24B show that platebound human CD47 fusion protein inhibited CD4 T cell proliferation mediated by dendritic cells in Mixed Lymphocyte Reaction, demonstrating that CD47-mediated signaling can be highly immune-suppressive. CD47-Fc mediated immunosuppression in these assays can be reverted to various degrees by anti-SIRPα antibodies (KWAR23, antibody A and E) alone or in combination with anti-PD1 antagonist.

Example 20. Crystallization of Anti-SIRPα Fab:SIRPα Complexes

To understand the mechanistic bases for antibody binding to SIRPα, an analysis was performed on the structure of the antibody-SIRPα complexes for Antibody E and Antibody A in complex with domain 1 of human SIRPα-V2 (FIGS. 25A-25F and FIGS. 26A-26B).

In order to obtain complex structures we generated a construct for expression of SIRPαV2 (Amino acids 31-148, comprising an N-terminal GST tag) using the Gateway cloning system. Protein was expressed in Origami B(DE3) cells and purified using standard protocols for GST-tagged proteins. Fractions were analyzed by SDS-PAGE and fractions containing the desired protein were pooled and concentrated to 24 mg/ml in 25 mM HEPES; 100 mM NaCl; 5% Glycerin; pH 7.0. SIRPαV2 protein was mixed with Fab fragments of Antibody A or E and purified by size-exclusion chromatography in 10 mM Tris; 150 mM NaCl; 1 mM TCEP; pH 7.5. Crystals of SIRPαV2 Fab complexes were obtained by vapor diffusion sitting drop method at a complex concentration of 5 mg/ml (reservoir solution: Antibody A: 20% PEG3350 and 180 mM tri-Ammonium citrate and Antibody E: 15% PEG 4000 and 100 mM HEPES, pH 7.0). Data was collected at the Swiss Light Source (SLS) and the structures were solved and modelled at resolutions of 1.4 Å (Antibody A) and 1.6 Å (Antibody E).

The crystal structure analysis demonstrated that the two antibodies can contact SIRPα on different areas and in different orientations. While both antibodies obstruct the 0047-binding site on SIRPα, Antibody A can contact most of the SIRPα residues that are engaged by 0047 indicating how this antibody can achieve complete 0047 antagonism. The SIRPα residues contacted by these antibodies explained how both alleles of SIRPα can be bound equally without detrimental effects by the variant residues between the alleles. The contact points also explain the selectivity against SIRPγ (FIGS. 25A-25F and FIGS. 26A-261B and Tables 51-52).

TABLE 51

Epitope, contact points on SIRPα-V2 and Antibody A

| Residues on SIRPα V2 that contact Antibody A | Residues on the Heavy Chain that contact SIRPα V2 | Residues on the Light Chain that contact SIRPα V2 |
|---|---|---|
| LEU 60 | H-SER 31 | L-ASP 28 |
| ILE 61 | H-TYR 32 | L-ASN 30 |
| VAL 63 | H-ASP 33 | L-ASN 31 |
| GLY 64 | H-THR 53 | L-TYR 32 |
| PRO 65 | H-ARG 97 | L-TYR 49 |
| GLN 82 | H-GLY 98 | L-THR 50 |
| LYS 83 | H-GLY 99 | L-TYR 91 |
| GLU 84 | H-VAL 100 | L-VAL 92 |
| THR 97 | H-TRP 101 | L-TYR 96 |
| LYS 98 | H-ASP 102 | |
| ARG 99 | H-ASP 103 | |
| GLU 100 (ASN 100 in V1) | | |
| LYS 126 | | |
| GLY 127 | | |
| SER 128 | | |
| PRO 129 | | |
| ASP 130 | | |

TABLE 52

Epitope, contact points on SIRPα-V2 and Antibody E

| Residues on SIRPα V2 that contact Antibody E | Residues on the Heavy Chain that contact SIRPα V2 | Residues on the Light Chain that contact SIRPα V2 |
|---|---|---|
| ARG 70 | H-ARG 30 | L-TYR 31 |
| GLY 71 | H-ASN 31 | L-SER 32 |
| ALA 72 | H-TYR 33 | L-ASN 33 |
| GLY 73 | H-TYR 52 | L-THR 99 |
| PRO 74 | H-TYR 53 | |
| ALA 75 (GLY 75 on V1) | H-ASN 54 | |
| ARG 76 | H-ARG 56 | |
| GLU 77 | H-PHE 58 | |
| ALA 114 | H-ALA 100 | |
| ALA 116 | H-TYR 101 | |
| GLY 117 | H-SER 102 | |
| THR 118 | H-GLY 103 | |

TABLE 52-continued

| Epitope, contact points on SIRPα-V2 and Antibody E | | |
|---|---|---|
| Residues on SIRPα V2 that contact Antibody E | Residues on the Heavy Chain that contact SIRPα V2 | Residues on the Light Chain that contact SIRPα V2 |
| TYR 120 | H-ILE 104 | |
| THR 131 (VAL 132 on V1) | H-GLY 105 | |
| GLU 132 (133 on V1) | H-LEU 106 | |
| PHE 133 (134 on V1) | | |
| SER 135 (136 on V1 | | |
| GLU 140 (141 on V1) | | |

See FIG. 26 for SIRPαV1 and SIRPαV2 alignment and numbering.

Example 21. Competition Assay with Commercial Anti-SIRP mAb, Clone SE5A5

Antibodies were assessed for their ability to compete with commercial anti-SIRP mAb, clone SE5A5, binding to V1- and V2-SIRPα-expressing U-937 cells. Cells blocked with Human TruStain FCX™ (Biolegend) are incubated with anti-SIRPα antibodies on ice for 30 minutes prior to the addition of fluorescently conjugated SE5A5 (Biolegend). Cells are washed, fixed, and analyzed by flow cytometry. Median fluorescent intensity is plotted.

Figure 27A:
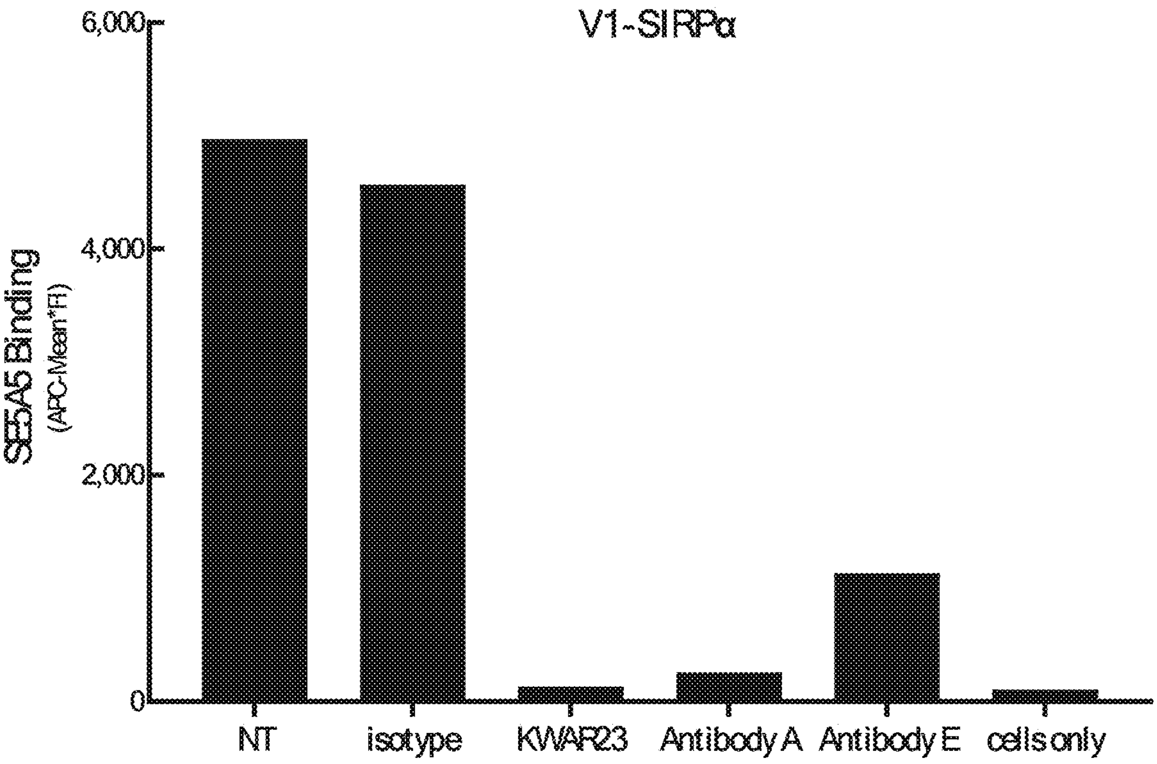
FIG. 27A and FIG. 27B, are series of histograms showing that anti-SIRPα antibodies block binding of SE5A5 to V1- or V2-expressing U-937 cells. Blockade of anti-SIRPα mAb, SE5A5, binding to (FIG. 27A) V1- or (FIG. 27B) V2-SIRPα expressing U-937 cells by anti-SIRPα antibodies.
Figure 27B:
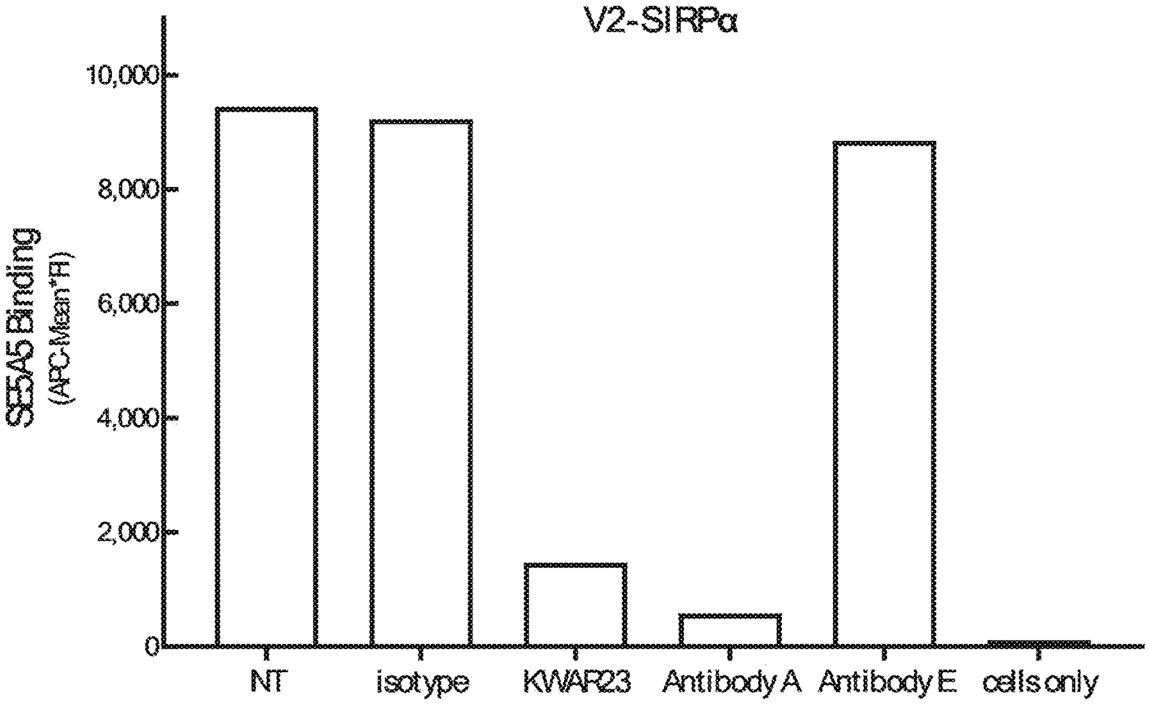

FIGS. 27A-27B show that KWAR23 and antibody A blocked the binding of fluorescently conjugated SE5A5 to both V1- and V2-SIRPα expressing U-937 cells. Antibody E blocked SE5A5 binding to V1-SIRPα-expressing U-937 cells, but not V2-SIRPα-expressing cells.

Example 22. Binding of Antibodies to Full-Length Cynomologus SIRPα Expressed on CHO Cells Antibody binding to cells expressing cynomolgus (cyno) SIRPα was evaluated by flow cytometry. CHO-K1 cells expressing full-length cyno SIRPα; derived from protein sequence accession numbers (A) EGM-02252; (B) XP_015313155; or (C) NP_001271679, are blocked with donkey IgG and incubated on ice with increasing concentrations of antibodies for 60 minutes, washed and stained with AF647-conjugated donkey $F(ab')_2$ anti-human IgG secondary reagent. Cells are washed, fixed, and analyzed by flow cytometry. Median fluorescent intensity is determined and used as a measure of antibody binding.

Figure 28A:
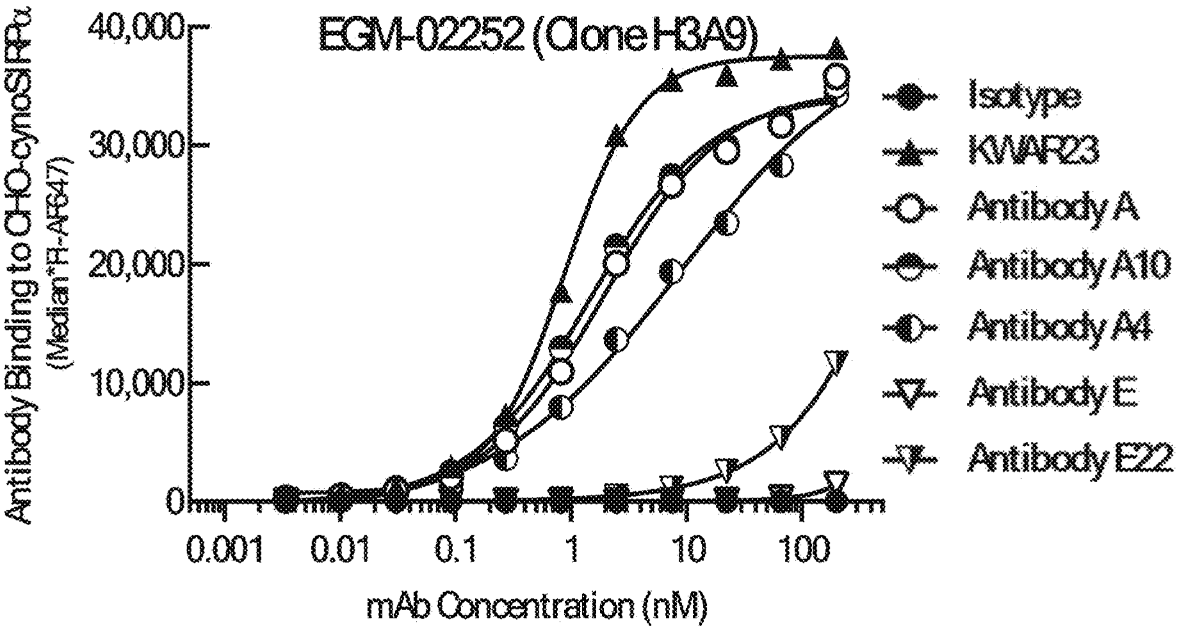
FIGS. 28A-28C are series of graphs depicting the binding of antibodies to full-length cyno SIRPα expressed on CHO cells.
Figure 28B:
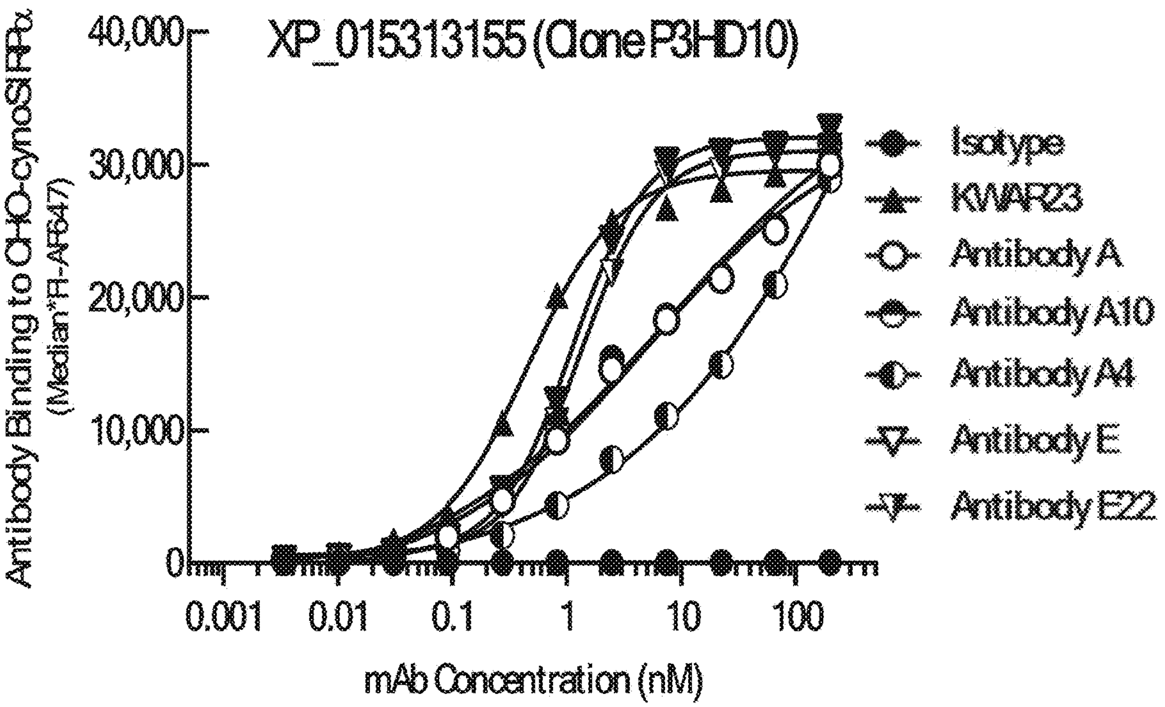
Figure 28C:
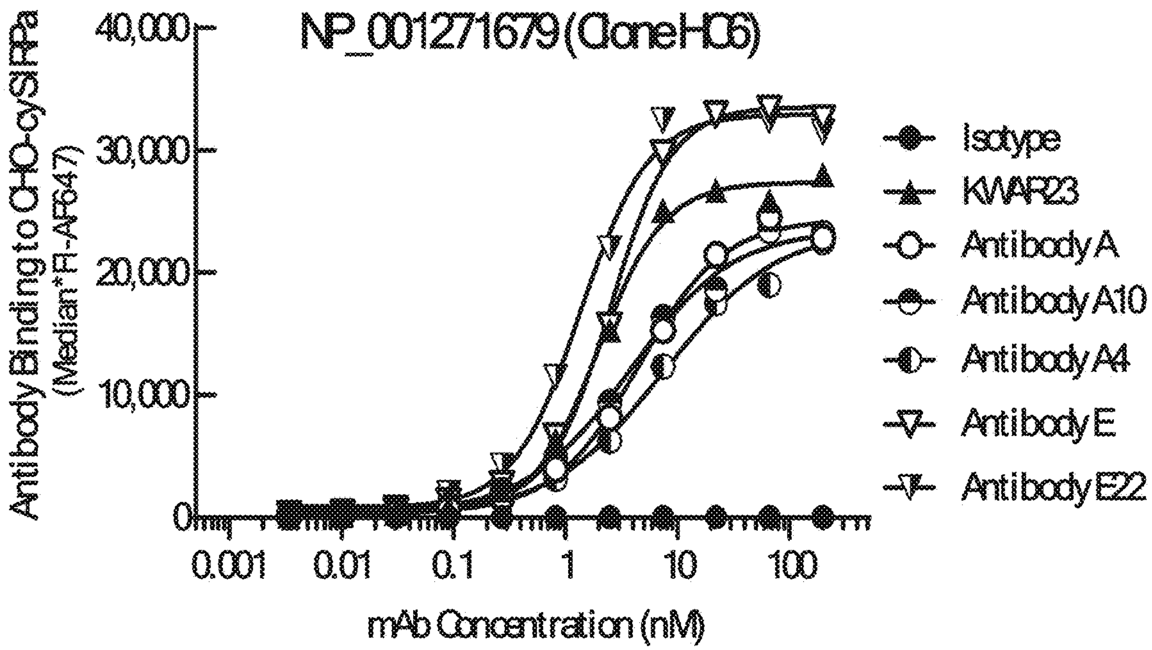

KWAR23 demonstrated dose-dependent binding to all cyno SIRPα-expressing CHO cells lines (H3A9, P3HD10, and HC6) encoding various cynomolgus SIRPα sequences (FIGS. 28A-28C) with $EC_{50}$ values ranging between 0.5-2.0 nM (Table 53). Antibodies E and E22 exhibited diverse binding profiles achieving saturable binding curves and $EC_{50}$ values between 1.1 and 2.5 for clones P3HD10 and HC6 and little to no binding to clone H3A9. While antibodies A and A10 exhibited binding to all 3 clones, binding was strongest to clone H3A9 and up to 5-fold weaker $EC_{50}$ values for clones P3HD10 and HC6. Titratable binding of antibody A4 was detected on each of the three cell lines but did not achieve saturation at concentrations as high as 200 nM.

TABLE 53

| $EC_{50}$ of Anti-SIRPα antibodies | | | |
|---|---|---|---|
| | Cynomolgus SIRPα; $EC_{50}$, nM | | |
| Antibody | EGM-02252 Clone H3A9 | XP_015313155 Clone P3HD10 | NP_001271679 Clone HC6 |
| Isotype | NB | NB | NB |
| KWAR23 | 0.9 | 0.5 | 2 |
| Antibody A | 1.9 | 5 | 4.5 |
| Antibody E | NS | 1.1 | 2.5 |
| Antibody A10 | 1.5 | 7.2 | 3.7 |
| Antibody A4 | NS | NS | NS |
| Antibody E22 | NS | 1.3 | 1.4 |

NB No binding
NS Non-saturable binding

Example 23. Binding of Antibodies to Full-Length Cynomologus SIRPβ1- and SIRPβ1v3 Expressed on CHO Cells Antibody binding to cells expressing full-length cynomolgus SIRPβ1 (XP_005568598) and SIRPβ1v3 (XP_005568593) is evaluated by flow cytometry. SIRPβ1- or SIRPβ1V3-expressing CHO cells are blocked with donkey IgG and incubated on ice with increasing concentrations of antibodies for 60 minutes, washed and stained with AF647-conjugated donkey $F(ab')_2$ anti-human IgG secondary reagent. Cells are washed, fixed, and analyzed by flow cytometry. Median fluorescent intensity is determined and used as a measure of antibody binding.

KWAR23 demonstrated dose-dependent binding to cyno SIRPβ1- and SIRPβ1v3-expressing CHO cells (FIGS. 29A and 29B, respectively) with subnanomolar $EC_{50}$ values (Table 54). Antibodies E and E22 exhibited diverse binding profiles achieving saturable binding curves and subnanomolar $EC_{50}$ values for SIRPβ1v3-expressing CHO cells (FIG. 29B, Table 54), but little to no detectable binding to SIRPβ1-expressing CHO cells (FIG. 29A). In contrast, antibodies A and A10 showed dose-dependent binding to SIRPβ1-expressing CHO cells (FIG. 29A) with subnanomolar $EC_{50}$ values (Table 54) and non-saturable binding to SIRPβ1v3-expressing cells (FIG. 29B). Dose-dependent binding of antibody A4 was detected on each of two cell lines but did not achieve saturation at concentrations as high as 67 nM.

TABLE 54

| $EC_{50}$ of Anti-SIRPα antibodies | | |
|---|---|---|
| | Cynomolgus SIRPβ1; $EC_{50}$, nM | |
| Antibody | SIRPβ1 XP_005568598 Clone PA2 | SIRPβ1v3 XP-005568593 Clone 1HC6 |
| Isotype | NB | NB |
| KWAR23 | 0.2 | 0.4 |
| Antibody A | 0.7 | NS |
| Antibody E | NB | 0.8 |
| Antibody A10 | 0.6 | NS |
| Antibody A4 | NS | NS |
| Antibody E22 | NB | 1 |

NB No binding
NS Non-saturable binding

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the invention. The appended claims are intended to be construed to include all such embodiments and equivalent variations.

Example 24. Pharmacokinetics (PK) in Cynomolgus Monkeys

A pharmacokinetic study is conducted in naïve male cynomolgus monkeys (*Macaca fascicularis*) 2-5 years of age with a body weight range between 2.1-6.0 kg. The monkeys are divided into two treatment groups that are administered Antibody A10. Group 1 (n=3) receives 1 mg/kg and Group 2 (n=3) receives 5 mg/kg of the antibody. The antibody is administered intravenously (i.v.) as a 2 mg/ml solution in citrate buffer (50 mM sodium citrate/115 mM sodium chloride, pH 5.0). Blood samples are collected over 6 weeks from a peripheral vein and serum is recovered for analysis.

Serum samples are analyzed using an ELISA format. Briefly, HuSIRPα-V1 is bound to a NUNC™ ELISA plate (Thermo Fisher Scientific). The plates are washed with 0.05% TWEEN™ 20 in phosphate buffered saline and blocked with 5% BSA Buffer (Sera Care cat #AP-4510-01), in PBS (Gibco ref 10010-023) prior to incubation with serum samples. The antibody is detected utilizing Novus, pAb anti-goat anti-human IgG HRP, Cat #NB7489 at 1:8000 dilution. PK parameters are determined by non-compartmental analysis using Phoenix WINNONLIN™ software (Version 8.2, Certara USA, Inc. Princeton, NJ).

The PK study results are shown FIG. 30 and the PK paramters are summarized in Table 55 below. The antibody demonstrated dose dependent CL between 1 and 5 mg/kg, suggestive of target-mediated drug distribution (TMDD) contributions to overall clearance.

TABLE 55

| Dose (mg/kg) | $AUC_{0\text{-}inf}$ (hr * ng/mL) | CL (mL/d/kg) | $t_{1/2z}$ (d) | $V_{ss}$ (mL/kg) | MRT (d) |
|---|---|---|---|---|---|
| 1.0 IV | 101000 (15800) | 24.2 (3.54) | 1.79 (0.79) | 34.7 (6.50) | 1.43 (0.157) |
| 5.0 IV | 11800000 (4260000) | 11.0 (3.79) | 3.4 (0.906) | 47.4 (4.04) | 4.58 (1.24) |

Abbreviations:
$AUC_{0\text{-}inf}$: area under the curve from dosing to the last measurement and extrapolated to infinity;
CL: Clearance;
$t_{1/2z}$: Terminal Half-life;
$V_{ss}$: volume distribution at steady state;
MRT: Mean Residence Time

Example 25. Toxicology in Cynomolgus Monkeys

A repeat dose toxicity study is conducted in cynomolgus monkeys with Antibody A10. Parameters evaluated in this study include bioanalysis, toxicokinetic, clinical observation, body weight, food consumption, hematology, blood chemistry, coagulation, urinalysis, immunophenotyping, neurobehavioral examination, electrocardiogram examination, and ophthalmic examination.

Groups of male and female cynomolgus monkeys (n=3/sex/group) receive the antibody at dose levels of 100 and 250 mg/kg/dose q1w for 4 weeks (5 dose administrations).

There were no antibody-related changes in body weight, clinical observations, food consumption, ophthalmic examination, neurobehavioral examination, electrocardiogram, immunophenotyping, hematology, coagulation, clinical chemistry, or urinalysis.

In conclusion, intravenous administration of the antibody at 100 and 250 mg/kg/dose q1w for 4 weeks (5 doses total) was tolerated in monkeys with no antibody-related adverse findings. Under the condition of this study, the no-observed-adverse-effect-level (NOAEL) at steady state (Day 22) was considered to be 250 mg/kg/dose q1w.

Example 26. Binding of Antibodies to Full-Length Human V1-SIRPα with Various Amino Acid Point Mutations Expressed on Expi-CHO Cells To study the structural basis of the observed antibody selectivity, antibody binding to cells engineered to express modified V1-SIRPα protein sequences is tested by flow cytometry. Expi-CHO parental cells are transduced with lentiviruses containing either full-length wild-type human SIRPαV1 allele (NP_542970.1) or full-length human SIRPαV1 with amino acid point mutations (Table 56) and sorted to achieve matching expression levels. These cells are blocked with donkey IgG and incubated on ice with increasing concentrations of antibodies for 60 minutes, washed and stained with AF647-conjugated donkey $F(ab')_2$ anti-human IgG antibodies. Stained cells are washed, fixed, and analyzed by flow cytometry. Median fluorescent intensity is determined and used as a measure of antibody binding.

Antibodies A-E, A4, A10, E22 and KWAR23, but not isotype control, showed dose-dependent binding to Expi-CHO cells expressing full-length wild-type human SIRPαV1 (FIG. 31A) with $EC_{50}$ values ranging between 0.3 to 3.8 nM (Table 57). Antibody binding to cells expressing SIRPαV1 N→E and D→E variants were comparable to binding to SIRPαV1 WT-expressing cells (FIGS. 31B-31C; Table 57). In contrast, binding of antibodies A-D, A4, and A10 to Expi-CHO cells expressing SIRPαV1 D→N and DD→EN variants was affected, showing abolished, weaker (>$EC_{50}$), or non-saturable binding (FIGS. 31D-31E; Table 57). None of the antibodies tested exhibited binding to parental CHO cells (FIG. 31F).

TABLE 56

| Target | Sequence | SEQ ID NO: |
|---|---|---|
| αV1 WT | EEELQVIQPDKSVLVAAGETATLRCTATSLIPVGPIQWFRGAGP GRELIYNQKEGHFPRVTTVSDLTKRNNMDFSIRIGNITPADAGT YYCVKFRKGSPDDVEFKSGAGTELSVRAKPSAPVVSGPAARATP QHTVSFTCESHGFSPRDITLKWFKNGNELSDFQTNVDPVGESVS YSIHSTAKVVLTREDVHSQVICEVAHVTLQGDPLRGTANLSETI RVPPTLEVTQQPVRAENQVNVTCQVRKFYPQRLQLTWLENGNVS RTETASTVTENKDGTYNWMSWLLVNVSAHRDDVKLTCQVEHDGQ PAVSKSHDLKVSAHPKEQGSNTAAENTGSNERNIYIVVGVVCTL LVALLMAALYLVRIRQKKAQGSTSSTRLHEPEKNAREITQDTND | 268 |

TABLE 56-continued

| Target | Sequence | SEQ ID NO: |
|---|---|---|
| | ITYADLNLPKGKKPAPQAAEPNNHTEYASIQTSPQPASEDTLTY<br>ADLDMVHLNRTPKQPAPKPEPSFSEYASVQVPRK | |
| αV1 N→E | EEELQVIQPDKSVLVAAGETATLRCTATSLIPVGPIQWFRGAGP<br>GRELIYNQKEGHFPRVTTVSDLTKR**E**NMDFSIRIGNITPADAGT<br>YYCVKFRKGSPDDVEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 269 |
| αV1 D→E | EEELQVIQPDKSVLVAAGETATLRCTATSLIPVGPIQWFRGAGP<br>GRELIYNQKEGHFPRVTTVSDLTKRNNMDFSIRIGNITPADAGT<br>YYCVKFRKGSP**E**DVEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 270 |
| αV1 D→N | EEELQVIQPDKSVLVAAGETATLRCTATSLIPVGPIQWFRGAGP<br>GRELIYNQKEGHFPRVTTVSDLTKRNNMDFSIRIGNITPADAGT<br>YYCVKFRKGSPD**N**VEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 271 |
| αV1 DD→EN | EEELQVIQPDKSVLVAAGETATLRCTATSLIPVGPIQWFRGAGP<br>GRELIYNQKEGHFPRVTTVSDLTKRNNMDFSIRIGNITPADAGT<br>YYCVKFRKGSP**EN**VEFKSGAGTELSVRAKPSAPVVSGPAARATP<br>QHTVSFTCESHGFSPRDITLKWFKNGNELSDFQTNVDPVGESVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTVTENKDGTYNWMSWLLVNVSAHRDDVKLTCQVEHDGQ<br>PAVSKSHDLKVSAHPKEQGSNTAAENTGSNERNIYIVVGVVCTL<br>LVALLMAALYLVRIRQKKAQGSTSSTRLHEPEKNAREITQDTND<br>ITYADLNLPKGKKPAPQAAEPNNHTEYASIQTSPQPASEDTLTY<br>ADLDMVHLNRTPKQPAPKPEPSFSEYASVQVPRK | 272 |

TABLE 57

| | Cell Binding $EC_{50}$ (nM) | | | | |
|---|---|---|---|---|---|
| Antibody | αV1 WT | αV1 N→E | αV1 D→E | αV1 D→N | αV1 DD→EN |
| Isotype | NB | NB | NB | NB | NB |
| KWAR23 | 0.3 | 0.5 | 0.2 | 0.2 | 0.2 |
| Antibody A | 0.4 | 0.4 | 0.3 | NS | NS |
| Antibody B | 3.8 | 4.5 | 3.7 | NS | NS |
| Antibody C | 0.3 | 0.3 | 0.2 | 2.7 | 1.1 |
| Antibody D | 0.3 | 0.3 | 0.2 | 9.6 | 6.6 |
| Antibody E | 0.5 | 0.5 | 0.4 | 0.4 | 0.4 |
| Antibody A4 | 0.4 | 0.4 | 0.3 | NS | NS |
| Antibody A10 | 0.4 | 0.4 | 0.3 | NS | NS |
| Antibody E22 | 0.8 | 0.9 | 0.7 | 0.8 | 0.6 |

NB: No binding

NS: Non-saturable binding at 67 nM

Example 27. Binding of Antibodies to Full-Length Human V2-SIRPα with Various Amino Acid Point Mutations Expressed on Expi-CHO Cells To study the structural basis of the observed antibody selectivity, antibody binding to cells engineered to express modified V2-SIRPα protein sequences is tested by flow cytometry. Expi-CHO parental cells are transduced with lentiviruses containing either full-length wild-type human SIRPαV2 allele (CAA71403.1) or full-length human SIRPαV2 with amino acid point mutations (Table 58) and sorted to achieve matching expression levels. These cells are blocked with donkey IgG and incubated on ice with increasing concentrations of antibodies for 60 minutes, washed and stained with AF647-conjugated donkey $F(ab')_2$ anti-human IgG antibodies. Stained cells are washed, fixed, and analyzed by flow cytometry. Median fluorescent intensity is determined and used as a measure of antibody binding.

Antibodies A-E, A4, A10, E22 and KWAR23, but not isotype control, showed dose-dependent binding to Expi-CHO cells expressing full-length wild-type human SIRPαV2 (FIG. 32A) with $EC_{50}$ values ranging between 0.2 to 3.6 nM (Table 59). Antibody binding to cells expressing SIRPαV2 E→N were comparable to binding to SIRPαV2 WT-expressing cells (FIG. 32B; Table 59). In contrast, binding of antibodies A, D, A4 and A10, but not B, C, E, E22, and KWAR23, to Expi-CHO cells expressing SIRPαV2 D→E was affected, showing 3.1 to 7.7 fold greater $EC_{50}$'s than $EC_{50}$ values observed for SIRPαV2 WT-expressing cells (FIG. 32C; Table 59).

TABLE 58

| Target | Sequence | SEQ ID NO: |
|---|---|---|
| αV2 WT | EEELQVIQPDKSVSVAAGESAILHCTVTSLIPVGPIQWFRGAGPA<br>RELIYNQKEGHFPRVTTVSESTKRENMDFSISISNITPADAGTYY<br>CVKFRKGSPDTEFKSGAGTELSVRAKPSAPVVSGPAARATPQHTV<br>SFTCESHGFSPRDITLKWFKNGNELSDFQTNVDPVGESVSYSIHS<br>TAKVVLTREDVHSQVICEVAHVTLQGDPLRGTANLSETIRVPPTL<br>EVTQQPVRAENQVNVTCQVRKFYPQRLQLTWLENGNVSRTETAST<br>VTENKDGTYNWMSWLLVNVSAHRDDVKLTCQVEHDGQPAVSKSHD<br>LKVSAHPKEQGSNTAAENTGSNERNIYIVVGVVCTLLVALLMAAL<br>YLVRIRQKKAQGSTSSTRLHEPEKNAREITQDTNDITYADLNLPK<br>GKKPAPQAAEPNNHTEYASIQTSPQPASEDTLTYADLDMVHLNRT<br>PKQPAPKPEPSFSEYASVQVPRK | 273 |
| αV2 E→N | EEELQVIQPDKSVSVAAGESAILHCTVTSLIPVGPIQWFRGAGPA<br>RELIYNQKEGHFPRVTTVSESTKR**N**NMDFSISISNITPADAGTYY<br>CVKFRKGSPDTEFKSGAGTELSVRAKPSAPVVSGPAARATPQHTV<br>SFTCESHGFSPRDITLKWFKNGNELSDFQTNVDPVGESVSYSIHS<br>TAKVVLTREDVHSQVICEVAHVTLQGDPLRGTANLSETIRVPPTL<br>EVTQQPVRAENQVNVTCQVRKFYPQRLQLTWLENGNVSRTETAST<br>VTENKDGTYNWMSWLLVNVSAHRDDVKLTCQVEHDGQPAVSKSHD<br>LKVSAHPKEQGSNTAAENTGSNERNIYIVVGVVCTLLVALLMAAL<br>YLVRIRQKKAQGSTSSTRLHEPEKNAREITQDTNDITYADLNLPK<br>GKKPAPQAAEPNNHTEYASIQTSPQPASEDTLTYADLDMVHLNRT<br>PKQPAPKPEPSFSEYASVQVPRK | 274 |
| αV2 D→E | EEELQVIQPDKSVSVAAGESAILHCTVTSLIPVGPIQWFRGAGPA<br>RELIYNQKEGHFPRVTTVSESTKRENMDFSISISNITPADAGTYY<br>CVKFRKGSP**E**TEFKSGAGTELSVRAKPSAPVVSGPAARATPQHTV<br>SFTCESHGFSPRDITLKWFKNGNELSDFQTNVDPVGESVSYSIHS<br>TAKVVLTREDVHSQVICEVAHVTLQGDPLRGTANLSETIRVPPTL<br>EVTQQPVRAENQVNVTCQVRKFYPQRLQLTWLENGNVSRTETAST<br>VTENKDGTYNWMSWLLVNVSAHRDDVKLTCQVEHDGQPAVSKSHD<br>LKVSAHPKEQGSNTAAENTGSNERNIYIVVGVVCTLLVALLMAAL<br>YLVRIRQKKAQGSTSSTRLHEPEKNAREITQDTNDITYADLNLPK<br>GKKPAPQAAEPNNHTEYASIQTSPQPASEDTLTYADLDMVHLNRT<br>PKQPAPKPEPSFSEYASVQVPRK | 275 |

TABLE 59

| | Cell Binding $EC_{50}$ (nM) | | |
|---|---|---|---|
| Antibody | αV2 WT | αV2 E→N | αV2 D→E |
| Isotype | NB | NB | NB |
| KWAR23 | 0.2 | 0.2 | 0.2 |
| Antibody A | 0.3 | 0.3 | 1.0 |
| Antibody B | 3.6 | 4.1 | 3.7 |
| Antibody C | 0.2 | 0.2 | 0.2 |
| Antibody D | 0.2 | 0.2 | 0.6 |
| Antibody E | 0.3 | 0.3 | 0.3 |
| Antibody A4 | 0.2 | 0.2 | 1.8 |
| Antibody A10 | 0.2 | 0.3 | 0.7 |
| Antibody E22 | 0.4 | 0.4 | 0.4 |

NB: No binding
NS: Non-saturable binding at 67 nM

Example 28. Binding of Antibodies to Full-Length Human SIRPβ1 with Various Amino Acid Point Mutations Expressed on Expi-CHO Cells To study the structural basis of the observed antibody selectivity, antibody binding to cells engineered to express modified SIRPβ1 protein sequences is tested by flow cytometry. Expi-CHO parental cells are transduced with lentiviruses containing either full-length wild-type human SIRPβ1 (000241) or full-length human SIRPβ1 with a single amino acid point mutation (Table 60) and sorted to achieve matching expression levels. These cells are blocked with donkey IgG and incubated on ice with increasing concentrations of antibodies for 60 minutes, washed and stained with AF647-conjugated donkey $F(ab')_2$ anti-human IgG antibodies. Stained cells are washed, fixed, and analyzed by flow cytometry. Median fluorescent intensity is determined and used as a measure of antibody binding.

Antibodies A-E, A4, A10 and KWAR23, but not isotype control or antibody E22, showed dose-dependent binding to full length wild-type human SIRPβ1 expressed on Expi-CHO cells (FIG. 33A). Table 61 highlights the binding $EC_{50}$ calculated for each of the antibodies. While antibodies A, C, D, A4, and A10 exhibited $EC_{50}$ values ranging between 0.2 to 1.6 nM on wild-type human SIRPβ1-expressing cells, binding of antibodies B and E were non-saturable and no $EC_{50}$ values were determined. Except for KWAR23, antibody binding was completely lost when a single amino acid substitution (D→H) was introduced within the loop region (FIG. 33B).

TABLE 60

| Target | Sequence | SEQ ID NO: |
|---|---|---|
| β1 WT | EDELQVIQPEKSVSVAAGESATLRCAMTSLIPVGPIMWFRGAGA<br>GRELIYNQKEGHFPRVTTVSELTKRNNLDFSISISNITPADAGT<br>YYCVKFRKGSPDDVEFKSGAGTELSVRAKPSAPVVSGPAVRATP<br>EHTVSFTCESHGFSPRDITLKWFKNGNELSDFQTNVDPAGDSVS<br>YSIHSTARVVLTRGDVHSQVICEIAHITLQGDPLRGTANLSEAI<br>RVPPTLEVTQQPMRAENQANVTCQVSNFYPRGLQLTWLENGNVS<br>RTETASTLIENKDGTYNWMSWLLVNTCAHRDDVVLTCQVEHDGQ<br>QAVSKSYALEISAHQKEHGSDITHEAALAPTAPLLVALLLGPKL<br>LLVVGVSAIYICWKQKA | 276 |
| β1 D→H | EDELQVIQPEKSVSVAAGESATLRCAMTSLIPVGPIMWFRGAGA<br>GRELIYNQKEGHFPRVTTVSELTKRNNLDFSISISNITPADAGT<br>YYCVKFRKGSPDHVEFKSGAGTELSVRAKPSAPVVSGPAVRATP<br>EHTVSFTCESHGFSPRDITLKWFKNGNELSDFQTNVDPAGDSVS<br>YSIHSTARVVLTRGDVHSQVICEIAHITLQGDPLRGTANLSEAI<br>RVPPTLEVTQQPMRAENQANVTCQVSNFYPRGLQLTWLENGNVS<br>RTETASTLIENKDGTYNWMSWLLVNTCAHRDDVVLTCQVEHDGQ<br>QAVSKSYALEISAHQKEHGSDITHEAALAPTAPLLVALLLGPKL<br>LLVVGVSAIYICWKQKA | 277 |

TABLE 61

| | Cell Binding $EC_{50}$ (nM) | |
|---|---|---|
| Antibody | β1 WT | β1 D→H |
| Isotype | NB | NB |
| KWAR23 | 0.2 | 0.01 |
| Antibody A | 1.6 | NB |
| Antibody B | NS | NB |
| Antibody C | 0.2 | NB |
| Antibody D | 0.2 | NB |
| Antibody E | NS | NB |
| Antibody A4 | 1.5 | NB |
| Antibody A10 | 1.6 | NB |
| Antibody E22 | NB | NB |

NB: No binding
NS: Non-saturable binding at 67 nM

Example 29. Binding of Antibodies to Full-Length Human SIRPβL with Various Amino Acid Point Mutations Expressed on Expi-CHO Cells To study the structural basis of the observed antibody selectivity, antibody binding to cells engineered to express modified SIRPβL protein sequences is tested by flow cytometry. Expi-CHO parental cells are transduced with lentiviruses containing either full-length wild-type human SIRPβL (Q5TFQ8) or full-length human SIRPβL with a single amino acid point mutation (Table 62) and sorted to achieve matching expression levels. These cells are blocked with donkey IgG and incubated on ice with increasing concentrations of antibodies for 60 minutes, washed and stained with AF647-conjugated donkey $F(ab')_2$ anti-human IgG antibodies. Stained cells are washed, fixed, and analyzed by flow cytometry. Median fluorescent intensity is determined and used as a measure of antibody binding.

Antibodies E, E22 and KWAR23 showed dose-dependent binding to full length human SIRPβL expressed on Expi-CHO cells (FIG. 34A) with $EC_{50}$ values less than 1.2 nM (Table 63). No binding of antibodies A, A4, and A10 could be detected on SIRPβL-expressing cells, while antibodies B, C, and D exhibited non-saturable binding (FIG. 34A, Table 63). A single amino acid substitution (H→D) introduced within the loop region maintained, strengthened, or facilitated antibody binding to these cells (FIG. 34B, Table 63).

TABLE 62

| Target | Sequence | SEQ ID NO: |
|---|---|---|
| βL WT | EEELQVIQPDKSISVAAGESATLHCTVTSLIPVGPIQWFRGAGP<br>GRELIYNQKEGHFPRVTTVSDLTKRNNMDFSIRISNITPADAGT<br>YYCVKFRKGSPDHVEFKSGAGTELSVRAKPSAPVVSGPAARATP<br>QHTVSFTCESHGFSPRDITLKWFKNGNELSDFQTNVDPAGDSVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTLTENKDGTYNWMSWLLVNVSAHRDDVKLTCQVEHDGQ<br>PAVSKSHDLKVSAHPKEQGSNTAPGPALASAAPLLIAFLLGPKV<br>LLVVGVSVIYVYWKQKA | 278 |
| βL H→D | EEELQVIQPDKSISVAAGESATLHCTVTSLIPVGPIQWFRGAGP<br>GRELIYNQKEGHFPRVTTVSDLTKRNNMDFSIRISNITPADAGT<br>YYCVKFRKGSPDDVEFKSGAGTELSVRAKPSAPVVSGPAARATP<br>QHTVSFTCESHGFSPRDITLKWFKNGNELSDFQTNVDPAGDSVS<br>YSIHSTAKVVLTREDVHSQVICEVAHVTLQGDPLRGTANLSETI<br>RVPPTLEVTQQPVRAENQVNVTCQVRKFYPQRLQLTWLENGNVS<br>RTETASTLTENKDGTYNWMSWLLVNVSAHRDDVKLTCQVEHDGQ<br>PAVSKSHDLKVSAHPKEQGSNTAPGPALASAAPLLIAFLLGPKV<br>LLVVGVSVIYVYWKQKA | 279 |

TABLE 63

| | Cell Binding $EC_{50}$ (nM) | |
|---|---|---|
| Antibody | βL WT | βL WT H→D |
| Isotype | NB | NB |
| KWAR23 | 1.0 | 0.5 |
| Antibody A | NB | 0.5 |
| Antibody B | NS | 6.7 |
| Antibody C | NS | 0.3 |
| Antibody D | NS | 0.2 |
| Antibody E | 1.0 | 0.5 |
| Antibody A4 | NB | 0.5 |
| Antibody A10 | NB | 0.6 |
| Antibody E22 | 1.2 | 0.7 |

NB: No binding
NS: Non-saturable binding at 67 nM

Example 30. Binding of Antibodies to Full-Length Human SIRPγ with Various Amino Acid Point Mutations Expressed on Expi-CHO Cells To study the structural basis of the observed antibody selectivity, antibody binding to cells engineered to express modified SIRPγ protein sequences is tested by flow cytometry. Expi-CHO parental cells are transduced with lentiviruses containing either full-length wild-type human SIRPγ (NP_542970.1) or full-length human SIRPγ with amino acid point mutations (Table 64) and sorted to achieve matching expression levels. These cells are blocked with donkey IgG and incubated on ice with increasing concentrations of antibodies for 60 minutes, washed and stained with AF647-conjugated donkey $F(ab')_2$ anti-human IgG antibodies. Stained cells are washed, fixed, and analyzed by flow cytometry. Median fluorescent intensity is determined and used as a measure of antibody binding.

Except KWAR23, none the antibodies tested (Antibodies A-E, A4, A10, E22) showed saturable binding to Expi-CHO cells expressing full-length wild-type human SIRPγ or SIRPγ E→D expressing cells (FIGS. 35A and 35B, respectively). In contrast, antibodies A-D, A4, and A10 showed saturable antibody binding to Expi-CHO cells expressing SIRPγ N→D and EN→DD variants with all but antibody B with sub nanomolar $EC_{50}$ values (FIGS. 35C and 35D, respectively, and Table 65).

TABLE 64

| Target | Sequence | SEQ ID NO: |
|---|---|---|
| γWT | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSPENVEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 280 |
| γE→D | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSPDNVEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 281 |
| γN→D | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSPEDVEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 282 |
| γEN→DD | EEELQMIQPEKLLLVTVGKTATLHCTVTSLLPVGPVLWFRGVGP GRELIYNQKEGHFPRVTTVSDLTKRNNMDFSIRISSITPADVGT YYCVKFRKGSPDDVEFKSGPGTEMALGAKPSAPVVLGPAARTTP EHTVSFTCESHGFSPRDITLKWFKNGNELSDFQTNVDPTGQSVA YSIRSTARVVLDPWDVRSQVICEVAHVTLQGDPLRGTANLSEAI RVPPTLEVTQQPMRVGNQVNVTCQVRKFYPQSLQLTWSENGNVC QRETASTLTENKDGTYNWTSWFLVNISDQRDDVVLTCQVKHDGQ LAVSKRLALEVTVHQKDQSSDATPGPASSLTALLLIAVLLGPIY VPWKQKT | 283 |

TABLE 65

| | Cell Binding $EC_{50}$ (nM) | | | |
|---|---|---|---|---|
| Antibody | γ WT | γ E→D | γ N→D | γ EN→DD |
| Isotype | NB | NB | NB | NB |
| KWAR23 | 0.113 | 0.3 | 0.3 | 0.3 |
| Antibody A | NB | NB | 0.4 | 0.6 |
| Antibody B | NS | NS | 4.8 | 5.3 |
| Antibody C | NS | NS | 0.2 | 0.2 |
| Antibody D | NS | NS | 0.3 | 0.3 |
| Antibody E | NB | NB | NB | NB |
| Antibody A4 | NB | NB | 0.5 | 0.7 |
| Antibody A10 | NB | NB | 0.5 | 0.7 |
| Antibody E22 | NB | NB | NB | NB |

NB: No binding
NS: Non-saturable binding at 67 nM

Example 31. Amino Acids 125-132 of SIRPαV1 and 125-131 of SIRPαV2 are Determinants for Antibody Selectivity A particular area of the SIRPα epitope bound by Antibody A was identified within the loop region located at amino acids 125-131 of SIRPαV2 (sequence RKGSPDT), corresponding to amino acids 125-132 of SIRPαV1 (sequence RKGSPDDV). We identified this loop as a determinant for the observed binding properties of Antibody A, including selective binding to SIRPαV1 and SIRPαV2, with no detectable binding to human SIRPγ and human SIRPβL (Table 37). The potential role of this loop in conferring binding selectivity was identified by determination of the crystal structure of Antibody A in complex SIRPαV2 (Example 20), and from the sequence comparison of epitope amino acids in related SIRP isoforms, and was confirmed by binding studies described above (Examples 26-30). Notably, this loop differs in length between SIRPαV1 and SIRPαV2, i.e., 8 amino acids in SIRPαV1 and 7 amino acids in SIRPαV2. Despite this difference in loop length, Antibody A shows similar binding affinity for both SIRPαV1 and SIRPαV2 (see, e.g., Table 37). FIG. 36A illustrates how Antibody A binds to this loop from the side, which is believed to allow for specific recognition of the loops with different length in SIRPαV1 and SIRPαV2. We observed that the general configuration of the SIRPα interaction with Antibody A is like the SIRPα interaction with the natural binding partner, CD47, where the loops of SIRPαV1 and SIRPαV2 are approached in a similar orientation (FIG. 36B). However, unlike Antibody A, CD47 also binds to SIRPγ, indicating that Antibody A can confer binding selectivity despite this general similarity.

Even though loops of different length can be recognized by Antibody A, this part of the epitope is nonetheless able to confer the selectivity observed for the SIRP proteins. We identified the sequence motif PDDV in SIRPαV1 as an important difference from SIRPγ and SIRPβL, where the corresponding sequences are PENV and PDHV respectively (FIGS. 37A-37F).

To further study the structural basis of the observed selectivity of Antibody A, we tested its ability to bind to cells engineered to expressed modified SIRP protein sequences (see Examples 26-30). The results of these experiments confirmed the importance of the variant residues in this loop to conferring binding selectivity. We observed that exchanging the respective sequence motif in SIRPαV1 (PDDV) to either PDNV or PENV sequence of SIRPγ strongly impaired binding to Antibody A (FIGS. 31D-31E). Similarly, binding of Antibody A to SIRPβ1 with its PDDV motif was completely abrogated by the exchange to PDHV motif of SIRPβL (FIG. 33B). Reciprocally, binding can be restored when exchanging the PENV motif of SIRPγ to either PEDV or PDDV of SIRPαV1 (FIGS. 35C-35D) or exchanging the PDHV motif of SIRPβL to PDDV of SIRPβ1 (FIG. 34B). These results highlight the properties of the epitope, allowing on the one hand for tolerance of two different loop length in the SIRPα proteins, but on the other hand providing high sensitivity to amino acid changes in the binding interface. Together, these properties result in the selectivity pattern described for Antibody A and its variants (e.g., A4 and A10), namely, strong binding to SIRPαV1, SIRPαV2 and SIRPβ1, complemented by pronounced absence of binding to SIRPγ and SIRPβL.

Example 32. Antibody Titer and Purity

Methods

Transfection. For transfection, combine heavy chain DNA, light chain DNA, Filler DNA and XBP-1 DNA with Opti-Pro SFM (Thermo Fisher) and sterilize by filtering through 0.2 μm filter. Prepare cells at $2\times10^6$ cells/mL or $4\times10^6$ cells/mL (in BalanCD Transfectory CHO (Irvine Scientific)+4 mM L-Glutamine) for required scale of transfection. Add the calculated volume of TransIT Pro (Mirus) transfection reagent to the prepared Opti-Pro SFM+DNA mix and immediately transfer to the prepared cells. Place the shake flask in incubator at 37° C., 5% $CO_2$, and 140 rpm or 200 rpm shake speed. 24 hours post-transfection, temperature is shifted to 30° C., and Transfectory Supplement and Anti-Clumping Supplement (both Irvine Scientific) are added to the transfected cells. CHO CD Efficient Feed B (Gibco) is added between day 5 or day 7, depending on when glucose levels drop between 2 g/L-1 g/L. The transfected culture is maintained for 7-10 days.

Harvest by centrifugation and sterile filtration. The clarified cell culture supernatant is sampled for titer by ForteBio/Pall Octet Red 96 instrument with Protein A biosensors. The measured antibody concentration is reported as the expression titer (mg/L).

Protein A (ProA) Purification: The purification is performed at room temperature (RT) using a GE AKTA Pure system. Each sample is captured from the harvested cell culture fluid (HCCF) by recombinant Protein-A affinity chromatography using MabSelect SuRe resin (GE Healthcare). Chromatography steps and buffer details can be found in Tables 66 and 67, respectively. Protein binds to Protein A at neutral pH at room temperature and is washed with high salt (1M NaCl). Each sample is eluted in an isocratic mode using 30 mM sodium acetate, pH 3.5. Eluted sample is neutralized to pH 5.0 using 1% solution of 3M sodium acetate, pH 9.0. Neutralized protein is sterile filtered with 0.22 μm filtration system. The concentration is calculated based on the absorbance measurement at 280 nm using a NanoDrop 8000 Spectrophotometer (Thermo Fisher).

TABLE 66

| Buffer | Composition |
|---|---|
| Equilibration/Wash 1 | DPBS: 8.05 mM sodium phosphate, 137 mM NaCl, 1.47 mM potassium phosphate, 2.6 mM potassium chloride, pH 7.4 |
| Wash 2 | 1M NaCl in DPBS |
| Wash 3 | DPBS: 8.05 mM sodium phosphate, 137 mM NaCl, 1.47 mM potassium phosphate, 2.6 mM potassium chloride, pH 7.2 |
| Elution | 30 mM Sodium Acetate, pH 3.5 |
| Neutralization | 3M Sodium Acetate, pH~9 |
| Regeneration | 0.25N NaOH |
| Storage | 20% Ethanol |

TABLE 67

| Step | Buffer/Solution | Volume |
|---|---|---|
| Equilibration | DPBS, pH 7.4 | ≥5 CV |
| Load | Media | varies |
| Wash 1 | DPBS, pH 7.4 | ≥5 CV |
| Wash 2 | DPBS + 1M NaCl | ≥5 CV |
| Wash 3 | DPBS, pH 7.4 | ≥5 CV |
| Elution | 30 mM sodium acetate, pH 3.5 | ≥5 CV Remark: OD wavelength 280 nm Start pool collection when OD ≥100 mAU End pool collection when OD ≥100 mAU |
| Neutralization | 3M sodium acetate, pH9 | 1% volume of pool post elution |
| Pre-regeneration wash | DPBS, pH 7.4 | ≥5 CV Remark: Ensure the column is equilibrated in DPBS, pH 7.2 by checking pH of the column wash |
| Regeneration | 0.25N NaOH | ≥5 CV Remark: Ensure the column is washed enough in 0.25N NaOH to clean from sticky contaminants Don't leave the column in regeneration buffer for ≥30 min |
| Post-regeneration wash | DPBS, pH 7.4 | ≥4 CV Remark: Ensure the column is equilibrated in DPBS, pH 7.2 by checking pH of the column wash |
| Storage | 20% Ethanol | ≥4 CV |

Cation exchange chromatography (CEX). Cation exchange chromatography is performed at room temperature. The buffers and process conditions are summarized in Tables 68 and 69. The Protein A affinity chromatography purified sample is polished using a Poros 50 XS column (Thermo Fisher) using an AKTA Avant chromatography system (Cytiva). The antibody is bound to the column which is pre-equilibrated with 5CV (column volumes) of 50 mM sodium acetate, pH5.0, washed with 5CV of the same buffer. The antibody is then eluted using gradient of 0 to 0.5M NaCl in 20 CV. Eluted sample is adjusted to the final ionic strength of ~100 mM NaC. Protein is sterile filtered into a 50 mL falcon tube by 0.22 μm Steriflip (Millipore) using vacuum filtration system. The antibody concentration is calculated based on the absorbance measured as 280 nm using the NanoDrop 8000 (Thermo Fisher). Purified antibody is stored at 4° C.

TABLE 68

| Buffer | Composition |
|---|---|
| Equilibration/Wash | 50 mM Sodium Acetate, pH 5.0 |
| Elution | 50 mM Sodium Acetate, 1M NaCl, pH 5.0 Gradient elution in 20 CV of 50% B |
| Regeneration | 0.25N NaOH |
| Storage | 20% Ethanol |

TABLE 69

| Step | Buffer | Volume |
|---|---|---|
| Equilibration | 50 mM sodium acetate, pH 5.0 | 5 CV |
| Load | 50 mM sodium acetate, pH 5.0 | varies |
| Wash | 50 mM sodiumm acetate, pH 5.0 | 5 CV |
| Elutions | 50 mM Sodium Acetate and 1M NaCl, pH 5.0 | 20 CV Remark: OD wavelength 280 nm Start pool collection when OD ≥100 mAU End pool collection when OD ≤100 mAU |
| Regeneration | 0.25N NaOH | ≥5 CV |
| Post-regeneration wash | DPBS, pH 7.4 | ≥5 CV |
| Storage | 20% Ethanol | ≥5 CV |

Analytical Size Exclusion Chromatography. Analytical Size Exclusion Chromatography (aSEC) is performed using a Acquity UPLC (Waters, Milford, MA) system using a Protein BEH SEC column 200 Å, 1.7 μm, 4.6×150 mm (Waters part #186005225). Running conditions are as follows: Mobile phase: 50 mM Sodium Phosphate, 200 mM Arginine and 0.05% Sodium Azide; Flow rate: 0.5 ml/min; Runtime: 5 minutes; Sample loading amount: 10 μg; Peak detection: A280 nm. The results are analyzed to determine the percentage of the antibody present as a monomer, low molecular weight (LMW), and high molecular weight (HMW).

Low pH hold is performed by adjusting the pH to 3.5 with 1M acetic acid, pH 2.45. After 90 minutes incubation at room temperature, the sample is neutralized to pH 5.0 by 1M Tris HCl, pH 9.0. Final concentration is determined using a NanoDrop 8000 (Thermo Fisher) by measuring absorbance at 280 nm. Size purity of the samples is characterized by analytical size exclusion chromatography.

Results

The above procedures are used to express and purify antibodies of the present disclosure. Tables 70 and 71 show the titer and size purity results from two different trials for the antibodies as indicated. Table 70 shows the expression titer and results of Protein A purification and cation exchange chromatography. Repeated rows for a given antibody indicate multiple replicates. Table 71 shows the expression titer and results of Protein A purification. Table 72 shows size purity results for the indicated antibodies following pH 3.5 treatment (2 replicates) compared to the same antibody held at pH 5.0.

TABLE 70

| Name | Titer (mg/L) | Pro A load amount (mg) | Recovery from ProA (%) | Monomer following ProA (%) | CEX Load Amount | Recovery from CEX (%) | Monomer following CEX (%) |
|---|---|---|---|---|---|---|---|
| A | 334 | 334 | 82.20% | 97.03 | 264.54 | 78.40% | 100 |
| B | 206 | 206 | 70.78% | 95.66 | 145.81 | 60.69% | 99.2 |
| C | 277 | 277 | 82.46% | 97.76 | 228.41 | 76.18% | 99.89 |
| D | 227 | 227 | 80.61% | 98.26 | 182.98 | 81.26% | 99.95 |

TABLE 70-continued

| Name | Titer (mg/L) | Pro A load amount (mg) | Recovery from ProA (%) | Monomer following ProA (%) | CEX Load Amount | Recovery from CEX (%) | Monomer following CEX (%) |
|---|---|---|---|---|---|---|---|
| E | 136 | 136 | 68.71% | 98.05 | 93.45 | 74.31% | 99.98 |
| A10 | 231 | 462 | 101% | 97.32 | 453 | 84.41% | 99.88 |
| A10 | 287 | 287 | 102% | 97.15 | 292 | 80.61% | 99.91 |
| A10 | 246.5 | 247 | 101.00% | 96.02 | 235 | 79.40% | 99.64 |
| A4 | 137 | 274 | 105.60% | 99.44 | 274 | 85.19% | 99.9 |
| E22 | 77 | 385 | 189.10% | 95.99 | 694 | 79.24% | 99.49 |

TABLE 71

| Antibody | Expression Titer (mg/L) | Purified Concentration (mg/mL) following Protein A purification | % Monomer (main peak) following Protein A purification |
|---|---|---|---|
| A | 286 | 3.68 | 98.57 |
| A1 | 215.1 | 3.61 | 98.62 |
| A2 | 199.4 | 3.57 | 99.11 |
| A3 | 222.6 | 3.64 | 98.78 |
| A4 | 230.5 | 3.67 | 98.69 |
| A5 | 254.7 | 3.72 | 98.13 |
| A6 | 226.5 | 3.62 | 98.59 |
| A7 | 256.2 | 3.58 | 98.37 |
| A8 | 249.8 | 3.59 | 98.58 |
| A9 | 251.1 | 3.68 | 98.03 |
| A10 | 256.3 | 3.67 | 97.54 |
| A12 | 271.6 | 3.68 | 98.57 |
| A13 | 259.2 | 3.67 | 98.39 |
| A14 | 261.4 | 3.72 | 98.48 |
| A15 | 249.2 | 3.63 | 97.56 |
| A16 | 281.3 | 3.7 | 98.64 |
| E | 146 | 3.19 | 99.09 |
| E1 | 216.1 | 3.24 | 87.86 |
| E2 | 157.6 | 3.37 | 97.12 |
| E3 | 237.7 | 3.27 | 88.32 |
| E4 | 169.8 | 3.31 | 97.58 |
| E5 | 240.6 | 3.26 | 88.92 |
| E6 | 193.4 | 3.37 | 98.51 |
| E7 | 209.2 | 3.44 | 86.42 |
| E8 | 92.8 | 3.12 | 98.9 |
| E9 | 209.7 | 3.39 | 88.79 |
| E10 | 162.9 | 3.28 | 100 |
| E11 | 58.6 | 1.95 | 100 |
| E12 | 235 | 3.43 | 88.83 |
| E13 | 204.6 | 3.3 | 89.09 |
| E14 | 227.5 | 3.41 | 92.98 |
| E15 | 118 | 3.21 | 99.14 |
| E16 | 245.2 | 3.35 | 88.1 |
| E17 | 84.9 | 2.93 | 92.69 |
| E18 | 183.8 | 3.35 | 97.63 |
| E19 | 230.3 | 3.39 | 87.89 |
| E20 | 208 | 3.49 | 89.2 |
| E21 | 237.5 | 3.46 | 91.24 |
| E22 | 78.5 | 2.89 | 97.27 |

TABLE 72

| | Monomer % | | | Avg. | HMW % | | |
|---|---|---|---|---|---|---|---|
| Antibody | pH 5.0 | pH 3.5 (trial #1) | pH 3.5 (trial #2) | Change in Monomer % | pH 5.0 | pH 3.5 (trial #1) | pH 3.5 (trial #2) |
| A10 | 97.49 | 97.37 | 97.40 | 0.10 | 2.52 | 2.62 | 2.60 |
| A4 | 99.29 | 99.13 | 98.40 | 0.53 | 0.71 | 0.87 | 1.60 |
| E22 | 96.64 | 96.33 | 96.98 | −0.02 | 3.36 | 3.66 | 3.03 |

Example 33. Antibody Binding Kinetics

Methods

The binding kinetics of anti-SIRPα antibodies to various SIRPα analytes are determined by surface plasmon resonance (SPR) using a Biacore 8K+ (Cytiva). 1×HBS-EP+ (Cytiva) is used as running buffer and for all the dilutions unless stated otherwise. The Series S CM5 sensorchip is activated with a 1:1 mixture of 0.1 M NHS (N-hydroxysuccinimide) and 0.4 M EDC (1-Ethyl-3-(3-dimethylaminopropyl) carbodiimide hydrochloride) for 420 seconds at a flow rate of 10 μl/min and immobilized with Protein A/G (Thermo Scientific, 10 μg/ml in 10 mM acetate pH 4.5) for 420 seconds at a flowrate of 10 μl/min resulting in approximately 3000 RU of Protein A/G on the surface. The sensorchip is then deactivated with 1 M ethanolamine HCl pH 8.5 for 420 seconds at a flowrate of 10 μl/min.

Antibodies (approximately 1 ug/ml) are captured on the Protein A/G surface for 60 seconds at a flowrate of 10 μl/min resulting in capture levels of approximately 240 RU. Dilutions of each SIRP protein (Extracellular Domain+His-Tag, with the concentrations as indicated) are injected as analytes over the captured antibody for 300 seconds of association at a flowrate of 30 μl/min, followed by a dissociation for 600 seconds. The surfaces are regenerated with a 30 second injection of 0.85% phosphoric acid at 30 μl/min. SPR sensorgrams are fit globally to 1:1 Langmuir binding to provide on-rate ($k_a$), off-rate ($k_d$), and dissociation constant ($K_D$) values or fit globally to a steady state affinity to provide $K_D$ in the Biacore Insight Evaluation software.

Results

The above procedures are used to measure binding properties of antibodies of the present disclosure. For each analyte used, the highest concentration was as indicated in Example 3 (see Table 36). On-rate, off-rate, and dissociation constant of each indicated antibody for each analyte measured are shown in Tables 73-74.

TABLE 73

| | huSIRPαV1 | | | huSIRPαV2 | | |
|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) |
| A | 4.97E+05 | 3.84E−03 | 7.72 | 8.07E+05 | 7.28E−03 | 9.03 |
| E | 4.79E+05 | 2.03E−04 | 0.43 | 5.47E+05 | 1.81E−04 | 0.33 |
| A1 | 7.27E+05 | 6.25E−03 | 8.60 | 8.69E+05 | 1.62E−02 | 18.6 |
| A2 | 7.29E+05 | 6.85E−03 | 9.39 | 8.83E+05 | 1.84E−02 | 20.9 |
| A3 | 7.30E+05 | 6.61E−03 | 9.06 | 9.07E+05 | 1.78E−02 | 19.6 |
| A4 | 7.29E+05 | 6.17E−03 | 8.46 | 8.92E+05 | 1.63E−02 | 18.3 |
| A5 | 6.84E+05 | 5.98E−03 | 8.75 | 9.09E+05 | 1.62E−02 | 17.8 |
| A6 | 7.66E+05 | 6.34E−03 | 8.28 | 9.47E+05 | 1.71E−02 | 18.1 |
| A7 | 7.16E+05 | 6.72E−03 | 9.38 | 9.33E+05 | 1.90E−02 | 20.4 |
| A8 | 7.08E+05 | 6.04E−03 | 8.53 | 8.59E+05 | 1.62E−02 | 18.8 |
| A9 | 4.95E+05 | 3.63E−03 | 7.34 | 7.91E+05 | 6.52E−03 | 8.25 |
| A10 | 5.98E+05 | 4.02E−03 | 6.75 | 6.93E+05 | 6.98E−03 | 10.6 |
| A11 | 5.86E+05 | 4.00E−03 | 6.87 | 6.80E+05 | 7.09E−03 | 10.9 |
| A12 | 4.82E+05 | 3.78E−03 | 7.83 | 7.69E+05 | 6.89E−03 | 8.96 |
| A13 | 4.84E+05 | 3.52E−03 | 7.28 | 7.60E+05 | 6.35E−03 | 8.36 |
| A14 | 4.88E+05 | 3.97E−03 | 8.13 | 8.16E+05 | 6.48E−03 | 7.95 |
| A15 | 5.26E+05 | 3.71E−03 | 7.06 | 8.48E+05 | 6.71E−03 | 7.91 |
| A16 | 4.72E+05 | 3.77E−03 | 7.98 | 7.66E+05 | 6.30E−03 | 8.22 |
| E1 | 4.14E+05 | 2.99E−04 | 0.72 | 5.23E+05 | 3.30E−04 | 0.63 |
| E2 | 4.59E+05 | 4.19E−04 | 0.91 | 5.35E+05 | 3.67E−04 | 0.69 |
| E3 | 3.85E+05 | 3.71E−04 | 0.96 | 4.72E+05 | 3.66E−04 | 0.78 |
| E4 | 4.38E+05 | 4.33E−04 | 0.99 | 5.11E+05 | 4.21E−04 | 0.82 |
| E5 | 3.31E+05 | 3.36E−04 | 1.02 | 4.06E+05 | 3.55E−04 | 0.87 |
| E6 | 3.74E+05 | 3.86E−04 | 1.03 | 4.29E+05 | 3.75E−04 | 0.88 |
| E7 | 3.78E+05 | 4.53E−04 | 1.20 | 4.68E+05 | 5.52E−04 | 1.18 |
| E8 | 3.22E+05 | 3.90E−04 | 1.21 | 4.35E+05 | 2.36E−04 | 0.54 |
| E9 | 5.18E+05 | 6.31E−04 | 1.22 | 5.83E+05 | 5.48E−04 | 0.94 |
| E10 | 4.22E+05 | 5.18E−04 | 1.23 | 4.98E+05 | 5.96E−04 | 1.20 |
| E11 | 3.52E+05 | 4.98E−04 | 1.41 | 4.53E+05 | 2.58E−04 | 0.57 |
| E12 | 4.90E+05 | 8.19E−04 | 1.67 | 5.62E+05 | 7.09E−04 | 1.26 |
| E13 | 3.94E+05 | 6.71E−04 | 1.70 | 4.90E+05 | 3.38E−04 | 0.69 |
| E14 | 4.03E+05 | 7.43E−04 | 1.84 | 4.53E+05 | 6.15E−04 | 1.36 |
| E15 | 4.21E+05 | 8.02E−04 | 1.91 | 5.01E+05 | 3.69E−04 | 0.74 |
| E16 | 4.90E+05 | 1.06E−03 | 2.15 | 5.47E+05 | 1.05E−03 | 1.93 |
| E17 | 4.05E+05 | 9.55E−04 | 2.36 | 5.08E+05 | 4.05E−04 | 0.80 |
| E18 | 4.10E+05 | 1.01E−03 | 2.46 | 4.93E+05 | 4.43E−04 | 0.90 |
| E19 | 3.34E+05 | 8.43E−04 | 2.52 | 4.11E+05 | 3.99E−04 | 0.97 |
| E20 | 4.80E+05 | 1.64E−03 | 3.42 | 5.63E+05 | 6.27E−04 | 1.11 |
| E21 | 4.76E+05 | 2.12E−03 | 4.46 | 5.49E+05 | 7.61E−04 | 1.39 |

TABLE 74

| | cynoSIRPα (NP_001271679) | | | cynoSIRPα (EGM_02252) | | | cynoSIRPα (XP_015313155) | | |
|---|---|---|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) |
| A | 8.73E+05 | 1.38E−01 | 158 | n/a | n/a | 258* | n/a | n/a | 165* |
| E | 2.35E+05 | 1.91E−03 | 8.14 | | NB | | 2.41E+05 | 1.70E−03 | 7.07 |
| A1 | n/a | n/a | 780* | n/a | n/a | 523* | n/a | n/a | 427* |
| A2 | n/a | n/a | 887* | n/a | n/a | 556* | n/a | n/a | 469* |
| A3 | n/a | n/a | 857* | n/a | n/a | 560* | n/a | n/a | 480* |
| A4 | n/a | n/a | 669* | n/a | n/a | 488* | n/a | n/a | 420* |
| A5 | n/a | n/a | 665* | n/a | n/a | 517* | n/a | n/a | 415* |
| A6 | n/a | n/a | 684* | n/a | n/a | 521* | n/a | n/a | 420* |
| A7 | n/a | n/a | 741* | n/a | n/a | 588* | n/a | n/a | 466* |
| A8 | n/a | n/a | 639* | n/a | n/a | 520* | n/a | n/a | 415* |
| A9 | n/a | n/a | 346* | n/a | n/a | 230* | n/a | n/a | 174* |
| A10 | n/a | n/a | 388* | n/a | n/a | 282* | n/a | n/a | 203* |
| A11 | n/a | n/a | 410* | n/a | n/a | 298* | n/a | n/a | 204* |
| A12 | n/a | n/a | 384* | n/a | n/a | 247* | n/a | n/a | 195* |
| A13 | n/a | n/a | 330* | n/a | n/a | 223* | n/a | n/a | 177* |
| A14 | n/a | n/a | 316* | n/a | n/a | 222* | n/a | n/a | 176* |
| A15 | n/a | n/a | 317* | n/a | n/a | 224* | n/a | n/a | 174* |
| A16 | n/a | n/a | 306* | n/a | n/a | 224* | n/a | n/a | 174* |
| E1 | 1.83E+05 | 3.27E−03 | 17.9 | | NB | | 1.90E+05 | 3.17E−03 | 16.7 |
| E2 | 2.54E+05 | 5.26E−03 | 20.7 | | NB | | 2.60E+05 | 5.12E−03 | 19.7 |
| E3 | 1.68E+05 | 2.91E−03 | 17.3 | | NB | | 1.70E+05 | 2.88E−03 | 16.9 |

TABLE 74-continued

| | cynoSIRPα (NP_001271679) | | | cynoSIRPα (EGM_02252) | | | cynoSIRPα (XP_015313155) | | |
|---|---|---|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) |
| E4 | 2.22E+05 | 4.68E−03 | 21.1 | | NB | | 2.28E+05 | 4.51E−03 | 19.8 |
| E5 | 1.23E+05 | 4.71E−03 | 38.2 | | NB | | 1.21E+05 | 4.59E−03 | 37.8 |
| E6 | 1.89E+05 | 7.74E−03 | 41.0 | | NB | | 1.75E+05 | 7.29E−03 | 41.6 |
| E7 | 1.58E+05 | 3.46E−03 | 21.9 | | NB | | 1.59E+05 | 3.37E−03 | 21.2 |
| E8 | 2.04E+05 | 3.60E−03 | 17.7 | | NB | | 2.07E+05 | 3.44E−03 | 16.6 |
| E9 | 3.21E+05 | 1.40E−02 | 43.7 | | NB | | 3.24E+05 | 1.32E−02 | 40.8 |
| E10 | 2.16E+05 | 5.45E−03 | 25.2 | | NB | | 2.22E+05 | 5.26E−03 | 23.7 |
| E11 | 2.67E+05 | 5.42E−03 | 20.3 | | NB | | 2.75E+05 | 5.49E−03 | 20.0 |
| E12 | 2.79E+05 | 1.29E−02 | 46.1 | | NB | | 2.97E+05 | 1.25E−02 | 42.2 |
| E13 | 1.97E+05 | 7.55E−03 | 38.3 | | NB | | 1.90E+05 | 7.11E−03 | 37.4 |
| E14 | 1.90E+05 | 1.73E−02 | 90.7 | | NB | | 2.00E+05 | 1.73E−02 | 86.3 |
| E15 | 2.43E+05 | 1.20E−02 | 49.4 | | NB | | 2.45E+05 | 1.13E−02 | 46.2 |
| E16 | 3.13E+05 | 1.58E−02 | 50.0 | | NB | | 3.00E+05 | 1.47E−02 | 48.8 |
| E17 | 2.82E+05 | 1.26E−02 | 44.8 | | NB | | 2.92E+05 | 1.26E−02 | 43.2 |
| E18 | 2.24E+05 | 1.18E−02 | 52.5 | | NB | | 2.26E+05 | 1.13E−02 | 50.0 |
| E19 | 1.56E+05 | 7.25E−03 | 46.6 | | NB | | 1.54E+05 | 6.87E−03 | 44.7 |
| E20 | 2.51E+05 | 2.78E−02 | 111.0 | | NB | | 2.51E+05 | 2.61E−02 | 104.0 |
| E21 | 2.25E+05 | 2.42E−02 | 107.0 | | NB | | 2.28E+05 | 2.45E−02 | 108.0 |

Abbreviations for Tables 73-74.
NB: No binding.
*indicates steady-state affinity ($k_a$ and $k_d$ values unavailable).

Example 34. Antibody Concentration Effects on Stability

Antibody A10 is prepared at varying concentrations in 10 mM histidine (pH 6.0). Each prepared sample is assessed for turbidity, viscosity, and for high molecular weight (HMW), antibody monomer, and low molecular weight (LMW) levels by size exclusion chromatography (SEC). SEC is performed initially and after one week at 25° C. Results are shown in Table 75 below.

Intrinsic fluorescence measurements are used to assess domain unfolding and aggregation formation as a function of temperature. Results are shown in Table 76 below.

TABLE 75

Antibody properties with varying concentration

| Nominal Conc [mg/mL] | Measured Conc [mg/mL] n = 2 | Turbidity [FNU] n = 2 | Viscosity @ 20°C [mPa * s] n = 2 | Initial HMW [%] | Initial Mono [%] | Initial LMW [%] | 1 wk @ 25° C. HMW [%] | 1 wk @ 25° C. Mono [%] | 1 wk @ 25° C. LMW [%] |
|---|---|---|---|---|---|---|---|---|---|
| 50 | 50.12 | 7.98 | 1.86 | 0.2 | 99.38 | 0.41 | 0.3 | 99.27 | 0.43 |
| 62.5 | 66.24 | 7.69 | 2.6 | 0.22 | 99.37 | 0.41 | 0.36 | 99.21 | 0.43 |
| 100 | 94.35 | 8.39 | 4.16 | 0.27 | 99.25 | 0.48 | 0.46 | 99.11 | 0.43 |
| 150 | 144.28 | 8.37 | 14.73 | 0.34 | 99.22 | 0.44 | 0.72 | 98.81 | 0.46 |
| 200 | 201.50 | 9.72 | 75.66** | 0.45 | 99.09 | 0.45 | 1 | 98.53 | 0.47 |
| 250 | 229.50 | 8.79 | 206.0** | 0.5 | 99.04 | 0.46 | 1.13 | 98.4 | 0.47 |

**viscosity measurement n = 1.
Abbreviations:
Conc: Concentration;
FNU: Formazin Nephelometric Unit;
HMW: High Molecular Weight;
Mono.: Monomer;
LMW: Low Molecular Weight.

TABLE 76

Intrinsic fluorescence measurement of antibody aggregation with varying concentration.

| Nominal Concentration [mg/mL] | Measured Concentration [mg/mL] n = 2 | IF $T_{off}$ [° C.] (n = 3) | IF $T_{m1}$ [° C.] (n = 3) | IF $T_{m2}$ [° C.] (n = 3) | IF $T_{agg}$ [° C.] (n = 3) |
|---|---|---|---|---|---|
| 50 | 50.12 | 63.4 | 69.3 | 80.0 | 76.5 |
| 62.5 | 66.24 | 63.4 | 69.3 | 80.3 | 76.4 |
| 100 | 94.35 | 63.4 | 69.2 | 80.5 | 75.7 |
| 150 | 144.28 | 63.6 | 68.8 | 80.7 | 75.4 |
| 200 | 201.50 | 63.6 | 68.3 | 81.0 | 76.0 |
| 250 | 229.50 | 63.4 | 68.1 | 81.2 | 74.5 |

Abbreviations:
$T_{off}$: transition onset point;
$T_{m1}$: first transition mid point;
$T_{m2}$: second transition mid point;
$T_{agg}$: transition onset of aggregation.

Methods

Turbidity. Turbidity is measured using a turbidity photometer. For each measurement, 130 µL of sample is placed in a single-use borosilicate glass round-bottom cuvette. The irradiation wavelength is 633 nm, and turbidity is measured by right angle light scattering. At least two replicates of each measurement are taken with a permitted deviation of ≤2%.

Viscosity. Viscosity is measured using the Haake MARS III Rheometer, Thermo Scientific. The measurement parameters are as follows: Con: C35/1 (Ø 35 mm and 1° angle), titanium. Volume=210 µL, undiluted. Data analysis: 100 data points at shear rate 1000 $s^{-1}$. Temperature: 20° C.

Size exclusion chromatography. Size exclusion chromatography is conducted on UPLC-System e.g. Agilent 1290 Infinity II using the pre-column KrudKatcher Ultra HPLC In-Line Filter 0.5 µm×0.004 µm ID (Phenomenex, Torrance, CA) and the column Acquity UPLC BEH200SEC 300×4.6 mm, (Waters Corp., Milford, MA). The mobile phase is 40 mM NaH2PO4×H2O, 0.4 M NaClO4, pH 6.8 and the flow rate is 0.3 mL/min. The autosampler is maintained at 5° C. and the column is at room temperature. The detection is done by UV detector at wavelength of 280 nm. Peakwidth is >0.05 min (1 s) (for EmPower) or approx. 10 Hz (other software). The slit is 4 nm. Samples are diluted to 5 mg/mL in the mobile phase. The load amount is 30 µg per injection. The run time is 15 min. Integration is performed automatically with the algorithm Apex Track as default, peak area is approximately within a retention time of 4.5-11.5 min, with activation of the "detect shoulders" setting. The peak width is 20 sec and the detection threshold is 14.

Intrinsic fluorescence. Intrinsic fluorescence is measured using the Prometheus NT. 48 nano DSF (NanoTemper Technologies GmbH, Munich, Germany) using a standardized method. The sample volume is 10 µL per capillary, and the sample concentration and formulation is as indicated. Prometheus NT.48 Series nanoDSF Grade Standard Capillaries is used for protein concentrations >0.2 mg/mL, and Prometheus NT.48 Series nanoDSF Grade High Sensitivity Capillaries for concentrations s 0.2 mg/mL. The temperature ramp is 20° C.-95° C. at 1° C./min. The excitation wavelength for intrinsic fluorescence is set to 285 nm and intensity is between 10%-30% (adapted depending on the optimal measuring range). The value of the detection ratio at 350/330 nm is plotted as a function against the temperature. The first derivation of this function is used for determination of Tonset and melting temperature, and Tonset is determined by light backscattering.

Example 35. Antibody Stability Testing

Antibody A10 is formulated at a concentration of 50 mg antibody/mL in 25 mM histidine and pH 6.0, with varying NaCl concentration. Properties of each formulation were assessed by SPR (Table 77) and SEC (Tables 78 and 79) initially and after 4 and 8 weeks held at 40° C.

TABLE 77

Change in binding activity (by SPR).

| NaCl [mM] | Activity [% change from baseline] 4 weeks@40° C. | 8 weeks@40° C. |
|---|---|---|
| 25 | 84.92 | 73.35 |
| 50 | 85.63 | 74.13 |
| 75 | 86.01 | 74.86 |
| 100 | 86.58 | 76.08 |
| 150 | 87.64 | 77.52 |
| 200 | 88.37 | 78.79 |
| 250 | 89.02 | 79.95 |
| 500 | 90.71 | 82.68 |

TABLE 78

High molecular weight species levels.

| NaCl [mM] | High Molecular Weight [%] 4 weeks@40° C. | 8 weeks@40° C. |
|---|---|---|
| 25 | 2.57 | 3.73 |
| 50 | 2.56 | 3.67 |
| 75 | 2.56 | 3.57 |
| 100 | 2.36 | 3.30 |
| 150 | 2.08 | 2.94 |
| 200 | 2.08 | 2.79 |
| 250 | 2.37 | 2.76 |
| 500 | 2.16 | 2.61 |

TABLE 79

Monomer levels.

| NaCl [mM] | Monomer [%] 4 weeks@40° C. | 8 weeks@40° C. |
|---|---|---|
| 25 | 95.26 | 92.87 |
| 50 | 95.24 | 92.87 |
| 75 | 95.22 | 92.94 |
| 100 | 95.39 | 93.16 |
| 150 | 95.68 | 93.50 |
| 200 | 95.64 | 93.61 |
| 250 | 95.35 | 93.64 |
| 500 | 95.50 | 93.63 |

Methods

Surface plasmon resonance. Surface plasmon resonance spectroscopy is performed using the Biacore T200 (Cytiva, Marlborough, MA). Running- and dilution buffer are HBS-EP+(Cytiva, Marlborough, MA). The analysis temperature was 25° C. and the data collection rate is 1 Hz using one flow cell. The Sensor Chip CM5 is used with high density Protein A/G immobilization. A predefined standard amine coupling method of the software is applied. The immobilization buffer is acetate at pH 4.5, 30 µg/ml, 420 s, 10 µl/min. Analysis is performed by preparing a calibration curve from 2000-62.5 ng/ml with factor 1:2 and additional blank injections. Antibody samples are diluted to 1 µg/ml. Human SIRPα V1 &

V2 antigens are diluted to 10 μg/ml. For the build method, one cycle includes: capture of the antibody for 180 s, 10 μl/min; injecting antigen for 180 s, 10 μl/min; and regeneration with 50 mM HCl for 12 s, 50p/min. Evaluation of the received sensorgram was performed using the calibration curve to calculate Biacore concentration of samples for Protein A/G and antigen and calculate the binding activity for the antigen binding site.

Size exclusion chromatography. Size exclusion chromatography is performed as described in Example 34, above.

Example 36. Intrinsic Biophysical Profile Analysis

Methods

Physicochemical descriptors for the variable regions of selected antibodies are computed according to the methods described in Ahmed et al., *Proc Natl Acad Sci USA.* 2021. September 14; 118(37):e2020577118 with a pH value of 7.4 and 137 mM salt. The five descriptors are: surface area buried between VL and VH domains (BSA_VL:VH), ratio of charged to hydrophobic surface patches (RP), ratio of dipole and hydrophobic moments (RM), hydrophobic anisotropy (Avg_HI), and structure-based isoelectric point (pIFv_3D). Each of these five descriptor values was used to compute Z-scores by comparing them with the average and standard deviation (SD) values of the corresponding descriptors for the 79 Fv regions contained in 77 approved antibody-based biotherapeutics (two of the approved biotherapeutics each contain two Fv regions). Each descriptor with a Z-score >1.96 or <−1.96 contributes a flag for an Fv region. The number of flags was summed for each selected antibody, such that an Fv region can collect up to five flags. The individual Z-scores for each Fv region are also combined to obtain its Z-distance as described (id.).

Results

The above procedures are used to evaluate intrinsic biophysical properties of selected antibodies. The variable region sequences of antibodies A-E, AN-A16, and E1-E22 are as disclosed above, and the sequence of antibodies L14, P11, S4, SB6, S7, S10, and S14 are as shown in Tables 80-81. Table 82 shows the values of each of the five descriptors. Table 83 shows the Z-score corresponding to each descriptor value, as well as the Z-distance computed from the five descriptors. Table 84 shows the flag values for each descriptor (0 indicate no flag and 1 indicates a flag, i.e., Z-score >1.96 or <−1.96) and the total number of flags for each antibody. For a given antibody, higher absolute Z-score values, higher numbers of flags, and higher Z-distance values each indicate greater deviation from the average properties of the 79 Fv regions contained in the 77 approved biotherapeutics used in the analysis.

TABLE 80

Sequences of Antibody Heavy Chain Variable Regions

| Antibody | Heavy Chain Variable Region Sequence | SEQ ID NO: |
|---|---|---|
| L14 | QVQLVQSGAEVKKPGASVKVSCKASGYNFNIYWINWVRQAPGQGL EWIGNIYPSSISTNYNEKFKTRATLTVDKSTSTVYMELSSLRSED TAVYYCARSEGTYYGGRYEGDWFGYWGQGTLVTVSS | 284 |
| P11 | EVQLVESGGGLVKPGGSLRLSCAASGFTFSSYVMSWVRQTPGKGL EWVATISSGGTYTYYPDSVKGRFTLSRDNAKNSLYLQMNSLRAED TAVYYCASQLTGSEFDYWGQGTTVTVSS | 286 |
| S4 | QSVEESGGRLGTPGTPLTLTCTVSGFSLSSYVMGWFRQAPGKGLE YIGIISSSGSPYYASWVNGRFTISKTSTTMDLKMNSPTTEDTATY FCARVGPLGVDYFNIWGPGTLVTVSL | 288 |
| SB6 | RQLVESGGGLVQPGGSLRLSCTASGFSLSSHGISWVRQAPGKGLE YIGTIGTGVITYFASWAKGRFTGSKTSSTAYMELSSLRSEDTAVY FCARGSAWNDPFDPWGQGTLVTVSS | 290 |
| S7 | RSVEESGGRLVTPGTPLTLTCTVSGFSLSSHGISWVRQAPGKGLE YIGTIGTGVITYFASWAKGRFTGSKTSTTVDLKITSPTTEDTATY FCARGSAWNDPFDPWGPGTLVTVSS | 292 |
| S10 | KVEESGGGLVQPGGSLRLSCAASGFSLSSYVMGWVRQAPGKGLEW VSIISSSGSPYYASWVNGRFTISKDNSEGMVYLQMNSLRAEDTAV YYCARVGPLGVDYFNIWGQGTTVTVSS | 294 |
| S14 | RQLVESGGGLVQPGGSLRLSCTASGFSLSSHGISWVRQAPGKGLE YIGTIGTGVITYFASWAKGRFTGSKTSSTAYMELSSLRSEDTAVY FCARGSAWNDPFDPWGQGTLVTVSS | 296 |

TABLE 81

Sequences of Antibody Light Chain Variable Regions

| Antibody | Light Chain Variable Region Sequence | SEQ ID NO: |
|---|---|---|
| L14 | DIQMTQSPSSLSASVGDRVTITCRASQDIRNYLNWYQQKPGKAPK LLIYFTSTLHSGVPSRFSGSGSGTDFTLTISSLQPEDFATYYCQQ GNTLPWTFGGGTKVEIK | 285 |

TABLE 81-continued

| Sequences of Antibody Light Chain Variable Regions | | |
|---|---|---|
| Antibody | Light Chain Variable Region Sequence | SEQ ID NO: |
| P11 | DIVITQSPASLAVSLGERATISCRASESVDSYGNSFMHWYQQKPG QPPKLLIYRASNLESGVPDRFSGSGSRTDFTLTINPLQAEDVATY YCHQSGDLPWTFGGGTKVEIK | 287 |
| S4 | DIVMTQTPSSVEAAVGGTVTIKCQAGQSINSYLAWYQQKPGQRPK LLIYYASTLESGVPSRFKGSGSGTDYTLTISDLESADAATYYCQS WHYISRSYAFGGGTEVVVK | 289 |
| SB6 | DIVMTQSPSSLSASVGDRVTITCQASQSVYGNNDLAWYQQKPGQA PKLLIYLASTLATGVPSRFSGSGSGTDFTLTISSLQPEDFATYYC LGGGDDEADNTFGQGTKVEIK | 291 |
| S7 | ALVMTQTPASVSAAVGGTVTTKCQASQSVYGNNDLAWYQHKPGQP PKLLIYLASTLATGVPSRFSGSGSGTQFTLTITGVQSDDAATYYC LGGGDDEADNVFGGGTEVVV | 293 |
| S10 | DIVMTQSPDSLAVSLGERATINCQAGQSINSYLAWYQQKPGQPPK LLIYYASTLESGVPDRFSGSGSGTDFTLTISSLQAEDVAVYYCQS WHYISRSYAFGGGTKLEIK | 295 |
| S14 | DIEMTQSPSSVSASVGDRVTLTCQASQSVYGNNDLAWYQQKPGQA PKLLIYLASTLATGVPSRFSGSGSGTDFTLTISSLQPEDFATYYC LGGGDDEADNVFGGGTKVEIK | 297 |

TABLE 82

| Intrinsic Biophysical Properties of Antibodies | | | | | |
|---|---|---|---|---|---|
| | Biophysical Property | | | | |
| Antibody | BSA_LC:HC | RP | RM | Avg_HI | pIFv_3D |
| A | 757.565 | 2.182 | 1.052 | 1.147 | 7.401 |
| B | 880.962 | 1.78 | 1.174 | 1.897 | 8.426 |
| C | 746.141 | 3.2 | 1.097 | 0.822 | 7.342 |
| D | 724.277 | 2.028 | 0.794 | 0.884 | 7.357 |
| E | 814.084 | 1.605 | 1.135 | 0.576 | 8.001 |
| A1 | 772.203 | 1.236 | 0.567 | 0.645 | 7.313 |
| A2 | 754.856 | 2.407 | 0.941 | 1.007 | 7.84 |
| A3 | 749.195 | 1.6 | 0.981 | 0.956 | 7.65 |
| A4 | 774.46 | 1.54 | 1.03 | 0.614 | 7.445 |
| A5 | 779.811 | 1.913 | 1.157 | 0.578 | 7.474 |
| A6 | 811.151 | 1.946 | 0.961 | 0.641 | 6.771 |
| A7 | 754.862 | 2.094 | 0.949 | 0.956 | 7.826 |
| A8 | 758.408 | 1.415 | 1.145 | 0.571 | 7.474 |
| A9 | 722.586 | 1.472 | 1.131 | 0.781 | 5.415 |
| A10 | 740.85 | 1.5 | 1.048 | 1.182 | 7.401 |
| A11 | 771.402 | 2.031 | 1.088 | 1.083 | 7.372 |
| A12 | 763.62 | 1.882 | 1.071 | 1.117 | 7.386 |
| A13 | 716.196 | 1.592 | 1.303 | 0.659 | 6.581 |
| A14 | 752.533 | 1.771 | 1.283 | 0.629 | 6.405 |
| A15 | 731.64 | 1.228 | 1.096 | 0.758 | 5.783 |
| A16 | 730.942 | 1.604 | 1.298 | 0.741 | 6.443 |
| E1 | 897.824 | 2 | 0.972 | 0.818 | 7.84 |
| E2 | 862.05 | 1.5 | 1.327 | 0.624 | 8.031 |
| E3 | 880.578 | 1.786 | 1.121 | 0.915 | 8.397 |
| E4 | 865.757 | 1.969 | 1.241 | 0.953 | 8.119 |
| E5 | 806.757 | 3 | 1.123 | 1.295 | 8.646 |

TABLE 82-continued

| Intrinsic Biophysical Properties of Antibodies | | | | | |
|---|---|---|---|---|---|
| | Biophysical Property | | | | |
| Antibody | BSA_LC:HC | RP | RM | Avg_HI | pIFv_3D |
| E6 | 871.934 | 3.333 | 1.292 | 1.147 | 8.529 |
| E7 | 858.2 | 2.152 | 0.991 | 0.996 | 8.368 |
| E8 | 892.703 | 2.086 | 0.745 | 0.553 | 7.518 |
| E9 | 848.808 | 1.426 | 1.155 | 0.659 | 8.001 |
| E10 | 849.995 | 2.194 | 1.133 | 1.144 | 8.397 |
| E11 | 842.435 | 1.789 | 0.796 | 0.685 | 7.401 |
| E12 | 910.73 | 1.478 | 1.219 | 0.883 | 8.353 |
| E13 | 827.903 | 1.744 | 0.928 | 0.567 | 8.148 |
| E14 | 835.996 | 2.3 | 1.314 | 1.12 | 8.646 |
| E15 | 817.36 | 1.639 | 1.007 | 1.031 | 8.031 |
| E16 | 874.806 | 1.795 | 1.236 | 0.971 | 8.397 |
| E17 | 847.622 | 1.65 | 0.94 | 0.514 | 7.606 |
| E18 | 840.334 | 1.933 | 1.234 | 1.14 | 8.236 |
| E19 | 871.606 | 1.634 | 1.124 | 0.756 | 8.294 |
| E20 | 821.97 | 1.465 | 0.903 | 0.447 | 7.928 |
| E21 | 842.136 | 1.477 | 1.447 | 0.956 | 8.382 |
| E22 | 886.351 | 2.793 | 1.236 | 0.985 | 7.987 |
| L14 | 992.129 | 1.929 | 0.654 | 1.426 | 8.617 |
| P11 | 759.501 | 1.795 | 1.69 | 0.685 | 6.481 |
| S4 | 893.191 | 1.829 | 1.359 | 1.002 | 6.756 |
| SB6 | 895.402 | 1.784 | 1.251 | 1.265 | 5.846 |
| S7 | 819.933 | 2.129 | 0.765 | 0.353 | 5.757 |
| S10 | 841.792 | 1.523 | 0.882 | 1.133 | 5.415 |
| S14 | 871.617 | 1.822 | 1.511 | 1.403 | 5.313 |

TABLE 83

| Z-scores and Z-distances Computed from Intrinsic Biophysical Properties of Antibodies | | | | | | |
|---|---|---|---|---|---|---|
| | Z score | | | | | Z- |
| Antibody | BSA_LC:HC | RP | RM | Avg_HI | pIFv_3D | distance |
| A | −0.813 | −0.003 | −0.098 | 0.551 | −0.306 | 1.034 |
| B | 0.678 | −0.315 | 0.068 | 2.503 | 0.515 | 2.664 |
| C | −0.952 | 0.787 | −0.038 | −0.293 | −0.353 | 1.318 |
| D | −1.216 | −0.123 | −0.454 | −0.131 | −0.342 | 1.354 |

TABLE 83-continued

Z-scores and Z-distances Computed from Intrinsic Biophysical Properties of Antibodies

| Antibody | Z score BSA_LC:HC | RP | RM | Avg_HI | pIFv_3D | Z-distance |
|---|---|---|---|---|---|---|
| E | −0.13 | −0.451 | 0.015 | −0.933 | 0.175 | 1.059 |
| A1 | −0.636 | −0.737 | −0.766 | −0.753 | −0.377 | 1.498 |
| A2 | −0.846 | 0.172 | −0.252 | 0.188 | 0.046 | 0.92 |
| A3 | −0.915 | −0.455 | −0.197 | 0.055 | −0.107 | 1.047 |
| A4 | −0.609 | −0.501 | −0.129 | −0.833 | −0.271 | 1.186 |
| A5 | −0.544 | −0.212 | 0.045 | −0.927 | −0.248 | 1.124 |
| A6 | −0.166 | −0.186 | −0.223 | −0.764 | −0.811 | 1.164 |
| A7 | −0.846 | −0.071 | −0.241 | 0.056 | 0.034 | 0.885 |
| A8 | −0.803 | −0.598 | 0.029 | −0.947 | −0.248 | 1.401 |
| A9 | −1.236 | −0.554 | 0.01 | −0.401 | −1.898 | 2.366 |
| A10 | −1.015 | −0.532 | −0.105 | 0.643 | −0.306 | 1.354 |
| A11 | −0.646 | −0.12 | −0.05 | 0.385 | −0.33 | 0.831 |
| A12 | −0.74 | −0.236 | −0.072 | 0.473 | −0.318 | 0.966 |
| A13 | −1.314 | −0.461 | 0.247 | −0.718 | −0.964 | 1.855 |
| A14 | −0.874 | −0.322 | 0.219 | −0.797 | −1.104 | 1.664 |
| A15 | −1.127 | −0.743 | −0.038 | −0.46 | −1.603 | 2.146 |
| A16 | −1.135 | −0.452 | 0.239 | −0.505 | −1.074 | 1.72 |
| E1 | 0.882 | −0.144 | −0.209 | −0.305 | 0.046 | 0.968 |
| E2 | 0.45 | −0.532 | 0.28 | −0.808 | 0.198 | 1.121 |
| E3 | 0.674 | −0.311 | −0.004 | −0.051 | 0.492 | 0.891 |
| E4 | 0.495 | −0.168 | 0.161 | 0.048 | 0.269 | 0.611 |
| E5 | −0.219 | 0.632 | −0.001 | 0.938 | 0.691 | 1.343 |
| E6 | 0.569 | 0.891 | 0.232 | 0.553 | 0.597 | 1.354 |
| E7 | 0.403 | −0.027 | −0.183 | 0.159 | 0.468 | 0.664 |
| E8 | 0.82 | −0.078 | −0.521 | −0.994 | −0.213 | 1.409 |
| E9 | 0.29 | −0.59 | 0.043 | −0.716 | 0.175 | 0.989 |
| E10 | 0.304 | 0.006 | 0.013 | 0.544 | 0.492 | 0.794 |
| E11 | 0.213 | −0.308 | −0.451 | −0.649 | −0.306 | 0.927 |
| E12 | 1.038 | −0.549 | 0.13 | −0.134 | 0.456 | 1.274 |
| E13 | 0.037 | −0.343 | −0.27 | −0.958 | 0.292 | 1.093 |
| E14 | 0.135 | 0.089 | 0.262 | 0.483 | 0.691 | 0.897 |
| E15 | −0.091 | −0.425 | −0.161 | 0.25 | 0.198 | 0.562 |
| E16 | 0.604 | −0.303 | 0.155 | 0.093 | 0.492 | 0.855 |
| E17 | 0.275 | −0.416 | −0.252 | −1.094 | −0.142 | 1.237 |
| E18 | 0.187 | −0.196 | 0.152 | 0.534 | 0.362 | 0.716 |
| E19 | 0.565 | −0.428 | 0.001 | −0.464 | 0.409 | 0.941 |
| E20 | −0.035 | −0.559 | −0.303 | −1.268 | 0.116 | 1.424 |
| E21 | 0.209 | −0.55 | 0.444 | 0.054 | 0.48 | 0.881 |
| E22 | 0.744 | 0.471 | 0.154 | 0.13 | 0.163 | 0.918 |
| L14 | 2.022 | −0.2 | −0.646 | 1.278 | 0.668 | 2.574 |
| P11 | −0.79 | −0.303 | 0.779 | −0.649 | −1.043 | 1.683 |
| S4 | 0.826 | −0.277 | 0.323 | 0.174 | −0.823 | 1.254 |
| SB6 | 0.853 | −0.312 | 0.176 | 0.858 | −1.552 | 2 |
| S7 | −0.059 | −0.044 | −0.494 | −1.513 | −1.623 | 2.275 |
| S10 | 0.205 | −0.515 | −0.333 | 0.515 | −1.898 | 2.07 |
| S14 | 0.565 | −0.282 | 0.533 | 1.218 | −1.979 | 2.467 |

TABLE 84

Flag Values Computed from Intrinsic Biophysical Properties of Antibodies

| Antibody | Flag BSA_LC:HC | RP | RM | Avg_HI | pIFv_3D | Total |
|---|---|---|---|---|---|---|
| A | 0 | 0 | 0 | 0 | 0 | 0 |
| B | 0 | 0 | 0 | 1 | 0 | 1 |
| C | 0 | 0 | 0 | 0 | 0 | 0 |
| D | 0 | 0 | 0 | 0 | 0 | 0 |
| E | 0 | 0 | 0 | 0 | 0 | 0 |
| A1 | 0 | 0 | 0 | 0 | 0 | 0 |
| A2 | 0 | 0 | 0 | 0 | 0 | 0 |
| A3 | 0 | 0 | 0 | 0 | 0 | 0 |
| A4 | 0 | 0 | 0 | 0 | 0 | 0 |
| A5 | 0 | 0 | 0 | 0 | 0 | 0 |
| A6 | 0 | 0 | 0 | 0 | 0 | 0 |
| A7 | 0 | 0 | 0 | 0 | 0 | 0 |
| A8 | 0 | 0 | 0 | 0 | 0 | 0 |
| A9 | 0 | 0 | 0 | 0 | 0 | 0 |

TABLE 84-continued

Flag Values Computed from Intrinsic Biophysical Properties of Antibodies

| Antibody | Flag BSA_LC:HC | RP | RM | Avg_HI | pIFv_3D | Total |
|---|---|---|---|---|---|---|
| A10 | 0 | 0 | 0 | 0 | 0 | 0 |
| A11 | 0 | 0 | 0 | 0 | 0 | 0 |
| A12 | 0 | 0 | 0 | 0 | 0 | 0 |
| A13 | 0 | 0 | 0 | 0 | 0 | 0 |
| A14 | 0 | 0 | 0 | 0 | 0 | 0 |
| A15 | 0 | 0 | 0 | 0 | 0 | 0 |
| A16 | 0 | 0 | 0 | 0 | 0 | 0 |
| E1 | 0 | 0 | 0 | 0 | 0 | 0 |
| E2 | 0 | 0 | 0 | 0 | 0 | 0 |
| E3 | 0 | 0 | 0 | 0 | 0 | 0 |
| E4 | 0 | 0 | 0 | 0 | 0 | 0 |
| E5 | 0 | 0 | 0 | 0 | 0 | 0 |
| E6 | 0 | 0 | 0 | 0 | 0 | 0 |
| E7 | 0 | 0 | 0 | 0 | 0 | 0 |

TABLE 84-continued

Flag Values Computed from Intrinsic Biophysical Properties of Antibodies

| Antibody | Flag | | | | | |
|---|---|---|---|---|---|---|
| | BSA_LC:HC | RP | RM | Avg_HI | pIFv_3D | Total |
| E8 | 0 | 0 | 0 | 0 | 0 | 0 |
| E9 | 0 | 0 | 0 | 0 | 0 | 0 |
| E10 | 0 | 0 | 0 | 0 | 0 | 0 |
| E11 | 0 | 0 | 0 | 0 | 0 | 0 |
| E12 | 0 | 0 | 0 | 0 | 0 | 0 |
| E13 | 0 | 0 | 0 | 0 | 0 | 0 |
| E14 | 0 | 0 | 0 | 0 | 0 | 0 |
| E15 | 0 | 0 | 0 | 0 | 0 | 0 |
| E16 | 0 | 0 | 0 | 0 | 0 | 0 |
| E17 | 0 | 0 | 0 | 0 | 0 | 0 |
| E18 | 0 | 0 | 0 | 0 | 0 | 0 |
| E19 | 0 | 0 | 0 | 0 | 0 | 0 |
| E20 | 0 | 0 | 0 | 0 | 0 | 0 |
| E21 | 0 | 0 | 0 | 0 | 0 | 0 |
| E22 | 0 | 0 | 0 | 0 | 0 | 0 |
| L14 | 1 | 0 | 0 | 0 | 0 | 1 |
| P11 | 0 | 0 | 0 | 0 | 0 | 0 |
| S4 | 0 | 0 | 0 | 0 | 0 | 0 |
| SB6 | 0 | 0 | 0 | 0 | 0 | 0 |
| S7 | 0 | 0 | 0 | 0 | 0 | 0 |
| S10 | 0 | 0 | 0 | 0 | 0 | 0 |
| S14 | 0 | 0 | 0 | 0 | 1 | 1 |

Example 37. Analysis of Humanness of Antibody Sequences

Methods

Percentage human identity ("humanness") values are computed for the variable light and variable heavy sequences of selected antibodies using the methods described in Jones et al. MAbs. 2016; 8(1):1-9. doi: 10.1080/19420862.2015.1114320. In brief, the humanized sequences are compared to their closest human germline counterparts, and percentage identity is determined for each.

Results

The above procedures are used to measure the percentage humanness of the light- and heavy-chain variable regions of selected antibodies. Results are shown in Table 85. Higher % Humanness values indicate greater similarity to human germline antibody sequences.

TABLE 85

Percentage Humanness Values of Antibodies

| Antibody | VH | | VL | |
|---|---|---|---|---|
| | Germ line | % Humanness | Germ line | % Humanness |
| A | IGHV3-13*01 | 96.907 | IGKV1-16*02 | 94.737 |
| B | IGHV1-2*02 | 98.958 | IGKV1-12*01 | 98.947 |
| C | IGHV3-13*01 | 96.907 | IGKV1-16*02 | 93.684 |
| D | IGHV3-13*01 | 94.845 | IGKV1-16*02 | 95.789 |
| E | IGHV4-59*01 | 86.598 | IGKV2-28*01 | 96 |
| A1 | IGHV3-13*01 | 94.845 | IGKV1-16*02 | 94.737 |
| A2 | IGHV3-13*01 | 95.876 | IGKV1-16*02 | 94.737 |
| A3 | IGHV3-13*01 | 95.876 | IGKV1-16*02 | 94.737 |
| A4 | IGHV3-13*01 | 94.845 | IGKV1-16*02 | 94.737 |
| A5 | IGHV3-13*01 | 94.845 | IGKV1-16*02 | 94.737 |
| A6 | IGHV3-13*01 | 94.845 | IGKV1-16*02 | 94.737 |
| A7 | IGHV3-13*01 | 96.907 | IGKV1-16*02 | 94.737 |
| A8 | IGHV3-13*01 | 95.876 | IGKV1-16*02 | 94.737 |
| A9 | IGHV3-13*01 | 94.845 | IGKV1-16*02 | 94.737 |
| A10 | IGHV3-13*01 | 95.876 | IGKV1-16*02 | 94.737 |
| A11 | IGHV3-13*01 | 95.876 | IGKV1-16*02 | 94.737 |
| A12 | IGHV3-13*01 | 95.876 | IGKV1-16*02 | 94.737 |
| A13 | IGHV3-13*01 | 94.845 | IGKV1-16*02 | 94.737 |
| A14 | IGHV3-13*01 | 94.845 | IGKV1-16*02 | 94.737 |
| A15 | IGHV3-13*01 | 94.845 | IGKV1-16*02 | 94.737 |
| A16 | IGHV3-13*01 | 95.876 | IGKV1-16*02 | 94.737 |
| E1 | IGHV4-59*01 | 87.629 | IGKV2-28*01 | 94 |
| E2 | IGHV4-59*01 | 87.629 | IGKV2-28*01 | 96 |
| E3 | IGHV4-59*01 | 88.66 | IGKV2-28*01 | 94 |
| E4 | IGHV4-59*01 | 88.66 | IGKV2-28*01 | 96 |
| E5 | IGHV4-59*01 | 88.66 | IGKV2-28*01 | 94 |
| E6 | IGHV4-59*01 | 88.66 | IGKV2-28*01 | 96 |
| E7 | IGHV4-59*01 | 89.691 | IGKV2-28*01 | 94 |
| E8 | IGHV4-4*08 | 85.567 | IGKV2-28*01 | 94 |
| E9 | IGHV4-59*01 | 87.629 | IGKV2-28*01 | 96 |
| E10 | IGHV4-59*01 | 89.691 | IGKV2-28*01 | 96 |
| E11 | IGHV4-4*08 | 85.567 | IGKV2-28*01 | 96 |
| E12 | IGHV4-59*01 | 88.66 | IGKV2-28*01 | 96 |
| E13 | IGHV4-59*01 | 87.629 | IGKV2-28*01 | 94 |
| E14 | IGHV4-59*01 | 88.66 | IGKV2-28*01 | 96 |
| E15 | IGHV4-59*01 | 87.629 | IGKV2-28*01 | 96 |
| E16 | IGHV4-59*01 | 89.691 | IGKV2-28*01 | 96 |
| E17 | IGHV4-4*08 | 85.567 | IGKV2-28*01 | 96 |
| E18 | IGHV4-59*01 | 88.66 | IGKV2-28*01 | 96 |
| E19 | IGHV4-59*01 | 88.66 | IGKV2-28*01 | 94 |
| E20 | IGHV4-59*01 | 87.629 | IGKV2-28*01 | 96 |
| E21 | IGHV4-59*01 | 88.66 | IGKV2-28*01 | 96 |
| E22 | IGHV4-59*01 | 88.66 | IGKV2-28*01 | 92 |
| L14 | IGHV1-46*02 | 80.612 | IGKV1-39*01 | 88.421 |
| P11 | IGHV3-2V01 | 88.66 | IGKV7-3*01 | 73.737 |
| S4 | IGHV3-64*04 | 60.215 | IGKV1-27*01 | 70.652 |
| SB6 | IGHV3-66*01 | 67.368 | IGKV1-6*01 | 85.556 |
| S7 | IGHV3-53*04 | 54.348 | IGKV1-6*01 | 65.934 |
| S10 | IGHV3-66*01 | 81.522 | IGKV4-1*01 | 82.653 |
| S14 | IGHV3-66*01 | 67.368 | IGKV1-6*01 | 83.333 |

What is claimed is:

1. An anti SIRPα antibody or an antigen-binding fragment thereof comprising:

a) a heavy chain variable region comprising the amino acid sequence of SEQ ID NO: 1 or SEQ ID NO: 223 (H-CDR1); the amino acid sequence of SEQ ID NO: 2, SEQ ID NO: 3, SEQ ID NO: 4, SEQ ID NO: 5 or SEQ ID NO: 224 (H-CDR2); and the amino acid sequence of SEQ ID NO: 6 (H-CDR3); and a light chain variable region comprising the amino acid sequence of SEQ ID NO: 7, SEQ ID NO: 8, SEQ ID NO: 9 or SEQ ID NO: 225 (L-CDR1); the amino acid sequence of SEQ ID NO: 10, SEQ ID NO: 11 or SEQ ID NO: 226 (L-CDR2); and the amino acid sequence of SEQ ID NO: 12 or SEQ ID NO: 227 (L-CDR3), or b) a heavy chain variable region comprising the amino acid sequence of SEQ ID NO: 52 (H-CDR1); the amino acid sequence of SEQ ID NO: 53 (H-CDR2); and the amino acid sequence of SEQ ID NO: 54 (H-CDR3); and a light chain variable region comprising the amino acid sequence of SEQ ID NO: 55 (L-CDR1); the amino acid sequence of SEQ ID NO: 56 (L-CDR2); and the amino acid sequence of SEQ ID NO: 57 (L-CDR3), or c) a heavy chain variable region comprising the amino acid sequence of SEQ ID NO: 33 (H-CDR1); the amino acid sequence of SEQ ID NO: 70 (H-CDR2); and the amino acid sequence of SEQ ID NO: 71 (H-CDR3); and a light chain variable region comprising the amino acid sequence of SEQ ID NO: 36 (L-CDR1); the amino acid sequence of SEQ ID NO: 72 (L-CDR2); and the amino acid sequence of SEQ ID NO: 39 (L-CDR3), or d) a heavy chain variable region comprising the amino acid sequence of SEQ ID NO: 262 (H-CDR1); the amino acid sequence of SEQ ID NO: 87 (H-CDR2); and the amino acid sequence of SEQ ID NO: 88 (H-CDR3); and a light chain variable region comprising the amino acid sequence of SEQ ID NO: 36 (L-CDR1); the amino acid sequence of SEQ ID NO: 72 (L-CDR2); and the amino acid sequence of SEQ ID NO: 89 (L-CDR3).

2. The anti SIRPα antibody or antigen-binding fragment thereof according to claim 1, wherein the anti-SIRPα antibody or antigen-binding fragment thereof comprises:

a heavy chain variable region comprising the amino acid sequence of SEQ ID NO: 1 or SEQ ID NO: 223 (H-CDR1); the amino acid sequence of SEQ ID NO: 2, SEQ ID NO: 3, SEQ ID NO: 4, SEQ ID NO: 5 or SEQ ID NO: 224 (H-CDR2); and the amino acid sequence of SEQ ID NO: 6 (H-CDR3); and a light chain variable region comprising the amino acid sequence of SEQ ID NO: 7, SEQ ID NO: 8, SEQ ID NO: 9 or SEQ ID NO: 225 (L-CDR1); the amino acid sequence of SEQ ID NO: 10, SEQ ID NO: 11 or SEQ ID NO: 226 (L-CDR2); and the amino acid sequence of SEQ ID NO: 12 or SEQ ID NO: 227 (L-CDR3).

3. The anti-SIRPα antibody or antigen-binding fragment thereof according to claim 1, wherein the anti-SIRPα antibody or antigen-binding fragment thereof comprises:

a heavy chain variable region comprising the amino acid sequence of SEQ ID NO: 52 (H-CDR1); the amino acid sequence of SEQ ID NO: 53 (H-CDR2); and the amino acid sequence of SEQ ID NO: 54 (H-CDR3); and a light chain variable region comprising the amino acid sequence of SEQ ID NO: 55 (L-CDR1); the amino acid sequence of SEQ ID NO: 56 (L-CDR2); and the amino acid sequence of SEQ ID NO: 57 (L-CDR3).

4. The anti-SIRPα antibody or antigen-binding fragment thereof according to claim 1, wherein the anti-SIRPα antibody or antigen-binding fragment thereof comprises:

a heavy chain variable region comprising the amino acid sequence of SEQ ID NO: 33 (H-CDR1); the amino acid sequence of SEQ ID NO: 70 (H-CDR2); and the amino acid sequence of SEQ ID NO: 71 (H-CDR3); and a light chain variable region comprising the amino acid sequence of SEQ ID NO: 36 (L-CDR1); the amino acid sequence of SEQ ID NO: 72 (L-CDR2); and the amino acid sequence of SEQ ID NO: 39 (L-CDR3).

5. The anti-SIRPα antibody or antigen-binding fragment thereof according to claim 1, wherein the anti-SIRPα antibody or antigen-binding fragment thereof comprises:

a heavy chain variable region comprising the amino acid sequence of SEQ ID NO: 262 (H-CDR1); the amino acid sequence of SEQ ID NO: 87 (H-CDR2); and the amino acid sequence of SEQ ID NO: 88 (H-CDR3); and a light chain variable region comprising the amino acid sequence of SEQ ID NO: 36 (L-CDR1); the amino acid sequence of SEQ ID NO: 72 (L-CDR2); and the amino acid sequence of SEQ ID NO: 89 (L-CDR3).

6. The anti-SIRPα antibody or antigen-binding fragment thereof according to claim 1, wherein the anti-SIRPα antibody or antigen-binding fragment thereof comprises:

a) a heavy chain variable region comprising the amino acid sequence of SEQ ID NO: 104; and a light chain variable region comprising the amino acid sequence of SEQ ID NO: 109; or b) a heavy chain variable region comprising the amino acid sequence of SEQ ID NO: 118; and a light chain variable region comprising the amino acid sequence of SEQ ID NO: 127; or c) a heavy chain variable region comprising the amino acid sequence of SEQ ID NO: 118; and a light chain variable region comprising the amino acid sequence of SEQ ID NO: 128; or d) a heavy chain variable region comprising the amino acid sequence of SEQ ID NO: 119; and a light chain variable region comprising the amino acid sequence of SEQ ID NO: 127; or e) a heavy chain variable region comprising the amino acid sequence of SEQ ID NO: 119; and a light chain variable region comprising the amino acid sequence of SEQ ID NO: 129; or f) a heavy chain variable region comprising the amino acid sequence of SEQ ID NO: 120; and a light chain variable region comprising the amino acid sequence of SEQ ID NO: 127; or g) a heavy chain variable region comprising the amino acid sequence of SEQ ID NO: 120; and a light chain variable region comprising the amino acid sequence of SEQ ID NO: 129; or h) a heavy chain variable region comprising the amino acid sequence of SEQ ID NO: 121; and a light chain variable region comprising the amino acid sequence of SEQ ID NO: 127; or i) a heavy chain variable region comprising the amino acid sequence of SEQ ID NO: 122; and a light chain variable region comprising the amino acid sequence of SEQ ID NO: 127; or j) a heavy chain variable region comprising the amino acid sequence of SEQ ID NO: 118; and a light chain variable region comprising the amino acid sequence of SEQ ID NO: 130; or k) a heavy chain variable region comprising the amino acid sequence of SEQ ID NO: 121; and a light chain variable region comprising the amino acid sequence of SEQ ID NO: 129; or l) a heavy chain variable region comprising the amino acid sequence of SEQ ID NO: 122; and a light chain variable region comprising the amino acid sequence of SEQ ID NO: 129; or m) a heavy chain variable region comprising the amino acid sequence of SEQ ID NO: 119; and a light chain variable region comprising the amino acid sequence of SEQ ID NO: 130; or n) a heavy chain variable region comprising the amino acid sequence of SEQ ID NO: 123; and a light chain variable region comprising the amino acid sequence of SEQ ID NO: 127; or o) a heavy chain variable region comprising the amino acid sequence of SEQ ID NO: 120; and a light chain variable region comprising the amino acid sequence of SEQ ID NO: 130; or p) a heavy chain variable region comprising the amino acid sequence of SEQ ID NO: 123; and a light chain variable region comprising the amino acid sequence of SEQ ID NO: 129; or q) a heavy chain variable region comprising the amino acid sequence of SEQ ID NO: 121; and a light chain variable region comprising the amino acid sequence of SEQ ID NO: 130; or r) a heavy chain variable region comprising the amino acid sequence of SEQ ID NO: 122; and a light chain variable region comprising the amino acid sequence of SEQ ID NO: 130; or s) a heavy chain variable region comprising the amino acid sequence of SEQ ID NO: 124; and a light chain variable region comprising the amino acid sequence of SEQ ID NO: 129; or t) a heavy chain variable region comprising the amino acid sequence of SEQ ID NO: 124; and a light chain variable region comprising the amino acid sequence of SEQ ID NO: 127; or u) a heavy chain variable region comprising the amino acid sequence of SEQ ID NO: 123; and a light chain variable region comprising the amino acid sequence of SEQ ID NO: 130; or v) a heavy chain variable region comprising the amino acid sequence of SEQ ID NO: 124; and a light chain variable region comprising the amino acid sequence of SEQ ID NO: 130; or w) a heavy chain variable region comprising the amino acid sequence of SEQ ID NO: 221; and a light chain variable region comprising the amino acid sequence of SEQ ID NO: 222.

7. The anti-SIRPα antibody or antigen-binding fragment thereof according to claim 1, wherein the anti-SIRPα antibody or antigen-binding fragment thereof comprises:

a) a heavy chain variable region comprising the amino acid sequence of SEQ ID NO: 101; and a light chain variable region comprising the amino acid sequence of SEQ ID NO: 106; or b) a heavy chain variable region comprising the amino acid sequence of SEQ ID NO: 102; and a light chain variable region comprising the amino acid sequence of SEQ ID NO: 107; or c) a heavy chain variable region comprising the amino acid sequence of SEQ ID NO: 103; and a light chain variable region comprising the amino acid sequence of SEQ ID NO: 108; or d) a heavy chain variable region comprising the amino acid sequence of SEQ ID NO: 104; and a light chain variable region comprising the amino acid sequence of SEQ ID NO: 109.

8. The anti-SIRPα antibody according to claim 1, wherein the anti-SIRPα antibody comprises:

a) a heavy chain comprising the amino acid sequence of SEQ ID NO: 135; and a light chain comprising the amino acid sequence of SEQ ID NO: 178; or b) a heavy chain comprising the amino acid sequence of SEQ ID NO: 153; and a light chain comprising the amino acid sequence of SEQ ID NO: 196; or c) a heavy chain comprising the amino acid sequence of SEQ ID NO: 154; and a light chain comprising the amino acid sequence of SEQ ID NO: 197; or d) a heavy chain comprising the amino acid sequence of SEQ ID NO: 155; and a light chain comprising the amino acid sequence of SEQ ID NO: 198; or e) a heavy chain comprising the amino acid sequence of SEQ ID NO: 156; and a light chain comprising the amino acid sequence of SEQ ID NO: 199; or f) a heavy chain comprising the amino acid sequence of SEQ ID NO: 157; and a light chain comprising the amino acid sequence of SEQ ID NO: 200; or g) a heavy chain comprising the amino acid sequence of SEQ ID NO: 158; and a light chain comprising the amino acid sequence of SEQ ID NO: 201; or h) a heavy chain comprising the amino acid sequence of SEQ ID NO: 159; and a light chain comprising the amino acid sequence of SEQ ID NO: 202; or i) a heavy chain comprising the amino acid sequence of SEQ ID NO: 160; and a light chain comprising the amino acid sequence of SEQ ID NO: 203; or j) a heavy chain comprising the amino acid sequence of SEQ ID NO: 161; and a light chain comprising the amino acid sequence of SEQ ID NO: 204; or k) a heavy chain comprising the amino acid sequence of SEQ ID NO: 162; and a light chain comprising the amino acid sequence of SEQ ID NO: 205; or l) a heavy chain comprising the amino acid sequence of SEQ ID NO: 163; and a light chain comprising the amino acid sequence of SEQ ID NO: 206; or m) a heavy chain comprising the amino acid sequence of SEQ ID NO: 164; and a light chain comprising the amino acid sequence of SEQ ID NO: 207; or n) a heavy chain comprising the amino acid sequence of SEQ ID NO: 165; and a light chain comprising the amino acid sequence of SEQ ID NO: 208; or o) a heavy chain comprising the amino acid sequence of SEQ ID NO: 166; and a light chain comprising the amino acid sequence of SEQ ID NO: 209; or p) heavy chain comprising the amino acid sequence of SEQ ID NO: 167; and a light chain comprising the amino acid sequence of SEQ ID NO: 210; or q) a heavy chain comprising the amino acid sequence of SEQ ID NO: 168; and a light chain comprising the amino acid sequence of SEQ ID NO: 211; or r) a heavy chain comprising the amino acid sequence of SEQ ID NO: 169; and a light chain comprising the amino acid sequence of SEQ ID NO: 212; or s) a heavy chain comprising the amino acid sequence of SEQ ID NO: 170; and a light chain comprising the amino acid sequence of SEQ ID NO: 213; or t) a heavy chain comprising the amino acid sequence of SEQ ID NO: 171; and a light chain comprising the amino acid sequence of SEQ ID NO: 214; or u) a heavy chain comprising the amino acid sequence of SEQ ID NO: 172; and a light chain comprising the amino acid sequence of SEQ ID NO: 215; or v) a heavy chain comprising the amino acid sequence of SEQ ID NO: 173; and a light chain comprising the amino acid sequence of SEQ ID NO: 216; or w) a heavy chain comprising the amino acid sequence of SEQ ID NO: 219; and a light chain comprising the amino acid sequence of SEQ ID NO: 220; or x) a heavy chain comprising the amino acid sequence of SEQ ID NO: 219; and a light chain comprising the amino acid sequence of SEQ ID NO: 220.

9. The anti-SIRPα antibody according to claim 1, wherein the anti-SIRPα antibody comprises:

a) a heavy chain comprising the amino acid sequence of SEQ ID NO: 133; and a light chain comprising the amino acid sequence of SEQ ID NO: 176; or b) a heavy chain comprising the amino acid sequence of SEQ ID NO: 134; and a light chain comprising the amino acid sequence of SEQ ID NO: 177; or c) a heavy chain comprising the amino acid sequence of SEQ ID NO: 137; and a light chain comprising the amino acid sequence of SEQ ID NO: 180; or d) a heavy chain comprising the amino acid sequence of SEQ ID NO: 135; and a light chain comprising the amino acid sequence of SEQ ID NO: 178; or e) a heavy chain comprising the amino acid sequence of SEQ ID NO: 219; and a light chain comprising the amino acid sequence of SEQ ID NO: 220.

10. The anti-SIRPα antibody or antigen-binding fragment thereof according to claim 1, wherein the anti-SIRPα antibody is a monoclonal antibody.

11. The anti-SIRPα antibody or antigen-binding fragment thereof according to claim 1, wherein the anti-SIRPα antibody is a human antibody.

12. The anti-SIRPα antibody or antigen-binding fragment thereof according to claim 1, wherein the anti-SIRPα antibody or antigen-binding fragment thereof binds to human SIRPα at a $K_D \leq 10$ nM.

13. The anti-SIRPα antibody or antigen-binding fragment thereof according to claim 1, wherein the anti-SIRPα antibody or antigen-binding fragment thereof binds to cynomolgus SIRPα at a $K_D \leq 400$ nM.

14. A pharmaceutical composition comprising the anti-SIRPα antibody or antigen-binding fragment thereof according to claim 1 and a pharmaceutically acceptable carrier.

15. A method of treating a cancer in a subject in need thereof, the method comprising administering a therapeutically effective amount of the anti-SIRPα antibody or antigen-binding fragment thereof according to claim 1 to the subject in need thereof.

16. An isolated polynucleotide composition, the isolated polynucleotide composition comprising:

a) a first isolated polynucleotide encoding the heavy chain variable region according to claim 1; and/or b) a second isolated polynucleotide encoding the light chain variable region according to claim 1.

17. An expression vector composition, the expression vector composition comprising:

a) a first expression vector comprising the first isolated polynucleotide of claim 16; and/or b) a second expression vector comprising the second isolated polynucleotide of claim 16.

18. A host cell comprising the isolated polynucleotide composition according to claim 16.

19. A method for the production of an anti-SIRPα antibody or antigen-binding fragment thereof, comprising the steps:

a) cultivating the host cell of claim 18 under conditions for expression of the anti-SIRPα antibody or antigen-binding fragment thereof; and b) recovering the anti-SIRPα antibody or antigen-binding fragment thereof.

* * * * *

SEQUENCE LISTING

```
Sequence total quantity: 297
SEQ ID NO: 1           moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1
NYYWS                                                      5

SEQ ID NO: 2           moltype = AA  length = 16
FEATURE                Location/Qualifiers
REGION                 1..16
                       note = Description of Artificial Sequence: Synthetic peptide
```

```
source                  1..16
                        mol_type = protein
                        organism = synthetic construct
SEQUENCE: 2
FIYYNGRTFY NSSLKS                                             16

SEQ ID NO: 3            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 3
FIYYNGRTFY NPSLKS                                             16

SEQ ID NO: 4            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 4
FIYDNGRTFY NPSLKS                                             16

SEQ ID NO: 5            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 5
FIYYTGRTFY NPSLKS                                             16

SEQ ID NO: 6            moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 6
VRAYSGIGLD GTDV                                               14

SEQ ID NO: 7            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 7
KSSQSLLYSN GYNYLD                                             16

SEQ ID NO: 8            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 8
KSSQSLLYSN GYAYLD                                             16

SEQ ID NO: 9            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 9
KSSQSLLYSN AYNYLD                                             16

SEQ ID NO: 10           moltype = AA  length = 7
FEATURE                 Location/Qualifiers
REGION                  1..7
```

```
                          note = Description of Artificial Sequence: Synthetic peptide
source                    1..7
                          mol_type = protein
                          organism = synthetic construct
SEQUENCE: 10
LGSNRAS                                                                   7

SEQ ID NO: 11             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 11
QGSNRAS                                                                   7

SEQ ID NO: 12             moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 12
MQALQTPLT                                                                 9

SEQ ID NO: 13             moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 13
GGSIRNYY                                                                  8

SEQ ID NO: 14             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 14
IYYNGRT                                                                   7

SEQ ID NO: 15             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 15
IYDNGRT                                                                   7

SEQ ID NO: 16             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 16
IYYTGRT                                                                   7

SEQ ID NO: 17             moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 17
ARVRAYSGIG LDGTDV                                                         16

SEQ ID NO: 18             moltype = AA  length = 11
FEATURE                   Location/Qualifiers
```

-continued

```
REGION                  1..11
                        note = Description of Artificial Sequence: Synthetic peptide
source                  1..11
                        mol_type = protein
                        organism = synthetic construct
SEQUENCE: 18
QSLLYSNGYN Y                                                          11

SEQ ID NO: 19           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 19
QSLLYSNGYA Y                                                          11

SEQ ID NO: 20           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 20
QSLLYSNAYN Y                                                          11

SEQ ID NO: 21           moltype =   length =
SEQUENCE: 21
000

SEQ ID NO: 22           moltype =   length =
SEQUENCE: 22
000

SEQ ID NO: 23           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 23
GGSIRNYYWS                                                            10

SEQ ID NO: 24           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 24
YYNGR                                                                 5

SEQ ID NO: 25           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 25
YDNGR                                                                 5

SEQ ID NO: 26           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 26
YYTGR                                                                 5

SEQ ID NO: 27           moltype = AA  length = 13
FEATURE                 Location/Qualifiers
REGION                  1..13
```

```
                        note = Description of Artificial Sequence: Synthetic peptide
source                  1..13
                        mol_type = protein
                        organism = synthetic construct
SEQUENCE: 27
TVSGGSIRNY YWS                                                      13

SEQ ID NO: 28           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 28
FIYYNGRTF                                                           9

SEQ ID NO: 29           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 29
FIYDNGRTF                                                           9

SEQ ID NO: 30           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 30
FIYYTGRTF                                                           9

SEQ ID NO: 31           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 31
YLGSNRAS                                                            8

SEQ ID NO: 32           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 32
YQGSNRAS                                                            8

SEQ ID NO: 33           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 33
SYDMH                                                               5

SEQ ID NO: 34           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 34
AIGTAGDTYY TGSVKG                                                   16

SEQ ID NO: 35           moltype = AA  length = 10
FEATURE                 Location/Qualifiers
```

```
REGION                1..10
                      note = Description of Artificial Sequence: Synthetic peptide
source                1..10
                      mol_type = protein
                      organism = synthetic construct
SEQUENCE: 35
GGVWDDAFDI                                                          10

SEQ ID NO: 36         moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 36
RASQDINNYL A                                                        11

SEQ ID NO: 37         moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 37
RASQGINNYA A                                                        11

SEQ ID NO: 38         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 38
TASSLHS                                                             7

SEQ ID NO: 39         moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 39
QQYVSYPYT                                                           9

SEQ ID NO: 40         moltype = AA  length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 40
GFTLSSYD                                                            8

SEQ ID NO: 41         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 41
IGTAGDT                                                             7

SEQ ID NO: 42         moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 42
VRGGVWDDAF DI                                                       12

SEQ ID NO: 43         moltype = AA  length = 6
```

```
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 43
QDINNY                                                                      6

SEQ ID NO: 44           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 44
QGINNY                                                                      6

SEQ ID NO: 45           moltype =   length =
SEQUENCE: 45
000

SEQ ID NO: 46           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 46
GFTLSSYDMH                                                                  10

SEQ ID NO: 47           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 47
GFTLSSY                                                                     7

SEQ ID NO: 48           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 48
GTAGD                                                                       5

SEQ ID NO: 49           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 49
AASGFTLSSY DMH                                                              13

SEQ ID NO: 50           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 50
AIGTAGDTY                                                                   9

SEQ ID NO: 51           moltype = AA  length = 8
FEATURE                 Location/Qualifiers
REGION                  1..8
                        note = Description of Artificial Sequence: Synthetic peptide
source                  1..8
                        mol_type = protein
```

```
                        organism = synthetic construct
SEQUENCE: 51
YTASSLHS                                                            8

SEQ ID NO: 52           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 52
GNYMH                                                               5

SEQ ID NO: 53           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 53
WINPNSGGTN YAQKFQG                                                  17

SEQ ID NO: 54           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 54
GSGWYENYYY YGMDV                                                    15

SEQ ID NO: 55           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 55
RASQGISSWL A                                                        11

SEQ ID NO: 56           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 56
AESSLQS                                                             7

SEQ ID NO: 57           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 57
QQANSFPLT                                                           9

SEQ ID NO: 58           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 58
GYTFTGNY                                                            8

SEQ ID NO: 59           moltype = AA  length = 8
FEATURE                 Location/Qualifiers
REGION                  1..8
                        note = Description of Artificial Sequence: Synthetic peptide
source                  1..8
```

```
                        mol_type = protein
                        organism = synthetic construct
SEQUENCE: 59
INPNSGGT                                                                8

SEQ ID NO: 60           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 60
VSGSGWYENY YYYGMDV                                                      17

SEQ ID NO: 61           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 61
QGISSW                                                                  6

SEQ ID NO: 62           moltype =   length =
SEQUENCE: 62
000

SEQ ID NO: 63           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 63
GFTFSSYDMH                                                              10

SEQ ID NO: 64           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 64
GYTFTGN                                                                 7

SEQ ID NO: 65           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 65
NPNSGG                                                                  6

SEQ ID NO: 66           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 66
KASGYTFTGN YMH                                                          13

SEQ ID NO: 67           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 67
WINPNSGGTN                                                              10
```

```
SEQ ID NO: 68           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 68
VSGSGWYENY YYYGMDV                                                 17

SEQ ID NO: 69           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 69
YAESSLQS                                                           8

SEQ ID NO: 70           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 70
VIGIAGDTYY PGSVKG                                                  16

SEQ ID NO: 71           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 71
GGSWDDAFDI                                                         10

SEQ ID NO: 72           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 72
TASSLQS                                                            7

SEQ ID NO: 73           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 73
GFTFSSYD                                                           8

SEQ ID NO: 74           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 74
IGIAGDT                                                            7

SEQ ID NO: 75           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 75
ARGGSWDDAF DI                                                      12
```

```
SEQ ID NO: 76           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 76
GFTFSSYDMH                                                          10

SEQ ID NO: 77           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 77
VIGIAGDTYY PGSVKG                                                   16

SEQ ID NO: 78           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 78
GGSWDDAFDI                                                          10

SEQ ID NO: 79           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 79
TASSLQS                                                             7

SEQ ID NO: 80           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 80
GFTFSSY                                                             7

SEQ ID NO: 81           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 81
GIAGD                                                               5

SEQ ID NO: 82           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 82
GGSWDDAFDI                                                          10

SEQ ID NO: 83           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 83
```

```
AASGFTFSSY DMH                                                  13

SEQ ID NO: 84           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 84
VIGIAGDTY                                                       9

SEQ ID NO: 85           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 85
ARGGSWDDAF DI                                                   12

SEQ ID NO: 86           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 86
YTASSLQS                                                        8

SEQ ID NO: 87           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 87
TIGIAGDTYF PGSVKG                                               16

SEQ ID NO: 88           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 88
GGNWDDALDI                                                      10

SEQ ID NO: 89           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 89
QQYNTYPYT                                                       9

SEQ ID NO: 90           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 90
ARGGNWDDAL DI                                                   12

SEQ ID NO: 91           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
```

SEQUENCE: 91
GFTFSSFDMH 10

SEQ ID NO: 92 moltype = AA length = 16
FEATURE Location/Qualifiers
REGION 1..16
note = Description of Artificial Sequence: Synthetic peptide
source 1..16
mol_type = protein
organism = synthetic construct
SEQUENCE: 92
TIGIAGDTYF PGSVKG 16

SEQ ID NO: 93 moltype = AA length = 10
FEATURE Location/Qualifiers
REGION 1..10
note = Description of Artificial Sequence: Synthetic peptide
source 1..10
mol_type = protein
organism = synthetic construct
SEQUENCE: 93
GGNWDDALDI 10

SEQ ID NO: 94 moltype = AA length = 7
FEATURE Location/Qualifiers
REGION 1..7
note = Description of Artificial Sequence: Synthetic peptide
source 1..7
mol_type = protein
organism = synthetic construct
SEQUENCE: 94
GFTFSSF 7

SEQ ID NO: 95 moltype = AA length = 10
FEATURE Location/Qualifiers
REGION 1..10
note = Description of Artificial Sequence: Synthetic peptide
source 1..10
mol_type = protein
organism = synthetic construct
SEQUENCE: 95
GGNWDDALDI 10

SEQ ID NO: 96 moltype = AA length = 13
FEATURE Location/Qualifiers
REGION 1..13
note = Description of Artificial Sequence: Synthetic peptide
source 1..13
mol_type = protein
organism = synthetic construct
SEQUENCE: 96
AASGFTFSSF DMH 13

SEQ ID NO: 97 moltype = AA length = 9
FEATURE Location/Qualifiers
REGION 1..9
note = Description of Artificial Sequence: Synthetic peptide
source 1..9
mol_type = protein
organism = synthetic construct
SEQUENCE: 97
TIGIAGDTY 9

SEQ ID NO: 98 moltype = AA length = 12
FEATURE Location/Qualifiers
REGION 1..12
note = Description of Artificial Sequence: Synthetic peptide
source 1..12
mol_type = protein
organism = synthetic construct
SEQUENCE: 98
ARGGNWDDAL DI 12

SEQ ID NO: 99 moltype = AA length = 11
FEATURE Location/Qualifiers
REGION 1..11
note = Description of Artificial Sequence: Synthetic peptide
source 1..11
mol_type = protein

```
                         organism = synthetic construct
SEQUENCE: 99
RASQDINNYL A                                                 11

SEQ ID NO: 100           moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 100
EVQLVESGGG LVQPGGSLRL SCAASGFTLS SYDMHWVRQA TGKGLEWVSA IGTAGDTYYT  60
GSVKGRFTIS RENAKNSLYL QMNSLRAGDT AVYYCVRGGV WDDAFDIWGQ GTMVTVSS    118

SEQ ID NO: 101           moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 101
QVQLVQSGAE VKKPGASVKV SCKASGYTFT GNYMHWVRQA PGQGLEWMGW INPNSGGTNY  60
AQKFQGRVTM TRDTSISTAY MELSRLRSDD TAVYYCVSGS GWYENYYYYG MDVWGQGTTV  120
TVSS                                                         124

SEQ ID NO: 102           moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 102
EVQLVESGGG LVQPGGSLRL SCAASGFTFS SYDMHWVRQA TGKGLEWVSV IGIAGDTYYP  60
GSVKGRFTIS RENAKNSLYL QMNSLRVGDT AVYYCARGGS WDDAFDIWGQ GTMVTVSS    118

SEQ ID NO: 103           moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 103
EVQLVESGGG LVQPGGSLRL SCAASGFTFS SFDMHWVRQP TGKGLEWVST IGIAGDTYFP  60
GSVKGRFTIS RENAKNSLYL QMNSLRAGDT AVYYCARGGN WDDALDIWGQ GTMVTVSS    118

SEQ ID NO: 104           moltype = AA  length = 179
FEATURE                  Location/Qualifiers
REGION                   1..179
                         note = Description of Artificial Sequence: Synthetic
                          polypeptide
source                   1..179
                         mol_type = protein
                         organism = synthetic construct
SEQUENCE: 104
QVQLQESGPG LVRPSETLSL TCTVSGGSIR NYYWSWIRQP PGKGLEWIGF IYYNGRTFYN  60
SSLKSRVTIS LDMSMNQFSL KMTSVTAADT AVYYCARVRA YSGIGLDGTD VWGQGTTVTV  120
SSARFTVDKS SSTAYMQFSS LTSEDTAVYF CARSGPYSYY AGGYALDYWG QGTSVTVSS   179

SEQ ID NO: 105           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 105
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIK                107

SEQ ID NO: 106           moltype = AA  length = 107
```

```
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 106
DIQMTQSPSS VSASVGDRVT ITCRASQGIS SWLAWYQQKP GKAPKLLIYA ESSLQSGVPS  60
RFSGSGSGTD FTLTISSLQP EDFATYYCQQ ANSFPLTFGG GTKVEIK                107

SEQ ID NO: 107         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 107
DIQMTQSPSS LSASIGDKVT ITCRASQDIN NYLAWFQQKP GKAPKSLIYT ASSLQSGVPS  60
KFSGSGSGTD FTLTISSLQP EDFATYYCQQ YVSYPYTFGQ GTKLEIK                107

SEQ ID NO: 108         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 108
DIQMTQSPSS LSASVGDRVT ITCRASQDIN NYLAWFQQKP GKAPKSLIYT ASSLQSGVPS  60
KFSGSGSGTD FTLTISSLQP EDFATYYCQQ YNTYPYTFGQ GTKLEIK                107

SEQ ID NO: 109         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 109
DIVMTQSPLS LPVTPGEPAS ISCKSSQSLL YSNGYNYLDW YLQRPGQSPQ LLIYLGSNRA  60
SGVPDRFSGS GSGTDFTLKI SRVEAEDVGV FYCMQALQTP LTFGGGTKVE IK          112

SEQ ID NO: 110         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 110
EVQLVESGGG LVQPGGSLRL SCAASGFTLS SYDMHWVRQA PGKGLEWVSA IGTAGDTYYT  60
GSVKGRFTIS RENAKNSLYL QMNSLRADDT AVYYCVRGGV WDDAFDIWGQ GTMVTVSS    118

SEQ ID NO: 111         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 111
EVQLVESGGG LVQPGGSLRL SCAASGFTLS SYDMHWVRQA TGKGLEWVSA IGTAGDTYYT  60
GSVKGRFTIS RENAKNSLYL QMNSLRAADT AVYYCVRGGV WDDAFDIWGQ GTMVTVSS    118

SEQ ID NO: 112         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
```

```
SEQUENCE: 112
EVQLVESGGG LVQPGGSLRL SCAASGFTLS SYDMHWVRQA TGKGLEWVSA IGTAGDTYYT  60
GSVKGRFTIS RENAKNSLYL QMNSLRASDT AVYYCVRGGV WDDAFDIWGQ GTMVTVSS    118

SEQ ID NO: 113         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 113
EVQLVESGGG LVQPGGSLRL SCAASGFTLS SYDMHWVRQA PGKGLEWVSA IGTAGDTYYT  60
GSVKGRFTIS RENAKNSLYL QMNSLRAADT AVYYCVRGGV WDDAFDIWGQ GTMVTVSS    118

SEQ ID NO: 114         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 114
EVQLVESGGG LVQPGGSLRL SCAASGFTLS SYDMHWVRQA PGKGLEWVSA IGTAGDTYYT  60
GSVKGRFTIS RENAKNSLYL QMNSLRASDT AVYYCVRGGV WDDAFDIWGQ GTMVTVSS    118

SEQ ID NO: 115         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 115
EVQLVESGGG LVQPGGSLRL SCAASGFTLS SYDMHWVRQA PGKGLEWVSA IGTAGDTYYT  60
GSVKGRFTIS RENAKNSLYL QMNSLRAEDT AVYYCVRGGV WDDAFDIWGQ GTMVTVSS    118

SEQ ID NO: 116         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 116
EVQLVESGGG LVQPGGSLRL SCAASGFTLS SYDMHWVRQA TGKGLEWVSA IGTAGDTYYT  60
GSVKGRFTIS RENAKNSLYL QMNSLRAGDT AVYYCVRGGV WDDAFDIWGQ GTMVTVSS    118

SEQ ID NO: 117         moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 117
EVQLVESGGG LVQPGGSLRL SCAASGFTLS SYDMHWVRQA PGKGLEWVSA IGTAGDTYYT  60
GSVKGRFTIS RENAKNSLYL QMNSLRAGDT AVYYCVRGGV WDDAFDIWGQ GTMVTVSS    118

SEQ ID NO: 118         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 118
QVQLQESGPG LVRPSETLSL TCTVSGGSIR NYYWSWIRQP PGKGLEWIGF IYYNGRTFYN  60
PSLKSRVTIS LDMSINQFSL KMTSVTAADT AVYYCARVRA YSGIGLDGTD VWGQGTTVTV  120
SS                                                                122

SEQ ID NO: 119         moltype = AA  length = 122
FEATURE                Location/Qualifiers
```

```
REGION                  1..122
                        note = Description of Artificial Sequence: Synthetic
                         polypeptide
source                  1..122
                        mol_type = protein
                        organism = synthetic construct
SEQUENCE: 119
QVQLQESGPG LVRPSETLSL TCTVSGGSIR NYYWSWIRQP PGKGLEWIGF IYYNGRTFYN  60
PSLKSRVTIS LDMSKNQFSL KMTSVTAADT AVYYCARVRA YSGIGLDGTD VWGQGTTVTV  120
SS                                                                  122

SEQ ID NO: 120          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 120
QVQLQESGPG LVRPSETLSL TCTVSGGSIR NYYWSWIRQP PGKGLEWIGF IYYNGRTFYN  60
PSLKSRVTIS LDKSKNQFSL KMTSVTAADT AVYYCARVRA YSGIGLDGTD VWGQGTTVTV  120
SS                                                                  122

SEQ ID NO: 121          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 121
QVQLQESGPG LVRPSETLSL TCTVSGGSIR NYYWSWIRQP PGKGLEWIGF IYYNGRTFYN  60
PSLKSRVTIS LDTSKNQFSL KMTSVTAADT AVYYCARVRA YSGIGLDGTD VWGQGTTVTV  120
SS                                                                  122

SEQ ID NO: 122          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 122
QVQLQESGPG LVRPSETLSL TCTVSGGSIR NYYWSWIRQP PGKGLEWMGF IYDNGRTFYN  60
PSLKSRVTIS LDMSMNQFSL KMTSVTAADT AVYYCARVRA YSGIGLDGTD VWGQGTTVTV  120
SS                                                                  122

SEQ ID NO: 123          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 123
QVQLQESGPG LVRPSETLSL TCTVSGGSIR NYYWSWIRQP PGKGLEWIGF IYYTGRTFYN  60
PSLKSRVTIS LDMSINQFSL KMTSVTAADT AVYYCARVRA YSGIGLDGTD VWGQGTTVTV  120
SS                                                                  122

SEQ ID NO: 124          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 124
QVQLQESGPG LVRPSETLSL TCTVSGGSIR NYYWSWIRQP PGKGLEWIGF IYYTGRTFYN  60
PSLKSRVTIS LDMSKNQFSL KMTSVTAADT AVYYCARVRA YSGIGLDGTD VWGQGTTVTV  120
SS                                                                  122

SEQ ID NO: 125          moltype = AA  length = 107
FEATURE                 Location/Qualifiers
REGION                  1..107
```

```
                         note = Description of Artificial Sequence: Synthetic
                          polypeptide
source                   1..107
                         mol_type = protein
                         organism = synthetic construct
SEQUENCE: 125
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIK                107

SEQ ID NO: 126           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 126
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIK                107

SEQ ID NO: 127           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 127
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IK          112

SEQ ID NO: 128           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 128
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IK          112

SEQ ID NO: 129           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 129
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IK          112

SEQ ID NO: 130           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 130
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IK          112

SEQ ID NO: 131           moltype = AA  length = 447
FEATURE                  Location/Qualifiers
REGION                   1..447
                         note = Description of Artificial Sequence: Synthetic
                          polypeptide
source                   1..447
                         mol_type = protein
                         organism = synthetic construct
SEQUENCE: 131
EVQLVESGGG LVQPGGSLRL SCAASGFTLS SYDMHWVRQA TGKGLEWVSA IGTAGDTYYT  60
```

```
GSVKGRFTIS RENAKNSLYL QMNSLRAGDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 132          moltype = AA  length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 132
EVQLVESGGG LVQPGGSLRL SCAASGFTLS SYDMHWVRQA TGKGLEWVSA IGTAGDTYYT  60
GSVKGRFTIS RENAKNSLYL QMNSLRAGDT AVYYCVRGGV WDDAFDIWGQ GTMVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                       444

SEQ ID NO: 133          moltype = AA  length = 453
FEATURE                 Location/Qualifiers
REGION                  1..453
                        note = Description of Artificial Sequence: Synthetic
                         polypeptide
source                  1..453
                        mol_type = protein
                        organism = synthetic construct
SEQUENCE: 133
QVQLVQSGAE VKKPGASVKV SCKASGYTFT GNYMHWVRQA PGQGLEWMGW INPNSGGTNY  60
AQKFQGRVTM TRDTSISTAY MELSRLRSDD TAVYYCVSGS GWYENYYYYG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCDKT HTCPPCPAPE  240
AAGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                             453

SEQ ID NO: 134          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 134
EVQLVESGGG LVQPGGSLRL SCAASGFTFS SYDMHWVRQA TGKGLEWVSV IGIAGDTYYP  60
GSVKGRFTIS RENAKNSLYL QMNSLRVGDT AVYYCARGGS WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 135          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 135
QVQLQESGPG LVRPSETLSL TCTVSGGSIR NYYWSWIRQP PGKGLEWIGF IYYNGRTFYN  60
SSLKSRVTIS LDMSMNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                               451
```

```
SEQ ID NO: 136          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 136
QVQLQESGPG LVRPSETLSL TCTVSGGSIR NYYWSWIRQP PGKGLEWIGF IYYNGRTFYN  60
SSLKSRVTIS LDMSMNQFSL KMTSVTAADT AVYYCARVRA YSGIGLDGTD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                    448

SEQ ID NO: 137          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 137
EVQLVESGGG LVQPGGSLRL SCAASGFTFS SFDMHWVRQP TGKGLEWVST IGIAGDTYFP  60
GSVKGRFTIS RENAKNSLYL QMNSLRAGDT AVYYCARGGN WDDALDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 138          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 138
EVQLVESGGG LVQPGGSLRL SCAASGFTLS SYDMHWVRQA PGKGLEWVSA IGTAGDTYYT  60
GSVKGRFTIS RENAKNSLYL QMNSLRADDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 139          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 139
EVQLVESGGG LVQPGGSLRL SCAASGFTLS SYDMHWVRQA TGKGLEWVSA IGTAGDTYYT  60
GSVKGRFTIS RENAKNSLYL QMNSLRAADT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 140          moltype = AA  length = 447
FEATURE                 Location/Qualifiers
REGION                  1..447
                        note = Description of Artificial Sequence: Synthetic
                         polypeptide
source                  1..447
```

```
                         mol_type = protein
                         organism = synthetic construct
SEQUENCE: 140
EVQLVESGGG LVQPGGSLRL SCAASGFTLS SYDMHWVRQA TGKGLEWVSA IGTAGDTYYT  60
GSVKGRFTIS RENAKNSLYL QMNSLRASDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 141          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 141
EVQLVESGGG LVQPGGSLRL SCAASGFTLS SYDMHWVRQA PGKGLEWVSA IGTAGDTYYT  60
GSVKGRFTIS RENAKNSLYL QMNSLRAADT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 142          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 142
EVQLVESGGG LVQPGGSLRL SCAASGFTLS SYDMHWVRQA PGKGLEWVSA IGTAGDTYYT  60
GSVKGRFTIS RENAKNSLYL QMNSLRASDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 143          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 143
EVQLVESGGG LVQPGGSLRL SCAASGFTLS SYDMHWVRQA PGKGLEWVSA IGTAGDTYYT  60
GSVKGRFTIS RENAKNSLYL QMNSLRAEDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 144          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 144
EVQLVESGGG LVQPGGSLRL SCAASGFTLS SYDMHWVRQA TGKGLEWVSA IGTAGDTYYT  60
GSVKGRFTIS RENAKNSLYL QMNSLRAGDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
```

```
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 145         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 145
EVQLVESGGG LVQPGGSLRL SCAASGFTLS SYDMHWVRQA PGKGLEWVSA IGTAGDTYYT  60
GSVKGRFTIS RENAKNSLYL QMNSLRAGDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 146         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 146
EVQLVESGGG LVQPGGSLRL SCAASGFTLS SYDMHWVRQA PGKGLEWVSA IGTAGDTYYT  60
GSVKGRFTIS RENAKNSLYL QMNSLRADDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 147         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 147
EVQLVESGGG LVQPGGSLRL SCAASGFTLS SYDMHWVRQA TGKGLEWVSA IGTAGDTYYT  60
GSVKGRFTIS RENAKNSLYL QMNSLRAADT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 148         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 148
EVQLVESGGG LVQPGGSLRL SCAASGFTLS SYDMHWVRQA TGKGLEWVSA IGTAGDTYYT  60
GSVKGRFTIS RENAKNSLYL QMNSLRASDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 149         moltype = AA  length = 447
FEATURE                Location/Qualifiers
```

```
REGION                1..447
                      note = Description of Artificial Sequence: Synthetic
                       polypeptide
source                1..447
                      mol_type = protein
                      organism = synthetic construct
SEQUENCE: 149
EVQLVESGGG LVQPGGSLRL SCAASGFTLS SYDMHWVRQA PGKGLEWVSA IGTAGDTYYT  60
GSVKGRFTIS RENAKNSLYL QMNSLRAADT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 150        moltype = AA  length = 447
FEATURE               Location/Qualifiers
REGION                1..447
                      note = Description of Artificial Sequence: Synthetic
                       polypeptide
source                1..447
                      mol_type = protein
                      organism = synthetic construct
SEQUENCE: 150
EVQLVESGGG LVQPGGSLRL SCAASGFTLS SYDMHWVRQA PGKGLEWVSA IGTAGDTYYT  60
GSVKGRFTIS RENAKNSLYL QMNSLRASDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 151        moltype = AA  length = 447
FEATURE               Location/Qualifiers
REGION                1..447
                      note = Description of Artificial Sequence: Synthetic
                       polypeptide
source                1..447
                      mol_type = protein
                      organism = synthetic construct
SEQUENCE: 151
EVQLVESGGG LVQPGGSLRL SCAASGFTLS SYDMHWVRQA PGKGLEWVSA IGTAGDTYYT  60
GSVKGRFTIS RENAKNSLYL QMNSLRAEDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 152        moltype = AA  length = 447
FEATURE               Location/Qualifiers
REGION                1..447
                      note = Description of Artificial Sequence: Synthetic
                       polypeptide
source                1..447
                      mol_type = protein
                      organism = synthetic construct
SEQUENCE: 152
EVQLVESGGG LVQPGGSLRL SCAASGFTLS SYDMHWVRQA PGKGLEWVSA IGTAGDTYYT  60
GSVKGRFTIS RENAKNSLYL QMNSLRAGDT AVYYCVRGGV WDDAFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 153        moltype = AA  length = 451
FEATURE               Location/Qualifiers
REGION                1..451
                      note = Description of Artificial Sequence: Synthetic
                       polypeptide
source                1..451
                      mol_type = protein
                      organism = synthetic construct
SEQUENCE: 153
```

```
QVQLQESGPG LVRPSETLSL TCTVSGGSIR NYYWSWIRQP PGKGLEWIGF IYYNGRTFYN  60
PSLKSRVTIS LDMSINQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 154         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 154
QVQLQESGPG LVRPSETLSL TCTVSGGSIR NYYWSWIRQP PGKGLEWIGF IYYNGRTFYN  60
PSLKSRVTIS LDMSINQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 155         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 155
QVQLQESGPG LVRPSETLSL TCTVSGGSIR NYYWSWIRQP PGKGLEWIGF IYYNGRTFYN  60
PSLKSRVTIS LDMSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 156         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 156
QVQLQESGPG LVRPSETLSL TCTVSGGSIR NYYWSWIRQP PGKGLEWIGF IYYNGRTFYN  60
PSLKSRVTIS LDMSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 157         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 157
QVQLQESGPG LVRPSETLSL TCTVSGGSIR NYYWSWIRQP PGKGLEWIGF IYYNGRTFYN  60
PSLKSRVTIS LDKSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
```

```
RWQQGNVFSC SVMHEALHNH YTQKSLSLSP G                                 451

SEQ ID NO: 158          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 158
QVQLQESGPG LVRPSETLSL TCTVSGGSIR NYYWSWIRQP PGKGLEWIGF IYYNGRTFYN  60
PSLKSRVTIS LDKSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 159          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 159
QVQLQESGPG LVRPSETLSL TCTVSGGSIR NYYWSWIRQP PGKGLEWIGF IYYNGRTFYN  60
PSLKSRVTIS LDTSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 160          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 160
QVQLQESGPG LVRPSETLSL TCTVSGGSIR NYYWSWIRQP PGKGLEWMGF IYDNGRTFYN  60
PSLKSRVTIS LDMSMNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 161          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 161
QVQLQESGPG LVRPSETLSL TCTVSGGSIR NYYWSWIRQP PGKGLEWIGF IYYNGRTFYN  60
PSLKSRVTIS LDMSINQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 162          moltype = AA  length = 451
FEATURE                 Location/Qualifiers
REGION                  1..451
                        note = Description of Artificial Sequence: Synthetic
                         polypeptide
```

```
source                  1..451
                        mol_type = protein
                        organism = synthetic construct
SEQUENCE: 162
QVQLQESGPG LVRPSETLSL TCTVSGGSIR NYYWSWIRQP PGKGLEWIGF IYYNGRTFYN  60
PSLKSRVTIS LDTSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 163          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 163
QVQLQESGPG LVRPSETLSL TCTVSGGSIR NYYWSWIRQP PGKGLEWMGF IYDNGRTFYN  60
PSLKSRVTIS LDMSMNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 164          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 164
QVQLQESGPG LVRPSETLSL TCTVSGGSIR NYYWSWIRQP PGKGLEWIGF IYYNGRTFYN  60
PSLKSRVTIS LDMSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 165          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 165
QVQLQESGPG LVRPSETLSL TCTVSGGSIR NYYWSWIRQP PGKGLEWIGF IYYTGRTFYN  60
PSLKSRVTIS LDMSINQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 166          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 166
QVQLQESGPG LVRPSETLSL TCTVSGGSIR NYYWSWIRQP PGKGLEWIGF IYYNGRTFYN  60
PSLKSRVTIS LDKSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
```

```
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 167         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 167
QVQLQESGPG LVRPSETLSL TCTVSGGSIR NYYWSWIRQP PGKGLEWIGF IYYTGRTFYN  60
PSLKSRVTIS LDMSINQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 168         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 168
QVQLQESGPG LVRPSETLSL TCTVSGGSIR NYYWSWIRQP PGKGLEWIGF IYYNGRTFYN  60
PSLKSRVTIS LDTSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 169         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 169
QVQLQESGPG LVRPSETLSL TCTVSGGSIR NYYWSWIRQP PGKGLEWMGF IYDNGRTFYN  60
PSLKSRVTIS LDMSMNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 170         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 170
QVQLQESGPG LVRPSETLSL TCTVSGGSIR NYYWSWIRQP PGKGLEWIGF IYYTGRTFYN  60
PSLKSRVTIS LDMSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 171         moltype = AA  length = 451
```

```
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 171
QVQLQESGPG LVRPSETLSL TCTVSGGSIR NYYWSWIRQP PGKGLEWIGF IYYTGRTFYN  60
PSLKSRVTIS LDMSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 172         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 172
QVQLQESGPG LVRPSETLSL TCTVSGGSIR NYYWSWIRQP PGKGLEWIGF IYYTGRTFYN  60
PSLKSRVTIS LDMSINQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 173         moltype = AA  length = 451
FEATURE                Location/Qualifiers
REGION                 1..451
                       note = Description of Artificial Sequence: Synthetic
                        polypeptide
source                 1..451
                       mol_type = protein
                       organism = synthetic construct
SEQUENCE: 173
QVQLQESGPG LVRPSETLSL TCTVSGGSIR NYYWSWIRQP PGKGLEWIGF IYYTGRTFYN  60
PSLKSRVTIS LDMSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 174         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 174
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 175         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 175
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
```

```
LSKADYEKHK VYACEVTHQG LSSPVTKSFN RGEC                              214

SEQ ID NO: 176          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 176
DIQMTQSPSS VSASVGDRVT ITCRASQGIS SWLAWYQQKP GKAPKLLIYA ESSLQSGVPS  60
RFSGSGSGTD FTLTISSLQP EDFATYYCQQ ANSFPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 177          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 177
DIQMTQSPSS LSASIGDKVT ITCRASQDIN NYLAWFQQKP GKAPKSLIYT ASSLQSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 178          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 178
DIVMTQSPLS LPVTPGEPAS ISCKSSQSLL YSNGYNYLDW YLQRPGQSPQ LLIYLGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 179          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 179
DIVMTQSPLS LPVTPGEPAS ISCKSSQSLL YSNGYNYLDW YLQRPGQSPQ LLIYLGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 180          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 180
DIQMTQSPSS LSASVGDRVT ITCRASQDIN NYLAWFQQKP GKAPKSLIYT ASSLQSGVPS  60
KFSGSGSGTD FTLTISSLQP EDFATYYCQQ YNTYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 181          moltype = AA  length = 214
FEATURE                 Location/Qualifiers
REGION                  1..214
                        note = Description of Artificial Sequence: Synthetic
                         polypeptide
source                  1..214
                        mol_type = protein
```

```
                        organism = synthetic construct
SEQUENCE: 181
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 182          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 182
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 183          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 183
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 184          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 184
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 185          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 185
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 186          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 186
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 187          moltype = AA  length = 214
FEATURE                 Location/Qualifiers
```

```
REGION                  1..214
                        note = Description of Artificial Sequence: Synthetic
                         polypeptide
source                  1..214
                        mol_type = protein
                        organism = synthetic construct
SEQUENCE: 187
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 188          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 188
DIQMTQSPSS LSASVGDRVT ITCRASQGIN NYAAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 189          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 189
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 190          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 190
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 191          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 191
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 192          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 192
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 193          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 193
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 194          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 194
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 195          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 195
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 196          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 196
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 197          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 197
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 198          moltype = AA  length = 219
FEATURE                 Location/Qualifiers
REGION                  1..219
                        note = Description of Artificial Sequence: Synthetic
                         polypeptide
source                  1..219
```

```
                         mol_type = protein
                         organism = synthetic construct
SEQUENCE: 198
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 199          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 199
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 200          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 200
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 201          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 201
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 202          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 202
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 203          moltype = AA  length = 219
FEATURE                 Location/Qualifiers
REGION                  1..219
                        note = Description of Artificial Sequence: Synthetic
                         polypeptide
source                  1..219
                        mol_type = protein
                        organism = synthetic construct
SEQUENCE: 203
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 204          moltype = AA  length = 219
```

```
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 204
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 205         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 205
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 206         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 206
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 207         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 207
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 208         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 208
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 209         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 209
DIVMTQSPLS LPVTPGEPAS ISCKSSQSLL YSNAYNYLDW YLQRPGQSPQ LLIYLGSNRA  60
```

```
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 210         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 210
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 211         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 211
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 212         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 212
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 213         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 213
DIVMTQSPLS LPVTPGEPAS ISCKSSQSLL YSNGYAYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 214         moltype = AA  length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 214
DIVMTQSPLS LPVTPGEPAS ISCKSSQSLL YSNGYAYLDW YLQRPGQSPQ LLIYQGSNRA  60
SGVPDRFSGS GSGTDFTLKI SRVEAEDVGV FYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 215         moltype = AA  length = 219
FEATURE                Location/Qualifiers
REGION                 1..219
                       note = Description of Artificial Sequence: Synthetic
                        polypeptide
```

```
source                1..219
                      mol_type = protein
                      organism = synthetic construct
SEQUENCE: 215
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 216        moltype = AA  length = 219
FEATURE               Location/Qualifiers
REGION                1..219
                      note = Description of Artificial Sequence: Synthetic
                       polypeptide
source                1..219
                      mol_type = protein
                      organism = synthetic construct
SEQUENCE: 216
DIVMTQSPLS LPVTPGEPAS ISCKSSQSLL YSNAYNYLDW YLQRPGQSPQ LLIYLGSNRA  60
SGVPDRFSGS GSGTDFTLKI SRVEAEDVGV YYCMQALQTP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 217        moltype = AA  length = 444
FEATURE               Location/Qualifiers
REGION                1..444
                      note = Description of Artificial Sequence: Synthetic
                       polypeptide
source                1..444
                      mol_type = protein
                      organism = synthetic construct
SEQUENCE: 217
EVQLVESGGG LVQPGGSLRL SCAASGFTLS SYDMHWVRQA TGKGLEWVSA IGTAGDTYYT  60
GSVKGRFTIS RENAKNSLYL QMNSLRAADT AVYYCVRGGV WDDAFDIWGQ GTMVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                        444

SEQ ID NO: 218        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 218
DIQMTQSPSS LSASVGDRVT ITCRASQDIN NYLAWFQQKP GKAPKSLIYT ASSLHSGVPS  60
KFSGSGSGTD FTLTISSLQP EDFATYYCQQ YVSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 219        moltype = AA  length = 451
FEATURE               Location/Qualifiers
REGION                1..451
                      note = Description of Artificial Sequence: Synthetic
                       polypeptide
source                1..451
                      mol_type = protein
                      organism = synthetic construct
SEQUENCE: 219
QVQLQESGPG LVKPSETLSL TCTVSGGSIR DYYWSWIRQP PGKGLEWIGF IYYNGRTFYQ  60
SSLKSRVTIS LDTSKNQFSL KMTSVTAADT AVYYCARVRA YSGIGLDGTD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 220        moltype = AA  length = 219
FEATURE               Location/Qualifiers
REGION                1..219
                      note = Description of Artificial Sequence: Synthetic
                       polypeptide
source                1..219
```

```
                         mol_type = protein
                         organism = synthetic construct
SEQUENCE: 220
DIVMTQSPLS LPVTPGEPAS ISCRSSQSLL YSTGYTYLDW YLQRPGQSPQ LLIYGGSSRA  60
SGVPDRFSGS GSGTDFTLKI SRVEAEDVGV FYCGQALQTP LTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 221           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 221
QVQLQESGPG LVKPSETLSL TCTVSGGSIR DYYWSWIRQP PGKGLEWIGF IYYNGRTFYQ  60
SSLKSRVTIS LDTSKNQFSL KMTSVTAADT AVYYCARVRA YSGIGLDGTD VWGQGTTVTV  120
SS                                                                 122

SEQ ID NO: 222           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 222
DIVMTQSPLS LPVTPGEPAS ISCRSSQSLL YSTGYTYLDW YLQRPGQSPQ LLIYGGSSRA  60
SGVPDRFSGS GSGTDFTLKI SRVEAEDVGV FYCGQALQTP LTFGQGTKVE IK          112

SEQ ID NO: 223           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 223
DYYWS                                                              5

SEQ ID NO: 224           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 224
FIYYNGRTFY QSSLKS                                                  16

SEQ ID NO: 225           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 225
RSSQSLLYST GYTYLD                                                  16

SEQ ID NO: 226           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 226
GGSSRAS                                                            7

SEQ ID NO: 227           moltype = AA  length = 9
FEATURE                  Location/Qualifiers
REGION                   1..9
                         note = Description of Artificial Sequence: Synthetic peptide
source                   1..9
                         mol_type = protein
```

```
                         organism = synthetic construct
SEQUENCE: 227
GQALQTPLT                                                              9

SEQ ID NO: 228           moltype = AA  length = 5
FEATURE                  Location/Qualifiers
REGION                   1..5
                         note = Description of Artificial Sequence: Synthetic peptide
MOD_RES                  1
                         note = N or D
source                   1..5
                         mol_type = protein
                         organism = synthetic construct
SEQUENCE: 228
XYYWS                                                                  5

SEQ ID NO: 229           moltype = AA  length = 16
FEATURE                  Location/Qualifiers
REGION                   1..16
                         note = Description of Artificial Sequence: Synthetic peptide
MOD_RES                  4
                         note = Y or D
MOD_RES                  5
                         note = N or T
MOD_RES                  11
                         note = N or Q
MOD_RES                  12
                         note = S or P
source                   1..16
                         mol_type = protein
                         organism = synthetic construct
SEQUENCE: 229
FIYXXGRTFY XXSLKS                                                      16

SEQ ID NO: 230           moltype = AA  length = 16
FEATURE                  Location/Qualifiers
REGION                   1..16
                         note = Description of Artificial Sequence: Synthetic peptide
MOD_RES                  1
                         note = K or R
MOD_RES                  10
                         note = N or T
MOD_RES                  11
                         note = G or A
MOD_RES                  13
                         note = N, A or T
source                   1..16
                         mol_type = protein
                         organism = synthetic construct
SEQUENCE: 230
XSSQSLLYSX XYXYLD                                                      16

SEQ ID NO: 231           moltype = AA  length = 7
FEATURE                  Location/Qualifiers
REGION                   1..7
                         note = Description of Artificial Sequence: Synthetic peptide
MOD_RES                  1
                         note = L, Q or G
MOD_RES                  4
                         note = N or S
source                   1..7
                         mol_type = protein
                         organism = synthetic construct
SEQUENCE: 231
XGSXRAS                                                                7

SEQ ID NO: 232           moltype = AA  length = 9
FEATURE                  Location/Qualifiers
REGION                   1..9
                         note = Description of Artificial Sequence: Synthetic peptide
MOD_RES                  1
                         note = M or G
source                   1..9
                         mol_type = protein
                         organism = synthetic construct
SEQUENCE: 232
XQALQTPLT                                                              9

SEQ ID NO: 233           moltype = AA  length = 11
```

```
FEATURE                Location/Qualifiers
REGION                 1..11
                       note = Description of Artificial Sequence: Synthetic peptide
MOD_RES                5
                       note = D or G
MOD_RES                10
                       note = L or A
source                 1..11
                       mol_type = protein
                       organism = synthetic construct
SEQUENCE: 233
RASQXINNYX A                                                     11

SEQ ID NO: 234         moltype = AA  length = 330
FEATURE                Location/Qualifiers
REGION                 1..330
                       note = Description of Artificial Sequence: Synthetic
                        polypeptide
source                 1..330
                       mol_type = protein
                       organism = synthetic construct
SEQUENCE: 234
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 235         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 235
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 236         moltype = AA  length = 327
FEATURE                Location/Qualifiers
REGION                 1..327
                       note = Description of Artificial Sequence: Synthetic
                        polypeptide
source                 1..327
                       mol_type = protein
                       organism = synthetic construct
SEQUENCE: 236
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                    327

SEQ ID NO: 237         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 237
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 238         moltype = AA  length = 330
FEATURE                Location/Qualifiers
REGION                 1..330
                       note = Description of Artificial Sequence: Synthetic
                        polypeptide
source                 1..330
                       mol_type = protein
                       organism = synthetic construct
SEQUENCE: 238
ASTKGPSVFP LAPSSKSTSG GTAALGCLVK DYFPEPVTVS WNSGALTSGV HTFPAVLQSS  60
```

-continued

```
GLYSLSSVVT VPSSSLGTQT YICNVNHKPS NTKVDKRVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 239         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 239
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 240         moltype = AA  length = 347
FEATURE                Location/Qualifiers
source                 1..347
                       mol_type = protein
                       organism = Homo sapiens
SEQUENCE: 240
EEELQVIQPD KSVLVAAGET ATLRCTATSL IPVGPIQWFR GAGPGRELIY NQKEGHFPRV  60
TTVSDLTKRN NMDFSIRIGN ITPADAGTYY CVKFRKGSPD DVEFKSGAGT ELSVRAKPSA  120
PVVSGPAARA TPQHTVSFTC ESHGFSPRDI TLKWFKNGNE LSDFQTNVDP VGESVSYSIH  180
STAKVVLTRE DVHSQVICEV AHVTLQGDPL RGTANLSETI RVPPTLEVTQ QPVRAENQVN  240
VTCQVRKFYP QRLQLTWLEN GNVSRTETAS TVTENKDGTY NWMSWLLVNV SAHRDDVKLT  300
CQVEHDGQPA VSKSHDLKVS AHPKEQGSNT AAENTGSNER NIYGGSG                347

SEQ ID NO: 241         moltype = AA  length = 346
FEATURE                Location/Qualifiers
source                 1..346
                       mol_type = protein
                       organism = Homo sapiens
SEQUENCE: 241
EEELQVIQPD KSVSVAAGES AILHCTVTSL IPVGPIQWFR GAGPARELIY NQKEGHFPRV  60
TTVSESTKRE NMDFSISISN ITPADAGTYY CVKFRKGSPD TEFKSGAGTE LSVRAKPSAP  120
VVSGPAARAT PQHTVSFTCE SHGFSPRDIT LKWFKNGNEL SDFQTNVDPV GESVSYSIHS  180
TAKVVLTRED VHSQVICEVA HVTLQGDPLR GTANLSETIR VPPTLEVTQQ PVRAENQVNV  240
TCQVRKFYPQ RLQLTWLENG NVSRTETAST VTENKDGTYN WMSWLLVNVS AHRDDVKLTC  300
QVEHDGQPAV SKSHDLKVSA HPKEQGSNTA AENTGSNERN IYGGSG                 346

SEQ ID NO: 242         moltype = AA  length = 346
FEATURE                Location/Qualifiers
source                 1..346
                       mol_type = protein
                       organism = Homo sapiens
SEQUENCE: 242
EDELQVIQPE KSVSVAAGES ATLRCAMTSL IPVGPIMWFR GAGAGRELIY NQKEGHFPRV  60
TTVSELTKRN NLDFSISISN ITPADAGTYY CVKFRKGSPD DVEFKSGAGT ELSVRAKPSA  120
PVVSGPAVRA TPEHTVSFTC ESHGFSPRDI TLKWFKNGNE LSDFQTNVDP AGDSVSYSIH  180
STARVVLTRG DVHSQVICEI AHITLQGDPL RGTANLSEAI RVPPTLEVTQ QPMRAENQAN  240
VTCQVSNFYP RGLQLTWLEN GNVSRTETAS TLIENKDGTY NWMSWLLVNT CAHRDDVVLT  300
CQVEHDGQQA VSKSYALEIS AHQKEHGSDI THEAALAPTA PLGGSG                 346

SEQ ID NO: 243         moltype = AA  length = 346
FEATURE                Location/Qualifiers
source                 1..346
                       mol_type = protein
                       organism = Homo sapiens
SEQUENCE: 243
EEELQVIQPD KSISVAAGES ATLHCTVTSL IPVGPIQWFR GAGPGRELIY NQKEGHFPRV  60
TTVSDLTKRN NMDFSIRISN ITPADAGTYY CVKFRKGSPD HVEFKSGAGT ELSVRAKPSA  120
PVVSGPAARA TPQHTVSFTC ESHGFSPRDI TLKWFKNGNE LSDFQTNVDP AGDSVSYSIH  180
STAKVVLTRE DVHSQVICEV AHVTLQGDPL RGTANLSETI RVPPTLEVTQ QPVRAENQVN  240
VTCQVRKFYP QRLQLTWLEN GNVSRTETAS TLTENKDGTY NWMSWLLVNV SAHRDDVKLT  300
CQVEHDGQPA VSKSHDLKVS AHPKEQGSNT APGPALASAA PLGGSG                 346

SEQ ID NO: 244         moltype = AA  length = 332
FEATURE                Location/Qualifiers
source                 1..332
                       mol_type = protein
                       organism = Homo sapiens
SEQUENCE: 244
EEELQMIQPE KLLLVTVGKT ATLHCTVTSL LPVGPVLWFR GVGPGRELIY NQKEGHFPRV  60
TTVSDLTKRN NMDFSIRISS ITPADVGTYY CVKFRKGSPE NVEFKSGPGT EMALGAKPSA  120
PVVLGPAART TPEHTVSFTC ESHGFSPRDI TLKWFKNGNE LSDFQTNVDP TGQSVAYSIR  180
```

```
STARVVLDPW DVRSQVICEV AHVTLQGDPL RGTANLSEAI RVPPTLEVTQ QPMRVGNQVN  240
VTCQVRKFYP QSLQLTWSEN GNVCQRETAS TLTENKDGTY NWTSWFLVNI SDQRDDVVLT  300
CQVKHDGQLA VSKRLALEVT VHQKDQSSDA TP                               332

SEQ ID NO: 245         moltype = AA  length = 120
FEATURE                Location/Qualifiers
source                 1..120
                       mol_type = protein
                       organism = Homo sapiens
SEQUENCE: 245
WQPPLLFNKT KSVEFTFGND TVVIPCFVTN MEAQNTTEVY VKWKFKGRDI YTFDGQANKS  60
TVPTDFSSAK IEVSQLLKGD ASLKMDKSDA VSHTGNYTCE VTELTREGET IIELKYRVVS  120

SEQ ID NO: 246         moltype = AA  length = 342
FEATURE                Location/Qualifiers
source                 1..342
                       mol_type = protein
                       organism = Mus musculus
SEQUENCE: 246
KELKVTQPEK SVSVAAGDST VLNCTLTSLL PVGPIKWYRG VGQSRLLIYS FTGEHFPRVT  60
NVSDATKRNN MDFSIRISNV TPEDAGTYYC VKFQKGPSEP DTEIQSGGGT EVYVLAKPSP  120
PEVSGPADRG IPDQKVNFTC KSHGFSPRNI TLKWFKDGQE LHHLETTVNP SGKNVSYNIS  180
STVRVVLNSM DVHSKVICEV AHITLDRSPL RGIANLSNFI RVSPTVKVTQ QSPTSMNQVN  240
LTCRAERFYP EDLQLIWLEN GNVSRNDTPK NLTKNTDGTY NYTSLFLVNS SAHREDVVFT  300
CQVKHDQQPA ITRNHTVLGL AHSSDQGSMQ TFPGNNATHN WN                    342

SEQ ID NO: 247         moltype = AA  length = 346
FEATURE                Location/Qualifiers
source                 1..346
                       mol_type = protein
                       organism = Macaca fascicularis
SEQUENCE: 247
EEELQVIQPE KSVSVAAGDS ATLNCTVSSL IPVGPIQWFR GAGPGRELIY NLKEGHFPRV  60
TAVSDPTKRN NMDFSIRISN ITPADAGTYY CVKFRKGSPD VELKSGAGTE LSVRAKPSAP  120
VVSGPAVRAT AEHTVSFTCE SHGFSPRDIT LKWFKNGNEL SDVQTNVDPA GKSVSYSIRS  180
TARVLLTRRD VHSQVICEVA HVTLQGDPLR GTANLSEAIR VPPFLEVTQQ SMRADNQVNV  240
TCQVTKFYPQ RLQLTWLENG NVSRTEMASA LPENKDGTYN WTSWLLVNVS AHRDDVKLTC  300
QVEHDGQPAV NKSFSVKVSA HPKEQGSNTA AENTGTNERN IYGGSG                346

SEQ ID NO: 248         moltype = AA  length = 346
FEATURE                Location/Qualifiers
source                 1..346
                       mol_type = protein
                       organism = Macaca fascicularis
SEQUENCE: 248
EEELQVIQPE KSVSVAAGES ATLNCTATSL IPVGPIQWFR GVGPGRELIY HQKEGHFPRV  60
TPVSDPTKRN NMDFSIRISN ITPADAGTYY CVKFRKGSPD VELKSGAGTE LSVRAKPSAP  120
VVSGPAVRAT AEHTVSFTCE SHGFSPRDIT LKWFKNGNEL SDFQTNVDPA GKSVSYSIRS  180
TARVVLTRRD VHSQVICEVA HVTLQGDPLR GTANLSEAIR VPPFLEFTQQ SMRADNQVNV  240
TCQVMKFYPQ RLQLTWLENG NVSRTEMASA LPENKDGTYN WTSWLLVNVS AHRDDVKLTC  300
QVEHDGQPAV NKSFSVKVSA HPKEQGSNTA AENTGTNERN IYGGSG                346

SEQ ID NO: 249         moltype = AA  length = 346
FEATURE                Location/Qualifiers
source                 1..346
                       mol_type = protein
                       organism = Macaca fascicularis
SEQUENCE: 249
EEELQVIQPE KSVSVAAGDS ATLNCTVSSL IPVGPIQWFR GAGPGRELIY NLKEGHFPRV  60
TPVSDPTKRN NMDFSIRISN ITPADAGTYY CVKFRKGSPD VELKSGAGTE LSVRAKPSAP  120
VVSGPAVRAT AEHTVSFTCE SHGFSPRDIT LKWFKNGNEL SDFQTNVDPA GKSVSYSIRS  180
TARVVLTRRD VHSQVICEVA HVTLQGDPLR GTANLSEAIR VPPFLEVTQQ SMRADNQVNV  240
TCQVTKFYPQ RLQLTWLENG NVSRTEMASA LPENKDGTYN WTSWLLVNVS AHRDDVKLTC  300
QVEHDGQPAV NKSFSVKVSA HPKEQGSNTA AENTGTNERN IYGGSG                346

SEQ ID NO: 250         moltype = AA  length = 345
FEATURE                Location/Qualifiers
source                 1..345
                       mol_type = protein
                       organism = Macaca fascicularis
SEQUENCE: 250
EEELQVIQPE KSVSVTAGES ATLNCTVTSL IPVGPIQWFR GAGPGRELIY NLKEGHFPRV  60
TTVLDPTKRN NMDFSIHISN ITPADAGTYY CVKFRKGSPD VELKSGAGTE LSVRAKPSAP  120
VVSGPTARAT PEHTVSFTCE SHGFSPRDIT LKWFKNGNEL SDFQTNVDPA GKSVSYSIRS  180
TARVVLTRRD VHSQVICEVA HVTLQGDPLR GTANLSEAIR VPPTLEVFQR PMRAENQVNV  240
TCQVRKFYPQ RLLLTWLENG NVSQTETAST LTENKDGTYN WRSWLLVNTC AHRDGVVLTC  300
QVEHDGQPAV SKSHALEVSA HQKEQCSDTT SGPVLAPTAP LGGSG                 345

SEQ ID NO: 251         moltype = AA  length = 345
```

```
FEATURE                Location/Qualifiers
source                 1..345
                       mol_type = protein
                       organism = Macaca fascicularis
SEQUENCE: 251
EEELQVIQPE KSISVAAGES ATLNCTVTSL IPVGPIQWFR GVGPGRELIF NLQEGHFPRV  60
TPVSDPTKRN NMDFSILISS ITPADAGTYY CVKFRKGSPD VELKSGAGTE LSVRAKPSAP  120
VVSGPAVRAT AEHTVSFTCE SHGFSPRDIT LKWFKNGNEL SDFQTSVDPA GKSVSYSIRS  180
TARVVLTRRD VHSQVICEVA HVTLQGDPLR GTANLSEAIR VPPFLEVTQQ SMRAENQANI  240
TCQVSNFYPQ RLLLTWLENG NVSQTETAST LTENKDGTYN WTSWLLVNIC AHRDDVVLTC  300
QVKHDGQPAV SKSHTLEISA HQKEQDSDVT HGLALAPTAP LGGSG                345

SEQ ID NO: 252         moltype = AA  length = 336
FEATURE                Location/Qualifiers
source                 1..336
                       mol_type = protein
                       organism = Macaca fascicularis
SEQUENCE: 252
EEELQMIQPE KLLLVAVGES ATLNCTVTSL LPVGPVLWFR GVGPGRELIY NQKEGHFPRV  60
TTVSDLTKRN NMDFSIRISS ITPADAGTYY CVKFRKGSPE NVEFKSGPGT EMALRAKPSA  120
PVVSGPAARA TPEHTVSFTC KSHGFSPRDI TLKWFKNGNE LSDFQTNVDP AGQSVSYSIR  180
STARVVLAPW DVRSQVTCEV AHVTLQGDPL RGTANLSEAI RVPPTLEVTQ QPMRAGNQVN  240
ITYQVRNFYP QNLQLTWLEN GNVCRTETAS TLTENKDGTY NWTSWLLVNT SDQRDDVVLT  300
CQVKHDGQLA VNKSLVLEVS AHQKDQSSDA THGGSG                          336

SEQ ID NO: 253         moltype = AA  length = 6
FEATURE                Location/Qualifiers
source                 1..6
                       mol_type = protein
                       organism = Homo sapiens
SEQUENCE: 253
LIPVGP                                                           6

SEQ ID NO: 254         moltype =   length =
SEQUENCE: 254
000

SEQ ID NO: 255         moltype = AA  length = 4
FEATURE                Location/Qualifiers
source                 1..4
                       mol_type = protein
                       organism = Homo sapiens
SEQUENCE: 255
TKRN                                                             4

SEQ ID NO: 256         moltype = AA  length = 5
FEATURE                Location/Qualifiers
source                 1..5
                       mol_type = protein
                       organism = Homo sapiens
SEQUENCE: 256
KGSPD                                                            5

SEQ ID NO: 257         moltype = AA  length = 8
FEATURE                Location/Qualifiers
source                 1..8
                       mol_type = protein
                       organism = Homo sapiens
SEQUENCE: 257
RGAGPGRE                                                         8

SEQ ID NO: 258         moltype = AA  length = 5
FEATURE                Location/Qualifiers
source                 1..5
                       mol_type = protein
                       organism = Homo sapiens
SEQUENCE: 258
AGTYY                                                            5

SEQ ID NO: 259         moltype = AA  length = 10
FEATURE                Location/Qualifiers
source                 1..10
                       mol_type = protein
                       organism = Homo sapiens
SEQUENCE: 259
VEFKSGAGTE                                                       10

SEQ ID NO: 260         moltype = AA  length = 10
FEATURE                Location/Qualifiers
```

```
source                  1..10
                        mol_type = protein
                        organism = Homo sapiens
SEQUENCE: 260
TEFKSGAGTE                                                      10

SEQ ID NO: 261          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 261
GGSIRNY                                                         7

SEQ ID NO: 262          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 262
SFDMH                                                           5

SEQ ID NO: 263          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 263
GFTFSSFD                                                        8

SEQ ID NO: 264          moltype = AA  length = 4
FEATURE                 Location/Qualifiers
source                  1..4
                        mol_type = protein
                        organism = Homo sapiens
SEQUENCE: 264
TKRE                                                            4

SEQ ID NO: 265          moltype = AA  length = 146
FEATURE                 Location/Qualifiers
source                  1..146
                        mol_type = protein
                        organism = Homo sapiens
SEQUENCE: 265
MEPAGPAPGR LGPLLCLLLA ASCAWSGVAG EEELQVIQPD KSVLVAAGET ATLRCTATSL  60
IPVGPIQWFR GAGPGRELIY NQKEGHFPRV TTVSDLTKRN NMDFSIRIGN ITPADAGTYY  120
CVKFRKGSPD DVEFKSGAGT ELSVRA                                      146

SEQ ID NO: 266          moltype = AA  length = 145
FEATURE                 Location/Qualifiers
source                  1..145
                        mol_type = protein
                        organism = Homo sapiens
SEQUENCE: 266
MEPAGPAPGR LGPLLCLLLA ASCAWSGVAG EEELQVIQPD KSVSVAAGES AILHCTVTSL  60
IPVGPIQWFR GAGPARELIY NQKEGHFPRV TTVSESTKRE NMDFSISISN ITPADAGTYY  120
CVKFRKGSPD TEFKSGAGTE LSVRA                                       145

SEQ ID NO: 267          moltype = AA  length = 144
FEATURE                 Location/Qualifiers
source                  1..144
                        mol_type = protein
                        organism = Homo sapiens
SEQUENCE: 267
MPVPASWPHP PGPFLLLTLL LGLTEVAGEE ELQMIQPEKL LLVTVGKTAT LHCTVTSLLP  60
VGPVLWFRGV GPGRELIYNQ KEGHFPRVTT VSDLTKRNNM DFSIRISSIT PADVGTYYCV  120
KFRKGSPENV EFKSGPGTEM ALGA                                        144

SEQ ID NO: 268          moltype = AA  length = 474
FEATURE                 Location/Qualifiers
source                  1..474
                        mol_type = protein
                        organism = Homo sapiens
```

SEQUENCE: 268
EEELQVIQPD KSVLVAAGET ATLRCTATSL IPVGPIQWFR GAGPGRELIY NQKEGHFPRV 60
TTVSDLTKRN NMDFSIRIGN ITPADAGTYY CVKFRKGSPD DVEFKSGAGT ELSVRAKPSA 120
PVVSGPAARA TPQHTVSFTC ESHGFSPRDI TLKWFKNGNE LSDFQTNVDP VGESVSYSIH 180
STAKVVLTRE DVHSQVICEV AHVTLQGDPL RGTANLSETI RVPPTLEVTQ QPVRAENQVN 240
VTCQVRKFYP QRLQLTWLEN GNVSRTETAS TVTENKDGTY NWMSWLLVNV SAHRDDVKLT 300
CQVEHDGQPA VSKSHDLKVS AHPKEQGSNT AAENTGSNER NIYIVVGVVC TLLVALLMAA 360
LYLVRIRQKK AQGSTSSTRL HEPEKNAREI TQDTNDITYA DLNLPKGKKP APQAAEPNNH 420
TEYASIQTSP QPASEDTLTY ADLDMVHLNR TPKQPAPKPE PSFSEYASVQ VPRK 474

SEQ ID NO: 269 moltype = AA length = 474
FEATURE Location/Qualifiers
REGION 1..474
note = SIRPaV1 mutant
SITE 70
note = Site - Mutated residue
source 1..474
mol_type = protein
organism = synthetic construct
SEQUENCE: 269
EEELQVIQPD KSVLVAAGET ATLRCTATSL IPVGPIQWFR GAGPGRELIY NQKEGHFPRV 60
TTVSDLTKRE NMDFSIRIGN ITPADAGTYY CVKFRKGSPD DVEFKSGAGT ELSVRAKPSA 120
PVVSGPAARA TPQHTVSFTC ESHGFSPRDI TLKWFKNGNE LSDFQTNVDP VGESVSYSIH 180
STAKVVLTRE DVHSQVICEV AHVTLQGDPL RGTANLSETI RVPPTLEVTQ QPVRAENQVN 240
VTCQVRKFYP QRLQLTWLEN GNVSRTETAS TVTENKDGTY NWMSWLLVNV SAHRDDVKLT 300
CQVEHDGQPA VSKSHDLKVS AHPKEQGSNT AAENTGSNER NIYIVVGVVC TLLVALLMAA 360
LYLVRIRQKK AQGSTSSTRL HEPEKNAREI TQDTNDITYA DLNLPKGKKP APQAAEPNNH 420
TEYASIQTSP QPASEDTLTY ADLDMVHLNR TPKQPAPKPE PSFSEYASVQ VPRK 474

SEQ ID NO: 270 moltype = AA length = 474
FEATURE Location/Qualifiers
REGION 1..474
note = SIRPaV1 mutant
SITE 100
note = Site - Mutated residue
source 1..474
mol_type = protein
organism = synthetic construct
SEQUENCE: 270
EEELQVIQPD KSVLVAAGET ATLRCTATSL IPVGPIQWFR GAGPGRELIY NQKEGHFPRV 60
TTVSDLTKRN NMDFSIRIGN ITPADAGTYY CVKFRKGSPE DVEFKSGAGT ELSVRAKPSA 120
PVVSGPAARA TPQHTVSFTC ESHGFSPRDI TLKWFKNGNE LSDFQTNVDP VGESVSYSIH 180
STAKVVLTRE DVHSQVICEV AHVTLQGDPL RGTANLSETI RVPPTLEVTQ QPVRAENQVN 240
VTCQVRKFYP QRLQLTWLEN GNVSRTETAS TVTENKDGTY NWMSWLLVNV SAHRDDVKLT 300
CQVEHDGQPA VSKSHDLKVS AHPKEQGSNT AAENTGSNER NIYIVVGVVC TLLVALLMAA 360
LYLVRIRQKK AQGSTSSTRL HEPEKNAREI TQDTNDITYA DLNLPKGKKP APQAAEPNNH 420
TEYASIQTSP QPASEDTLTY ADLDMVHLNR TPKQPAPKPE PSFSEYASVQ VPRK 474

SEQ ID NO: 271 moltype = AA length = 474
FEATURE Location/Qualifiers
REGION 1..474
note = SIRPaV1 mutant
SITE 101
note = Site - Mutated residue
source 1..474
mol_type = protein
organism = synthetic construct
SEQUENCE: 271
EEELQVIQPD KSVLVAAGET ATLRCTATSL IPVGPIQWFR GAGPGRELIY NQKEGHFPRV 60
TTVSDLTKRN NMDFSIRIGN ITPADAGTYY CVKFRKGSPD NVEFKSGAGT ELSVRAKPSA 120
PVVSGPAARA TPQHTVSFTC ESHGFSPRDI TLKWFKNGNE LSDFQTNVDP VGESVSYSIH 180
STAKVVLTRE DVHSQVICEV AHVTLQGDPL RGTANLSETI RVPPTLEVTQ QPVRAENQVN 240
VTCQVRKFYP QRLQLTWLEN GNVSRTETAS TVTENKDGTY NWMSWLLVNV SAHRDDVKLT 300
CQVEHDGQPA VSKSHDLKVS AHPKEQGSNT AAENTGSNER NIYIVVGVVC TLLVALLMAA 360
LYLVRIRQKK AQGSTSSTRL HEPEKNAREI TQDTNDITYA DLNLPKGKKP APQAAEPNNH 420
TEYASIQTSP QPASEDTLTY ADLDMVHLNR TPKQPAPKPE PSFSEYASVQ VPRK 474

SEQ ID NO: 272 moltype = AA length = 474
FEATURE Location/Qualifiers
REGION 1..474
note = SIRPaV1 mutant
REGION 100..101
note = Site - Mutated residue
source 1..474
mol_type = protein
organism = synthetic construct
SEQUENCE: 272
EEELQVIQPD KSVLVAAGET ATLRCTATSL IPVGPIQWFR GAGPGRELIY NQKEGHFPRV 60
TTVSDLTKRN NMDFSIRIGN ITPADAGTYY CVKFRKGSPE NVEFKSGAGT ELSVRAKPSA 120

```
PVVSGPAARA TPQHTVSFTC ESHGFSPRDI TLKWFKNGNE LSDFQTNVDP VGESVSYSIH  180
STAKVVLTRE DVHSQVICEV AHVTLQGDPL RGTANLSETI RVPPTLEVTQ QPVRAENQVN  240
VTCQVRKFYP QRLQLTWLEN GNVSRTETAS TVTENKDGTY NWMSWLLVNV SAHRDDVKLT  300
CQVEHDGQPA VSKSHDLKVS AHPKEQGSNT AAENTGSNER NIYIVVGVVC TLLVALLMAA  360
LYLVRIRQKK AQGSTSSTRL HEPEKNAREI TQDTNDITYA DLNLPKGKKP APQAAEPNNH  420
TEYASIQTSP QPASEDTLTY ADLDMVHLNR TPKQPAPKPE PSFSEYASVQ VPRK        474

SEQ ID NO: 273         moltype = AA  length = 473
FEATURE                Location/Qualifiers
source                 1..473
                       mol_type = protein
                       organism = Homo sapiens
SEQUENCE: 273
EEELQVIQPD KSVSVAAGES AILHCTVTSL IPVGPIQWFR GAGPARELIY NQKEGHFPRV  60
TTVSESTKRE NMDFSISISN ITPADAGTYY CVKFRKGSPD TEFKSGAGTE LSVRAKPSAP  120
VVSGPAARAT PQHTVSFTCE SHGFSPRDIT LKWFKNGNEL SDFQTNVDPV GESVSYSIHS  180
TAKVVLTRED VHSQVICEVA HVTLQGDPLR GTANLSETIR VPPTLEVTQQ PVRAENQVNV  240
TCQVRKFYPQ RLQLTWLENG NVSRTETAST VTENKDGTYN WMSWLLVNVS AHRDDVKLTC  300
QVEHDGQPAV SKSHDLKVSA HPKEQGSNTA AENTGSNERN IYIVVGVVCT LLVALLMAAL  360
YLVRIRQKKA QGSTSSTRLH EPEKNAREIT QDTNDITYAD LNLPKGKKPA PQAAEPNNHT  420
EYASIQTSPQ PASEDTLTYA DLDMVHLNRT PKQPAPKPEP SFSEYASVQV PRK         473

SEQ ID NO: 274         moltype = AA  length = 473
FEATURE                Location/Qualifiers
REGION                 1..473
                       note = SIRPaV2 mutant
SITE                   70
                       note = Site - Mutated residue
source                 1..473
                       mol_type = protein
                       organism = synthetic construct
SEQUENCE: 274
EEELQVIQPD KSVSVAAGES AILHCTVTSL IPVGPIQWFR GAGPARELIY NQKEGHFPRV  60
TTVSESTKRN NMDFSISISN ITPADAGTYY CVKFRKGSPD TEFKSGAGTE LSVRAKPSAP  120
VVSGPAARAT PQHTVSFTCE SHGFSPRDIT LKWFKNGNEL SDFQTNVDPV GESVSYSIHS  180
TAKVVLTRED VHSQVICEVA HVTLQGDPLR GTANLSETIR VPPTLEVTQQ PVRAENQVNV  240
TCQVRKFYPQ RLQLTWLENG NVSRTETAST VTENKDGTYN WMSWLLVNVS AHRDDVKLTC  300
QVEHDGQPAV SKSHDLKVSA HPKEQGSNTA AENTGSNERN IYIVVGVVCT LLVALLMAAL  360
YLVRIRQKKA QGSTSSTRLH EPEKNAREIT QDTNDITYAD LNLPKGKKPA PQAAEPNNHT  420
EYASIQTSPQ PASEDTLTYA DLDMVHLNRT PKQPAPKPEP SFSEYASVQV PRK         473

SEQ ID NO: 275         moltype = AA  length = 473
FEATURE                Location/Qualifiers
REGION                 1..473
                       note = SIRPaV2 mutant
SITE                   100
                       note = Site - Mutated residue
source                 1..473
                       mol_type = protein
                       organism = synthetic construct
SEQUENCE: 275
EEELQVIQPD KSVSVAAGES AILHCTVTSL IPVGPIQWFR GAGPARELIY NQKEGHFPRV  60
TTVSESTKRE NMDFSISISN ITPADAGTYY CVKFRKGSPE TEFKSGAGTE LSVRAKPSAP  120
VVSGPAARAT PQHTVSFTCE SHGFSPRDIT LKWFKNGNEL SDFQTNVDPV GESVSYSIHS  180
TAKVVLTRED VHSQVICEVA HVTLQGDPLR GTANLSETIR VPPTLEVTQQ PVRAENQVNV  240
TCQVRKFYPQ RLQLTWLENG NVSRTETAST VTENKDGTYN WMSWLLVNVS AHRDDVKLTC  300
QVEHDGQPAV SKSHDLKVSA HPKEQGSNTA AENTGSNERN IYIVVGVVCT LLVALLMAAL  360
YLVRIRQKKA QGSTSSTRLH EPEKNAREIT QDTNDITYAD LNLPKGKKPA PQAAEPNNHT  420
EYASIQTSPQ PASEDTLTYA DLDMVHLNRT PKQPAPKPEP SFSEYASVQV PRK         473

SEQ ID NO: 276         moltype = AA  length = 369
FEATURE                Location/Qualifiers
source                 1..369
                       mol_type = protein
                       organism = Homo sapiens
SEQUENCE: 276
EDELQVIQPE KSVSVAAGES ATLRCAMTSL IPVGPIMWFR GAGAGRELIY NQKEGHFPRV  60
TTVSELTKRN NLDFSISISN ITPADAGTYY CVKFRKGSPD DVEFKSGAGT ELSVRAKPSA  120
PVVSGPAVRA TPEHTVSFTC ESHGFSPRDI TLKWFKNGNE LSDFQTNVDP AGDSVSYSIH  180
STARVVLTRG DVHSQVICEI AHITLQGDPL RGTANLSEAI RVPPTLEVTQ QPMRAENQAN  240
VTCQVSNFYP RGLQLTWLEN GNVSRTETAS TLIENKDGTY NWMSWLLVNT CAHRDDVVLT  300
CQVEHDGQQA VSKSYALEIS AHQKEHGSDI THEAALAPTA PLLVALLLGP KLLLVVGVSA  360
IYICWKQKA                                                          369

SEQ ID NO: 277         moltype = AA  length = 369
FEATURE                Location/Qualifiers
REGION                 1..369
                       note = SIRPb1 mutant
SITE                   101
```

```
                         note = Site - Mutated residue
source                   1..369
                         mol_type = protein
                         organism = synthetic construct
SEQUENCE: 277
EDELQVIQPE KSVSVAAGES ATLRCAMTSL IPVGPIMWFR GAGAGRELIY NQKEGHFPRV  60
TTVSELTKRN NLDFSISISN ITPADAGTYY CVKFRKGSPD HVEFKSGAGT ELSVRAKPSA  120
PVVSGPAVRA TPEHTVSFTC ESHGFSPRDI TLKWFKNGNE LSDFQTNVDP AGDSVSYSIH  180
STARVVLTRG DVHSQVICEI AHITLQGDPL RGTANLSEAI RVPPTLEVTQ QPMRAENQAN  240
VTCQVSNFYP RGLQLTWLEN GNVSRTETAS TLIENKDGTY NWMSWLLVNT CAHRDDVVLT  300
CQVEHDGQQA VSKSYALEIS AHQKEHGSDI THEAALAPTA PLLVALLLGP KLLLVVGVSA  360
IYICWKQKA                                                         369

SEQ ID NO: 278           moltype = AA  length = 369
FEATURE                  Location/Qualifiers
source                   1..369
                         mol_type = protein
                         organism = Homo sapiens
SEQUENCE: 278
EEELQVIQPD KSISVAAGES ATLHCTVTSL IPVGPIQWFR GAGPGRELIY NQKEGHFPRV  60
TTVSDLTKRN NMDFSIRISN ITPADAGTYY CVKFRKGSPD HVEFKSGAGT ELSVRAKPSA  120
PVVSGPAARA TPQHTVSFTC ESHGFSPRDI TLKWFKNGNE LSDFQTNVDP AGDSVSYSIH  180
STAKVVLTRE DVHSQVICEV AHVTLQGDPL RGTANLSETI RVPPTLEVTQ QPVRAENQVN  240
VTCQVRKFYP QRLQLTWLEN GNVSRTETAS TLTENKDGTY NWMSWLLVNV SAHRDDVKLT  300
CQVEHDGQPA VSKSHDLKVS AHPKEQGSNT APGPALASAA PLLIAFLLGP KVLLVVGVSV  360
IYVYWKQKA                                                         369

SEQ ID NO: 279           moltype = AA  length = 369
FEATURE                  Location/Qualifiers
REGION                   1..369
                         note = SIRPbL mutant
SITE                     101
                         note = Site - Mutated residue
source                   1..369
                         mol_type = protein
                         organism = synthetic construct
SEQUENCE: 279
EEELQVIQPD KSISVAAGES ATLHCTVTSL IPVGPIQWFR GAGPGRELIY NQKEGHFPRV  60
TTVSDLTKRN NMDFSIRISN ITPADAGTYY CVKFRKGSPD DVEFKSGAGT ELSVRAKPSA  120
PVVSGPAARA TPQHTVSFTC ESHGFSPRDI TLKWFKNGNE LSDFQTNVDP AGDSVSYSIH  180
STAKVVLTRE DVHSQVICEV AHVTLQGDPL RGTANLSETI RVPPTLEVTQ QPVRAENQVN  240
VTCQVRKFYP QRLQLTWLEN GNVSRTETAS TLTENKDGTY NWMSWLLVNV SAHRDDVKLT  300
CQVEHDGQPA VSKSHDLKVS AHPKEQGSNT APGPALASAA PLLIAFLLGP KVLLVVGVSV  360
IYVYWKQKA                                                         369

SEQ ID NO: 280           moltype = AA  length = 359
FEATURE                  Location/Qualifiers
source                   1..359
                         mol_type = protein
                         organism = Homo sapiens
SEQUENCE: 280
EEELQMIQPE KLLLVTVGKT ATLHCTVTSL LPVGPVLWFR GVGPGRELIY NQKEGHFPRV  60
TTVSDLTKRN NMDFSIRISS ITPADVGTYY CVKFRKGSPE NVEFKSGPGT EMALGAKPSA  120
PVVLGPAART TPEHTVSFTC ESHGFSPRDI TLKWFKNGNE LSDFQTNVDP TGQSVAYSIR  180
STARVVLDPW DVRSQVICEV AHVTLQGDPL RGTANLSEAI RVPPTLEVTQ QPMRVGNQVN  240
VTCQVRKFYP QSLQLTWSEN GNVCQRETAS TLTENKDGTY NWTSWFLVNI SDQRDDVVLT  300
CQVKHDGQLA VSKRLALEVT VHQKDQSSDA TPGPASSLTA LLLIAVLLGP IYVPWKQKT   359

SEQ ID NO: 281           moltype = AA  length = 359
FEATURE                  Location/Qualifiers
REGION                   1..359
                         note = SIRPg mutant
SITE                     100
                         note = Site - Mutated residue
source                   1..359
                         mol_type = protein
                         organism = synthetic construct
SEQUENCE: 281
EEELQMIQPE KLLLVTVGKT ATLHCTVTSL LPVGPVLWFR GVGPGRELIY NQKEGHFPRV  60
TTVSDLTKRN NMDFSIRISS ITPADVGTYY CVKFRKGSPD NVEFKSGPGT EMALGAKPSA  120
PVVLGPAART TPEHTVSFTC ESHGFSPRDI TLKWFKNGNE LSDFQTNVDP TGQSVAYSIR  180
STARVVLDPW DVRSQVICEV AHVTLQGDPL RGTANLSEAI RVPPTLEVTQ QPMRVGNQVN  240
VTCQVRKFYP QSLQLTWSEN GNVCQRETAS TLTENKDGTY NWTSWFLVNI SDQRDDVVLT  300
CQVKHDGQLA VSKRLALEVT VHQKDQSSDA TPGPASSLTA LLLIAVLLGP IYVPWKQKT   359

SEQ ID NO: 282           moltype = AA  length = 359
FEATURE                  Location/Qualifiers
REGION                   1..359
                         note = SIRPg mutant
```

```
SITE                    101
                        note = Site - Mutated residue
source                  1..359
                        mol_type = protein
                        organism = synthetic construct
SEQUENCE: 282
EEELQMIQPE KLLLVTVGKT ATLHCTVTSL LPVGPVLWFR GVGPGRELIY NQKEGHFPRV  60
TTVSDLTKRN NMDFSIRISS ITPADVGTYY CVKFRKGSPE DVEFKSGPGT EMALGAKPSA  120
PVVLGPAART TPEHTVSFTC ESHGFSPRDI TLKWFKNGNE LSDFQTNVDP TGQSVAYSIR  180
STARVVLDPW DVRSQVICEV AHVTLQGDPL RGTANLSEAI RVPPTLEVTQ QPMRVGNQVN  240
VTCQVRKFYP QSLQLTWSEN GNVCQRETAS TLTENKDGTY NWTSWFLVNI SDQRDDVVLT  300
CQVKHDGQLA VSKRLALEVT VHQKDQSSDA TPGPASSLTA LLLIAVLLGP IYVPWKQKT   359

SEQ ID NO: 283          moltype = AA  length = 359
FEATURE                 Location/Qualifiers
REGION                  1..359
                        note = SIRPg mutant
REGION                  100..101
                        note = Site - Mutated residue
source                  1..359
                        mol_type = protein
                        organism = synthetic construct
SEQUENCE: 283
EEELQMIQPE KLLLVTVGKT ATLHCTVTSL LPVGPVLWFR GVGPGRELIY NQKEGHFPRV  60
TTVSDLTKRN NMDFSIRISS ITPADVGTYY CVKFRKGSPD DVEFKSGPGT EMALGAKPSA  120
PVVLGPAART TPEHTVSFTC ESHGFSPRDI TLKWFKNGNE LSDFQTNVDP TGQSVAYSIR  180
STARVVLDPW DVRSQVICEV AHVTLQGDPL RGTANLSEAI RVPPTLEVTQ QPMRVGNQVN  240
VTCQVRKFYP QSLQLTWSEN GNVCQRETAS TLTENKDGTY NWTSWFLVNI SDQRDDVVLT  300
CQVKHDGQLA VSKRLALEVT VHQKDQSSDA TPGPASSLTA LLLIAVLLGP IYVPWKQKT   359

SEQ ID NO: 284          moltype = AA  length = 126
FEATURE                 Location/Qualifiers
REGION                  1..126
                        note = Artificial antibody sequence
source                  1..126
                        mol_type = protein
                        organism = synthetic construct
SEQUENCE: 284
QVQLVQSGAE VKKPGASVKV SCKASGYNFN IYWINWVRQA PGQGLEWIGN IYPSSISTNY  60
NEKFKTRATL TVDKSTSTVY MELSSLRSED TAVYYCARSE GTYYGGRYEG DWFGYWGQGT  120
LVTVSS                                                            126

SEQ ID NO: 285          moltype = AA  length = 107
FEATURE                 Location/Qualifiers
REGION                  1..107
                        note = Artificial antibody sequence
source                  1..107
                        mol_type = protein
                        organism = synthetic construct
SEQUENCE: 285
DIQMTQSPSS LSASVGDRVT ITCRASQDIR NYLNWYQQKP GKAPKLLIYF TSTLHSGVPS  60
RFSGSGSGTD FTLTISSLQP EDFATYYCQQ GNTLPWTFGG GTKVEIK               107

SEQ ID NO: 286          moltype = AA  length = 118
FEATURE                 Location/Qualifiers
REGION                  1..118
                        note = Artificial antibody sequence
source                  1..118
                        mol_type = protein
                        organism = synthetic construct
SEQUENCE: 286
EVQLVESGGG LVKPGGSLRL SCAASGFTFS SYVMSWVRQT PGKGLEWVAT ISSGGTYTYY  60
PDSVKGRFTL SRDNAKNSLY LQMNSLRAED TAVYYCASQL TGSEFDYWGQ GTTVTVSS    118

SEQ ID NO: 287          moltype = AA  length = 111
FEATURE                 Location/Qualifiers
REGION                  1..111
                        note = Artificial antibody sequence
source                  1..111
                        mol_type = protein
                        organism = synthetic construct
SEQUENCE: 287
DIVITQSPAS LAVSLGERAT ISCRASESVD SYGNSFMHWY QQKPGQPPKL LIYRASNLES  60
GVPDRFSGSG SRTDFTLTIN PLQAEDVATY YCHQSGDLPW TFGGGTKVEI K           111

SEQ ID NO: 288          moltype = AA  length = 116
FEATURE                 Location/Qualifiers
source                  1..116
                        mol_type = protein
```

```
                         organism = Oryctolagus cuniculus
SEQUENCE: 288
QSVEESGGRL GTPGTPLTLT CTVSGFSLSS YVMGWFRQAP GKGLEYIGII SSSGSPYYAS  60
WVNGRFTISK TSTTMDLKMN SPTTEDTATY FCARVGPLGV DYFNIWGPGT LVTVSL      116

SEQ ID NO: 289           moltype = AA  length = 109
FEATURE                  Location/Qualifiers
source                   1..109
                         mol_type = protein
                         organism = Oryctolagus cuniculus
SEQUENCE: 289
DIVMTQTPSS VEAAVGGTVT IKCQAGQSIN SYLAWYQQKP GQRPKLLIYY ASTLESGVPS  60
RFKGSGSGTD YTLTISDLES ADAATYYCQS WHYISRSYAF GGGTEVVVK              109

SEQ ID NO: 290           moltype = AA  length = 115
FEATURE                  Location/Qualifiers
REGION                   1..115
                         note = Artificial antibody sequence
source                   1..115
                         mol_type = protein
                         organism = synthetic construct
SEQUENCE: 290
RQLVESGGGL VQPGGSLRLS CTASGFSLSS HGISWVRQAP GKGLEYIGTI GTGVITYFAS  60
WAKGRFTGSK TSSTAYMELS SLRSEDTAVY FCARGSAWND PFDPWGQGTL VTVSS       115

SEQ ID NO: 291           moltype = AA  length = 111
FEATURE                  Location/Qualifiers
REGION                   1..111
                         note = Artificial antibody sequence
source                   1..111
                         mol_type = protein
                         organism = synthetic construct
SEQUENCE: 291
DIVMTQSPSS LSASVGDRVT ITCQASQSVY GNNDLAWYQQ KPGQAPKLLI YLASTLATGV  60
PSRFSGSGSG TDFTLTISSL QPEDFATYYC LGGGDDEADN TFGQGTKVEI K           111

SEQ ID NO: 292           moltype = AA  length = 115
FEATURE                  Location/Qualifiers
source                   1..115
                         mol_type = protein
                         organism = Oryctolagus cuniculus
SEQUENCE: 292
RSVEESGGRL VTPGTPLTLT CTVSGFSLSS HGISWVRQAP GKGLEYIGTI GTGVITYFAS  60
WAKGRFTGSK TSTTVDLKIT SPTTEDTATY FCARGSAWND PFDPWGPGTL VTVSS       115

SEQ ID NO: 293           moltype = AA  length = 110
FEATURE                  Location/Qualifiers
source                   1..110
                         mol_type = protein
                         organism = Oryctolagus cuniculus
SEQUENCE: 293
ALVMTQTPAS VSAAVGGTVT TKCQASQSVY GNNDLAWYQH KPGQPPKLLI YLASTLATGV  60
PSRFSGSGSG TQFTLTITGV QSDDAATYYC LGGGDDEADN VFGGGTEVVV             110

SEQ ID NO: 294           moltype = AA  length = 117
FEATURE                  Location/Qualifiers
REGION                   1..117
                         note = Artificial antibody sequence
source                   1..117
                         mol_type = protein
                         organism = synthetic construct
SEQUENCE: 294
KVEESGGGLV QPGGSLRLSC AASGFSLSSY VMGWVRQAPG KGLEWVSIIS SSGSPYYASW  60
VNGRFTISKD NSEGMVYLQM NSLRAEDTAV YYCARVGPLG VDYFNIWGQG TTVTVSS     117

SEQ ID NO: 295           moltype = AA  length = 109
FEATURE                  Location/Qualifiers
REGION                   1..109
                         note = Artificial antibody sequence
source                   1..109
                         mol_type = protein
                         organism = synthetic construct
SEQUENCE: 295
DIVMTQSPDS LAVSLGERAT INCQAGQSIN SYLAWYQQKP GQPPKLLIYY ASTLESGVPD  60
RFSGSGSGTD FTLTISSLQA EDVAVYYCQS WHYISRSYAF GGGTKLEIK              109

SEQ ID NO: 296           moltype = AA  length = 115
FEATURE                  Location/Qualifiers
REGION                   1..115
```

-continued

```
                        note = Artificial antibody sequence
source                  1..115
                        mol_type = protein
                        organism = synthetic construct
SEQUENCE: 296
RQLVESGGGL VQPGGSLRLS CTASGFSLSS HGISWVRQAP GKGLEYIGTI GTGVITYFAS  60
WAKGRFTGSK TSSTAYMELS SLRSEDTAVY FCARGSAWND PFDPWGQGTL VTVSS       115

SEQ ID NO: 297          moltype = AA  length = 111
FEATURE                 Location/Qualifiers
REGION                  1..111
                        note = Artificial antibody sequence
source                  1..111
                        mol_type = protein
                        organism = synthetic construct
SEQUENCE: 297
DIEMTQSPSS VSASVGDRVT LTCQASQSVY GNNDLAWYQQ KPGQAPKLLI YLASTLATGV  60
PSRFSGSGSG TDFTLTISSL QPEDFATYYC LGGGDDEADN VFGGGTKVEI K           111
```